US008497273B2

(12) United States Patent
Grandel et al.

(10) Patent No.: US 8,497,273 B2
(45) Date of Patent: *Jul. 30, 2013

(54) HETEROCYCLIC COMPOUNDS SUITABLE FOR TREATING DISORDERS THAT RESPOND TO MODULATION OF THE SEROTONIN 5HT6 RECEPTOR

(75) Inventors: Roland Grandel, Dossenheim (DE); Wilfried Martin Braje, Rinteln (DE); Andreas Haupt, Schwetzingen (DE); Sean Colm Turner, Mannheim (DE); Udo Lange, Berlin (DE); Karla Drescher, Dossenheim (DE); Liliane Unger, Ludwigshafen (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/297,328

(22) PCT Filed: Apr. 18, 2007

(86) PCT No.: PCT/EP2007/053808
§ 371 (c)(1),
(2), (4) Date: Nov. 4, 2009

(87) PCT Pub. No.: WO2007/118900
PCT Pub. Date: Oct. 25, 2007

(65) Prior Publication Data
US 2010/0048582 A1 Feb. 25, 2010

Related U.S. Application Data

(60) Provisional application No. 60/793,047, filed on Apr. 19, 2006.

(51) Int. Cl.
| | |
|---|---|
| A61K 31/496 | (2006.01) |
| C07D 401/04 | (2006.01) |
| C07D 401/14 | (2006.01) |
| A61K 31/4439 | (2006.01) |
| A61K 31/4545 | (2006.01) |
| C07D 413/14 | (2006.01) |
| C07D 417/14 | (2006.01) |

(52) U.S. Cl.
USPC .......... 514/253.01; 514/253.11; 514/318; 514/343; 544/360; 544/364; 546/194; 546/268.1; 546/276.4

(58) Field of Classification Search
None
See application file for complete search history.

(56) References Cited

U.S. PATENT DOCUMENTS

| | | | | |
|---|---|---|---|---|
| 7,320,979 B2 * | 1/2008 | Braje et al. | ............... | 514/252.14 |
| 7,713,978 B2 * | 5/2010 | King et al. | ............... | 514/253.11 |
| 2004/0204422 A1 * | 10/2004 | Braje et al. | ............... | 514/254.01 |

FOREIGN PATENT DOCUMENTS

| | | |
|---|---|---|
| WO | 95/04713 A1 | 2/1995 |
| WO | 96/23760 A1 | 8/1996 |
| WO | 97/45503 A1 | 12/1997 |
| WO | 98/27081 A1 | 6/1998 |
| WO | 99/58499 A1 | 11/1999 |
| WO | 00/05225 A1 | 2/2000 |
| WO | 2005/026125 A1 | 3/2005 |
| WO | 2005/037830 A1 | 4/2005 |
| WO | 2005/113539 A1 | 12/2005 |
| WO | 2006/040182 A1 | 4/2006 |
| WO | 2006/063718 A1 | 6/2006 |

OTHER PUBLICATIONS

Robichaud et al. in Annual Reports in Medicinal Chemistry, vol. 36, p. 11-20 (2000).*
Rogers et al. Psychopharmacology, vol. 158, p. 114-119 (2001).*
Holenz et al. Drug Discovery Today, vol. 11, pp. 283-299 (2006).*
Sokoloff, et al., Localization and Function of the D3 Dopamine Receptor, Drug Res. 42(1), 224 (1992).
Sokoloff, et al., Molecular Cloning and Characterization of a Novel Dopamine Receptor (D3) as a Target for Neuroleptics, Nature, 347, 146 (1990).
International Search Report as filed Jul. 20, 2007 in PCT/EP2007/053808.
Written Opinion for Application No. PCT/EP2007/053808 dated Jul. 20, 2007 (5 pages).

* cited by examiner

*Primary Examiner* — Emily Bernhardt
(74) *Attorney, Agent, or Firm* — Lisa V. Mueller; Michael Best & Friedrich LLP

(57) ABSTRACT

The invention relates to compounds of the formula (I)

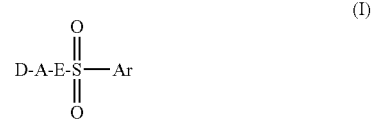

(I)

wherein the variables have meanings given in the claims and the description.
The invention also relates to the use of a compound of the formula I or a pharmaceutically acceptable salt thereof for preparing a medicament for the treatment of a medical disorder susceptible to the treatment with a $5HT_6$ receptor ligand.

11 Claims, No Drawings

HETEROCYCLIC COMPOUNDS SUITABLE FOR TREATING DISORDERS THAT RESPOND TO MODULATION OF THE SEROTONIN 5HT6 RECEPTOR

CROSS REFERENCE TO RELATED APPLICATION

This application is a 371 national stage filing based upon International PCT Application No. PCT/EP2007/053808, with an international filing date of Apr. 18, 2007, which claims the benefit of priority to U.S. Provisional Application No. 60/793,047, filed Apr. 19, 2006, each of which are fully incorporated herein by reference as though fully set forth herein.

BACKGROUND OF THE INVENTION

The present invention relates to novel heterocyclic compounds. The compounds possess valuable therapeutic properties and are suitable, in particular, for treating diseases that respond to modulation of the serotonine 5-HT6 receptor.

Serotonin (5-hydroxytryptamine, 5HT), a monoamine neurotransmitter and local hormone, is formed by the hydroxylation and decarboxylation of tryptophan. The greatest concentration is found in the enterochromaffin cells of the gastrointestinal tract, the remainder being predominantly present in platelets and in the Central Nervous System (CNS). 5HT is implicated in a vast array of physiological and pathophysiological path-ways. In the periphery, it contracts a number of smooth muscles and induces endothelium-dependent vasodilation. In the CNS, it is believed to be involved in a wide range of functions, including the control of appetite, mood, anxiety, hallucinations, sleep, vomiting and pain perception.

Neurons that secrete 5HT are termed serotonergic. The function of 5HT is exerted upon ist interaction with specific (serotonergic) neurons. Until now, seven types of 5HT receptors have been identified: $5HT_1$ (with subtypes $5HT_{1A}$, $5HT_{1B}$, $5HT_{1D}$, $5HT_{1E}$ and $5HT_{1F}$), $5HT_2$ (with subtypes $5HT_{2A}$, $5HT_{2B}$ and $5HT_{1C}$), $5HT_3$, $5HT_4$, $5HT_5$ (with subtypes $5HT_{1A}$ and $5HT_{1B}$), $5HT_6$ and $5HT_7$). Most of these receptors are coupled to G-proteins that affect the activities of either adenylate cyclase or phospholipase Cγ.

The human $5HT_6$ receptors are positively coupled to adenylyl cyclase. They are distributed throughout the limbic, striatal and cortical regions of the brain and show a high affinity to antipsychotics.

The modulation of the $5HT_6$ receptor by suitable substances is expected to improve certain disorders including cognitive dysfunctions, such as a deficit in memory, cognition and learning, in particular associated with Alzheimer's disease, age-related cognitive decline and mild cognitive impairment, attention deficit disorder/hyperactivity syndrome, personality disorders, such as schizophrenia, in particular cognitive deficits related with schizophrenia, affective disorders such as depression, anxiety and obsessive compulsive disorders, motion or motor disorders such as Parkinson's disease and epilepsy, migraine, sleep disorders (including disturbances of the Circadian rhythm), feeding disorders, such as anorexia and bulimia, certain gastrointestinaldisorders such as Irritable Bowel Syndrome, diseases associated with neurodegeneration, such as stroke, spinal or head trauma and head injuries, such as hydrocephalus, drug addiction and obesity.

Another neurotransmitter with implications on the CNS is dopamine. Disorders in the dopaminergic transmitter system result in diseases of the central nervous system which include, for example, schizophrenia, depression and Parkinson's disease. These diseases, and others, are treated with drugs which interact with the dopamine receptors. The dopamine receptors are divided into two families. On the one hand, there is the $D_2$ group, consisting of $D_2$, $D_3$ and $D_4$ receptors, and, on the other hand, the $D_1$ group, consisting of $D_1$ and $D_5$ receptors. Whereas $D_1$ and $D_2$ receptors are widely distributed, $D_3$ receptors appear to be expressed regioselectively. Thus, these receptors are preferentially to be found in the limbic system and the projection regions of the mesolimbic dopamine system, especially in the nucleus accumbens, but also in other regions, such as the amygdala. Because of this comparatively regioselective expression, $D_3$ receptors are regarded as being a target having few side-effects and it is assumed that while a selective $D_3$ ligand would have the properties of known antipsychotics, it would not have their dopamine $D_2$ receptor-mediated neurological side-effects (P. Sokoloff et al., Localization and Function of the $D_3$ Dopamine Receptor, *Arzneim. Forsch./Drug Res.* 42(1), 224 (1992); P. Sokoloff et al. Molecular Cloning and Characterization of a Novel Dopamine Receptor ($D_3$) as a Target for Neuroleptics, *Nature*, 347, 146 (1990)).

Compounds having an affinity for the dopamine $D_3$ receptor have been described in the prior art on various occasions, e.g. in WO 95/04713, WO 96/23760, WO 97/45503, WO 99/58499 and in the unpublished international patent application PCT/EP 2005/011106.

Compounds having an affinity for the $5HT_6$ receptor have also been described in the prior art, e.g. in WO 2005/037830, WO 2005/026125, WO 00/05225 and WO 98/27081. However, their affinity and selectivity towards the $5HT_6$ receptor or their pharmacological profile is not yet satisfactory.

It is an object of the present invention to provide compounds which have a high affinity and selectivity for the $5HT_6$ receptor and optionally a high affinity and selectivity (in particular versus $D_2$) for the dopamine $D_3$ receptor, thus allowing the treatment of disorders related to or affected by the $5HT_6$ receptor. Compounds having an affinity for both receptors are expected to be suitable for treating disorders related to or affected by both the $5HT_6$ receptor and the $D_3$ receptor, thus allowing the treatment of more than one aspect of the respective disorder.

The compounds should also have good pharmacological profile, e.g. a good brain plasma ratio, a good bioavailability, good metabolic stability, or a decreased inhibition of the mitochondrial respiration.

SUMMARY OF THE INVENTION

The invention is based on the object of providing compounds which act as $5HT_6$ receptor ligands. This object is surprisingly achieved by means of compounds of the formula I

wherein
D is a group of the formula B or C

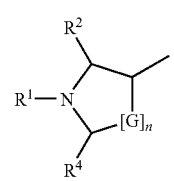

B

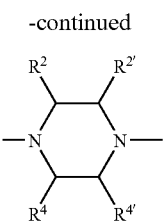

n is or 2;

G is $CH_2$ or $CHR^3$;

$R^1$ is H, $C_1$-$C_6$-alkyl, $C_1$-$C_6$-alkyl substituted by $C_3$-$C_6$-cycloalkyl, $C_1$-$C_6$-hydroxyalkyl, fluorinated $C_1$-$C_6$-alkyl, $C_3$-$C_6$-cycloalkyl, fluorinated $C_3$-$C_6$-cycloalkyl, $C_3$-$C_6$-alkenyl, fluorinated $C_3$-$C_6$-alkenyl, formyl, acetyl, propionyl or benzyl;

$R^2$, $R^{2'}$, $R^3$, $R^4$ and $R^{4'}$ are, independently of each other, H, methyl, fluoromethyl, difluoromethyl, or trifluoromethyl;

A is 2,4-pyridylene, 3,5-pyridylene or 2,6-pyridylene, which is optionally substituted by one, two or three substituents selected from halogen, $C_1$-$C_4$-alkyl, $C_1$-$C_4$-alkoxy, fluorinated $C_1$-$C_4$-alkyl and fluorinated $C_1$-$C_4$-alkoxy;

E is $NR^5$ or $CH_2$, wherein $R^5$ is H or $C_1$-$C_3$-alkyl;

Ar is a cyclic radical selected from the group consisting of phenyl, a 5- or 6-membered heteroaromatic radical comprising as ring members 1, 2 or 3 heteroatoms selected from N, O and S and a phenyl ring fused to a saturated or unsaturated 5- or 6-membered carbocyclic or heterocyclic ring, where the heterocyclic ring comprises as ring members 1, 2 or 3 heteroatoms selected from N, O and S and/or 1, 2 or 3 heteroatom-containing groups each independently selected from $NR^8$, where $R^8$ is H, $C_1$-$C_4$-alkyl, fluorinated $C_1$-$C_4$-alkyl, $C_1$-$C_4$-alkylcarbonyl or fluorinated $C_1$-$C_4$-alkylcarbonyl, and where the cyclic radical Ar may carry 1, 2 or 3 substituents $R^a$;

each $R^a$ is independently halogen, hydroxyl, $C_1$-$C_6$-alkyl, fluorinated $C_1$-$C_6$-alkyl, $C_1$-$C_6$-hydroxyalkyl, $C_1$-$C_6$-alkoxy-$C_1$-$C_6$-alkyl, $C_2$-$C_6$-alkenyl, fluorinated $C_2$-$C_6$-alkenyl, $C_3$-$C_6$-cycloalkyl, fluorinated $C_3$-$C_6$-cycloalkyl, $C_1$-$C_6$-alkoxy, $C_1$-$C_6$-hydroxyalkoxy, $C_1$-$C_6$-alkoxy-$C_1$-$C_6$-alkoxy, fluorinated $C_1$-$C_6$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, phenylsulfonyl, pyridylsulfonyl, benzyloxy, phenoxy, phenyl, where the phenyl and the pyridyl radical in the 5 last-mentioned radicals may be unsubstituted or may carry 1 to 3 substituents selected from $C_1$-$C_4$-alkyl, fluorinated $C_1$-$C_4$-alkyl and halogen, CN, nitro, $C_1$-$C_6$-alkylcarbonyl, fluorinated $C_1$-$C_6$-alkylcarbonyl, $C_1$-$C_6$-alkylcarbonylamino, fluorinated $C_1$-$C_6$-alkylcarbonylamino, carboxy, NH—C(O)—$NR^6R^7$, $NR^6R^7$, $NR^6R^7$—$C_1$-$C_6$-alkylene, O—$NR^6R^7$, where $R^6$ and $R^7$ are, independently of each other, H, $C_1$-$C_4$-alkyl, fluorinated $C_1$-$C_4$-alkyl or $C_1$-$C_4$-alkoxy or may form, together with N, a 4-, 5- or 6-membered saturated or unsaturated ring, $R^{10}$—CO—$NR^6$—$C_1$-$C_6$-alkylene, where $R^6$ is as defined above and $R^{10}$ is $C_1$-$C_4$-alkyl or phenyl, where the phenyl radical may be unsubstituted or may carry 1 to 3 substituents selected from $C_1$-$C_4$-alkyl, fluorinated $C_1$-$C_4$-alkyl and halogen, $CH_2$-pyridyl, where the pyridyl radical may be unsubstituted or may carry 1 to 3 substituents selected from $C_1$-$C_4$-alkyl, fluorinated $C_1$-$C_4$-alkyl and halogen, or is a saturated or unsaturated aromatic or non-aromatic 3- to 7-membered heterocyclic ring comprising as ring members 1, 2, 3 or 4 heteroatoms selected from N, O and S and/or 1, 2 or 3 heteroatom-containing groups selected from $NR^9$, where $R^9$ has one of the meanings given for $R^8$, SO, $SO_2$ and CO, and where the heterocyclic ring may carry 1, 2 or 3 substituents selected from hydroxy, halogen, $C_1$-$C_6$-alkyl, fluorinated $C_1$-$C_6$-alkyl, $C_1$-$C_6$-alkoxy, fluorinated $C_1$-$C_6$-alkoxy, $C_1$-$C_6$-alkylthio, fluorinated $C_1$-$C_6$-alkylthio, $NR^6R^7$—$C_1$-$C_6$-alkylene, where $R^6$ and $R^7$ are as defined above, carboxyl and $C_1$-$C_4$-alkoxycarbonyl;

and physiologically tolerated acid addition salts thereof.

The present invention therefore relates to compounds of the general formula I and to their physiologically tolerated acid addition salts.

In a specific embodiment of compounds I, $R^1$ is H, $C_1$-$C_6$-alkyl, $C_1$-$C_6$-alkyl substituted by $C_3$-$C_6$-cycloalkyl, $C_1$-$C_6$-hydroxyalkyl, fluorinated $C_1$-$C_6$-alkyl, $C_3$-$C_6$-cycloalkyl, fluorinated $C_3$-$C_6$-cycloalkyl, $C_3$-$C_6$-alkenyl, fluorinated $C_3$-$C_6$-alkenyl, formyl, acetyl or propionyl; and $R^a$ is halogen, $C_1$-$C_6$-alkyl, fluorinated $C_1$-$C_6$-alkyl, $C_1$-$C_6$-hydroxyalkyl, $C_1$-$C_6$-alkoxy-$C_1$-$C_6$-alkyl, $C_2$-$C_6$-alkenyl, fluorinated $C_2$-$C_6$-alkenyl, $C_3$-$C_6$-cycloalkyl, fluorinated $C_3$-$C_6$-cycloalkyl, $C_1$-$C_6$-alkoxy, $C_1$-$C_6$-hydroxyalkoxy, $C_1$-$C_6$-alkoxy-$C_1$-$C_6$-alkoxy, fluorinated $C_1$-$C_6$-alkoxy, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, phenylsulfonyl, benzyloxy, phenoxy, where the phenyl radical in the 3 last-mentioned radicals may be unsubstituted or may carry 1 to 3 substituents selected from $C_1$-$C_4$-alkyl, fluorinated $C_1$-$C_4$-alkyl and halogen, CN, nitro, $C_1$-$C_6$-alkylcarbonyl, fluorinated $C_1$-$C_6$-alkylcarbonyl, $C_1$-$C_6$-alkylcarbonylamino, fluorinated $C_1$-$C_6$-alkylcarbonylamino, carboxy, NH—C(O)—$NR^6R^7$, $NR^6R^7$, $NR^6R^7$—$C_1$-$C_6$-alkylene, O—$NR^6R^7$, where $R^6$ and $R^7$ are, independently of each other, H, $C_1$-$C_4$-alkyl, fluorinated $C_1$-$C_4$-alkyl or $C_1$-$C_4$-alkoxy or may form, together with N, a 4-, 5- or 6-membered saturated or unsaturated ring, or is a saturated or unsaturated 3- to 7-membered heterocyclic ring comprising as ring members 1, 2, 3 or 4 heteroatoms selected from N, O and S and/or 1, 2 or 3 heteroatom-containing groups selected from $NR^9$, where $R^9$ has one of the meanings given for $R^8$, SO, $SO_2$ and CO, and where the heterocyclic ring may carry 1, 2 or 3 substituents selected from hydroxy, halogen, $C_1$-$C_6$-alkyl, fluorinated $C_1$-$C_6$-alkyl and $C_1$-$C_6$-alkoxy.

The present invention also relates to a pharmaceutical composition which comprises at least one compound of the formula I and/or at least one physiologically tolerated acid addition salt of I, where appropriate together with physiologically acceptable carriers and/or auxiliary substances.

The present invention also relates to a method for treating disorders which respond to influencing by $5HT_6$ receptor antagonists or $5HT_6$ agonists, said method comprising administering an effective amount of at least one compound of the formula I and/or at least one physiologically tolerated acid addition salt of I to a subject in need thereof.

The present invention further relates to the use of a compound of the formula I and/or physiologically tolerated acid addition salts thereof, for preparing a medicament for the treatment of a medical disorder susceptible to treatment with a 5-$HT_6$ receptor ligand.

DETAILED DESCRIPTION OF THE INVENTION

The remarks made in the following with respect to preferred aspects of the invention, e.g. to preferred meanings of the variables of compound I, to preferred compounds I and to preferred embodiments of the method or the use according to the invention, apply in each case on their own or to combinations thereof.

The diseases which respond to the influence of $5HT_6$ receptor antagonists or agonists include, in particular, disorders and diseases of the central nervous system, in particular cognitive dysfunctions, such as a deficit in memory, cognition and learning, in particular associated with Alzheimer's disease, age-related cognitive decline and mild cognitive impairment, attention deficit disorder/hyperactivity syndrome, personality disorders, such as schizophrenia, in particular cognitive deficits related with schizophrenia, affective disorders such as depression, bipolar disorder, anxiety and obsessive compulsive disorders, motion or motor disorders such as Parkinson's disease and epilepsy, migraine, sleep disorders (including disturbances of the Circadian rhythm), feeding disorders, such as anorexia and bulimia, certain gastrointestinaldisorders such as Irritable Bowel Syndrome, diseases associated with neurodegeneration, such as stroke, spinal or head trauma and head injuries, such as hydrocephalus, drug addiction and obesity.

According to the invention, at least one compound of the general formula I having the meanings mentioned at the outset is used for treating the above mentioned indications. Provided the compounds of the formula I of a given constitution may exist in different spatial arrangements, for example if they possess one or more centers of asymmetry, polysubstituted rings or double bonds, or as different tautomers, it is also possible to use enantiomeric mixtures, in particular racemates, diastereomeric mixtures and tautomeric mixtures, preferably, however, the respective essentially pure enantiomers, diastereomers and tautomers of the compounds of formula I and/or of their salts.

Particularly, the carbon atom of the nitrogen-containing ring D carrying the group A may have (S) or (R) configuration. However, the (S) configuration is preferred.

Moreover, the radical A may be in a cis or trans position to either of the substituents $R^2$, $R^3$ or $R^4$ (if at least one of those is not hydrogen). However, the cis position is preferred.

It is likewise possible to use physiologically tolerated salts of the compounds of the formula I, especially acid addition salts with physiologically tolerated acids. Examples of suitable physiologically tolerated organic and inorganic acids are hydrochloric acid, hydrobromic acid, phosphoric acid, sulfuric acid, $C_1$-$C_4$-alkylsulfonic acids, such as methanesulfonic acid, aromatic sulfonic acids, such as benzenesulfonic acid and toluenesulfonic acid, oxalic acid, maleic acid, fumaric acid, lactic acid, tartaric acid, adipic acid and benzoic acid. Other utilizable acids are described in Fortschritte der Arzneimittelforschung [Advances in drug research], Volume 10, pages 224 ff., Birkhäuser Verlag, Basel and Stuttgart, 1966.

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine, in particular fluorine, chlorine or bromine.

$C_1$-$C_4$ Alkyl is a straight-chain or branched alkyl group having from 1 to 4 carbon atoms. Examples of an alkyl group are methyl, ethyl, n-propyl, iso-propyl, n-butyl, 2-butyl, isobutyl or tert-butyl. $C_1$-$C_2$ Alkyl is methyl or ethyl, $C_1$-$C_3$ alkyl is additionally n-propyl or isopropyl.

$C_1$-$C_6$ Alkyl is a straight-chain or branched alkyl group having from 1 to 6 carbon atoms. Examples include $C_1$-$C_4$ alkyl as mentioned above and also pentyl, 1-methylbutyl, 2-methylbutyl, 3-methylbutyl, 2,2-dimethylpropyl, 1-ethyl-propyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

Fluorinated $C_1$-$C_6$ alkyl is a straight-chain or branched alkyl group having from 1 to 6, especially 1 to 4 carbon atoms (=fluorinated $C_1$-$C_4$ alkyl), in particular 1 to 3 carbon atoms (=fluorinated $C_1$-$C_3$ alkyl), wherein at least one, e.g. 1, 2, 3, 4 or all of the hydrogen atoms are replaced by a fluorine atom such as in fluoromethyl, difluoromethyl, trifluoromethyl, (R)-1-fluoroethyl, (S)-1-fluoroethyl, 2-fluoroethyl, 1,1-difluoroethyl, 2,2-difluoroethyl, 2,2,2-trifluoroethyl, 1,1,2,2-tetrafluoroethyl, (R)-1-fluoropropyl, (S)-1-fluoropropyl, 2-fluoropropyl, 3-fluoropropyl, 1,1-difluoropropyl, 2,2-difluoropropyl, 3,3-difluoropropyl, 3,3,3-trifluoropropyl, (R)-2-fluoro-1-methylethyl, (S)-2-fluoro-1-methylethyl, (R)-2,2-difluoro-1-methylethyl, (S)-2,2-difluoro-1-methylethyl, (R)-1,2-difluoro-1-methylethyl, (S)-1,2-difluoro-1-methylethyl, (R)-2,2,2-trifluoro-1-methylethyl, (S)-2,2,2-trifluoro-1-methylethyl, 2-fluoro-1-(fluoromethyl)ethyl, 1-(difluoromethyl)-2,2-difluoroethyl, 1-(trifluoromethyl)-2,2,2-trifluoroethyl, 1-(trifluoromethyl)-1,2,2,2-tetrafluoroethyl, (R)-1-fluorobutyl, (S)-1-fluorobutyl, 2-fluorobutyl, 3-fluorobutyl, 4-fluorobutyl, 1,1-difluorobutyl, 2,2-difluorobutyl, 3,3-difluorobutyl, 4,4-difluorobutyl, 4,4,4-trifluorobutyl, and the like.

Branched $C_3$-$C_6$ alkyl is alkyl having 3 to 6 carbon atoms at least one being a secondary or tertiary carbon atom. Examples are isopropyl, tert.-butyl, 2-butyl, isobutyl, 2-pentyl, 2-hexyl, 3-methylpentyl, 1,1-dimethylbutyl, 1,2-dimethylbutyl, 1-methyl-1-ethylpropyl.

Fluorinated branched $C_3$-$C_6$ alkyl is alkyl having 3 to 6 carbon atoms at least one being a secondary or tertiary carbon atom wherein at least one, e.g. 1, 2, 3, 4 or all of the hydrogen atoms are replaced by a fluorine atom.

$C_1$-$C_6$ Alkoxy is a straight-chain or branched alkyl group having from 1 to 6, in particular 1 to 4 carbon atoms (=$C_1$-$C_4$ alkoxy), which is bound to the remainder of the molecule via an oxygen atom. Examples include methoxy, ethoxy, n-propoxy, isopropoxy, n-butoxy, 2-butoxy, iso-butoxy, tert.-butoxy pentyloxy, 1-methylbutoxy, 2-methylbutoxy, 3-methylbutoxy, 2,2-dimethylbutoxy, 1-ethylpropoxy, hexyloxy, 1,1-dimethylpropoxy, 1,2-dimethylpropoxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 2-ethylbutyloxy, 1,1,2-trimethylpropoxy, 1,2,2-trimethylpropoxy, 1-ethyl-1-methylpropoxy and 1-ethyl-2-methylpropoxy.

Fluorinated $C_1$-$C_6$ alkoxy is a straight-chain or branched alkoxy group having from 1 to 6, in particular 1 to 4 carbon atoms (=fluorinated $C_1$-$C_4$ alkoxy), wherein at least one, e.g. 1, 2, 3, 4 or all of the hydrogen atoms are replaced by a fluorine atoms such as in fluoromethoxy, difluoromethoxy, trifluoromethoxy, (R)-1-fluoroethoxy, (S)-1-fluoroethoxy, 2-fluoroethoxy, 1,1-difluoroethoxy, 2,2-difluoroethoxy, 2,2,2-trifluoroethoxy, 1,1,2,2-tetrafluoroethoxy, (R)-1-fluoropropoxy, (S)-1-fluoropropoxy, (R)-2-fluoropropoxy, (S)-2-fluoropropoxy, 3-fluoropropoxy, 1,1-difluoropropoxy, 2,2-difluoropropoxy, 3,3-difluoropropoxy, 3,3,3-trifluoropropoxy, (R)-2-fluoro-1-methylethoxy, (S)-2-fluoro-1-methylethoxy, (R)-2,2-difluoro-1-methylethoxy, (S)-2,2-difluoro-1-methylethoxy, (R)-1,2-difluoro-1-methylethoxy, (S)-1,2-difluoro-1-methylethoxy, (R)-2,2,2-trifluoro-1-methylethoxy, (S)-2,2,2-trifluoro-1-methylethoxy, 2-fluoro-1-(fluoromethyl)ethoxy, 1-(difluoromethyl)-2,2-difluoroethoxy, (R)-1-fluorobutoxy, (S)-1-fluorobutoxy, 2-fluorobutoxy, 3-fluorobutoxy, 4-fluorobutoxy, 1,1-difluorobutoxy, 2,2-difluorobutoxy, 3,3-difluorobutoxy, 4,4-difluorobutoxy, 4,4,4-trifluorobutoxy, and the like.

$C_1$-$C_6$ Hydroxyalkyl is a straight-chain or branched alkyl group having from 1 to 6, especially 1 to 4 carbon atoms (=$C_1$-$C_4$ hydroxyalkyl), in particular 1 to 3 carbon atoms (=$C_1$-$C_3$ hydroxyalkyl), wherein one of the hydrogen atoms is replaced by a hydroxy group, such as in 2-hydroxyethyl or 3-hydroxypropyl.

$C_1$-$C_6$-Alkoxy-$C_1$-$C_6$-alkyl is a straight-chain or branched alkyl group having from 1 to 6, especially 1 to 4 carbon atoms, in particular 1 to 3 carbon atoms, wherein one of the hydrogen atoms is replaced by a $C_1$-$C_6$-alkoxy group, such as in methoxymethyl, 2-methoxyethyl, ethoxymethyl, 3-methoxypropyl, 3-ethoxypropyl and the like.

$C_1$-$C_6$-Alkoxy-$C_1$-$C_6$-alkoxy is a straight-chain or branched alkyl group having from 1 to 6, especially 1 to 4 carbon atoms, in particular 1 to 3 carbon atoms, wherein one of the hydrogen atoms is replaced by a $C_1$-$C_6$-alkoxy group, such as in 2-methoxyethoxy, ethoxymethoxy, 2-ethoxyethoxy, 3-methoxypropoxy, 3-ethoxypropoxy and the like.

$C_1$-$C_6$-Alkylcarbonyl is a straight-chain or branched alkyl group having from 1 to 6, especially 1 to 4 carbon atoms, in particular 1 to 3 carbon atoms, wherein one of the hydrogen atoms is replaced by a carbonyl group (CO), such as in acetyl and propionyl.

Fluorinated $C_1$-$C_6$-alkylcarbonyl is a straight-chain or branched alkyl group having from 1 to 6, especially 1 to 4 carbon atoms (=fluorinated $C_1$-$C_4$ alkylcarbonyl), in particular 1 to 3 carbon atoms (=fluorinated $C_1$-$C_3$ alkylcarbonyl), wherein one of the hydrogen atoms is replaced by a carbonyl group (CO) and wherein at least one of the remaining hydrogen atoms, e.g. 1, 2, 3, or 4 of the hydrogen atoms are replaced by a fluorine atom, such as in trifluoroacetyl and 3,3,3-trifluoropropionyl.

$C_1$-$C_6$-Alkylcarbonylamino is a straight-chain or branched alkyl group having from 1 to 6, especially 1 to 4 carbon atoms (=$C_1$-$C_4$ alkylcarbonylamino), in particular 1 to 3 carbon atoms (=$C_1$-$C_3$ alkylcarbonylamino), wherein one of the hydrogen atoms is replaced by a carbonylamino group (CO—NH—), such as in acetamido (acetylamino) ($CH_3CONH$—) and propionamido ($CH_3CH_2CONH$—).

Fluorinated $C_1$-$C_6$-alkylcarbonylamino is a straight-chain or branched alkyl group having from 1 to 6, especially 1 to 4 carbon atoms (=fluorinated $C_1$-$C_4$ alkylcarbonylamino), in particular 1 to 3 carbon atoms (=fluorinated $C_1$-$C_3$ alkylcarbonylamino), wherein one of the hydrogen atoms is replaced by a carbonylamino group (CO—NH—) and wherein at least one of the remaining hydrogen atoms, e.g. 1, 2, 3, or 4 of the hydrogen atoms are replaced by a fluorine atom, such as in trifluoroacetylamino and 3,3,3-trifluoropropionylamino.

$C_1$-$C_6$ Alkylthio (also termed as $C_1$-$C_6$-alkylsulfanyl) (or $C_1$-$C_6$-alkylsulfinyl or $C_1$-$C_6$-alkylsulfonyl, respectively) refer to straight-chain or branched alkyl groups having 1 to 6 carbon atoms, e.g. 1 to 4 carbon atoms, which are bound to the remainder of the molecule via a sulfur atom (or S(O)O in case of alkylsulfinyl or $S(O)_2O$ in case of alkylsulfonyl, respectively), at any bond in the alkyl group. Examples for $C_1$-$C_4$-alkylthio include methylthio, ethylthio, propylthio, isopropylthio, and n-butylthio. Examples for $C_1$-$C_4$-alkylsulfinyl include methylsulfinyl, ethylsulfinyl, propylsulfinyl, isopropylsulfinyl, and n-butylsulfinyl. Examples for $C_1$-$C_4$-alkylsulfonyl include methylsulfonyl, ethylsulfonyl, propylsulfonyl, isopropylsulfonyl, and n-butylsulfonyl.

Fluorinated $C_1$-$C_6$ alkylthio (also termed fluorinated $C_1$-$C_6$-alkylsulfanyl) is a straight-chain or branched alkylthio group having from 1 to 6, in particular 1 to 4 carbon atoms, wherein at least one, e.g. 1, 2, 3, 4 or all of the hydrogen atoms are replaced by fluorine atoms. Fluorinated $C_1$-$C_6$ alkylsulfinyl is a straight-chain or branched alkylsulfinyl group having from 1 to 6, in particular 1 to 4 carbon atoms, wherein at least one, e.g. 1, 2, 3, 4 or all of the hydrogen atoms are replaced by fluorine atoms. Fluorinated $C_1$-$C_6$ alkylsulfonyl is a straight-chain or branched alkylsulfonyl group having from 1 to 6, in particular 1 to 4 carbon atoms, wherein at least one, e.g. 1, 2, 3, 4 or all of the hydrogen atoms are replaced by fluorine atoms.

$C_3$-$C_6$ Cycloalkyl is a cycloaliphatic radical having from 3 to 6 C atoms, such as cyclo-propyl, cyclobutyl, cyclopentyl and cyclohexyl. The cycloalkyl radical may be unsubstituted or may carry 1, 2, 3 or 4 $C_1$-$C_4$ alkyl radicals, preferably a methyl radical. One alkyl radical is preferably located in the 1-position of the cycloalkyl radical, such as in 1-methylcyclopropyl or 1-methylcyclobutyl.

Fluorinated $C_3$-$C_6$ cycloalkyl is a cycloaliphatic radical having from 3 to 6 C atoms, such as cyclopropyl, cyclobutyl, cyclopentyl and cyclohexyl, wherein at least one, e.g. 1, 2, 3, 4 or all of the hydrogen atoms are replaced by a fluorine atoms such as in 1-fluorocyclopropyl, 2-fluorocyclopropyl, (S)- and (R)-2,2-difluorocyclopropyl, 1,2-difluorocyclopropyl, 2,3-difluorocyclopropyl, pentafluorocyclopropyl, 1-fluorocyclobutyl, 2-fluorocyclobutyl, 3-fluorocyclobutyl, 2,2-difluorocyclobutyl, 3,3-difluorocyclobutyl, 1,2-difluorocyclobutyl, 1,3-difluorocyclobutyl, 2,3-difluorocyclobutyl, 2,4-difluorocyclobutyl, or 1,2,2-trifluorocyclobutyl.

$C_2$-$C_6$-Alkenyl is a singly unsaturated hydrocarbon radical having 2, 3, 4, 5 or 6 C-atoms, e.g. vinyl, allyl (2-propen-1-yl), 1-propen-1-yl, 2-propen-2-yl, methallyl (2-methylprop-2-en-1-yl) and the like. $C_3$-$C_6$-Alkenyl is, in particular, allyl, 1-methylprop-2-en-1-yl, 2-buten-1-yl, 3-buten-1-yl, methallyl, 2-penten-1-yl, 3-penten-1-yl, 4-penten-1-yl, 1-methylbut-2-en-1-yl or 2-ethylprop-2-en-1-yl.

Fluorinated $C_2$-$C_6$-alkenyl is a singly unsaturated hydrocarbon radical having 2, 3, 4, 5 or 6 C-atoms, I, wherein at least one, e.g. 1, 2, 3, 4 or all of the hydrogen atoms are replaced by a fluorine atoms such as in 1-fluorovinyl, 2-fluorovinyl, 2,2-fluorovinyl, 3,3,3-fluoropropenyl, 1,1-difluoro-2-propenyl 1-fluoro-2-propenyl and the like.

$C_1$-$C_6$-Alkylene is a hydrocarbon bridging group having 1, 2, 3, 4, 5 or 6 carbon atoms, like methylene, ethylene, 1,2- and 1,3-propylene, 1,4-butylene and the like.

Examples of 5- or 6-membered heteroaromatic radicals comprise 2-, 3-, or 4-pyridyl, 2-, 4- or 5-pyrimidinyl, pyrazinyl, 3- or 4-pyridazinyl, 2- or 3-thienyl, 2- or 3-furyl, 2- or 3-pyrrolyl, 2-, 3- or 5-oxazolyl, 3-, 4- or 5-isoxazolyl, 2-, 3- or 5-thiazolyl, 3-, 4- or 5-isothiazolyl, 3-, 4- or 5-pyrazolyl, 2-, 4- or 5-imidazolyl, 2- or 5-[1,3,4]oxadiazolyl, 4- or 5-[1,2,3]oxadiazolyl, 3- or 5-[1,2,4]oxadiazolyl, 2- or 5-[1,3,4]thiadiazolyl, 2- or 5-[1,3,4]thiadiazolyl, 4- or 5-[1,2,3]thiadiazolyl, 3- or 5-[1,2,4]thiadiazolyl 1H-, 2H- or 3H-1,2,3-triazol-4-yl, 2H-triazol-3-yl, 1H-, 2H-, or 4H-1,2,4-triazolyl and 1H- or 2H-tetrazolyl, which may be unsubstituted or which may carry 1, 2 or 3 of the aforementioned radicals $R^a$.

Examples of a phenyl ring fused to a saturated or unsaturated 5- or 6-membered carbocyclic or heterocyclic ring comprise indenyl, indanyl, naphthyl, 1,2- or 2,3-dihydronaphthyl, tetralin, benzofuranyl, 2,3-dihydrobenzofuranyl, benzothienyl, indolyl, indazolyl, benzimidazolyl, benzoxathiazolyl, benzoxadiazolyl, benzothiadiazolyl, benzoxazinyl, dihydrobenzoxazinyl, chinolinyl, isochinolinyl, tetrahydroisochinolinyl, chromenyl, chromanyl and the like, which may be unsubstituted or which may carry 1, 2 or 3 of the aforementioned radicals $R^a$. This fused system may be bonded to the remainder of the molecule (more precisely to the sulfonyl group) via carbon atoms of the phenyl moiety or via ring atoms (C- or N-atoms) of the ring fused to phenyl.

Examples for saturated or unsaturated 3- to 7-membered heterocyclic rings (as radicals $R^a$) comprise saturated or unsaturated, aromatic or non-aromatic heterocyclic rings. Examples therefore include, apart from the above-defined 5- or 6-membered heteroaromatic radicals, aziridyl, diaziridinyl, oxiranyl, azetidinyl, azetinyl, di- and tetrahy-drofuranyl, pyrrolinyl, pyrrolidinyl, oxopyrrolidinyl, pyrazolinyl, pyrazolidinyl, imidazolinyl, imidazolidinyl, oxazolinyl, oxazolidinyl, oxo-oxazolidinyl, isoxazolinyl, isoxazolidinyl, piperidinyl, piperazinyl, morpholinyl, thiomorpholinyl, oxothiomorpholinyl, dioxothiomorpholinyl and the like.

If $R^6$ and $R^7$ form together with N a 4-, 5- or 6-membered ring, examples for this type of radical comprise, apart from the above-defined 5- or 6-membered heteroaromatic radicals containing at least one N atom as ring member, azetidinyl, azetinyl, pyrrolinyl, pyrrolidinyl, pyrazolinyl, pyrazolidinyl, imidazolinyl, imidazolidinyl, oxazolinyl, oxazolidinyl, piperidinyl, piperazinyl, morpholinyl and the like.

In compounds of formula I, n preferably is 0 or 1; i.e. the nitrogen-containing ring B is an azetidinyl group or a pyrrolidinyl group; and particularly, n is 1, which means that in a particularly preferred embodiment, the nitrogen-containing ring B is a pyrrolidinyl ring.

Preferably, the radical $R^1$ is selected from H, $C_1$-$C_4$-alkyl, $C_1$-$C_4$-alkyl which is substituted by $C_3$-$C_6$-cycloalkyl or hydroxy, fluorinated $C_1$-$C_4$-alkyl and $C_2$-$C_4$-alkenyl. More preference is given to H, propyl, cyclopropylmethylene, fluorinated ethyl, e.g. 2-fluoroethyl, fluorinated propyl, e.g. 3-fluoropropyl, hydroxypropyl, e.g. 3-hydroxypropyl, propionyl and allyl. More preferably, $R^1$ is selected from H, propyl, ethyl, methyl, cyclo-propylmethylene, 2-fluoroethyl, 3-fluoropropyl, 3-hydroxypropyl, and allyl. Even more preferably, $R^1$ is selected from H, propyl, cyclopropylmethylene, 2-fluoroethyl, 3-fluoropropyl, 3-hydroxypropyl, and allyl. In a particularly preferred embodiment, $R^1$ is H, n-propyl or allyl, in particular H or n-propyl and especially H.

Preferably, $R^2$, $R^{2'}$, $R^3$, $R^4$ and $R^{4'}$ are H.

In one preferred embodiment, D is a group of the formula B.

In an alternative preferred embodiment, D is a group of the formula C.

If the group A is substituted, preferred substituents are selected from halogen, in particular fluorine, methyl, difluoromethyl, trifluoromethyl, methoxy, difluoromethoxy and trifluoromethoxy. More preferred substituents are selected from halogen, in particular fluorine, methyl and methoxy. Specifically, the substituent is methoxy. Examples include 2-methoxy-3,5-pyridylene, 4-methoxy-3,5-pyridylene, 3-methoxy-2,4-pyridylene, 5-methoxy-2,4-pyridylene, 6-methoxy-2,4-pyridylene, 3-methoxy-2,6-pyridylene, 4-methoxy-2,6-pyridylene, 2-fluoro-3,5-pyridylene, 4-fluoro-3,5-pyridylene, 3-fluoro-2,4-pyridylene, 5-fluoro-2,4-pyridylene, 6-fluoro-2,4-pyridylene, 3-fluoro-2,6-pyridylene, 4-fluoro-2,6-pyridylene, 2-methyl-3,5-pyridylene, 4-methyl-3,5-pyridylene, 3-methyl-2,4-pyridylene, 5-methyl-2,4-pyridylene, 6-methyl-2,4-pyridylene, 3-methyl-2,6-pyridylene, 4-methyl-2,6-pyridylene. In a specific embodiment, A is 2,4- or 3,5-pyridylene which is unsubstituted or substituted by methoxy.

A is 2,4-pyridylene 3,5-pyridylene or 2,6-pyridylene, relating to the 1-position of the nitrogen atom. This corresponds to following binding positions:

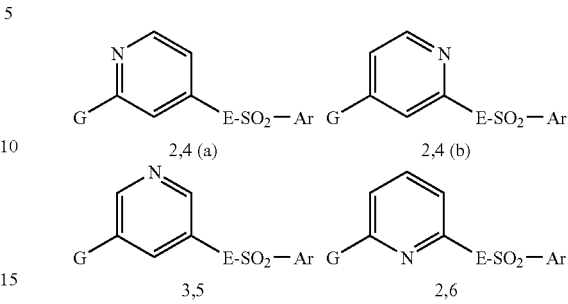

Preferably, A is 2,4-pyridylene (preferably (a)) or 3,5-pyridylene, which is optionally substituted by one or more substituents selected from halogen, $C_1$-$C_4$-alkyl, $C_1$-$C_4$-alkoxy, fluorinated $C_1$-$C_4$-alkyl and fluorinated $C_1$-$C_4$-alkoxy. Preferably, the substituents are selected from halogen, in particular fluorine, methyl, difluoromethyl, trifluoromethyl, methoxy, difluoromethoxy and trifluoromethoxy. More preferred substituents are selected from halogen, in particular fluorine, methyl and methoxy. More preferably, A is 2,4-pyridylene (preferably (a)) or 3,5-pyridylene, which is optionally substituted by one or more substituents selected from halogen, $C_1$-$C_4$-alkyl, $C_1$-$C_4$-alkoxy, fluorinated $C_1$-$C_4$-alkyl and fluorinated $C_1$-$C_4$-alkoxy. Preferably, the substituents are selected from halogen, in particular fluorine, methyl, difluoromethyl, trifluoromethyl, methoxy, di-fluoromethoxy and trifluoromethoxy. More preferred substituents are selected from halogen, in particular fluorine, methyl and methoxy. In particular, A is 2,4- or 3,5-pyridylene, which is unsubstituted or substituted by one methoxy group. In a specific embodiment, A is 3,5-pyridylene which is unsubstituted or substituted by methoxy.

The group E is preferably $NR^5$, more preferably NH or $NCH_3$ and in particular NH. Preferred cyclic radicals of the group Ar are phenyl, 2- or 3-thienyl, in particular 2-thienyl, imidazolyl, in particular 4-imidazolyl, isoxazolyl, in particular 4-isoxazolyl, thiazolyl, in particular 2-thiazolyl, triazolyl, in particular 3-[1,2,4]triazolyl, thiadiazolyl, in particular 3- and 5-[1,2,4]thiadiazolyl and 2-[1,3,4]thiadiazolyl, 2-, 3- or 4-pyridyl, 2- and 5-pyrimidinl, 1-, 2-, 3-, 4- or 5-indanyl, 2-, 3-, 4- or 5-benzofuranyl, quinolinyl, in particular 8-quinolinyl, isoquinolinyl, in particular 5-isoquinolinyl, 1,2,3,4-tetrahydroisoquinolinyl, in particular 7-1,2,3,4-tetrahydroisoquinolin-7-yl, benzothienyl, in particular 2-benzothienyl, benzothiazolyl, in particular 6-benzothiazolyl, benzoxadiazolyl, in particular 4-[2,1,3]benzoxadiazolyl, benzothiadiazolyl, in particular 4-[2,1,3]benzothiadiazolyl, benzoxazin and dihydrobenzoxazin. The numbers indicate the position at which Ar is bound to the sulfonyl group. More preferred radicals Ar are phenyl, 2-thienyl, 2-pyridyl, 3-pyridyl, 4-pyridyl, 5-indanyl, 2-benzofuranyl, 2-benzothienyl and 2,3-dihydrobenzofuran-2-yl. Even more preferred radicals Ar are phenyl, thienyl, in particular 2-thienyl, 2-pyridyl, 3-pyridyl, 4-pyridyl, 5-indanyl, benzofuran-2-yl, 2-benzothienyl and 2,3-dihydrobenzofuran-2-yl. Particularly preferred radicals Ar are phenyl, 2-pyridyl, 3-pyridyl, 4-pyridyl, thienyl, in particular 2-thienyl, and 2-benzothienyl and in particular phenyl, thienyl, in particular 2-thienyl, and 2-benzothienyl. Specifically, Ar is phenyl or thienyl, in particular 2-thienyl, and more specifically phenyl.

In a preferred embodiment, the cyclic radical Ar is unsubstituted or substituted by 1, 2 or 3 substituents $R^a$ selected from the group consisting of halogen, $C_1$-$C_6$-alkyl, $C_1$-$C_6$-hydroxyalkyl, fluorinated $C_1$-$C_4$-alkyl, $C_1$-$C_4$-alkoxy, fluorinated $C_1$-$C_4$-alkoxy, $C_1$-$C_4$-alkoxy-$C_1$-$C_4$-alkoxy, $C_2$-$C_4$-alkenyl, fluorinated $C_2$-$C_4$-alkenyl, $NR^6R^7$, $ONR^6R^7$, $C_1$-$C_6$-alkylene-$NR^6R^7$, where $R^6$ and $R^7$ are independently of each other H, $C_1$-$C_4$-alkyl or or $C_1$-$C_4$-alkoxy, ureido (NH-$CONH_2$)$C_3$-$C_6$-cycloalkyl, fluorinated $C_3$-$C_6$-cycloalkyl, acetyl, carboxyl, hydroxy, cyano, nitro, benzoxy, methylsulfanyl, fluoromethylsulfanyl, di-fluoromethylsulfanyl, trifluoromethylsulfanyl, methylsulfonyl and one of the above-mentioned saturated or unsaturated 3- to 7-membered heterocyclic rings, which may be substituted as defined above. In a more preferred embodiment, $R^a$ is selected from the group consisting of halogen, $C_1$-$C_6$-alkyl, fluorinated $C_1$-$C_4$-alkyl, $C_1$-$C_4$-alkoxy, $OCF_3$, $OCHF_2$, $OCH_2F$, $C_2$-$C_4$-alkenyl, $C_3$-$C_6$-cycloalkyl, fluorinated $C_3$-$C_6$-cycloalkyl, ureido, acetyl, carboxyl, hydroxy, cyano, benzoxy, trifluoromethylsulfanyl, methylsulfonyl, azetidin-1-yl, 2,2-difluoroazetidin-1-yl, pyrrolidin-1-yl, 3,3-difluoropyrrolidin-1-yl, 2-oxo-pyrrolidin-1-yl, 2-oxo-oxazolidin-1-yl, piperidin-1-yl, 2-fluoropiperidin-1-yl, 2,2-difluoropiperidin-1-yl, morpholin-4-yl, and a 5- or 6-membered heteroaromatic ring containing 1, 2, 3 or 4 heteroatoms or heteroatom containing groups selected from O, S, N and $NR^9$ where $R^9$ is as defined above, which may be substituted as defined above.

Examples for such 5- or 6-membered heteroaromatic rings are pyrrolyl, such as pyrrol-1-yl, pyrrol-2-yl, or pyrrol-3-yl, furanyl, such as 2-furanyl, or furan-3-yl, thienyl, such as thien-2-yl, thien-3-yl, or 5-propylthien-2-yl, pyrazolyl, such as pyrazol-1-yl, pyrazol-3-yl, pyrazol-4-yl, pyrazol-5-yl, 1-methylpyrazol-4-yl, 1-ethylpyrazol-4-yl, or 4-fluoropyrazol-1-yl, imidazolyl, such as imidazol-1-yl, imidazol-2-yl, imidazol-4-yl, or imidazol-5-yl, oxazolyl, such as oxazol-2-yl, oxazol-4-yl, or oxazol-5-yl, isoxazolyl, such as isoxazol-3-yl, isoxazol-4-yl, or isoxazol-5-yl, thiazolyl, such as thiazol-2-yl, thiazol-4-yl, thiazol-5-yl, 2-methylthiazol-4-yl, or 2-methylthiazol-5-yl, isothiazolyl, such as isothiazol-3-yl, isothiazol-4-yl, or isothiazol-5-yl, triazolyl, such as [1,2,3]-1H-triazol-1-yl, [1,2,3]-1H-triazol-4-yl, [1,2,3]-1H-triazol-5-yl, [1,2,4]-1H-triazol-1-yl, [1,2,4]-1H-triazol-3-yl, [1,2,4]-1H-triazol-5-yl, [1,3,4]-1H-triazol-1-yl, [1,3,4]-1H-triazol-2-yl, [1,3,4]-1H-triazol-5-yl, [1,2,3]-2H-triazol-2-yl, [1,2,3]-2H-triazol-4-yl, and [1,2,3]-2H-triazol-5-yl, oxadiazolyl, such as [1,2,3]oxadiazol-4-yl, [1,2,3]oxadiazol-5-yl, [1,2,4]oxadiazol-3-yl, [1,2,4]oxadiazol-5-yl, [1,3,4]oxadiazol-2-yl, and [1,3,4]oxadiazol-5-yl, thiadiazolyl, such as [1,2,3]thiadiazol-4-yl, [1,2,3]thiadiazol-5-yl, [1,2,4]thiadiazol-3-yl, [1,2,4]thiadiazol-5-yl, [1,3,4]thiadiazol-2-yl, and [1,3,4]thiadiazol-5-yl, tetrazolyl, pyridyl, such as pyridin-2-yl, pyridin-3-yl, pyridin-3-yl, pyrimidinyl, such as pyrimidin-2-yl, pyrimidin-4-yl, pyrimidin-5-yl, pyrazinyl and pyridazinyl. Even more preferably, $R^a$ is selected from the group consisting of halogen, $C_1$-$C_6$-alkyl, fluorinated $C_1$-$C_4$-alkyl, $C_1$-$C_4$-alkoxy, $OCF_3$, $OCHF_2$, $OCH_2F$, $C_2$-$C_4$-alkenyl, $C_3$-$C_6$-cycloalkyl, fluorinated $C_3$-$C_6$— cycloalkyl, ureido, acetyl, carboxyl, hydroxy, benzoxy, trifluoromethylsulfanyl, azetidin-1-yl, 2,2-difluoroazetidin-1-yl, pyrrolidin-1-yl, 3,3-difluoropyrrolidin-1-yl, 2-oxo-pyrrolidin-1-yl, 2-fluoropiperidin-1-yl, 2,2-difluoropiperidin-1-yl, morpholin-4-yl, pyrrol-1-yl, furan-2-yl, pyrazol-1-yl, 1-methylpyrazol-4-yl, 4-fluoropyrazol-1-yl, oxazol-5-yl, isoxazol-5-yl, thiazol-2-yl, thiazol-4-yl, thiazol-5-yl, 2-methylthiazol-4-yl, 2-methylthiazol-5-yl, and 4-[1,2,3]thiadiazolyl.

If Ar is a heteroaromatic ring, $R^a$ in this case is in particular selected from halogen, $C_1$-$C_6$-alkyl, fluorinated $C_1$-$C_4$-alkyl, $C_1$-$C_4$-alkoxy, $OCF_3$, $OCHF_2$, $OCH_2F$, $C_2$-$C_4$-alkenyl, phenyl, phenylsulfonyl, pyridylsulfonyl, pyridylmethyl, where the pyridyl radical in the two last-mentioned radicals may be substituted as defined above, aminomethyl, acetylaminomethyl, benzoylaminomethyl, where the benzene ring in the last-mentioned radical may be substituted as defined above, and a 5- or 6-membered heteroaromatic ring which may be substituted as defined above for $R^a$ being a 3- to 7-membered heterocyclic ring. More preferably, $R^a$ in this case is in particular selected from halogen, $C_1$-$C_6$-alkyl, fluorinated $C_1$-$C_4$-alkyl, $C_1$-$C_4$-alkoxy, $OCF_3$, $OCHF_2$, $OCH_2F$ and a 5- or 6-membered heteroaromatic ring which may be substituted as defined above.

Preferred 5- or 6-membered heteroaromatic rings $R^a$ are selected from pyrrolyl, such as pyrrol-1-yl, pyrrol-2-yl, or pyrrol-3-yl, furanyl, such as furan-2-yl, or furan-3-yl, thienyl, such as thien-2-yl, or thien-3-yl, pyrazolyl, such as pyrazol-1-yl, pyrazol-3-yl, pyrazol-4-yl, or pyrazol-5-yl, imidazolyl, such as imidazol-1-yl, imidazol-2-yl, imidazol-4-yl, or imidazol-5-yl, oxazolyl, such as oxazol-2-yl, oxazol-4-yl, or oxazol-5-yl, isoxazolyl, such as isoxazol-3-yl, isoxazol-4-yl, or isoxazol-5-yl, thiazolyl, such as thiazol-2-yl, thiazol-4-yl, or thiazol-5-yl, isothiazolyl, such as isothiazol-3-yl, isothiazol-4-yl, or isothiazol-5-yl, triazolyl, such as [1,2,3]-1H-triazol-1-yl, [1,2,3]-1H-triazol-4-yl, [1,2,3]-1H-triazol-5-yl, [1,2,4]-1H-triazol-1-yl, [1,2,4]-1H-triazol-3-yl, [1,2,4]-1H-triazol-5-yl, [1,3,4]-1H-triazol-1-yl, [1,3,4]-1H-triazol-2-yl, [1,3,4]-1H-triazol-5-yl, [1,2,3]-2H-triazol-2-yl, [1,2,3]-2H-triazol-4-yl, and [1,2,3]-2H-triazol-5-yl, oxadiazolyl, such as [1,2,3]oxadiazol-4-yl, [1,2,3]oxadiazol-5-yl, [1,2,4]oxadiazol-3-yl, [1,2,4]oxadiazol-5-yl, [1,3,4]oxadiazol-2-yl, and [1,3,4]oxadiazol-5-yl, thiadiazolyl, such as [1,2,3]thiadiazol-4-yl, [1,2,3]thiadiazol-5-yl, [1,2,4]thiadiazol-3-yl, [1,2,4]thiadiazol-5-yl, [1,3,4]thiadiazol-2-yl, and [1,3,4]thiadiazol-5-yl, tetrazolyl, pyridyl, such as pyridin-2-yl, pyridin-3-yl, pyridin-3-yl, pyrimidinyl, such as pyrimidin-2-yl, pyrimidin-4-yl, pyrimidin-5-yl, pyrazinyl and pyridazinyl.

Preferably, the 5- or 6-membered heteroaromatic rings $R^a$ contain one N atom as ring member (in 5-membered rings possibly also in the form of a group $NR^9$) and optionally one or two further heteroatoms as ring members selected from O, N and S, such as pyrrolyl, such as pyrrol-1-yl, pyrrol-2-yl, or pyrrol-3-yl, pyrazolyl, such as pyrazol-1-yl, pyrazol-3-yl, pyrazol-4-yl, or pyrazol-5-yl, imidazolyl, such as imidazol-1-yl, imidazol-2-yl, imidazol-4-yl, or imidazol-5-yl, oxazolyl, such as oxazol-2-yl, oxazol-4-yl, or oxazol-5-yl, isoxazolyl, such as isoxazol-3-yl, isoxazol-4-yl, or isoxazol-5-yl, thiazolyl, such as thiazol-2-yl, thiazol-4-yl, or thiazol-5-yl, isothiazolyl, such as isothiazol-3-yl, isothiazol-4-yl, or isothiazol-5-yl, triazolyl, oxadiazolyl, thiadiazolyl, tetrazolyl, pyridyl, such as pyridin-2-yl, pyridin-3-yl, pyridin-3-yl, pyrimidinyl, such as pyrimidin-2-yl, pyrimidin-4-yl, pyrimidin-5-yl, pyrazinyl and pyridazinyl.

More preferably, the heteroaromatc ring $R^a$ is 5-membered. Preferred 5-membered heteroaromatc rings contain one N atom as ring member (possibly also in the form of a group $NR^9$) and optionally one or two further heteroatoms as ring members selected from O, N and S, e.g. pyrrolyl, such as pyrrol-1-yl, pyrrol-2-yl, or pyrrol-3-yl, pyrazolyl, such as pyrazol-1-yl, pyrazol-3-yl, pyrazol-4-yl, or pyrazol-5-yl, imidazolyl, such as imidazol-1-yl, imidazol-2-yl, imidazol-4-yl, or imidazol-5-yl, oxazolyl, such as oxazol-2-yl, oxazol-4-yl, or oxazol-5-yl, isoxazolyl, such as isoxazol-3-yl, isoxazol-4-yl, or isoxazol-5-yl, thiazolyl, such as thiazol-2-yl, thiazol-4-yl, or thiazol-5-yl, isothiazolyl, such as isothiazol-3-yl, isothiazol-4-yl, or isothiazol-5-yl, triazolyl, oxadiazolyl and thiadiazolyl. A particularly preferred 5-membered heteroaromatic ring is thiazolyl, such as thiazol-2-yl, thiazol-4-yl, or specifically thiazol-5-yl.

Preferably, the 5- or 6-membered heteroaromatic ring $R^a$ is unsubstituted or carries one, two or three, preferably one, substituents selected from halogen, $C_1$-$C_4$-alkyl, fluorinated $C_1$-$C_4$-alkyl, $C_1$-$C_4$-alkoxy, fluorinated $C_1$-$C_4$-alkoxy, $C_1$-$C_4$-thioalkyl, fluorinated $C_1$-$C_4$-thioalkyl, and amino-$C_1$-$C_2$-alkylene.

If Ar is a fused system, it is preferentially not substituted or is substituted by one or two substituents which are preferably selected from halogen, $C_1$-$C_4$-alkyl and fluorinated $C_1$-$C_4$-alkyl.

If Ar is a phenyl ring fused to a heteroaromatic ring, it is preferably bound via a carbon atom of the heteroaromatic ring to the $SO_2$ group.

In the aforementioned 5-membered heteroaromatic radicals, Ar preferably is unsubstituted or carries one radical $R^a$ in the 5-position (related to the 2-position of the $SO_2$-radical) and optionally one or two further radicals selected from halogen, in particular fluorine or chlorine.

Phenyl and the aforementioned 6-membered heteroaromatic radicals Ar preferably carry one radical $R^a$ in the 2-, 3- or 4-position, preferably 3- or 4-(related to the 1-position of the $SO_2$-radical) and optionally one or two further radicals selected from halogen, in particular fluorine, $C_1$-$C_4$-alkyl, in particular methyl, $C_1$-$C_4$-alkoxy, in particular methoxy, fluorinated $C_1$-$C_4$-alkyl, in particular $CHF_2$ or $CF_3$, and fluorinated $C_1$-$C_4$-alkoxy, in particular $OCHF_2$ or $OCF_3$.

If D is a group C, A is unsubstituted 2,4-, 2,6- or 3,5-pyridylene and Ar is phenyl or one of the aforementioned 6-membered heteroaromatic radicals, it is preferred that Ar carries one radical $R^a$ in the 3- or in the 4-position, more preferably in the 3-position (related to the 1-position of the $SO_2$-radical) and optionally one or two further radicals selected from halogen, in particular fluorine, $C_1$-$C_4$-alkyl, in particular methyl, $C_1$-$C_4$-alkoxy, in particular methoxy, fluorinated $C_1$-$C_4$-alkyl, in particular $CHF_2$ or $CF_3$, and fluorinated $C_1$-$C_4$-alkoxy, in particular $OCHF_2$ or $OCF_3$.

Also for the case that D is a group C and Ar is phenyl or one of the aforementioned 6-membered heteroaromatic radicals, it is preferred that Ar carries one radical $R^a$ in the 3- or in the 4-position, more preferably in the 3-position (related to the 1-position of the $SO_2$-radical) and optionally one or two further radicals selected from halogen, in particular fluorine, $C_1$-$C_4$-alkyl, in particular methyl, $C_1$-$C_4$-alkoxy, in particular methoxy, fluorinated $C_1$-$C_4$-alkyl, in particular $CHF_2$ or $CF_3$, and fluorinated $C_1$-$C_4$-alkoxy, in particular $OCHF_2$ or $OCF_3$.

In a very preferred embodiment of the invention Ar is phenyl that carries one radical $R^a$ in the 4-position of the phenyl ring and optionally 1 or 2 further radicals selected from halogen, in particular fluorine, $C_1$-$C_4$-alkyl, in particular methyl, $C_1$-$C_4$-alkoxy, in particular methoxy, fluorinated $C_1$-$C_4$-alkyl, in particular $CHF_2$ or $CF_3$, and fluorinated $C_1$-$C_4$-alkoxy, in particular $OCHF_2$ or $OCF_3$. If in this case, A is furthermore unsubstituted unsubstituted 2,4-, 2,6- or 3,5-pyridylene, it is preferred that D is not a group C.

Alternatively, in a very preferred embodiment of the invention Ar is phenyl that carries one radical $R^a$ in the 3-position of the phenyl ring and optionally 1 or 2 further radicals selected from halogen, in particular fluorine, $C_1$-$C_4$-alkyl, in particular methyl, $C_1$-$C_4$-alkoxy, in particular methoxy, fluorinated $C_1$-$C_4$-alkyl, in particular $CHF_2$ or $CF_3$, and fluorinated $C_1$-$C_4$-alkoxy, in particular $OCHF_2$ or $OCF_3$.

Alternatively, in a very preferred embodiment of the invention Ar is 2-pyridyl (related to the 1-position of the nitrogen atom of pyridyl) that carries one radical $R^a$ in the 4- or 6-position of the pyridyl ring and optionally 1 or 2 further radicals selected from halogen, in particular fluorine, $C_1$-$C_4$-alkyl, in particular methyl, $C_1$-$C_4$-alkoxy, in particular methoxy, fluorinated $C_1$-$C_4$-alkyl, in particular $CHF_2$ or $CF_3$, and fluorinated $C_1$-$C_4$-alkoxy, in particular $OCHF_2$ or $OCF_3$.

Alternatively, in a very preferred embodiment of the invention Ar is 2-pyridyl (related to the 1-position of the nitrogen atom of pyridyl) that carries one radical $R^a$ in the 5-position of the pyridyl ring and optionally 1 or 2 further radicals selected from halogen, in particular fluorine, $C_1$-$C_4$-alkyl, in particular methyl, $C_1$-$C_4$-alkoxy, in particular methoxy, fluorinated $C_1$-$C_4$-alkyl, in particular $CHF_2$ or $CF_3$, and fluorinated $C_1$-$C_4$-alkoxy, in particular $OCHF_2$ or $OCF_3$. If in this case, A is furthermore unsubstituted unsubstituted 2,4-, 2,6- or 3,5-pyridylene, it is preferred that D is not a group C.

Alternatively, in a very preferred embodiment of the invention Ar is 3-pyridyl (related to the 1-position of the nitrogen atom of pyridyl) that carries one radical $R^a$ in the 5-position of the pyridyl ring and optionally 1 or 2 further radicals selected from halogen, in particular fluorine, $C_1$-$C_4$-alkyl, in particular methyl, $C_1$-$C_4$-alkoxy, in particular methoxy, fluorinated $C_1$-$C_4$-alkyl, in particular $CHF_2$ or $CF_3$, and fluorinated $C_1$-$C_4$-alkoxy, in particular $OCHF_2$ or $OCF_3$.

Alternatively, in a very preferred embodiment of the invention Ar is 3-pyridyl (related to the 1-position of the nitrogen atom of pyridyl) that carries one radical $R^a$ in the 6-position of the pyridyl ring and optionally 1 or 2 further radicals selected from halogen, in particular fluorine, $C_1$-$C_4$-alkyl, in particular methyl, $C_1$-$C_4$-alkoxy, in particular methoxy, fluorinated $C_1$-$C_4$-alkyl, in particular $CHF_2$ or $CF_3$, and fluorinated $C_1$-$C_4$-alkoxy, in particular $OCHF_2$ or $OCF_3$. If in this case, A is furthermore unsubstituted unsubstituted 2,4-, 2,6- or 3,5-pyridylene, it is preferred that D is not a group C.

Alternatively, in a very preferred embodiment of the invention Ar is 4-pyridyl (related to the 1-position of the nitrogen atom of pyridyl) that carries one radical $R^a$ in the 2-position of the pyridyl ring and optionally 1 or 2 further radicals selected from halogen, in particular fluorine, $C_1$-$C_4$-alkyl, in particular methyl, $C_1$-$C_4$-alkoxy, in particular methoxy, fluorinated $C_1$-$C_4$-alkyl, in particular $CHF_2$ or $CF_3$, and fluorinated $C_1$-$C_4$-alkoxy, in particular $OCHF_2$ or $OCF_3$.

Alternatively, in a very preferred embodiment of the invention Ar is 2- or 3-thienyl, preferably 2-thienyl (related to the 1-position of the sulfur atom of thienyl) that is unsubstituted or carries 1, 2 or 3 substituents $R^a$. Preferred meaning of $R^a$ are defined above for Ar being a heteroaromatic ring. If the thienyl ring Ar carries one substituent $R^a$, this is preferably bound at the 5-position.

Preferably, $R^1$ is selected from the group consisting of halogen, $C_1$-$C_6$-alkyl, fluorinated $C_1$-$C_6$-alkyl, $C_1$-$C_6$-hydroxyalkyl, $C_1$-$C_6$-alkoxy-$C_1$-$C_6$-alkyl, $C_2$-$C_6$-alkenyl, $C_3$-$C_6$-cycloalkyl, fluorinated $C_3$-$C_6$-cycloalkyl, $C_1$-$C_6$-alkoxy, $C_1$-$C_6$-alkoxy-$C_1$-$C_6$-alkoxy, fluorinated $C_1$-$C_6$-alkoxy, fluorinated $C_1$-$C_6$-alkylthio, $C_1$-$C_6$-alkylsulfonyl, phenylsulfonyl, benzyloxy, phenoxy, CN, nitro, acetyl, trifluoroacetyl, acetamido, carboxy, NH—C(O)—$NH_2$, $NR^6R^7$, $NR^6R^7$—$C_1$-$C_6$-alkylene, O—$NR^6R^7$, where $R^6$ and $R^7$ are, independently of each other, H, $C_1$-$C_4$-alkyl, fluorinated $C_1$-$C_4$-alkyl or $C_1$-$C_4$-alkoxy, and a saturated or unsaturated 3- to 7-membered heterocyclic ring comprising as ring members 1, 2, 3 or 4 heteroatoms selected from N, O and S and/or 1, 2 or 3 heteroatom-containing groups selected from $NR^9$, where $R^9$ has one of the meanings given for $R^8$, SO, $SO_2$ and CO, and where the 3- to 7-membered heterocyclic ring may carry 1, 2 or 3 substituents selected from hydroxy, halogen, $C_1$-$C_6$-alkyl, fluorinated $C_1$-$C_6$-alkyl and $C_1$-$C_6$-alkoxy.

Preferably, the saturated or unsaturated 3- to 7-membered heterocyclic ring $R^a$ is selected from azetidin-1-yl, 2-methylazetidinyl, 3-methoxyazetidinyl, 3-hydroxyazetidinyl, 3-fluoroazetidinyl, pyrrolidin-1-yl, pyrrolidin-2-yl, pyrrolidin-3-yl, 2- and 3-fluoropyrrolidin-1-yl, 2,2-difluoropyrrolidin-1-yl 3,3-difluoropyrrolidin-1-yl, 2- and 3-methylpyrrolidin-1-yl, 1-methylpyrrolidin-2-yl, 2,2-dimethylpyrrolidin-1-yl, 3,3-dimethylpyrrolidin-1-yl, 2-oxo-pyrrolidin-1-yl, 2- and 3-trifluoromethylpyrrolidin-1-yl, 2-oxo-oxazolidin-1-yl, piperidin-1-yl, 2-methylpiperidin-1-yl, piperazin-1-yl, 4-methylpiperazin-1-yl, morpholin-4-yl, thiomorpholin-4-yl, 1-oxothiomorpholin-4-yl, 1,1-dioxothiomorpholin-4-yl, pyrrol-1-yl, pyrrol-2-yl, pyrrol-3-yl, 1-methylpyrrol-2-yl, 1-methylpyrrol-3-yl, furan-2-yl, furan-3-yl, thiophen-2-yl, thiophen-3-yl, 5-propylthiophen-2-yl, pyrazol-1-yl, pyrazol-3-yl, pyrazol-4-yl, pyrazol-5-yl, 1-methylpyrazol-4-yl, 1-methylpyrazol-5-yl, imidazol-1-yl, imidazol-2-yl, imidazol-4-yl, imidazol-5-yl, 1-methylimidazol-2-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, 2-methylthiazol-4-yl, [1,2,3]-1H-triazol-1-yl, [1,2,3]-1H-triazol-4-yl, [1,2,3]-1H-triazol-5-yl, [1,2,3]-2H-triazol-2-yl, [1,2,4]-1H-triazol-1-yl, [1,2,4]-1H-triazol-3-yl, [1,2,4]-1H-triazol-5-yl, 4-methyl-[1,2,4]triazol-3-yl, 2-methyl-[1,2,3]triazol-4-yl, [1,3,4]-oxadiazol-2-yl, [1,2,4]-oxadiazol-3-yl, [1,2,4]-oxadiazol-5-yl, [1,2,3]-oxadiazol-5-yl, [1,3,4]-oxadiazol-2-yl, 5-methyl-[1,3,4]-oxadiazol-2-yl, 5-methyl-[1,2,4]-oxadiazol-3-yl, [1,2,3]thiadiazol-4-yl, [1,2,3]thiadiazol-5-yl, [1,2,4]thiadiazol-3-yl, [1,2,4]thiadiazol-5-yl, [1,3,4]thiadiazol-2-yl, tetrazol-1-yl, tetrazol-5-yl, 2-methyltetrazol-5-yl, 1-methyltetrazol-5-yl, furazan-3-yl, pyrid-2-yl, pyrid-3-yl, pyrid-4-yl, pyrimidin-2-yl, pyrimidin-4-yl, pyrimidin-5-yl and 2-methylpyrimidin-4-yl.

More preferably, the saturated or unsaturated 3- to 7-membered heterocyclic ring $R^a$ is selected from nitrogen containing rings such as azetidin-1-yl, 2-methylazetidinyl, 3-methoxyazetidinyl, 3-hydroxyazetidinyl, 3-fluoroazetidinyl, pyrrolidin-1-yl, pyrrolidin-2-yl, pyrrolidin-3-yl, 2- and 3-fluoropyrrolidin-1-yl, 2,2-difluoropyrrolidin-1-yl 3,3-difluoropyrrolidin-1-yl, 2- and 3-methylpyrrolidin-1-yl, 1-methylpyrrolidin-2-yl, 2,2-dimethylpyrrolidin-1-yl, 3,3-dimethylpyrrolidin-1-yl, 2-oxo-pyrrolidin-1-yl, 2- and 3-trifluoromethylpyrrolidin-1-yl, 2-oxo-oxazolidin-1-yl, piperidin-1-yl, 2-methylpiperidin-1-yl, piperazin-1-yl, 4-methylpiperazin-1-yl, morpholin-4-yl, thiomorpholin-4-yl, 1-oxothiomorpholin-4-yl, 1,1-dioxothiomorpholin-4-yl, pyrrol-1-yl, pyrrol-2-yl, pyrrol-3-yl, 1-methylpyrrol-2-yl, 1-methylpyrrol-3-yl, pyrazol-1-yl, pyrazol-3-yl, pyrazol-4-yl, 1-methylpyrazol-4-yl, imidazol-1-yl, imidazol-2-yl, 1-methylimidazol-2-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, 2-methylthiazol-4-yl, [1,2,3]triazol-1-yl, [1,2,4]triazol-1-yl, [1,2,3]triazol-2-yl, [1,2,4]triazol-3-yl, [1,2,4]triazol-4-yl, 4-methyl-[1,2,4]triazol-3-yl, 2-methyl-[1,2,3]triazol-4-yl, [1,3,4]-oxadiazol-2-yl, [1,2,4]-oxadiazol-3-yl, [1,2,4]-oxadiazol-5-yl, [1,2,3]-oxadiazol-5-yl, [1,3,4]-oxadiazol-2-yl, 5-methyl-[1,3,4]-oxadiazol-2-yl, 5-methyl-[1,2,4]-oxadiazol-3-yl, [1,2,3]thiadiazol-4-yl, tetrazol-1-yl, tetrazol-5-yl, 2-methyltetrazol-5-yl, 1-methyltetrazol-5-yl, furazan-3-yl, pyrid-2-yl, pyrid-3-yl, pyrid-4-yl, pyrimidin-2-yl, pyrimidin-4-yl, pyrimidin-5-yl and 2-methylpyrimidin-4-yl.

Even more preferably, the saturated or unsaturated 3- to 7-membered heterocyclic ring $R^a$ is selected from nitrogen containing rings which are bound to the phenyl or pyridyl ring of the group Ar via their nitrogen atom, such as azetidin-1-yl, 2-methylazetidin-1-yl, 3-methoxyazetidin-1-yl, 3-hydroxyazetidin-1-yl, 3-fluoroazetidin-1-yl, pyrrolidin-1-yl, 2- and 3-fluoropyrrolidin-1-yl, 2,2-difluoropyrrolidin-1-yl 3,3-difluoropyrrolidin-1-yl, 2- and 3-methylpyrrolidin-1-yl, 2,2-dimethylpyrrolidin-1-yl, 3,3-dimethylpyrrolidin-1-yl, 2-oxo-pyrrolidin-1-yl, 2- and 3-trifluoromethylpyrrolidin-1-yl, 2-oxo-oxazolidin-1-yl, piperidin-1-yl, 2-methylpiperidin-1-yl, piperazin-1-yl, 4-methylpiperazin-1-yl, morpholin-4-yl, thiomorpholin-4-yl, 1-oxothiomorpholin-4-yl, 1,1-dioxothiomorpholin-4-yl, pyrrol-1-yl, pyrazol-1-yl, imidazol-1-yl, [1,2,3]triazol-1-yl, [1,2,4]triazol-1-yl, [1,2,3]triazol-2-yl, [1,2,4]triazol-3-yl, [1,2,4]triazol-4-yl, 4-methyl-[1,2,4]triazol-3-yl, 2-methyl-[1,2,3]triazol-4-yl, tetrazol-1-yl and tetrazol-2-yl.

In another even more preferred embodiment, the saturated or unsaturated 3- to 7-membered heterocyclic ring $R^a$ is a 5- or 6-membered heteroaromatic ring, where the 5- or 6-membered heteroaromatic ring is preferably selected from pyrrolyl, such as pyrrol-1-yl, pyrrol-2-yl, or pyrrol-3-yl, furanyl, such as furan-2-yl, or furan-3-yl, thienyl, such as thien-2-yl, or thien-3-yl, pyrazolyl, such as pyrazol-1-yl, pyrazol-3-yl, pyrazol-4-yl, or pyrazol-5-yl, imidazolyl, such as imidazol-1-yl, imidazol-2-yl, imidazol-4-yl, or imidazol-5-yl, oxazolyl, such as oxazol-2-yl, oxazol-4-yl, or oxazol-5-yl, isoxazolyl, such as isoxazol-3-yl, isoxazol-4-yl, or isoxazol-5-yl, thiazolyl, such as thiazol-2-yl, thiazol-4-yl, or thiazol-5-yl, isothiazolyl, such as isothiazol-3-yl, isothiazol-4-yl, or isothiazol-5-yl, triazolyl, such as [1,2,3]-1H-triazol-1-yl, [1,2,3]-1H-triazol-4-yl, [1,2,3]-1H-triazol-5-yl, [1,2,4]-1H-triazol-1-yl, [1,2,4]-1H-triazol-3-yl, [1,2,4]-1H-triazol-5-yl, [1,3,4]-1H-triazol-1-yl, [1,3,4]-1H-triazol-2-yl, [1,3,4]-1H-triazol-5-yl, [1,2,3]-2H-triazol-2-yl, [1,2,3]-2H-triazol-4-yl, and [1,2,3]-2H-triazol-5-yl, oxadiazolyl, such as [1,2,3]oxadiazol-4-yl, [1,2,3]oxadiazol-5-yl, [1,2,4]oxadiazol-3-yl, [1,2,4]oxadiazol-5-yl, [1,3,4]oxadiazol-2-yl, and [1,3,4]oxadiazol-5-yl, thiadiazolyl, such as [1,2,3]thiadiazol-4-yl, [1,2,3]thiadiazol-5-yl, [1,2,4]thiadiazol-3-yl, [1,2,4]thiadiazol-5-yl, [1,3,4]thiadiazol-2-yl, and [1,3,4]thiadiazol-5-yl, tetrazolyl, pyridyl, such as pyridin-2-yl, pyridin-3-yl, pyridin-3-yl, pyrimidinyl, such as pyrimidin-2-yl, pyrimidin-4-yl, pyrimidin-5-yl, pyrazinyl and pyridazinyl.

Preferably, the 5- or 6-membered heteroaromatic rings $R^a$ contain one N atom as ring member (in 5-membered rings possibly also in the form of a group $NR^9$) and optionally one or two further heteroatoms as ring members selected from O, N and S, such as pyrrolyl, such as pyrrol-1-yl, pyrrol-2-yl, or pyrrol-3-yl, pyrazolyl, such as pyrazol-1-yl, pyrazol-3-yl, pyrazol-4-yl, or pyrazol-5-yl, imidazolyl, such as imidazol-1-yl, imidazol-2-yl, imidazol-4-yl, or imidazol-5-yl, oxazolyl, such as oxazol-2-yl, oxazol-4-yl, or oxazol-5-yl, isoxazolyl, such as isoxazol-3-yl, isoxazol-4-yl, or isoxazol-5-yl, thiazolyl, such as thiazol-2-yl, thiazol-4-yl, or thiazol-5-yl, isothiazolyl, such as isothiazol-3-yl, isothiazol-4-yl, or isothiazol-5-yl, triazolyl, oxadiazolyl, thiadiazolyl, tetrazolyl, pyridyl, such as pyridin-2-yl, pyridin-3-yl, pyridin-3-yl, pyrimidinyl, such as pyrimidin-2-yl, pyrimidin-4-yl, pyrimidin-5-yl, pyrazinyl and pyridazinyl.

More preferably, the heteroaromatc ring $R^a$ is 5-membered. Preferred 5-membered heteroaromatc rings contain one N atom as ring member (possibly also in the form of a group $NR^9$) and optionally one or two further heteroatoms as ring members selected from O, N and S, e.g. pyrrolyl, such as pyrrol-1-yl, pyrrol-2-yl, or pyrrol-3-yl, pyrazolyl, such as pyrazol-1-yl, pyrazol-3-yl, pyrazol-4-yl, or pyrazol-5-yl, imidazolyl, such as imidazol-1-yl, imidazol-2-yl, imidazol-4-yl, or imidazol-5-yl, oxazolyl, such as oxazol-2-yl, oxazol-4-yl, or oxazol-5-yl, isoxazolyl, such as isoxazol-3-yl, isoxazol-4-yl, or isoxazol-5-yl, thiazolyl, such as thiazol-2-yl, thiazol-4- yl, or thiazol-5-yl, isothiazolyl, such as isothiazol-3-yl, isothiazol-4-yl, or isothiazol-5-yl, triazolyl, oxadiazolyl and thiadiazolyl. A particularly preferred 5-membered heteroaromatic ring is thiazolyl, such as thiazol-2-yl, thiazol-4-yl, or specifically thiazol-5-yl.

Preferably, the 5- or 6-membered heteroaromatic ring $R^a$ is unsubstituted or carries one, two or three, preferably one, substituents selected from halogen, $C_1$-$C_4$-alkyl, fluorinated $C_1$-$C_4$-alkyl, $C_1$-$C_4$-alkoxy, fluorinated $C_1$-$C_4$-alkoxy, $C_1$-$C_4$-thioalkyl, fluorinated $C_1$-$C_4$-thioalkyl, and amino-$C_1$-$C_2$-alkylene.

In a preferred embodiment, $R^a$ is selected from the group consisting of halogen, $C_1$-$C_6$-alkyl, $C_1$-$C_6$-hydroxyalkyl, fluorinated $C_1$-$C_4$-alkyl, $C_1$-$C_4$-alkoxy, fluorinated $C_1$-$C_4$-alkoxy, $C_1$-$C_4$-alkoxy-$C_1$-$C_4$-alkoxy, $C_2$-$C_4$-alkenyl, fluorinated $C_2$-$C_4$-alkenyl, $NR^6R^7$, $ONR^6R^7$, $C_1$-$C_6$-alkylene-$NR^6R^7$, where $R^6$ and $R^7$ are independently of each other H, $C_1$-$C_4$-alkyl or or $C_1$-$C_4$-alkoxy, ureido ($NHCONH_2$)$C_3$-$C_6$-cycloalkyl, fluorinated $C_3$-$C_6$-cycloalkyl, acetyl, carboxyl, hydroxy, cyano, nitro, benzoxy, methylsulfanyl, fluoro-methylsulfanyl, difluoromethylsulfanyl, trifluoromethylsulfanyl, methylsulfonyl and one of the above-mentioned saturated or unsaturated 3- to 7-membered heterocyclic rings, in particular azetidin-1-yl, 2-methylazetidinyl, 3-methoxyazetidinyl, 3-hydroxyazetidinyl, 3-fluoroazetidinyl, pyrrolidin-1-yl, pyrrolidin-2-yl, pyrrolidin-3-yl, 2- and 3-fluoropyrrolidin-1-yl, 2,2-difluoropyrrolidin-1-y 3,3-difluoropyrrolidin-1-yl, 2- and 3-methylpyrrolidin-1-yl, 1-methylpyrrolidin-2-yl, 2,2-dimethylpyrrolidin-1-yl, 3,3-dimethylpyrrolidin-1-yl, 2-oxo-pyrrolidin-1-yl, 2- and 3-trifluoromethylpyrrolidin-1-yl, 2-oxo-oxazolidin-1-yl, piperidin-1-yl, 2-methylpiperidin-1-yl, piperazin-1-yl, 4-methylpiperazin-1-yl, morpholin-4-yl, thiomorpholin-4-yl, 1-oxothiomorpholin-4-yl, 1,1-dioxothiomorpholin-4-yl, pyrrol-1-yl, pyrrol-2-yl, pyrrol-3-yl, 1-methylpyrrol-2-yl, 1-methylpyrrol-3-yl, pyrazol-1-yl, pyrazol-3-yl, pyrazol-4-yl, 1-methylpyrazol-4-yl, imidazol-1-yl, imidazol-2-yl, 1-methylimidazol-2-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, 2-methylthiazol-4-yl, [1,2,3]triazol-1-yl, [1,2,4]triazol-1-yl, [1,2,3]triazol-2-yl, [1,2,4]triazol-3-yl, [1,2,4]triazol-4-yl, 4-methyl-[1,2,4]triazol-3-yl, 2-methyl-[1,2,3]triazol-4-yl, [1,3,4]-oxadiazol-2-yl, [1,2,4]-oxadiazol-3-yl, [1,2,4]-oxadiazol-5-yl, [1,2,3]-oxadiazol-5-yl, [1,3,4]-oxadiazol-2-yl, 5-methyl-[1,3,4]-oxadiazol-2-yl, 5-methyl-[1,2,4]-oxadiazol-3-yl, [1,2,3]thiadiazol-4-yl, tetrazol-1-yl, tetrazol-5-yl, 2-methyltetrazol-5-yl, 1-methyltetrazol-5-yl, furazan-3-yl, pyrid-2-yl, pyrid-3-yl, pyrid-4-yl, pyrimidin-2-yl, pyrimidin-4-yl, pyrimidin-5-yl and 2-methylpyrimidin-4-yl.

In a more preferred embodiment, $R^a$ is selected from the group consisting of halogen, $C_1$-$C_6$-alkyl, fluorinated $C_1$-$C_4$-alkyl, $C_1$-$C_4$-alkoxy, $OCF_3$, $OCHF_2$, $OCH_2F$, 2-fluoroethoxy, 2,2-difluoroethoxy, 2,2,2-trifluoroethoxy, 1,1,2,2-tetrafluoroethoxy, 1,1,2,2,2-pentafluoroethoxy, $C_2$-$C_4$-alkenyl, $C_3$-$C_6$-cycloalkyl, fluorinated $C_3$-$C_6$-cycloalkyl, ureido, acetyl, acetylamino, carboxyl, hydroxy, cyano, nitro, benzoxy, trifluoro-methylsulfanyl, methylsulfonyl, azetidin-1-yl, 2-methylazetidinyl, 3-methoxyazetidinyl, 3-hydroxyazetidinyl, 3-fluoroazetidinyl, 2,2-difluoroazetidin-1-yl, pyrrolidin-1-yl, pyrrolidin-2-yl, pyrrolidin-3-yl, 2- and 3-fluoropyrrolidin-1-yl, 2,2-difluoropyrrolidin-1-y 3,3-difluoropyrrolidin-1-yl, 2- and 3-methylpyrrolidin-1-yl, 1-methylpyrrolidin-2-yl, 2,2-dimethylpyrrolidin-1-yl, 3,3-dimethylpyrrolidin-1-yl, 2-oxo-pyrrolidin-1-yl, 2- and 3-trifluoromethylpyrrolidin-1-yl, 2-oxo-oxazolidin-1-yl, piperidin-1-yl, 2-methylpiperidin-1-yl, 2-fluoropiperidin-1-yl, 2,2-difluoropiperidin-1-yl, piperazin-1-yl, 4-methylpiperazin-1-yl, morpholin-4-yl, thiomorpholin-4-yl, 1-oxothiomorpholin-4-yl, 1,1-dioxothiomorpholin-4-yl, pyrrol-1-yl, pyrrol-2-yl, pyrrol-3-yl, 1-methylpyrrol-2-yl, 1-methylpyrrol-3-yl, pyrazol-1-yl, pyrazol-3-yl, pyrazol-4-yl, 1-methylpyrazol-4-yl, 4-fluoropyrazol-1-yl, imidazol-1-yl, imidazol-2-yl, 1-methylimidazol-2-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, 2-methylthiazol-4-yl, 2-methylthiazol-5-yl, [1,2,3]triazol-1-yl, [1,2,4]triazol-1-yl, [1,2,3]triazol-2-yl, [1,2,4]triazol-3-yl, [1,2,4]triazol-4-yl, 4-methyl-[1,2,4]triazol-3-yl, 2-methyl-[1,2,3]triazol-4-yl, [1,3,4]-oxadiazol-2-yl, [1,2,4]-oxadiazol-3-yl, [1,2,4]-oxadiazol-5-yl, [1,2,3]-oxadiazol-5-yl, [1,3,4]-oxadiazol-2-yl, 5-methyl-[1,3,4]-oxadiazol-2-yl, 5-methyl-[1,2,4]-oxadiazol-3-yl, [1,2,3]thiadiazol-4-yl, [1,2,3]thiadiazol-5-yl, [1,2,4]thiadiazol-3-yl, [1,2,4]thiadiazol-5-yl, [1,3,4]thiadiazol-2-yl, tetrazol-1-yl, tetrazol-5-yl, 2-methyltetrazol-5-yl, 1-methyltetrazol-5-yl, furazan-3-yl, pyrid-2-yl, pyrid-3-yl, pyrid-4-yl, pyrimidin-2-yl, pyrimidin-4-yl, pyrimidin-5-yl and 2-methylpyrimidin-4-yl.

In an alternatively preferred embodiment, $R^a$ has the formula $R^{a'}$

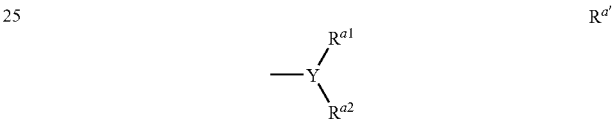

wherein

Y is N, CH or CF, $R^{a1}$ and $R^{a2}$ are independently of each other selected from $C_1$-$C_2$-alkyl, in particular methyl, fluorinated $C_1$-$C_2$-alkyl, in particular fluoromethyl, difluoromethyl or trifluoromethyl, provided for Y being CH or CF one of the radicals $R^{a1}$ or $R^{a2}$ may also be hydrogen or fluorine, or $R^{a1}$ and $R^{a2}$ form a radical $(CH_2)_m$ wherein 1 or 2 of the hydrogen atoms may be replaced by fluorine and wherein m is 2, 3 or 4, in particular $CH_2$—$CH_2$, $CHF$—$CH_2$ $CF_2$—$CH_2$, $CH_2$—$CH_2$—$CH_2$, $CHF$—$CH_2$—$CH_2$, $CF_2$—$CH_2$—$CH_2$, $CH_2$—$CHF$—$CH_2$, $CH_2$—$CF_2$—$CH_2$.

In case $R^{a1}$ and $R^{a2}$ are different from each other, the radical of the aforementioned formula Ra may have either (R)- or (S)-configuration with regard to the Y-moiety.

Examples for preferred radicals of the formula $R^{a'}$ comprise isopropyl, (R)-1-fluoroethyl, (S)-1-fluoroethyl, 2-fluoroethyl, 1,1-difluoroethyl, 2,2-difluoroethyl, 2,2,2-trifluoroethyl, (R)-1-fluoropropyl, (S)-1-fluoropropyl, 2-fluoropropyl, 3-fluoropropyl, 1,1-difluoropropyl, 2,2-difluoropropyl, 3,3-difluoropropyl, 3,3,3-trifluoropropyl, cyclopropyl, cyclobutyl, 1-fluorocyclopropyl, (S)- and (R)-2,2-difluorocyclopropyl and 2-fluorocyclopropyl.

Amongst the radicals of the formula R" those are preferred which carry 1, 2, 3 or 4, in particular 1, 2 or 3 fluorine atoms.

Preferred examples for Ar are in particular the following: 3-methylphenyl, 3-ethylphenyl, 3-propylphenyl, 3-isopropylphenyl, 3-sec-butylphenyl, 3-isobutylphenyl, 3-tert-butylphenyl, 3-(1,1-dimethylpropyl)-phenyl, 3-vinylphenyl, 3-isopropenylphenyl, 2-fluorophenyl, 3-fluorophenyl, 3-chlorophenyl, 3-bromophenyl, 3-iodophenyl, 3-(fluoromethyl)phenyl, 3-(difluoromethyl)phenyl, 3-(trifluoromethyl)phenyl, 3,5-bis(trifluoromethyl)phenyl, 3-(1-fluoroethyl)-phenyl, 3-((S)-1-fluoroethyl)-phenyl, 3-((R)-1-fluoroethyl)-phenyl, 3-(2-fluoroethyl)-phenyl, 3-(1,1-difluoroethyl)-phenyl, 3-(2,2-difluoroethyl)-phenyl, 3-(2,2,2-trifluoroethyl)-phenyl, 3-(3-fluoropropyl)-phenyl, 3-(2- fluoropropyl)-phenyl, 3-((S)-2-fluoropropyl)-phenyl, 3-((R)-2-fluoropropyl)-phenyl, 3-(3,3-difluoropropyl)-phenyl, 3-(3,3,3-trifluoropropyl)-phenyl, 3-(1-fluoro-1-methylethyl)-phenyl, 3-(2-fluoro-1-methylethyl)-phenyl, 3-((S)-2-fluoro-1-methylethyl)-phenyl, 3-((R)-2-fluoro-1-methylethyl)-phenyl, 3-(2,2-difluoro-1-methylethyl)-phenyl, 3-((S)-2,2-difluoro-1-methylethyl)-phenyl, 3-((R)-2,2-difluoro-1-methylethyl)-phenyl, 3-(2,2,2-trifluoro-1-methylethyl)-phenyl, 3-((S)-2,2,2-trifluoro-1-methylethyl)-phenyl, 3-((R)-2,2,2-trifluoro-1-methylethyl)-phenyl, 3-(2-fluoro-1-fluoromethylethyl)-phenyl, 3-(1-difluoromethyl-2,2-difluoroethyl)-phenyl, 3-(1,1-dimethyl-2-fluoroethyl)-phenyl, 3-methoxyphenyl, 3-ethoxyphenyl, 3-propoxyphenyl, 3-isopropoxyphenyl, 3-butoxyphenyl, 3-(fluoromethoxy)-phenyl, 3-(difluoromethoxy)-phenyl, 3-(trifluoromethoxy)-phenyl, 3-(2-fluoroethoxy)-phenyl, 3-(2,2-difluoroethoxy)-phenyl, 3-(2,2,2-trifluoroethoxy)-phenyl, 3-(1,1,2,2-tetrafluoroethoxy)-phenyl, 3-cyclopropylphenyl, 3-cyclobutylphenyl, 3-cyclopentylphenyl, 3-(2,2-difluorocyclopropyl)-phenyl, 3,4-difluorophenyl, 3,5-dichlorophenyl, 2,3-dichlorophenyl, 2,5-dichlorophenyl, 4-bromo-3-fluorophenyl, 3-bromo-2-fluorophenyl, 2-bromo-3-fluorophenyl, 3-chloro-4-fluorophenyl, 3-bromo-2,5-difluorophenyl, 4-bromo-2,5-difluorophenyl, 5-bromo-2,4-difluorophenyl, 3-bromo-2,4-difluorophenyl, 4-chloro-3-(trifluoromethyl)-phenyl, 2-chloro-5-(trifluoromethyl)-phenyl, 2-fluoro-5-(trifluoromethyl)-phenyl, 4-fluoro-3-(trifluoromethyl)-phenyl, 3-fluoro-5-(trifluoromethyl)-phenyl, 4-bromo-3-(trifluoromethyl)-phenyl, 3-bromo-5-(trifluoromethyl)-phenyl, 2-bromo-5-(trifluoromethyl)-phenyl, 5-bromo-2-methoxyphenyl, 3-bromo-4-methoxyphenyl, 3-bromo-4-(trifluoromethoxy)-phenyl, 3,5-dibromo-4-(2-fluoroethoxy)-phenyl, 2-fluoro-3-isopropylphenyl, 4-fluoro-3-isopropylphenyl, 3-(1-hydroxy-1-methylethyl)-phenyl, 3-(2-hydroxy-2-methylpropyl)-phenyl, 3-acetylphenyl, 3-acetylaminophenyl, 3-carboxyphenyl, 3-cyanophenyl, 3-nitrophenyl, 3-hydroxyphenyl, 3-(O-benzyl)-phenyl, 3-(2-methoxyethoxy)-phenyl, 3-($CH_2$—$N(CH_3)_2$)-phenyl, 3-(NH—CO—$NH_2$)-phenyl, 3-(methylsulfanyl)-phenyl, 3-(fluoromethylsulfanyl)-phenyl, 3-(difluoromethylsulfanyl)-phenyl, 3-(trifluoromethylsulfanyl)-phenyl, 3-(methylsulfonyl)-phenyl, 3-(N-methoxy-N-methyl-amino)-phenyl, 3-(methoxyamino)-phenyl, 3-(ethoxyamino)-phenyl, 3-(N-methylaminooxy)-phenyl, 3-(N,N-dimethylaminooxy)-phenyl, 3-cyanophenyl, 2,5-dimethylphenyl, 2,5-di-(trifluoromethyl)-phenyl, 3,5-di-(trifluoromethyl)-phenyl, 2,5-dimethoxyphenyl, 2-methoxy-5-methylphenyl, 2-methoxy-5-(trifluoromethyl)-phenyl, 3-(azetidin-1-yl)-phenyl, 3-(2-methylazetidin-1-yl)-phenyl, 3-((S)-2-methylazetidin-1-yl)-phenyl, 3-((R)-2-methylazetidin-1-yl)-phenyl, 3-(3-fluoroazetidin-1-yl)-phenyl, 3-(2,2-difluoroazetidin-1-yl)-phenyl, 3-(3-methoxyazetidin-1-yl)-phenyl, 3-(3-hydroxyazetidin-1-yl)-phenyl, 3-(pyrrolidin-1-yl)-phenyl, 3-(pyrrolidin-2-yl)-phenyl, 3-((S)-pyrrolidin-2-yl)-phenyl, 3-((R)-pyrrolidin-2-yl)-phenyl, 3-(pyrrolidin-3-yl)-phenyl, 3-((S)-pyrrolidin-3-yl)-phenyl, 3-((R)-pyrrolidin-3-yl)-phenyl, 3-(pyrrolidin-1-yl)-5-(trifluoromethyl)-phenyl, 5-(pyrrolidin-1-yl)-2-methoxyphenyl, 3-(pyrrolidin-1-yl)-4-methoxyphenyl, 5-(pyrrolidin-1-yl)-2,4-difluorophenyl, 3-(pyrrolidin-1-yl)-2,4-difluorophenyl, 3-(2-fluoropyrrolidin-1-yl)-phenyl, 3-((S)-2-fluoropyrrolidin-1-yl)-phenyl, 3-((R)-2-fluoropyrrolidin-1-yl)-phenyl, 3-(3-fluoropyrrolidin-1-yl)-phenyl, 3-((S)-3-fluoropyrrolidin-1-yl)-phenyl, 3-((R)-3-fluoropyrrolidin-1-yl)-phenyl, 3-(2,2-difluoropyrrolidin-1-yl)-phenyl, 3-(3,3-difluoropyrrolidin-1-yl)-phenyl, 3-(2-methylpyrrolidin-1-yl)-phenyl, 3-((S)-2-methylpyrrolidin-1-yl)-phenyl, 3-((R)-2-methylpyrrolidin-1-yl)-phenyl, 3-(3-methylpyrrolidin-1-yl)-phenyl, 3-((S)-3-methylpyrrolidin-1-yl)-phenyl, 3-((R)-3-methylpyrrolidin-1-yl)-phenyl, 3-(1-methylpyrrolidin-2-yl)-phenyl, 3-((S)-1-methylpyrrolidin-2-yl)-phenyl, 3-((R)-1-methylpyrrolidin-2-yl)-phenyl, 3-(1-methylpyrrolidin-3-yl)-phenyl, 3-((S)-1-methylpyrrolidin-3-yl)-phenyl, 3-((R)-1-methylpyrrolidin-3-yl)-phenyl, 3-(2,2-dimethylpyrrolidin-1-yl)-phenyl, 3-(3,3-dimethylpyrrolidin-1-yl)-phenyl, 3-(2-trifluoromethylpyrrolidin-1-yl)-phenyl, 3-((S)-2-trifluoromethylpyrrolidin-1-yl)-phenyl, 3-((R)-2-trifluoromethylpyrrolidin-1-yl)-phenyl, 3-(3-trifluoromethylpyrrolidin-1-yl)-phenyl, 3-((S)-3-trifluoromethylpyrrolidin-1-yl)-phenyl, 3-((R)-3-trifluoromethylpyrrolidin-1-yl)-phenyl, 3-(2-oxopyrrolidin-1-yl)-phenyl, 3-(2-oxo-oxazolidin-3-yl)-phenyl, 3-(piperidin-1-yl)-phenyl, 3-(2-methylpiperidin-1-yl)-phenyl, 3-((S)-2-methylpiperidin-1-yl)-phenyl, 3-((R)-2-methylpiperidin-1-yl)-phenyl, 3-(2-fluoropiperidin-1-yl)-phenyl, 3-((S)-2-fluoropiperidin-1-yl)-phenyl, 3-((R)-2-fluoropiperidin-1-yl)-phenyl, 3-(2,2-difluoropiperidin-1-yl)-phenyl, 3-(piperazin-1-yl)-phenyl, 3-(4-methylpiperazin-1-yl)-phenyl, 3-(morpholin-4-yl)-phenyl, 3-(morpholin-4-yl)-5-(trifluoromethyl)-phenyl, 5-(morpholin-4-yl)-2-methoxyphenyl, 3-(morpholin-4-yl)-4-methoxyphenyl, 5-(morpholin-4-yl)-2,4-difluorophenyl, 3-(morpholin-4-yl)-2,4-difluorophenyl, 3-(thiomorpholin-4-yl)-phenyl, 3-(1-oxo-thiomorpholin-4-yl)-phenyl, 3-(1,1-dioxo-thiomorpholin-4-yl)-phenyl, 3-(pyrrol-1-yl)-phenyl, 3-(pyrrol-2-yl)-phenyl, 3-(pyrrol-3-yl)-phenyl, 3-(1-methylpyrrol-2-yl)-phenyl, 3-(1-methylpyrrol-3-yl)-phenyl, 3-(furan-2-yl)-phenyl, 3-(furan-3-yl)-phenyl, 3-(thiophen-2-yl)-phenyl, 3-(thiophen-3-yl)-phenyl, 3-(5-propylthien-2-yl)-phenyl, 3-(pyrazol-1-yl)-phenyl, 3-(pyrazol-3-yl)-phenyl, 3-(pyrazol-4-yl)-phenyl, 3-(1-methyl-1H-pyrazol-4-yl)-phenyl, 3-(1-ethyl-1H-pyrazol-4-yl)-phenyl, 3-(1-methyl-1H-pyrazol-5-yl)-phenyl, 3-(4-fluoropyrazol-1-yl)-phenyl, 3-(1H-imidazol-2-yl)-phenyl, 3-(imidazol-1-yl)-phenyl, 3-(1-methylimidazol-2-yl)-phenyl, 3-(oxazol-2-yl)-phenyl, 3-(oxazol-4-yl)-phenyl, 3-(oxazol-5-yl)-phenyl, 4-fluoro-3-(oxazol-4-yl)-phenyl, 3-(isoxazol-3-yl)-phenyl, 3-(isoxazol-4-yl)-phenyl, 3-(isoxazol-5-yl)-phenyl, 3-(thiazol-2-yl)-phenyl, 3-(thiazol-4-yl)-phenyl, 3-(thiazol-5-yl)-phenyl, 3-(2-methylthiazol-4-yl)-phenyl, 3-(2-methylthiazol-5-yl)-phenyl, 3-([1,2,3]-triazol-1-yl)-phenyl, 3-([1,2,4]-triazol-1-yl)-phenyl, 3-([1,2,3]-triazol-2-yl)-phenyl, 3-(4H-[1,2,4]-triazol-3-yl)-phenyl, 3-([1,2,4]-triazol-4-yl)-phenyl, 3-(2H-[1,2,3]-triazol-4-yl)-phenyl, 3-(4-methyl-4H-[1,2,4]-triazol-3-yl)-phenyl, 3-(2-methyl-2H-[1,2,3]-triazol-4-yl)-phenyl, 3-([1,3,4]-oxadiazol-2-yl)-phenyl, 3-(5-methyl-[1,3,4]-oxadiazol-2-yl)-phenyl, 3-([1,2,4]-oxadiazol-3-yl)-phenyl, 3-(5-methyl-[1,2,4]-oxadiazol-3-yl)-phenyl, 3-([1,2,4]-oxadiazol-5-yl)-phenyl, 3-([1,2,3]-oxadiazol-4-yl)-phenyl, 3-([1,2,3]-oxadiazol-5-yl)-phenyl, 3-([1,2,3]-thiadiazol-4-yl)-phenyl, 3-(1H-tetrazol-5-yl)-phenyl, 3-(tetrazol-1-yl)-phenyl, 3-(2-methyl-2H-tetrazol-5-yl)-phenyl, 3-(1-methyl-1H-tetrazol-5-yl)-phenyl, 3-furazan-3-yl-phenyl, 3-(pyrid-2-yl)-phenyl, 3-(pyrid-3-yl)-phenyl, 3-(pyrid-4-yl)-phenyl, 3-(pyrimidin-2-yl)-phenyl, 3-(pyrimidin-4-yl)-phenyl, 3-(2-methylpyrimidin-4-yl)-phenyl, 3-(pyrimidin-5-yl)-phenyl, 5-bromopyridin-3-yl, 3-bromo-2-chloropyridin-5-yl, 4-methylpyridin-2-yl, 6-methylpyridin-2-yl, 4-(trifluoromethyl)-pyridin-2-yl, 6-(trifluoromethyl)-pyridin-2-yl, 5-(trifluoromethyl)-pyridin-3-yl, 5-(pyrrolidin-1-yl)-pyridin-3-yl, 3-(pyrrolidin-1-yl)-2-chloropyridin-5-yl, 3-(morpholin-4-yl)-2-chloropyridin-5-yl, 4-methylphenyl, 4-ethylphenyl, 4-propylphenyl, 4-isopropylphenyl, 4-sec-butylphenyl, 4-tert-butylphenyl, 4-isobutylphenyl, 4-(1,1-dimethylpropyl)-phenyl, 4-vinylphenyl, 4-isopropenylphenyl, 4-fluorophenyl, 4-chlorophenyl, 4-bromophenyl, 4-iodophenyl, 4-(fluoromethyl)phenyl, 4-(difluoromethyl)phenyl, 4-(trifluoromethyl)phenyl, 2,4-bis(trifluoroethyl)phenyl, 4-(1-fluoroethyl)-phenyl, 4-((S)-1-fluoroethyl)-phenyl, 4-((R)-1-fluoroethyl)-phenyl, 4-(2-fluoroethyl)-phenyl, 4-(1,1-difluoroethyl)-phenyl, 4-(2,2-difluoroethyl)-phenyl, 4-(2,2,2-trifluoroethyl)-phenyl, 4-(3-fluoropropyl)-phenyl, 4-(2-fluoropropyl)-phenyl, 4-((S)-2-fluoropropyl)-phenyl, 4-((R)-2-fluoropropyl)-phenyl, 4-(3,3-difluoropropyl)-phenyl, 4-(3,3,3-trifluoropropyl)-phenyl, 4-(1-fluoro-1-methylethyl)-phenyl, 4-(2-fluoro-1-methylethyl)-phenyl, 4-((S)-2-fluoro-1-methylethyl)-phenyl, 4-((R)-2-fluoro-1-methylethyl)-phenyl, 4-(2,2-difluoro-1-methylethyl)-phenyl, 4-((S)-2,2-difluoro-1-methylethyl)-phenyl, 4-((R)-2,2-difluoro-1-methylethyl)-phenyl, 4-(2,2,2-trifluoro-1-methylethyl)-phenyl, 4-((S)-2,2,2-trifluoro-1-methylethyl)-phenyl, 4-((R)-2,2,2-trifluoro-1-methylethyl)-phenyl, 4-(2-fluoro-1-fluoromethylethyl)-phenyl, 4-(1-difluoromethyl-2,2-difluoroethyl)-phenyl, 4-(1,1-dimethyl-2-fluoroethyl)-phenyl, 4-methoxyphenyl, 4-ethoxyphenyl, 4-propoxyphenyl, 4-isopropoxyphenyl, 4-butoxyphenyl, 4-(fluoromethoxy)-phenyl, 4-(difluoromethoxy)-phenyl, 4-(trifluoromethoxy)-phenyl, 4-(2-fluoroethoxy)-phenyl, 4-(2,2-difluoroethoxy)-phenyl, 4-(2,2,2-trifluoroethoxy)-phenyl, 4-(1,1,2,2-tetrafluoroethoxy)-phenyl, 4-cyclopropylphenyl, 4-cyclobutylphenyl, 4-cyclopentylphenyl, 4-(2,2-difluorocyclopropyl)-phenyl, 3,4-difluorophenyl, 4-bromo-2-fluorophenyl, 2-bromo-4-fluorophenyl, 4-bromo-2,5-difluorophenyl, 5-bromo-2,4-difluorophenyl, 3-bromo-2,4-difluorophenyl, 3-chloro-4-(trifluoromethyl)-phenyl, 4-fluoro-3-(trifluoromethyl)-phenyl, 3-fluoro-5-(trifluoromethyl)-phenyl, 3-bromo-4-(trifluoromethyl)-phenyl, 5-bromo-3-(trifluoromethyl)-phenyl, 5-bromo-2-(trifluoromethyl)-phenyl, 2-bromo-5-methoxyphenyl, 4-bromo-3-methoxyphenyl, 3-fluoro-2-isopropylphenyl, 3-fluoro-4-isopropylphenyl, 4-(1-hydroxy-1-methylethyl)-phenyl, 4-(2-hydroxy-2-methylpropyl)-phenyl, 4-acetylphenyl, 4-acetylaminophenyl, 4-carboxyphenyl, 4-cyanophenyl, 4-nitrophenyl, 4-hydroxyphenyl, 4-(O-benzyl)-phenyl, 4-(2-methoxyethoxy)-phenyl, 4-($CH_2$—$N(CH_3)_2$)-phenyl, 4-(NH—CO—$NH_2$)-phenyl, 4-(methylsulfanyl)-phenyl, 4-(fluoromethylsulfanyl)-phenyl, 4-(difluoromethylsulfanyl)-phenyl, 4-(trifluoromethylsulfanyl)-phenyl, 4-(methylsulfonyl)-phenyl, 4-(N-methoxy-N-methyl-amino)-phenyl, 4-(methoxyamino)-phenyl, 4-(ethoxyamino)-phenyl, 4-(N-methylaminooxy)-phenyl, 4-(N,N-dimethylaminooxy)-phenyl, 4-(azetidin-1-yl)-phenyl, 4-(2-methylazetidin-1-yl)-phenyl, 4-((S)-2-methylazetidin-1-yl)-phenyl, 4-((R)-2-methylazetidin-1-yl)-phenyl, 4-(3-fluoroazetidin-1-yl)-phenyl, 4-(3-methoxyazetidin-1-yl)-phenyl, 4-(3-hydroxyazetidin-1-yl)-phenyl, 4-(pyrrolidin-1-yl)-phenyl, 4-(pyrrolidin-2-yl)-phenyl, 4-((S)-pyrrolidin-2-yl)-phenyl, 4-((R)-pyrrolidin-2-yl)-phenyl, 4-(pyrrolidin-3-yl)-phenyl, 4-((S)-pyrrolidin-3-yl)-phenyl, 4-((R)-pyrrolidin-3-yl)-phenyl, 4-(pyrrolidin-1-yl)-5-(trifluoromethyl)-phenyl, 4-(pyrrolidin-1-yl)-2-methoxyphenyl, 4-(pyrrolidin-1-yl)-34-methoxyphenyl, 4-(pyrrolidin-1-yl)-2,5-difluorophenyl, 4-(pyrrolidin-1-yl)-2,6-difluorophenyl, 4-(2-fluoropyrrolidin-1-yl)-phenyl, 4-((S)-2-fluoropyrrolidin-1-yl)-phenyl, 4-((R)-2-fluoropyrrolidin-1-yl)-phenyl, 4-(3-fluoropyrrolidin-1-yl)-phenyl, 4-((S)-3-fluoropyrrolidin-1-yl)-phenyl, 4-((R)-3-fluoropyrrolidin-1-yl)-phenyl, 4-(2,2-difluoropyrrolidin-1-yl)-phenyl, 4-(3,3-difluoropyrrolidin-1-yl)-phenyl, 4-(2-methylpyrrolidin-1-yl)-phenyl, 4-((S)-2-methylpyrrolidin-1-yl)-phenyl, 4-((R)-2-methylpyrrolidin-1-yl)-phenyl, 4-(3-methylpyrrolidin-1-yl)-phenyl, 4-((S)-3-methylpyrrolidin-1-yl)-phenyl, 4-((R)-3-methylpyrrolidin-1-yl)-phenyl, 4-(1-methylpyrrolidin-2-yl)-phenyl, 4-((S)-1-methylpyrrolidin-2-yl)-phenyl, 4-((R)-1-methylpyrrolidin-2-yl)-phenyl, 4-(1-methylpyrrolidin-3-yl)-phenyl, 4-((S)-1-methylpyrrolidin-3-yl)-phenyl, 4-((R)-1-methylpyrrolidin-3-yl)-phenyl, 4-(2,2-dimethylpyrrolidin-1-yl)-phenyl, 4-(3,3-dimethylpyrrolidin-1-yl)-phenyl, 4-(2-trifluoromethylpyrrolidin-1-yl)-phenyl, 4-((S)-2-trifluoromethylpyrrolidin-1-yl)-phenyl, 4-((R)-2-trifluoromethylpyrrolidin-1-yl)-phenyl, 4-(3-trifluoromethylpyrrolidin-1-yl)-phenyl, 4-((S)-3-trifluoromethylpyrrolidin-1-yl)-phenyl, 4-((R)-3-trifluoromethylpyrrolidin-1-yl)-phenyl, 4-(2-oxopyrrolidin-1-yl)-phenyl, 4-(2-oxo-oxazolidin-3-yl)-phenyl, 4-(piperidin-1-yl)-phenyl, 4-(2-methylpiperidin-1-yl)-phenyl, 4-((S)-2-methylpiperidin-1-yl)-phenyl, 4-((R)-2-methylpiperidin-1-yl)-phenyl, 4-(piperazin-1-yl)-phenyl, 4-(4-methylpiperazin-1-yl)-phenyl, 4-(morpholin-4-yl)-phenyl, 4-(morpholin-4-yl)-5-(trifluoromethyl)-phenyl, 4-(morpholin-4-yl)-2-methoxyphenyl, 4-(morpholin-4-yl)-3-methoxyphenyl, 4-(morpholin-4-yl)-2,5-difluorophenyl, 4-(morpholin-4-yl)-2,6-difluorophenyl, 4-(thiomorpholin-4-yl)-phenyl, 4-(1-oxo-thiomorpholin-4-yl)-phenyl, 4-(1,1-dioxo-thiomorpholin-4-yl)-phenyl, 4-(pyrrol-1-yl)-phenyl, 4-(pyrrol-2-yl)-phenyl, 4-(pyrrol-3-yl)-phenyl, 4-(1-methylpyrrol-2-yl)-phenyl, 4-(1-methylpyrrol-3-yl)-phenyl, 4-(furan-2-yl)-phenyl, 4-(furan-3-yl)-phenyl, 4-(thiophen-2-yl)-phenyl, 4-(thiophen-3-yl)-phenyl, 4-(5-propylthien-2-yl)-phenyl, 4-(pyrazol-1-yl)-phenyl, 4-(pyrazol-3-yl)-phenyl, 4-(pyrazol-4-yl)-phenyl, 4-(1-methyl-1H-pyrazol-4-yl)-phenyl, 4-(1-ethyl-1H-pyrazol-4-yl)-phenyl, 4-(1-methyl-1H-pyrazol-5-yl)-phenyl, 4-(1H-imidazol-2-yl)-phenyl, 4-(imidazol-1-yl)-phenyl, 4-(1-methylimidazol-2-yl)-phenyl, 4-(oxazol-2-yl)-phenyl, 4-(oxazol-4-yl)-phenyl, 4-(oxazol-5-yl)-phenyl, 4-(isoxazol-3-yl)-phenyl, 4-(isoxazol-4-yl)-phenyl, 4-(isoxazol-5-yl)-phenyl, 4-(thiazol-2-yl)-phenyl, 4-(thiazol-4-yl)-phenyl, 4-(thiazol-5-yl)-phenyl, 4-(2-methylthiazol-4-yl)-phenyl, 4-([1,2,3]-triazol-1-yl)-phenyl, 4-([1,2,4]-triazol-1-yl)-phenyl, 4-([1,2,3]-triazol-2-yl)-phenyl, 4-(4H-[1,2,4]-triazol-3-yl)-phenyl, 4-([1,2,4]-triazol-4-yl)-phenyl, 4-(2H-[1,2,3]-triazol-4-yl)-phenyl, 4-(4-methyl-4H-[1,2,4]-triazol-3-yl)-phenyl, 4-(2-methyl-2H-[1,2,3]-triazol-4-yl)-phenyl, 4-([1,3,4]-oxadiazol-2-yl)-phenyl, 4-(5-methyl-[1,3,4]-oxadiazol-2-yl)-phenyl, 4-([1,2,4]-oxadiazol-3-yl)-phenyl, 4-(5-methyl-[1,2,4]-oxadiazol-3-yl)-phenyl, 4-([1,2,4]-oxadiazol-5-yl)-phenyl, 4-([1,2,3]-oxadiazol-4-yl)-phenyl, 4-([1,2,3]-oxadiazol-5-yl)-phenyl, 4-([1,2,3]-thiadiazol-4-yl)-phenyl, 4-(1H-tetrazol-5-yl)-phenyl, 4-(tetrazol-1-yl)-phenyl, 4-(2-methyl-2H-tetrazol-5-yl)-phenyl, 4-(1-methyl-1H-tetrazol-5-yl)-phenyl, 4-furazan-3-yl-phenyl, 4-(pyrid-2-yl)-phenyl, 4-(pyrid-3-yl)-phenyl, 4-(pyrid-4-yl)-phenyl, 4-(pyrimidin-2-yl)-phenyl, 4-(2-methylpyrimidin-4-yl)-phenyl, 4-(pyrimidin-4-yl)-phenyl, 4-(pyrimidin-5-yl)-phenyl, 4-bromo-2-chloropyridin-5-yl, 4-methylpyridin-2-yl, 5-methylpyridin-2-yl, 4-(pyrrolidin-1-yl)-2-chloropyridin-5-yl, 4-(morpholin-4-yl)-2-chloropyridin-5-yl, 2-(morpholin-4-yl)-pyridin-5-yl, 2-phenoxypyridin-5-yl, thien-2-yl, thien-3-yl, 3-chlorothien-2-yl, 4-chlorothien-2-yl, 5-chlorothien-2-yl, 3-bromothien-2-yl, 4-bromothien-2-yl, 5-bromothien-2-yl, 4,5-dichlorothien-2-yl, 4,5-dibromothien-2-yl, 4-bromo-5-chlorothien-2-yl, 3-bromo-5-chlorothien-2-yl, 5-methylthien-2-yl, 5-ethylthien-2-yl, 5-propylthien-2-yl, 5-trifluoromethylthien-2-yl, 5-phenylthien-2-yl, 5-(pyrid-2-yl)-thien-2-yl, 5-(phenylsulfonyl)-thien-2-yl, 4-(phenylsulfonyl)-thien-2-yl, 5-(pyrid-2-ylsulfonyl)-thien-2-yl, 5-(3-chloro-5-trifluoro-pyrid-2-ylsulfonyl)-thien-2-yl, 5-(benzoylaminomethyl)-thien-2-yl, 5-((4-chlorobenzoyl)aminomethyl)-thien-2-yl, 5-(acetylaminomethyl)-thien-2-yl, 5-(pyrazol-1-yl)-thien-2-yl, 5-(pyrazol-3-yl)-thien-2-yl, 5-(pyrazol-4-yl)-thien-2-yl, 5-(pyrazol-5-yl)-thien-2-yl, 5-(4-fluoropyrazol-1-yl)-thien-2-yl, 5-(1-methyl-5-trifluoromethyl-(1H)-pyrazol-3-yl)-thien-2-yl, 5-(1-methyl-3-trifluoromethyl-(1H)-pyrazol-5-yl)-thien-2-yl, 5-(4-carboxy-1-methyl-5-methylthio-(1H)-pyrazol-3-yl)-thien-2-yl, 5-(4-aminomethyl-1-methyl-5-methylthio-(1H)-pyrazol-3-yl)-thien-2-yl, 5-(isoxazol-3-yl)-thien-2-yl, 5-(isoxazol-4-yl)-thien-2-yl, 5-(isoxazol-5-yl)-thien-2-yl, 5-(5-trifluoromethylisoxazol-3-yl)-thien-2-yl, 5-(oxazol-2-yl)-thien-2-yl, 5-(oxazol-4-yl)-thien-2-yl, 5-(oxazol-5-yl)-thien-2-yl, 5-(2-methyloxazol-4-yl)-thien-2-yl, 5-(2-methyloxazol-5-yl)-thien-2-yl, 5-(isothiazol-3-yl)-thien-2-yl, 5-(isothiazol-4-yl)-thien-2-yl, 5-(isothiazol-5-yl)-thien-2-yl, 5-(5-trifluoromethylisothiazol-3-yl)-thien-2-yl, 5-(thiazol-2-yl)-thien-2-yl, 5-(thiazol-4-yl)-thien-2-yl, 5-(thiazol-5-yl)-thien-2-yl, 5-(2-methylthiazol-4-yl)-thien-2-yl, 5-(2-methylthiazol-5-yl)-thien-2-yl, 5-([1,2,3]-oxadiazol-4-yl)-thien-2-yl, 5-([1,2,3]-thiadiazol-4-yl)-thien-2-yl, 5-(pyrimidin-2-yl)-thien-2-yl, 5-(pyrimidin-4-yl)-thien-2-yl, 5-(pyrimidin-5-yl)-thien-2-yl, 5-(2-methylthiopyrimidin-4-yl)-thien-2-yl, 5-([1,3]-dioxolan-2-yl)-thien-2-yl, 3-([1,3]-dioxolan-2-yl)-thien-2-yl thien-2-yl, 5-((3-chloro-5-(trifluoromethyl)-pyridin-2-yl)-methyl)-thien-2-yl, 5-[3-chloro-5-(trifluoromethyl)-pyrid-2-ylsulfonyl]-thien-2-yl, 2-chlorothien-3-yl, 4-chlorothien-3-yl, 5-chlorothien-3-yl, 2-bromothien-3-yl, 4-bromothien-3-yl, 5-bromothien-3-yl, 2,5-dichlorothien-3-yl, 2,5-dibromothien-3-yl, 2,4,5-trichlorothien-3-yl, 4-bromo-2,5-dichlorothien-3-yl, 2-chloro-5-methylsulfonylthien-3-yl, 2,5-dimethylthien-3-yl, 4-hydroxythien-3-yl, 2-phenylthien-3-yl, 4-phenyl-5-(trofluoromethyl)-thien-3-yl, 2-methoxycarbonyl-4-phenyl-5-(trifluoromethyl)-thien-3-yl, benzo[b]thiophen-2-yl, benzo[b]thiophen-3-yl, 3-methyl-benzo[b]thiophen-2-yl, 5-methyl-benzo[b]thiophen-2-yl, 5-fluoro-3-methyl-benzo[b]thiophen-2-yl, 5-chloro-3-methyl-benzo[b]thiophen-2-yl and 5-bromo-3-methyl-benzo[b]thiophen-2-yl.

Particularly preferred compounds I are those of formulae I.a.1, I.a.2, I.a.3, I.a.4, I.a.5, I.a.6, I.a.7, I.a.8, I.a.9, I.a.10, I.a.11, I.a.12, I.a.13, I.a.14, I.a.15, I.a.16, I.b.1, I.b.2, I.b.3, I.b.4, I.b.5, I.b.6, I.b.7, I.b.8, I.b.9, I.b.10, I.b.11, I.b.12, I.b.13, I.b.14, I.b.15, I.b.16, I.c.1, I.c.2, I.c.3, I.c.4, I.c.5, I.c.6, I.c.7, I.c.8, I.d.1, I.d.2, I.d.3, I.d.4, I.d.5, I.d.6, I.d.7, I.d.8, I.d.9, I.d.10, I.d.11, I.12, I.d.13, I.d.14, I.d.15, I.d.16, I.d.17, I.d.18, I.d.19, I.d.20, I.d.21, I.d.22, I.d.23 and I.d.24, wherein $R^1$ and Ar have the above-defined meanings. Preferred meanings of $R^1$ and Ar are as defined above.

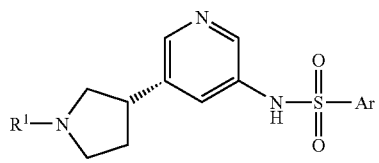

I.a.1

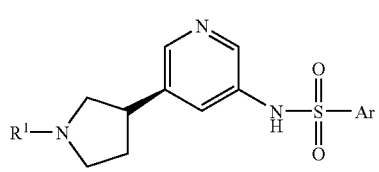

I.a.2

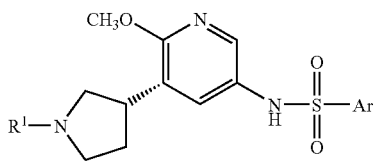

I.a.3

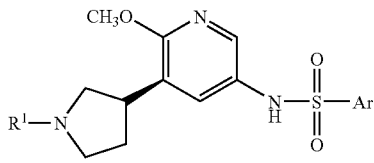

I.a.4

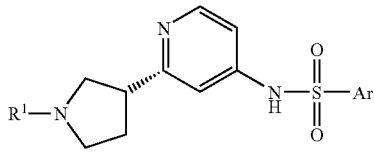

I.a.5

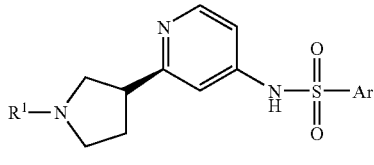

I.a.6

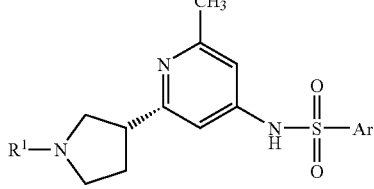

I.a.7

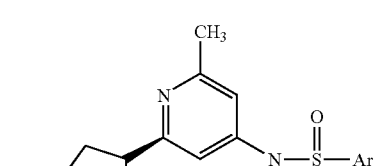

I.a.8

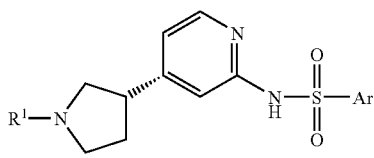

I.a.9

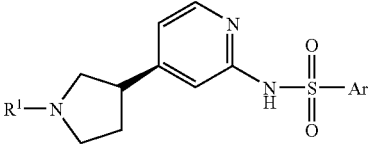

I.a.10

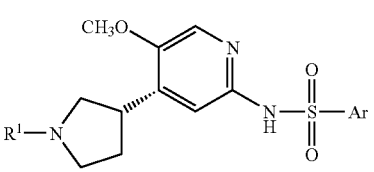

I.a.11

I.a.12
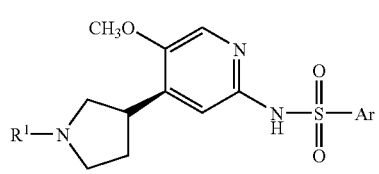
I.a.13
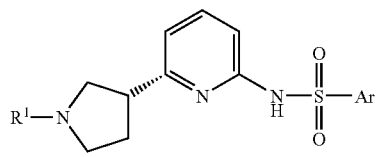
I.a.14
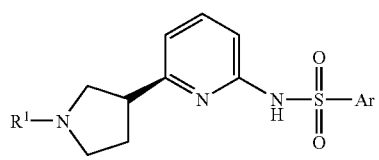
I.a.15
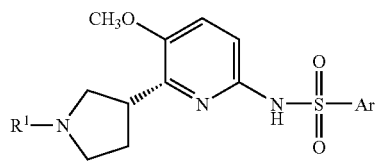
I.a.16
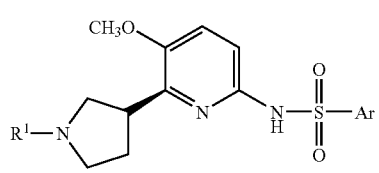
I.b.1
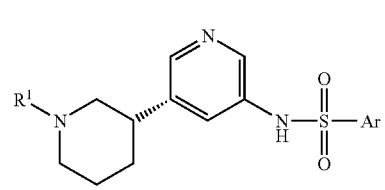
I.b.2
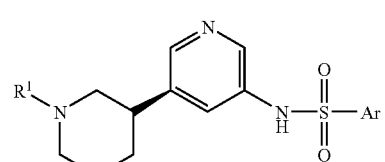
I.b.3
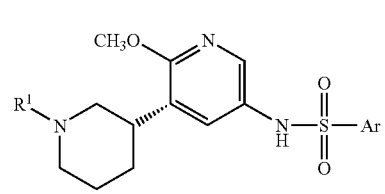
I.b.4
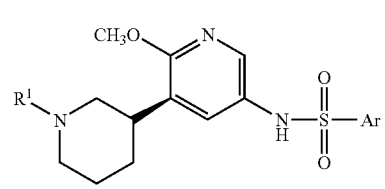
I.b.5
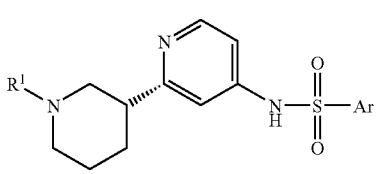
I.b.6
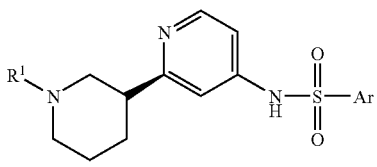
I.b.7
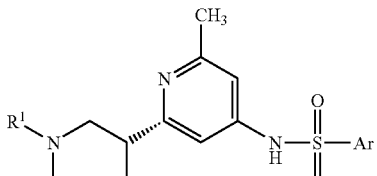
I.b.8
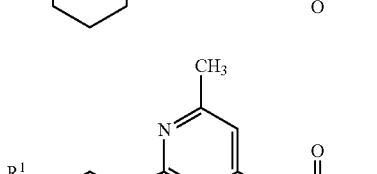
I.b.9
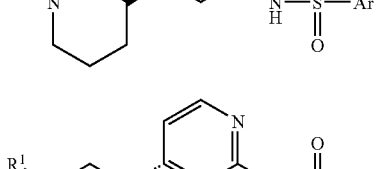
I.b.10
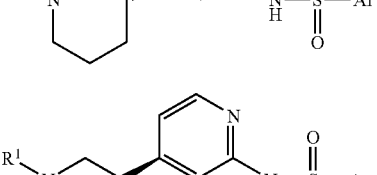
I.b.11
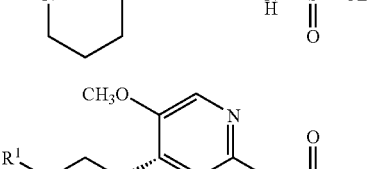
I.b.12
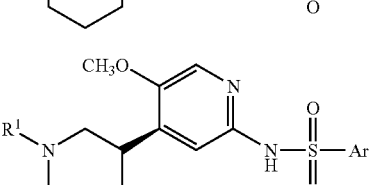
I.b.13
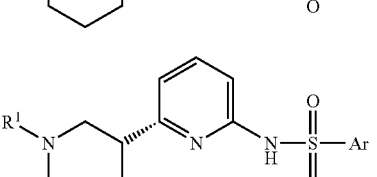

-continued
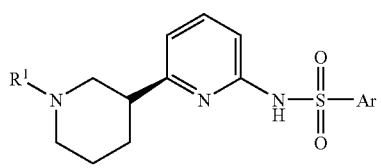 I.b.14
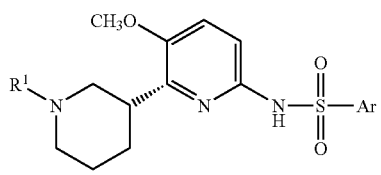 I.b.15
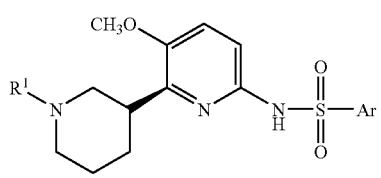 I.b.16
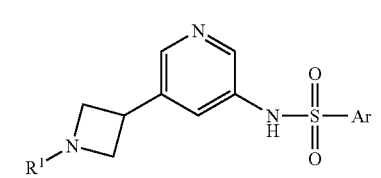 I.c.1
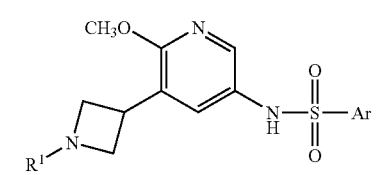 I.c.2
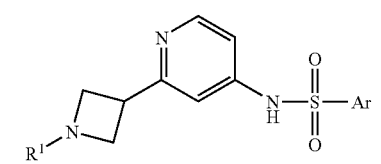 I.c.3
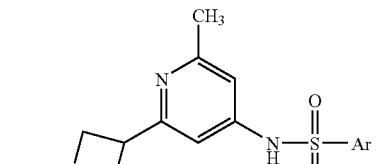 I.c.4
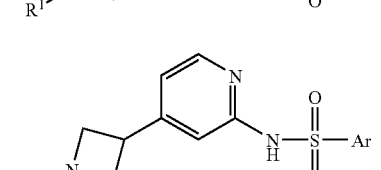 I.c.5
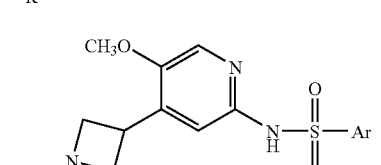 I.c.6
-continued
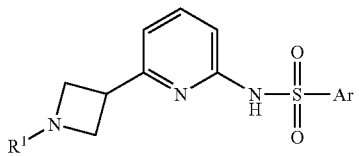 I.c.7
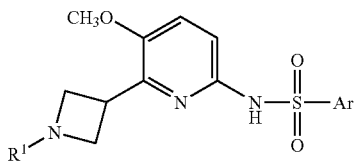 I.c.8
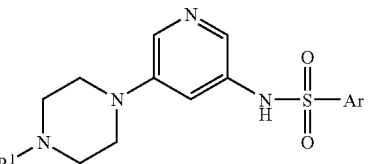 I.d.1
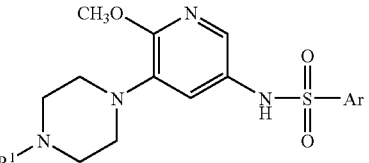 I.d.2
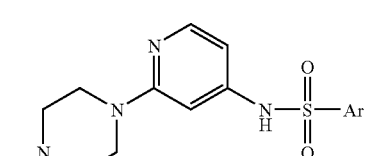 I.d.3
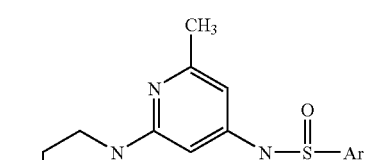 I.d.4
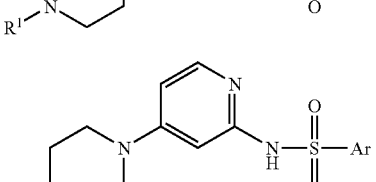 I.d.5
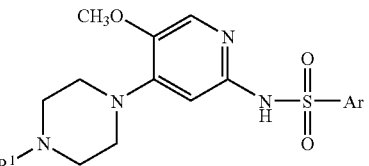 I.d.6
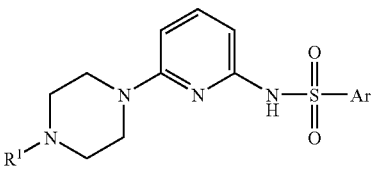 I.d.7

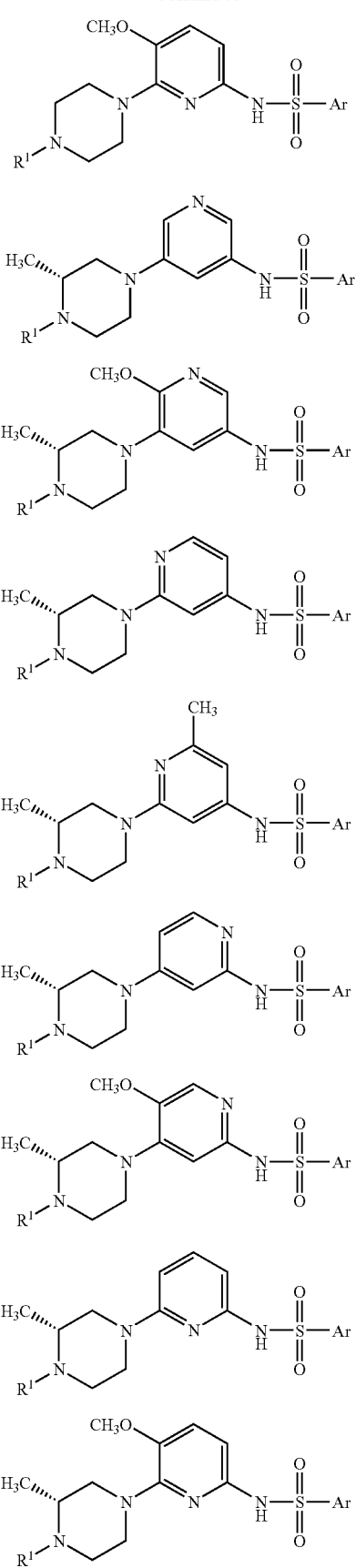
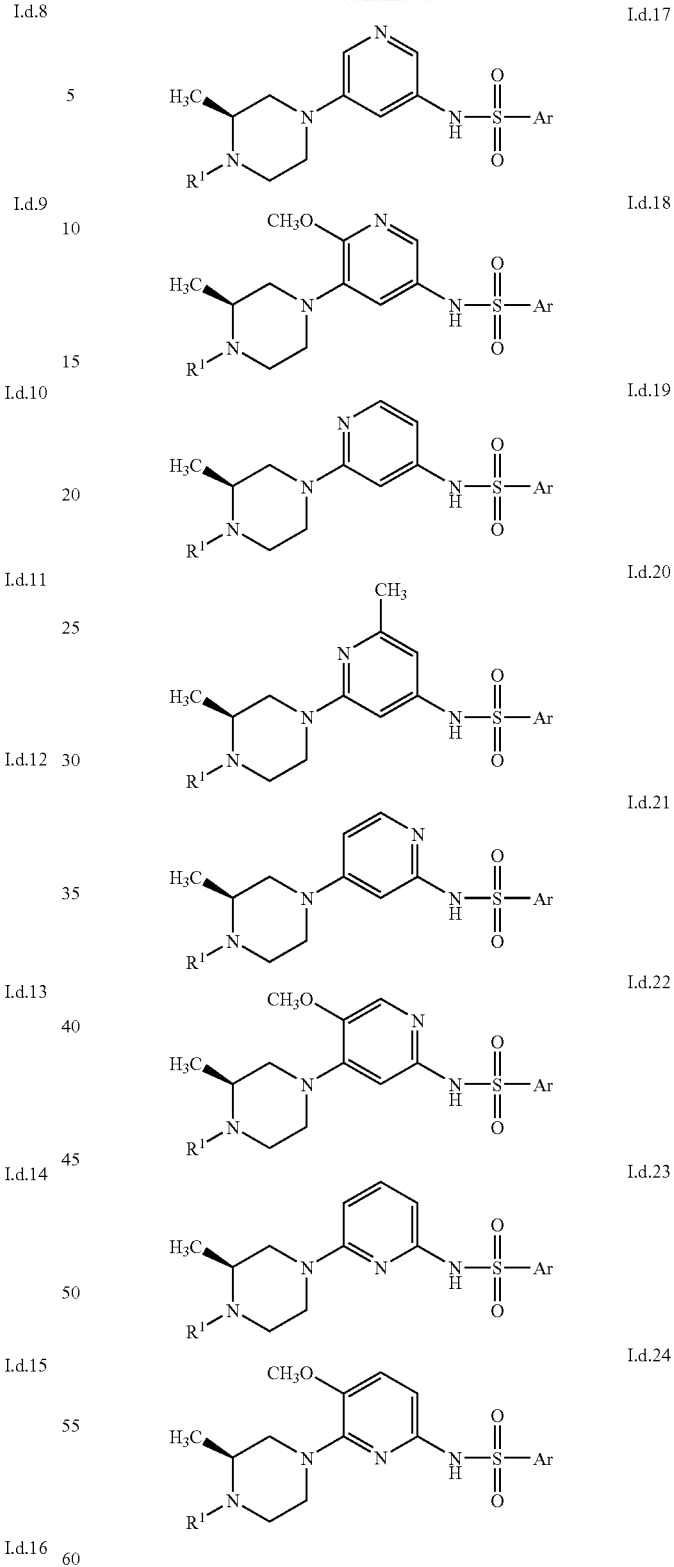
Examples of preferred compounds which are represented by the formulae I.a.1, I.a.2, I.a.3, I.a.4, I.a.5, I.a.6, I.a.7, I.a.8, I.a.9, I.a.10, I.a.11, I.a.12, I.a.13, I.a.14, I.a.15, I.a.16, I.b.1, I.b.2, I.b.3, I.b.4, I.b.5, I.b.6, I.b.7, I.b.8, I.b.9, I.b.10, I.b.11, I.b.12, I.b.13, I.b.14, I.b.15, I.b.16, I.c.1, I.c.2, I.c.3, I.c.4, I.c.5, I.c.6, I.c.7, I.c.8, I.d.1, I.d.2, I.d.3, I.d.4, I.d.5, I.d.6, I.d.7, I.d.8, I.d.9, I.d.10, I.d.11, I.12, I.d.13, I.d.14, I.d.15, I.d.16, I.d.17, I.d.18, I.d.19, I.d.20, I.d.21, I.d.22, I.d.23 and I.d.24, are the individual compounds listed above, where the variables Ar and $R^1$ have the meanings given in one row of table A.

TABLE A

| No. | $R^1$ | Ar |
|---|---|---|
| 1. | propyl | 3-methylphenyl |
| 2. | propyl | 3-ethylphenyl |
| 3. | propyl | 3-propylphenyl |
| 4. | propyl | 3-isopropylphenyl |
| 5. | propyl | 3-sec-butylphenyl |
| 6. | propyl | 3-tert-butylphenyl |
| 7. | propyl | 3-isobutylphenyl |
| 8. | propyl | 3-(1,1-dimethylpropyl)-phenyl |
| 9. | propyl | 3-vinylphenyl |
| 10. | propyl | 3-isopropenylphenyl |
| 11. | propyl | 3-fluorophenyl |
| 12. | propyl | 2-fluorophenyl |
| 13. | propyl | 3-chlorophenyl |
| 14. | propyl | 3-bromophenyl |
| 15. | propyl | 3-iodophenyl |
| 16. | propyl | 3-(fluoromethyl)phenyl |
| 17. | propyl | 3-(difluoromethyl)phenyl |
| 18. | propyl | 3-(trifluoromethyl)phenyl |
| 19. | propyl | 3,5-bis(trifluoromethyl)phenyl |
| 20. | propyl | 3-(1-fluoroethyl)-phenyl |
| 21. | propyl | 3-((S)-1-fluoroethyl)-phenyl |
| 22. | propyl | 3-((R)-1-fluoroethyl)-phenyl |
| 23. | propyl | 3-(2-fluoroethyl)-phenyl |
| 24. | propyl | 3-(1,1-difluoroethyl)-phenyl |
| 25. | propyl | 3-(2,2-difluoroethyl)-phenyl |
| 26. | propyl | 3-(2,2,2-trifluoroethyl)-phenyl |
| 27. | propyl | 3-(3-fluoropropyl)-phenyl |
| 28. | propyl | 3-(2-fluoropropyl)-phenyl |
| 29. | propyl | 3-((S)-2-fluoropropyl)-phenyl |
| 30. | propyl | 3-((R)-2-fluoropropyl)-phenyl |
| 31. | propyl | 3-(3,3-difluoropropyl)-phenyl |
| 32. | propyl | 3-(3,3,3-trifluoropropyl)-phenyl |
| 33. | propyl | 3-(1-fluoro-1-methylethyl)-phenyl |
| 34. | propyl | 3-(2-fluoro-1-methylethyl)-phenyl |
| 35. | propyl | 3-((S)-2-fluoro-1-methylethyl)-phenyl |
| 36. | propyl | 3-((R)-2-fluoro-1-methylethyl)-phenyl |
| 37. | propyl | 3-(2,2-difluoro-1-methylethyl)-phenyl |
| 38. | propyl | 3-((S)-2,2-difluoro-1-methylethyl)-phenyl |
| 39. | propyl | 3-((R)-2,2-difluoro-1-methylethyl)-phenyl |
| 40. | propyl | 3-(2,2,2-trifluoro-1-methylethyl)-phenyl |
| 41. | propyl | 3-((S)-2,2,2-trifluoro-1-methylethyl)-phenyl |
| 42. | propyl | 3-((R)-2,2,2-trifluoro-1-methylethyl)-phenyl |
| 43. | propyl | 3-(2-fluoro-1-fluoromethylethyl)-phenyl |
| 44. | propyl | 3-(1-difluoromethyl-2,2-difluoroethyl)-phenyl |
| 45. | propyl | 3-(1,1-dimethyl-2-fluoroethyl)-phenyl |
| 46. | propyl | 3-methoxyphenyl |
| 47. | propyl | 3-ethoxyphenyl |
| 48. | propyl | 3-propoxyphenyl |
| 49. | propyl | 3-isopropoxyphenyl |
| 50. | propyl | 3-butoxyphenyl |
| 51. | propyl | 3-(fluoromethoxy)-phenyl |
| 52. | propyl | 3-(difluoromethoxy)-phenyl |
| 53. | propyl | 3-(trifluoromethoxy)-phenyl |
| 54. | propyl | 3-(2-fluoroethoxy)-phenyl |
| 55. | propyl | 3-(2,2-difluoroethoxy)-phenyl |
| 56. | propyl | 3-(2,2,2-trifluoroethoxy)-phenyl |
| 57. | propyl | 3-(1,1,2,2-tetrafluoroethoxy)-phenyl |
| 58. | propyl | 3-cyclopropylphenyl |
| 59. | propyl | 3-cyclobutylphenyl |
| 60. | propyl | 3-cyclopentylphenyl |
| 61. | propyl | 3-(2,2-difluorocyclopropyl)-phenyl |
| 62. | propyl | 3,4-difluorophenyl |
| 63. | propyl | 3-bromo-2-fluorophenyl |
| 64. | propyl | 2-bromo-3-fluorophenyl |
| 65. | propyl | 3-bromo-2,5-difluorophenyl |
| 66. | propyl | 5-bromo-2,4-difluorophenyl |
| 67. | propyl | 3-bromo-2,4-difluorophenyl |
| 68. | propyl | 4-chloro-3-(trifluoromethyl)-phenyl |
| 69. | propyl | 2-chloro-5-(trifluoromethyl)-phenyl |
| 70. | propyl | 2-fluoro-5-(trifluoromethyl)-phenyl |
| 71. | propyl | 4-fluoro-3-(trifluoromethyl)-phenyl |
| 72. | propyl | 3-fluoro-5-(trifluoromethyl)-phenyl |
| 73. | propyl | 4-bromo-3-(trifluoromethyl)-phenyl |
| 74. | propyl | 3-bromo-5-(trifluoromethyl)-phenyl |
| 75. | propyl | 2-bromo-5-(trifluoromethyl)-phenyl |

TABLE A-continued

| No. | R¹ | Ar |
|---|---|---|
| 76. | propyl | 5-bromo-2-methoxyphenyl |
| 77. | propyl | 3-bromo-4-methoxyphenyl |
| 78. | propyl | 2-fluoro-3-isopropylphenyl |
| 79. | propyl | 4-fluoro-3-isopropylphenyl |
| 80. | propyl | 3-(1-hydroxy-1-methylethyl)-phenyl |
| 81. | propyl | 3-(2-hydroxy-2-methylpropyl)-phenyl |
| 82. | propyl | 3-acetylphenyl |
| 83. | propyl | 3-acetylaminophenyl |
| 84. | propyl | 3-carboxyphenyl |
| 85. | propyl | 3-cyanophenyl |
| 86. | propyl | 3-nitrophenyl |
| 87. | propyl | 3-hydroxyphenyl |
| 88. | propyl | 3-(O-benzyl)-phenyl |
| 89. | propyl | 3-(2-methoxyethoxy)-phenyl |
| 90. | propyl | 3-($CH_2$—$N(CH_3)_2$)-phenyl |
| 91. | propyl | 3-(NH—CO—$NH_2$)-phenyl |
| 92. | propyl | 3-(methylsulfanyl)-phenyl |
| 93. | propyl | 3-(fluoromethylsulfanyl)-phenyl |
| 94. | propyl | 3-(difluoromethylsulfanyl)-phenyl |
| 95. | propyl | 3-(trifluoromethylsulfanyl)-phenyl |
| 96. | propyl | 3-(methylsulfonyl)-phenyl |
| 97. | propyl | 3-(N-methoxy-N-methyl-amino)-phenyl |
| 98. | propyl | 3-(methoxyamino)-phenyl |
| 99. | propyl | 3-(ethoxyamino)-phenyl |
| 100. | propyl | 3-(N-methylaminooxy)-phenyl |
| 101. | propyl | 3-(N,N-dimethylaminooxy)-phenyl |
| 102. | propyl | 3-(azetidin-1-yl)-phenyl |
| 103. | propyl | 3-(2-methylazetidin-1-yl)-phenyl |
| 104. | propyl | 3-((S)-2-methylazetidin-1-yl)-phenyl |
| 105. | propyl | 3-((R)-2-methylazetidin-1-yl)-phenyl |
| 106. | propyl | 3-(3-fluoroazetidin-1-yl)-phenyl |
| 107. | propyl | 3-(2,2-difluoroazetidin-1-yl)-phenyl |
| 108. | propyl | 3-(3-methoxyazetidin-1-yl)-phenyl |
| 109. | propyl | 3-(3-hydroxyazetidin-1-yl)-phenyl |
| 110. | propyl | 3-(pyrrolidin-1-yl)-phenyl |
| 111. | propyl | 3-(pyrrolidin-2-yl)-phenyl |
| 112. | propyl | 3-((S)-pyrrolidin-2-yl)-phenyl |
| 113. | propyl | 3-((R)-pyrrolidin-2-yl)-phenyl |
| 114. | propyl | 3-(pyrrolidin-3-yl)-phenyl |
| 115. | propyl | 3-((S)-pyrrolidin-3-yl)-phenyl |
| 116. | propyl | 3-((R)-pyrrolidin-3-yl)-phenyl |
| 117. | propyl | 3-(pyrrolidin-1-yl)-5-(trifluoromethyl)-phenyl |
| 118. | propyl | 5-(pyrrolidin-1-yl)-2-methoxyphenyl |
| 119. | propyl | 3-(pyrrolidin-1-yl)-4-methoxyphenyl |
| 120. | propyl | 5-(pyrrolidin-1-yl)-2,4-difluorophenyl |
| 121. | propyl | 3-(pyrrolidin-1-yl)-2,4-difluorophenyl |
| 122. | propyl | 3-(2-fluoropyrrolidin-1-yl)-phenyl |
| 123. | propyl | 3-((S)-2-fluoropyrrolidin-1-yl)-phenyl |
| 124. | propyl | 3-((R)-2-fluoropyrrolidin-1-yl)-phenyl |
| 125. | propyl | 3-(3-fluoropyrrolidin-1-yl)-phenyl |
| 126. | propyl | 3-((S)-3-fluoropyrrolidin-1-yl)-phenyl |
| 127. | propyl | 3-((R)-3-fluoropyrrolidin-1-yl)-phenyl |
| 128. | propyl | 3-(2,2-difluoropyrrolidin-1-yl)-phenyl |
| 129. | propyl | 3-(3,3-difluoropyrrolidin-1-yl)-phenyl |
| 130. | propyl | 3-(2-methylpyrrolidin-1-yl)-phenyl |
| 131. | propyl | 3-((S)-2-methylpyrrolidin-1-yl)-phenyl |
| 132. | propyl | 3-((R)-2-methylpyrrolidin-1-yl)-phenyl |
| 133. | propyl | 3-(3-methylpyrrolidin-1-yl)-phenyl |
| 134. | propyl | 3-((S)-3-methylpyrrolidin-1-yl)-phenyl |
| 135. | propyl | 3-((R)-3-methylpyrrolidin-1-yl)-phenyl |
| 136. | propyl | 3-(1-methylpyrrolidin-2-yl)-phenyl |
| 137. | propyl | 3-((S)-1-methylpyrrolidin-2-yl)-phenyl |
| 138. | propyl | 3-((R)-1-methylpyrrolidin-2-yl)-phenyl |
| 139. | propyl | 3-(1-methylpyrrolidin-3-yl)-phenyl |
| 140. | propyl | 3-((S)-1-methylpyrrolidin-3-yl)-phenyl |
| 141. | propyl | 3-((R)-1-methylpyrrolidin-3-yl)-phenyl |
| 142. | propyl | 3-(2,2-dimethylpyrrolidin-1-yl)-phenyl |
| 143. | propyl | 3-(3,3-dimethylpyrrolidin-1-yl)-phenyl |
| 144. | propyl | 3-(2-trifluoromethylpyrrolidin-1-yl)-phenyl |
| 145. | propyl | 3-((S)-2-trifluoromethylpyrrolidin-1-yl)-phenyl |
| 146. | propyl | 3-((R)-2-trifluoromethylpyrrolidin-1-yl)-phenyl |
| 147. | propyl | 3-(3-trifluoromethylpyrrolidin-1-yl)-phenyl |
| 148. | propyl | 3-((S)-3-trifluoromethylpyrrolidin-1-yl)-phenyl |
| 149. | propyl | 3-((R)-3-trifluoromethylpyrrolidin-1-yl)-phenyl |
| 150. | propyl | 3-(2-oxopyrrolidin-1-yl)-phenyl |
| 151. | propyl | 3-(2-oxo-oxazolidin-3-yl)-phenyl |
| 152. | propyl | 3-(piperidin-1-yl)-phenyl |
| 153. | propyl | 3-(2-methylpiperidin-1-yl)-phenyl |

TABLE A-continued

| No. | R¹ | Ar |
|---|---|---|
| 154. | propyl | 3-((S)-2-methylpiperidin-1-yl)-phenyl |
| 155. | propyl | 3-((R)-2-methylpiperidin-1-yl)-phenyl |
| 156. | propyl | 3-(2-fluoropiperidin-1-yl)-phenyl |
| 157. | propyl | 3-((S)-2-fluoropiperidin-1-yl)-phenyl |
| 158. | propyl | 3-((R)-2-fluoropiperidin-1-yl)-phenyl |
| 159. | propyl | 3-(2,2-difluoropiperidin-1-yl)-phenyl |
| 160. | propyl | 3-(piperazin-1-yl)-phenyl |
| 161. | propyl | 3-(4-methylpiperazin-1-yl)-phenyl |
| 162. | propyl | 3-(morpholin-4-yl)-phenyl |
| 163. | propyl | 3-(morpholin-4-yl)-5-(trifluoromethyl)-phenyl |
| 164. | propyl | 5-(morpholin-4-yl)-2-methoxyphenyl |
| 165. | propyl | 3-(morpholin-4-yl)-4-methoxyphenyl |
| 166. | propyl | 5-(morpholin-4-yl)-2,4-difluorophenyl |
| 167. | propyl | 3-(morpholin-4-yl)-2,4-difluorophenyl |
| 168. | propyl | 3-(thiomorpholin-4-yl)-phenyl |
| 169. | propyl | 3-(1-oxo-thiomorpholin-4-yl)-phenyl |
| 170. | propyl | 3-(1,1-dioxo-thiomorpholin-4-yl)-phenyl |
| 171. | propyl | 3-(pyrrol-1-yl)-phenyl |
| 172. | propyl | 3-(pyrrol-2-yl)-phenyl |
| 173. | propyl | 3-(pyrrol-3-yl)-phenyl |
| 174. | propyl | 3-(1-methylpyrrol-2-yl)-phenyl |
| 175. | propyl | 3-(1-methylpyrrol-3-yl)-phenyl |
| 176. | propyl | 3-(furan-2-yl)-phenyl |
| 177. | propyl | 3-(furan-3-yl)-phenyl |
| 178. | propyl | 3-(thiophen-2-yl)-phenyl |
| 179. | propyl | 3-(thiophen-3-yl)-phenyl |
| 180. | propyl | 3-(5-propylthien-2-yl)-phenyl |
| 181. | propyl | 3-(pyrazol-1-yl)-phenyl |
| 182. | propyl | 3-(pyrazol-3-yl)-phenyl |
| 183. | propyl | 3-(pyrazol-4-yl)-phenyl |
| 184. | propyl | 3-(4-fluoropyrazol-1-yl)-phenyl |
| 185. | propyl | 3-(1-methyl-1H-pyrazol-4-yl)-phenyl |
| 186. | propyl | 3-(1-ethyl-1H-pyrazol-4-yl)-phenyl |
| 187. | propyl | 3-(1-methyl-1H-pyrazol-5-yl)-phenyl |
| 188. | propyl | 3-(1H-imidazol-2-yl)-phenyl |
| 189. | propyl | 3-(imidazol-1-yl)-phenyl |
| 190. | propyl | 3-(1-methylimidazol-2-yl)-phenyl |
| 191. | propyl | 3-(oxazol-2-yl)-phenyl |
| 192. | propyl | 3-(oxazol-4-yl)-phenyl |
| 193. | propyl | 3-(oxazol-5-yl)-phenyl |
| 194. | propyl | 3-(isoxazol-3-yl)-phenyl |
| 195. | propyl | 3-(isoxazol-4-yl)-phenyl |
| 196. | propyl | 3-(isoxazol-5-yl)-phenyl |
| 197. | propyl | 3-(thiazol-2-yl)-phenyl |
| 198. | propyl | 3-(thiazol-4-yl)-phenyl |
| 199. | propyl | 3-(thiazol-5-yl)-phenyl |
| 200. | propyl | 3-(2-methylthiazol-4-yl)-phenyl |
| 201. | propyl | 3-(2-methylthiazol-5-yl)-phenyl |
| 202. | propyl | 3-([1,2,3]-triazol-1-yl)-phenyl |
| 203. | propyl | 3-([1,2,4]-triazol-1-yl)-phenyl |
| 204. | propyl | 3-([1,2,3]-triazol-2-yl)-phenyl |
| 205. | propyl | 3-(4H-[1,2,4]-triazol-3-yl)-phenyl |
| 206. | propyl | 3-([1,2,4]-triazol-4-yl)-phenyl |
| 207. | propyl | 3-(2H-[1,2,3]-triazol-4-yl)-phenyl |
| 208. | propyl | 3-(4-methyl-4H-[1,2,4]-triazol-3-yl)-phenyl |
| 209. | propyl | 3-(2-methyl-2H-[1,2,3]-triazol-4-yl)-phenyl |
| 210. | propyl | 3-([1,3,4]-oxadiazol-2-yl)-phenyl |
| 211. | propyl | 3-(5-methyl-[1,3,4]-oxadiazol-2-yl)-phenyl |
| 212. | propyl | 3-([1,2,4]-oxadiazol-3-yl)-phenyl |
| 213. | propyl | 3-(5-methyl-[1,2,4]-oxadiazol-3-yl)-phenyl |
| 214. | propyl | 3-([1,2,4]-oxadiazol-5-yl)-phenyl |
| 215. | propyl | 3-([1,2,3]-oxadiazol-4-yl)-phenyl |
| 216. | propyl | 3-([1,2,3]-oxadiazol-5-yl)-phenyl |
| 217. | propyl | 3-([1,2,3]-thiadiazol-4-yl)-phenyl |
| 218. | propyl | 3-(1H-tetrazol-5-yl)-phenyl |
| 219. | propyl | 3-(tetrazol-1-yl)-phenyl |
| 220. | propyl | 3-(2-methyl-2H-tetrazol-5-yl)-phenyl |
| 221. | propyl | 3-(1-methyl-1H-tetrazol-5-yl)-phenyl |
| 222. | propyl | 3-furazan-3-yl-phenyl |
| 223. | propyl | 3-(pyrid-2-yl)-phenyl |
| 224. | propyl | 3-(pyrid-3-yl)-phenyl |
| 225. | propyl | 3-(pyrid-4-yl)-phenyl |
| 226. | propyl | 3-(pyrimidin-2-yl)-phenyl |
| 227. | propyl | 3-(2-methylpyrimidin-4-yl)-phenyl |
| 228. | propyl | 3-(pyrimidin-4-yl)-phenyl |
| 229. | propyl | 3-(pyrimidin-5-yl)-phenyl |
| 230. | propyl | 5-bromopyridin-3-yl |
| 231. | propyl | 3-bromo-2-chloropyridin-5-yl |

TABLE A-continued

| No. | R¹ | Ar |
|---|---|---|
| 232. | propyl | 4-methylpyridin-2-yl |
| 233. | propyl | 6-methylpyridin-2-yl |
| 234. | propyl | 4-(trifluoromethyl)-pyridin-2-yl |
| 235. | propyl | 6-(trifluoromethyl)-pyridin-2-yl |
| 236. | propyl | 5-(trifluoromethyl)-pyridin-3-yl |
| 237. | propyl | 5-(pyrrolidin-1-yl)-pyridin-3-yl |
| 238. | propyl | 3-(pyrrolidin-1-yl)-2-chloropyridin-5-yl |
| 239. | propyl | 3-(morpholin-4-yl)-2-chloropyridin-5-yl |
| 240. | propyl | 2-(morpholin-4-yl)-pyridin-5-yl |
| 241. | propyl | 2-phenoxypyridin-5-yl |
| 242. | propyl | 4-methylphenyl |
| 243. | propyl | 4-ethylphenyl |
| 244. | propyl | 4-propylphenyl |
| 245. | propyl | 4-isopropylphenyl |
| 246. | propyl | 4-sec-butylphenyl |
| 247. | propyl | 4-tert-butylphenyl |
| 248. | propyl | 4-isobutylphenyl |
| 249. | propyl | 4-(1,1-dimethylpropyl)-phenyl |
| 250. | propyl | 4-vinylphenyl |
| 251. | propyl | 4-isopropenylphenyl |
| 252. | propyl | 4-fluorophenyl |
| 253. | propyl | 4-chlorophenyl |
| 254. | propyl | 4-bromophenyl |
| 255. | propyl | 4-iodophenyl |
| 256. | propyl | 4-(fluoromethyl)phenyl |
| 257. | propyl | 4-(difluoromethyl)phenyl |
| 258. | propyl | 4-(trifluoromethyl)phenyl |
| 259. | propyl | 2,4-bis(trifluoromethyl)phenyl |
| 260. | propyl | 4-(1-fluoroethyl)-phenyl |
| 261. | propyl | 4-((S)-1-fluoroethyl)-phenyl |
| 262. | propyl | 4-((R)-1-fluoroethyl)-phenyl |
| 263. | propyl | 4-(2-fluoroethyl)-phenyl |
| 264. | propyl | 4-(1,1-difluoroethyl)-phenyl |
| 265. | propyl | 4-(2,2-difluoroethyl)-phenyl |
| 266. | propyl | 4-(2,2,2-trifluoroethyl)-phenyl |
| 267. | propyl | 4-(3-fluoropropyl)-phenyl |
| 268. | propyl | 4-(2-fluoropropyl)-phenyl |
| 269. | propyl | 4-((S)-2-fluoropropyl)-phenyl |
| 270. | propyl | 4-((R)-2-fluoropropyl)-phenyl |
| 271. | propyl | 4-(3,3-difluoropropyl)-phenyl |
| 272. | propyl | 4-(3,3,3-trifluoropropyl)-phenyl |
| 273. | propyl | 4-(1-fluoro-1-methylethyl)-phenyl |
| 274. | propyl | 4-(2-fluoro-1-methylethyl)-phenyl |
| 275. | propyl | 4-((S)-2-fluoro-1-methylethyl)-phenyl |
| 276. | propyl | 4-((R)-2-fluoro-1-methylethyl)-phenyl |
| 277. | propyl | 4-(2,2-difluoro-1-methylethyl)-phenyl |
| 278. | propyl | 4-((S)-2,2-difluoro-1-methylethyl)-phenyl |
| 279. | propyl | 4-((R)-2,2-difluoro-1-methylethyl)-phenyl |
| 280. | propyl | 4-(2,2,2-trifluoro-1-methylethyl)-phenyl |
| 281. | propyl | 4-((S)-2,2,2-trifluoro-1-methylethyl)-phenyl |
| 282. | propyl | 4-((R)-2,2,2-trifluoro-1-methylethyl)-phenyl |
| 283. | propyl | 4-(2-fluoro-1-fluoromethylethyl)-phenyl |
| 284. | propyl | 4-(1-difluoromethyl-2,2-difluoroethyl)-phenyl |
| 285. | propyl | 4-(1,1-dimethyl-2-fluoroethyl)-phenyl |
| 286. | propyl | 4-methoxyphenyl |
| 287. | propyl | 4-ethoxyphenyl |
| 288. | propyl | 4-propoxyphenyl |
| 289. | propyl | 4-isopropoxyphenyl |
| 290. | propyl | 4-butoxyphenyl |
| 291. | propyl | 4-(fluoromethoxy)-phenyl |
| 292. | propyl | 4-(difluoromethoxy)-phenyl |
| 293. | propyl | 4-(trifluoromethoxy)-phenyl |
| 294. | propyl | 4-(2-fluoroethoxy)-phenyl |
| 295. | propyl | 4-(2,2-difluoroethoxy)-phenyl |
| 296. | propyl | 4-(2,2,2-trifluoroethoxy)-phenyl |
| 297. | propyl | 4-(1,1,2,2-tetrafluoroethoxy)-phenyl |
| 298. | propyl | 4-cyclopropylphenyl |
| 299. | propyl | 4-cyclobutylphenyl |
| 300. | propyl | 4-cyclopentylphenyl |
| 301. | propyl | 4-(2,2-difluorocyclopropyl)-phenyl |
| 302. | propyl | 3,4-difluorophenyl |
| 303. | propyl | 4-bromo-2-fluorophenyl |
| 304. | propyl | 2-bromo-4-fluorophenyl |
| 305. | propyl | 4-bromo-2,5-difluorophenyl |
| 306. | propyl | 5-bromo-2,4-difluorophenyl |
| 307. | propyl | 3-bromo-2,4-difluorophenyl |
| 308. | propyl | 3-chloro-4-(trifluoromethyl)-phenyl |
| 309. | propyl | 4-fluoro-3-(trifluoromethyl)-phenyl |

TABLE A-continued

| No. | R¹ | Ar |
|---|---|---|
| 310. | propyl | 3-fluoro-5-(trifluoromethyl)-phenyl |
| 311. | propyl | 3-bromo-4-(trifluoromethyl)-phenyl |
| 312. | propyl | 5-bromo-3-(trifluoromethyl)-phenyl |
| 313. | propyl | 5-bromo-2-(trifluoromethyl)-phenyl |
| 314. | propyl | 2-bromo-5-methoxyphenyl |
| 315. | propyl | 4-bromo-3-methoxyphenyl |
| 316. | propyl | 3-fluoro-2-isopropylphenyl |
| 317. | propyl | 3-fluoro-4-isopropylphenyl |
| 318. | propyl | 4-(1-hydroxy-1-methylethyl)-phenyl |
| 319. | propyl | 4-(2-hydroxy-2-methylpropyl)-phenyl |
| 320. | propyl | 4-acetylphenyl |
| 321. | propyl | 4-acetylaminophenyl |
| 322. | propyl | 4-carboxyphenyl |
| 323. | propyl | 4-cyanophenyl |
| 324. | propyl | 4-nitrophenyl |
| 325. | propyl | 4-hydroxyphenyl |
| 326. | propyl | 4-(O-benzyl)-phenyl |
| 327. | propyl | 4-(2-methoxyethoxy)-phenyl |
| 328. | propyl | 4-($CH_2$—$N(CH_3)_2$)-phenyl |
| 329. | propyl | 4-(NH—CO—$NH_2$)-phenyl |
| 330. | propyl | 4-(methylsulfanyl)-phenyl |
| 331. | propyl | 4-(fluoromethylsulfanyl)-phenyl |
| 332. | propyl | 4-(difluoromethylsulfanyl)-phenyl |
| 333. | propyl | 4-(trifluoromethylsulfanyl)-phenyl |
| 334. | propyl | 4-(methylsulfonyl)-phenyl |
| 335. | propyl | 4-(N-methoxy-N-methyl-amino)-phenyl |
| 336. | propyl | 4-(methoxyamino)-phenyl |
| 337. | propyl | 4-(ethoxyamino)-phenyl |
| 338. | propyl | 4-(N-methylaminooxy)-phenyl |
| 339. | propyl | 4-(N,N-dimethylaminooxy)-phenyl |
| 340. | propyl | 4-(azetidin-1-yl)-phenyl |
| 341. | propyl | 4-(2-methylazetidin-1-yl)-phenyl |
| 342. | propyl | 4-((S)-2-methylazetidin-1-yl)-phenyl |
| 343. | propyl | 4-((R)-2-methylazetidin-1-yl)-phenyl |
| 344. | propyl | 4-(3-fluoroazetidin-1-yl)-phenyl |
| 345. | propyl | 4-(2,2-difluoroazetidin-1-yl)-phenyl |
| 346. | propyl | 4-(3-methoxyazetidin-1-yl)-phenyl |
| 347. | propyl | 4-(3-hydroxyazetidin-1-yl)-phenyl |
| 348. | propyl | 4-(pyrrolidin-1-yl)-phenyl |
| 349. | propyl | 4-(pyrrolidin-2-yl)-phenyl |
| 350. | propyl | 4-((S)-pyrrolidin-2-yl)-phenyl |
| 351. | propyl | 4-((R)-pyrrolidin-2-yl)-phenyl |
| 352. | propyl | 4-(pyrrolidin-3-yl)-phenyl |
| 353. | propyl | 4-((S)-pyrrolidin-3-yl)-phenyl |
| 354. | propyl | 4-((R)-pyrrolidin-3-yl)-phenyl |
| 355. | propyl | 4-(pyrrolidin-1-yl)-5-(trifluoromethyl)-phenyl |
| 356. | propyl | 4-(pyrrolidin-1-yl)-2-methoxyphenyl |
| 357. | propyl | 4-(pyrrolidin-1-yl)-34-methoxyphenyl |
| 358. | propyl | 4-(pyrrolidin-1-yl)-2,5-difluorophenyl |
| 359. | propyl | 4-(pyrrolidin-1-yl)-2,6-difluorophenyl |
| 360. | propyl | 4-(2-fluoropyrrolidin-1-yl)-phenyl |
| 361. | propyl | 4-((S)-2-fluoropyrrolidin-1-yl)-phenyl |
| 362. | propyl | 4-((R)-2-fluoropyrrolidin-1-yl)-phenyl |
| 363. | propyl | 4-(3-fluoropyrrolidin-1-yl)-phenyl |
| 364. | propyl | 4-((S)-3-fluoropyrrolidin-1-yl)-phenyl |
| 365. | propyl | 4-((R)-3-fluoropyrrolidin-1-yl)-phenyl |
| 366. | propyl | 4-(2,2-difluoropyrrolidin-1-yl)-phenyl |
| 367. | propyl | 4-(3,3-difluoropyrrolidin-1-yl)-phenyl |
| 368. | propyl | 4-(2-methylpyrrolidin-1-yl)-phenyl |
| 369. | propyl | 4-((S)-2-methylpyrrolidin-1-yl)-phenyl |
| 370. | propyl | 4-((R)-2-methylpyrrolidin-1-yl)-phenyl |
| 371. | propyl | 4-(3-methylpyrrolidin-1-yl)-phenyl |
| 372. | propyl | 4-((S)-3-methylpyrrolidin-1-yl)-phenyl |
| 373. | propyl | 4-((R)-3-methylpyrrolidin-1-yl)-phenyl |
| 374. | propyl | 4-(1-methylpyrrolidin-2-yl)-phenyl |
| 375. | propyl | 4-((S)-1-methylpyrrolidin-2-yl)-phenyl |
| 376. | propyl | 4-((R)-1-methylpyrrolidin-2-yl)-phenyl |
| 377. | propyl | 4-(1-methylpyrrolidin-3-yl)-phenyl |
| 378. | propyl | 4-((S)-1-methylpyrrolidin-3-yl)-phenyl |
| 379. | propyl | 4-((R)-1-methylpyrrolidin-3-yl)-phenyl |
| 380. | propyl | 4-(2,2-dimethylpyrrolidin-1-yl)-phenyl |
| 381. | propyl | 4-(3,3-dimethylpyrrolidin-1-yl)-phenyl |
| 382. | propyl | 4-(2-trifluoromethylpyrrolidin-1-yl)-phenyl |
| 383. | propyl | 4-((S)-2-trifluoromethylpyrrolidin-1-yl)-phenyl |
| 384. | propyl | 4-((R)-2-trifluoromethylpyrrolidin-1-yl)-phenyl |
| 385. | propyl | 4-(3-trifluoromethylpyrrolidin-1-yl)-phenyl |
| 386. | propyl | 4-((S)-3-trifluoromethylpyrrolidin-1-yl)-phenyl |
| 387. | propyl | 4-((R)-3-trifluoromethylpyrrolidin-1-yl)-phenyl |

TABLE A-continued

| No. | R¹ | Ar |
|---|---|---|
| 388. | propyl | 4-(2-oxopyrrolidin-1-yl)-phenyl |
| 389. | propyl | 4-(2-oxo-oxazolidin-3-yl)-phenyl |
| 390. | propyl | 4-(piperidin-1-yl)-phenyl |
| 391. | propyl | 4-(2-methylpiperidin-1-yl)-phenyl |
| 392. | propyl | 4-((S)-2-methylpiperidin-1-yl)-phenyl |
| 393. | propyl | 4-((R)-2-methylpiperidin-1-yl)-phenyl |
| 394. | propyl | 4-(2-fluoropiperidin-1-yl)-phenyl |
| 395. | propyl | 4-((S)-2-fluoropiperidin-1-yl)-phenyl |
| 396. | propyl | 4-((R)-2-fluoropiperidin-1-yl)-phenyl |
| 397. | propyl | 4-(2,2-difluoropiperidin-1-yl)-phenyl |
| 398. | propyl | 4-(piperazin-1-yl)-phenyl |
| 399. | propyl | 4-(4-methylpiperazin-1-yl)-phenyl |
| 400. | propyl | 4-(morpholin-4-yl)-phenyl |
| 401. | propyl | 4-(morpholin-4-yl)-5-(trifluoromethyl)-phenyl |
| 402. | propyl | 4-(morpholin-4-yl)-2-methoxyphenyl |
| 403. | propyl | 4-(morpholin-4-yl)-3-methoxyphenyl |
| 404. | propyl | 4-(morpholin-4-yl)-2,5-difluorophenyl |
| 405. | propyl | 4-(morpholin-4-yl)-2,6-difluorophenyl |
| 406. | propyl | 4-(thiomorpholin-4-yl)-phenyl |
| 407. | propyl | 4-(1-oxo-thiomorpholin-4-yl)-phenyl |
| 408. | propyl | 4-(1,1-dioxo-thiomorpholin-4-yl)-phenyl |
| 409. | propyl | 4-(pyrrol-1-yl)-phenyl |
| 410. | propyl | 4-(pyrrol-2-yl)-phenyl |
| 411. | propyl | 4-(pyrrol-3-yl)-phenyl |
| 412. | propyl | 4-(1-methylpyrrol-2-yl)-phenyl |
| 413. | propyl | 4-(1-methylpyrrol-3-yl)-phenyl |
| 414. | propyl | 4-(furan-2-yl)-phenyl |
| 415. | propyl | 4-(furan-3-yl)-phenyl |
| 416. | propyl | 4-(thiophen-2-yl)-phenyl |
| 417. | propyl | 4-(thiophen-3-yl)-phenyl |
| 418. | propyl | 4-(5-propylthien-2-yl)-phenyl |
| 419. | propyl | 4-(pyrazol-1-yl)-phenyl |
| 420. | propyl | 4-(pyrazol-3-yl)-phenyl |
| 421. | propyl | 4-(pyrazol-4-yl)-phenyl |
| 422. | propyl | 4-(4-fluoropyrazol-1-yl)-phenyl |
| 423. | propyl | 4-(1-methyl-1H-pyrazol-4-yl)-phenyl |
| 424. | propyl | 4-(1-ethyl-1H-pyrazol-4-yl)-phenyl |
| 425. | propyl | 4-(1-methyl-1H-pyrazol-5-yl)-phenyl |
| 426. | propyl | 4-(1H-imidazol-2-yl)-phenyl |
| 427. | propyl | 4-(imidazol-1-yl)-phenyl |
| 428. | propyl | 4-(1-methylimidazol-2-yl)-phenyl |
| 429. | propyl | 4-(oxazol-2-yl)-phenyl |
| 430. | propyl | 4-(oxazol-4-yl)-phenyl |
| 431. | propyl | 4-(oxazol-5-yl)-phenyl |
| 432. | propyl | 4-(isoxazol-3-yl)-phenyl |
| 433. | propyl | 4-(isoxazol-4-yl)-phenyl |
| 434. | propyl | 4-(isoxazol-5-yl)-phenyl |
| 435. | propyl | 4-(thiazol-2-yl)-phenyl |
| 436. | propyl | 4-(thiazol-4-yl)-phenyl |
| 437. | propyl | 4-(thiazol-5-yl)-phenyl |
| 438. | propyl | 4-(2-methylthiazol-4-yl)-phenyl |
| 439. | propyl | 4-(2-methylthiazol-5-yl)-phenyl |
| 440. | propyl | 4-([1,2,3]-triazol-1-yl)-phenyl |
| 441. | propyl | 4-([1,2,4]-triazol-1-yl)-phenyl |
| 442. | propyl | 4-([1,2,3]-triazol-2-yl)-phenyl |
| 443. | propyl | 4-(4H-[1,2,4]-triazol-3-yl)-phenyl |
| 444. | propyl | 4-([1,2,4]-triazol-4-yl)-phenyl |
| 445. | propyl | 4-(2H-[1,2,3]-triazol-4-yl)-phenyl |
| 446. | propyl | 4-(4-methyl-4H-[1,2,4]-triazol-3-yl)-phenyl |
| 447. | propyl | 4-(2-methyl-2H-[1,2,3]-triazol-4-yl)-phenyl |
| 448. | propyl | 4-([1,3,4]-oxadiazol-2-yl)-phenyl |
| 449. | propyl | 4-(5-methyl-[1,3,4]-oxadiazol-2-yl)-phenyl |
| 450. | propyl | 4-([1,2,4]-oxadiazol-3-yl)-phenyl |
| 451. | propyl | 4-(5-methyl-[1,2,4]-oxadiazol-3-yl)-phenyl |
| 452. | propyl | 4-([1,2,4]-oxadiazol-5-yl)-phenyl |
| 453. | propyl | 4-([1,2,3]-oxadiazol-4-yl)-phenyl |
| 454. | propyl | 4-([1,2,3]-oxadiazol-5-yl)-phenyl |
| 455. | propyl | 4-([1,2,3]-thiadiazol-4-yl)-phenyl |
| 456. | propyl | 4-(1H-tetrazol-5-yl)-phenyl |
| 457. | propyl | 4-(tetrazol-1-yl)-phenyl |
| 458. | propyl | 4-(2-methyl-2H-tetrazol-5-yl)-phenyl |
| 459. | propyl | 4-(1-methyl-1H-tetrazol-5-yl)-phenyl |
| 460. | propyl | 4-furazan-3-yl-phenyl |
| 461. | propyl | 4-(pyrid-2-yl)-phenyl |
| 462. | propyl | 4-(pyrid-3-yl)-phenyl |
| 463. | propyl | 4-(pyrid-4-yl)-phenyl |
| 464. | propyl | 4-(pyrimidin-2-yl)-phenyl |
| 465. | propyl | 4-(2-methylpyrimidin-4-yl)-phenyl |

TABLE A-continued

| No. | R¹ | Ar |
|---|---|---|
| 466. | propyl | 4-(pyrimidin-4-yl)-phenyl |
| 467. | propyl | 4-(pyrimidin-5-yl)-phenyl |
| 468. | propyl | 5-bromopyridin-3-yl |
| 469. | propyl | 4-bromo-2-chloropyridin-5-yl |
| 470. | propyl | 4-methylpyridin-2-yl |
| 471. | propyl | 5-methylpyridin-2-yl |
| 472. | propyl | 4-(trifluoromethyl)-pyridin-2-yl |
| 473. | propyl | 6-(trifluoromethyl)-pyridin-2-yl |
| 474. | propyl | 5-(trifluoromethyl)-pyridin-3-yl |
| 475. | propyl | 5-(pyrrolidin-1-yl)-pyridin-3-yl |
| 476. | propyl | 4-(pyrrolidin-1-yl)-2-chloropyridin-5-yl |
| 477. | propyl | 4-(morpholin-4-yl)-2-chloropyridin-5-yl |
| 478. | propyl | 2-(morpholin-4-yl)-pyridin-5-yl |
| 479. | propyl | 5-(morpholin-4-yl)-pyridin-2-yl |
| 480. | propyl | 2-phenoxypyridin-5-yl |
| 481. | propyl | 2,3-dichlorophenyl |
| 482. | propyl | 2,5-dichlorophenyl |
| 483. | propyl | 3,5-dichlorophenyl |
| 484. | propyl | 3-chloro-4-fluorophenyl |
| 485. | propyl | 4-bromo-2,5-dichlorophenyl |
| 486. | propyl | 3-bromo-4-(trifluoromethoxy)phenyl |
| 487. | propyl | 3,5-dibromo-4-(2-fluoroethoxy)-phenyl |
| 488. | propyl | 2,5-dimethylphenyl |
| 489. | propyl | 2,5-di-(trifluoromethyl)-phenyl |
| 490. | propyl | 3,5-di-(trifluoromethyl)-phenyl |
| 491. | propyl | 2,5-dimethoxyphenyl |
| 492. | propyl | 2-methoxy-5-methylphenyl |
| 493. | propyl | 2-methoxy-5-(trifluoromethyl)-phenyl |
| 494. | propyl | 4-fluoro-3-(oxazol-4-yl)-phenyl |
| 495. | propyl | thien-2-yl |
| 496. | propyl | thien-3-yl |
| 497. | propyl | 3-chlorothien-2-yl |
| 498. | propyl | 4-chlorothien-2-yl |
| 499. | propyl | 5-chlorothien-2-yl |
| 500. | propyl | 3-bromothien-2-yl |
| 501. | propyl | 4-bromothien-2-yl |
| 502. | propyl | 5-bromothien-2-yl |
| 503. | propyl | 4,5-dichlorothien-2-yl |
| 504. | propyl | 4,5-dibromothien-2-yl |
| 505. | propyl | 4-bromo-5-chlorothien-2-yl |
| 506. | propyl | 3-bromo-5-chlorothien-2-yl |
| 507. | propyl | 5-methylthien-2-yl |
| 508. | propyl | 5-ethylthien-2-yl |
| 509. | propyl | 5-propylthien-2-yl |
| 510. | propyl | 5-(trifluoromethyl)-thien-2-yl |
| 511. | propyl | 5-phenylthien-2-yl |
| 512. | propyl | 5-(pyrid-2-yl)-thien-2-yl |
| 513. | propyl | 5-(phenylsulfonyl)-thien-2-yl |
| 514. | propyl | 4-(phenylsulfonyl)-thien-2-yl |
| 515. | propyl | 5-(pyrid-2-ylsulfonyl)-thien-2-yl |
| 516. | propyl | 5-(3-chloro-5-trifluoro-pyrid-2-ylsulfonyl)-thien-2-yl |
| 517. | propyl | 5-(benzoylaminomethyl)-thien-2-yl |
| 518. | propyl | 5-((4-chlorobenzoyl)aminomethyl)-thien-2-yl |
| 519. | propyl | 5-(acetylaminomethyl)-thien-2-yl |
| 520. | propyl | 5-(pyrazol-1-yl)-thien-2-yl |
| 521. | propyl | 5-(pyrazol-3-yl)-thien-2-yl |
| 522. | propyl | 5-(pyrazol-4-yl)-thien-2-yl |
| 523. | propyl | 5-(pyrazol-5-yl)-thien-2-yl |
| 524. | propyl | 5-(4-fluoropyrazol-1-yl)-thien-2-yl |
| 525. | propyl | 5-(1-methyl-5-trifluoromethyl-(1H)-pyrazol-3-yl)-thien-2-yl |
| 526. | propyl | 5-(1-methyl-3-trifluoromethyl-(1H)-pyrazol-5-yl)-thien-2-yl |
| 527. | propyl | 5-(4-carboxy-1-methyl-5-methylthio-(1H)-pyrazol-3-yl)-thien-2-yl |
| 528. | propyl | 5-(4-aminomethyl-1-methyl-5-methylthio-(1H)-pyrazol-3-yl)-thien-2-yl |
| 529. | propyl | 5-(isoxazol-3-yl)-thien-2-yl |
| 530. | propyl | 5-(isoxazol-4-yl)-thien-2-yl |
| 531. | propyl | 5-(isoxazol-5-yl)-thien-2-yl |
| 532. | propyl | 5-(5-trifluoromethylisoxazol-3-yl)-thien-2-yl |
| 533. | propyl | 5-(oxazol-2-yl)-thien-2-yl |
| 534. | propyl | 5-(oxazol-4-yl)-thien-2-yl |
| 535. | propyl | 5-(oxazol-5-yl)-thien-2-yl |
| 536. | propyl | 5-(2-methyloxazol-4-yl)-thien-2-yl |
| 537. | propyl | 5-(2-methyloxazol-5-yl)-thien-2-yl |
| 538. | propyl | 5-(isothiazol-3-yl)-thien-2-yl |

TABLE A-continued

| No. | R¹ | Ar |
|---|---|---|
| 539. | propyl | 5-(isothiazol-4-yl)-thien-2-yl |
| 540. | propyl | 5-(isothiazol-5-yl)-thien-2-yl |
| 541. | propyl | 5-(5-trifluoromethylisothiazol-3-yl)-thien-2-yl |
| 542. | propyl | 5-(thiazol-2-yl)-thien-2-yl |
| 543. | propyl | 5-(thiazol-4-yl)-thien-2-yl |
| 544. | propyl | 5-(thiazol-5-yl)-thien-2-yl |
| 545. | propyl | 5-(2-methylthiazol-4-yl)-thien-2-yl |
| 546. | propyl | 5-(2-methylthiazol-5-yl)-thien-2-yl |
| 547. | propyl | 5-([1,2,3]-oxadiazol-4-yl)-thien-2-yl |
| 548. | propyl | 5-([1,2,3]-thiadiazol-4-yl)-thien-2-yl |
| 549. | propyl | 5-(pyrimidin-2-yl)-thien-2-yl |
| 550. | propyl | 5-(pyrimidin-4-yl)-thien-2-yl |
| 551. | propyl | 5-(pyrimidin-5-yl)-thien-2-yl |
| 552. | propyl | 5-(2-methylthiopyrimidin-4-yl)-thien-2-yl |
| 553. | propyl | 5-([1,3]-dioxolan-2-yl)-thien-2-yl |
| 554. | propyl | 3-([1,3]-dioxolan-2-yl)-thien-2-yl thien-2-yl |
| 555. | propyl | 5-((3-chloro-5-(trifluoromethyl)-pyridin-2-yl)-methyl)-thien-2-yl |
| 556. | propyl | 5-[3-chloro-5-(trifluoromethyl)-pyrid-2-ylsulfonyl]-thien-2-yl |
| 557. | propyl | 2-chlorothien-3-yl |
| 558. | propyl | 4-chlorothien-3-yl |
| 559. | propyl | 5-chlorothien-3-yl |
| 560. | propyl | 2-bromothien-3-yl |
| 561. | propyl | 4-bromothien-3-yl |
| 562. | propyl | 5-bromothien-3-yl |
| 563. | propyl | 2,5-dichlorothien-3-yl |
| 564. | propyl | 2,5-dibromothien-3-yl |
| 565. | propyl | 2,4,5-trichlorothien-3-yl |
| 566. | propyl | 4-bromo-2,5-dichlorothien-3-yl |
| 567. | propyl | 2-chloro-5-methylsulfonylthien-3-yl |
| 568. | propyl | 2,5-dimethylthien-3-yl |
| 569. | propyl | 4-hydroxythien-3-yl |
| 570. | propyl | 2-phenylthien-3-yl |
| 571. | propyl | 4-phenyl-5-(trofluoromethyl)-thien-3-yl |
| 572. | propyl | 2-methoxycarbonyl-4-phenyl-5-(trifluoromethyl)-thien-3-yl |
| 573. | propyl | benzo[b]thiophen-2-yl |
| 574. | propyl | benzo[b]thiophen-3-yl |
| 575. | propyl | 3-methyl-benzo[b]thiophen-2-yl |
| 576. | propyl | 5-methyl-benzo[b]thiophen-2-yl |
| 577. | propyl | 5-fluoro-3-methyl-benzo[b]thiophen-2-yl |
| 578. | propyl | 5-chloro-3-methyl-benzo[b]thiophen-2-yl |
| 579. | propyl | 5-bromo-3-methyl-benzo[b]thiophen-2-yl |
| 580. | ethyl | 3-methylphenyl |
| 581. | ethyl | 3-ethylphenyl |
| 582. | ethyl | 3-propylphenyl |
| 583. | ethyl | 3-isopropylphenyl |
| 584. | ethyl | 3-sec-butylphenyl |
| 585. | ethyl | 3-tert-butylphenyl |
| 586. | ethyl | 3-isobutylphenyl |
| 587. | ethyl | 3-(1,1-dimethylpropyl)-phenyl |
| 588. | ethyl | 3-vinylphenyl |
| 589. | ethyl | 3-isopropenylphenyl |
| 590. | ethyl | 3-fluorophenyl |
| 591. | ethyl | 2-fluorophenyl |
| 592. | ethyl | 3-chlorophenyl |
| 593. | ethyl | 3-bromophenyl |
| 594. | ethyl | 3-iodophenyl |
| 595. | ethyl | 3-(fluoromethyl)phenyl |
| 596. | ethyl | 3-(difluoromethyl)phenyl |
| 597. | ethyl | 3-(trifluoromethyl)phenyl |
| 598. | ethyl | 3,5-bis(trifluoromethyl)phenyl |
| 599. | ethyl | 3-(1-fluoroethyl)-phenyl |
| 600. | ethyl | 3-((S)-1-fluoroethyl)-phenyl |
| 601. | ethyl | 3-((R)-1-fluoroethyl)-phenyl |
| 602. | ethyl | 3-(2-fluoroethyl)-phenyl |
| 603. | ethyl | 3-(1,1-difluoroethyl)-phenyl |
| 604. | ethyl | 3-(2,2-difluoroethyl)-phenyl |
| 605. | ethyl | 3-(2,2,2-trifluoroethyl)-phenyl |
| 606. | ethyl | 3-(3-fluoropropyl)-phenyl |
| 607. | ethyl | 3-(2-fluoropropyl)-phenyl |
| 608. | ethyl | 3-((S)-2-fluoropropyl)-phenyl |
| 609. | ethyl | 3-((R)-2-fluoropropyl)-phenyl |
| 610. | ethyl | 3-(3,3-difluoropropyl)-phenyl |
| 611. | ethyl | 3-(3,3,3-trifluoropropyl)-phenyl |
| 612. | ethyl | 3-(1-fluoro-1-methylethyl)-phenyl |
| 613. | ethyl | 3-(2-fluoro-1-methylethyl)-phenyl |

TABLE A-continued

| No. | R¹ | Ar |
|---|---|---|
| 614. | ethyl | 3-((S)-2-fluoro-1-methylethyl)-phenyl |
| 615. | ethyl | 3-((R)-2-fluoro-1-methylethyl)-phenyl |
| 616. | ethyl | 3-(2,2-difluoro-1-methylethyl)-phenyl |
| 617. | ethyl | 3-((S)-2,2-difluoro-1-methylethyl)-phenyl |
| 618. | ethyl | 3-((R)-2,2-difluoro-1-methylethyl)-phenyl |
| 619. | ethyl | 3-(2,2,2-trifluoro-1-methylethyl)-phenyl |
| 620. | ethyl | 3-((S)-2,2,2-trifluoro-1-methylethyl)-phenyl |
| 621. | ethyl | 3-((R)-2,2,2-trifluoro-1-methylethyl)-phenyl |
| 622. | ethyl | 3-(2-fluoro-1-fluoromethylethyl)-phenyl |
| 623. | ethyl | 3-(1-difluoromethyl-2,2-difluoroethyl)-phenyl |
| 624. | ethyl | 3-(1,1-dimethyl-2-fluoroethyl)-phenyl |
| 625. | ethyl | 3-methoxyphenyl |
| 626. | ethyl | 3-ethoxyphenyl |
| 627. | ethyl | 3-propoxyphenyl |
| 628. | ethyl | 3-isopropoxyphenyl |
| 629. | ethyl | 3-butoxyphenyl |
| 630. | ethyl | 3-(fluoromethoxy)-phenyl |
| 631. | ethyl | 3-(difluoromethoxy)-phenyl |
| 632. | ethyl | 3-(trifluoromethoxy)-phenyl |
| 633. | ethyl | 3-(2-fluoroethoxy)-phenyl |
| 634. | ethyl | 3-(2,2-difluoroethoxy)-phenyl |
| 635. | ethyl | 3-(2,2,2-trifluoroethoxy)-phenyl |
| 636. | ethyl | 3-(1,1,2,2-tetrafluoroethoxy)-phenyl |
| 637. | ethyl | 3-cyclopropylphenyl |
| 638. | ethyl | 3-cyclobutylphenyl |
| 639. | ethyl | 3-cyclopentylphenyl |
| 640. | ethyl | 3-(2,2-difluorocyclopropyl)-phenyl |
| 641. | ethyl | 3,4-difluorophenyl |
| 642. | ethyl | 3-bromo-2-fluorophenyl |
| 643. | ethyl | 2-bromo-3-fluorophenyl |
| 644. | ethyl | 3-bromo-2,5-difluorophenyl |
| 645. | ethyl | 5-bromo-2,4-difluorophenyl |
| 646. | ethyl | 3-bromo-2,4-difluorophenyl |
| 647. | ethyl | 4-chloro-3-(trifluoromethyl)-phenyl |
| 648. | ethyl | 2-chloro-5-(trifluoromethyl)-phenyl |
| 649. | ethyl | 2-fluoro-5-(trifluoromethyl)-phenyl |
| 650. | ethyl | 4-fluoro-3-(trifluoromethyl)-phenyl |
| 651. | ethyl | 3-fluoro-5-(trifluoromethyl)-phenyl |
| 652. | ethyl | 4-bromo-3-(trifluoromethyl)-phenyl |
| 653. | ethyl | 3-bromo-5-(trifluoromethyl)-phenyl |
| 654. | ethyl | 2-bromo-5-(trifluoromethyl)-phenyl |
| 655. | ethyl | 5-bromo-2-methoxyphenyl |
| 656. | ethyl | 3-bromo-4-methoxyphenyl |
| 657. | ethyl | 2-fluoro-3-isopropylphenyl |
| 658. | ethyl | 4-fluoro-3-isopropylphenyl |
| 659. | ethyl | 3-(1-hydroxy-1-methylethyl)-phenyl |
| 660. | ethyl | 3-(2-hydroxy-2-methylpropyl)-phenyl |
| 661. | ethyl | 3-acetylphenyl |
| 662. | ethyl | 3-acetylaminophenyl |
| 663. | ethyl | 3-carboxyphenyl |
| 664. | ethyl | 3-cyanophenyl |
| 665. | ethyl | 3-nitrophenyl |
| 666. | ethyl | 3-hydroxyphenyl |
| 667. | ethyl | 3-(O-benzyl)-phenyl |
| 668. | ethyl | 3-(2-methoxyethoxy)-phenyl |
| 669. | ethyl | 3-($CH_2$—$N(CH_3)_2$)-phenyl |
| 670. | ethyl | 3-(NH—CO—$NH_2$)-phenyl |
| 671. | ethyl | 3-(methylsulfanyl)-phenyl |
| 672. | ethyl | 3-(fluoromethylsulfanyl)-phenyl |
| 673. | ethyl | 3-(difluoromethylsulfanyl)-phenyl |
| 674. | ethyl | 3-(trifluoromethylsulfanyl)-phenyl |
| 675. | ethyl | 3-(methylsulfonyl)-phenyl |
| 676. | ethyl | 3-(N-methoxy-N-methyl-amino)-phenyl |
| 677. | ethyl | 3-(methoxyamino)-phenyl |
| 678. | ethyl | 3-(ethoxyamino)-phenyl |
| 679. | ethyl | 3-(N-methylaminooxy)-phenyl |
| 680. | ethyl | 3-(N,N-dimethylaminooxy)-phenyl |
| 681. | ethyl | 3-(azetidin-1-yl)-phenyl |
| 682. | ethyl | 3-(2-methylazetidin-1-yl)-phenyl |
| 683. | ethyl | 3-((S)-2-methylazetidin-1-yl)-phenyl |
| 684. | ethyl | 3-((R)-2-methylazetidin-1-yl)-phenyl |
| 685. | ethyl | 3-(3-fluoroazetidin-1-yl)-phenyl |
| 686. | ethyl | 3-(2,2-difluoroazetidin-1-yl)-phenyl |
| 687. | ethyl | 3-(3-methoxyazetidin-1-yl)-phenyl |
| 688. | ethyl | 3-(3-hydroxyazetidin-1-yl)-phenyl |
| 689. | ethyl | 3-(pyrrolidin-1-yl)-phenyl |
| 690. | ethyl | 3-(pyrrolidin-2-yl)-phenyl |
| 691. | ethyl | 3-((S)-pyrrolidin-2-yl)-phenyl |

TABLE A-continued

| No. | R¹ | Ar |
|---|---|---|
| 692. | ethyl | 3-((R)-pyrrolidin-2-yl)-phenyl |
| 693. | ethyl | 3-(pyrrolidin-3-yl)-phenyl |
| 694. | ethyl | 3-((S)-pyrrolidin-3-yl)-phenyl |
| 695. | ethyl | 3-((R)-pyrrolidin-3-yl)-phenyl |
| 696. | ethyl | 3-(pyrrolidin-1-yl)-5-(trifluoromethyl)-phenyl |
| 697. | ethyl | 5-(pyrrolidin-1-yl)-2-methoxyphenyl |
| 698. | ethyl | 3-(pyrrolidin-1-yl)-4-methoxyphenyl |
| 699. | ethyl | 5-(pyrrolidin-1-yl)-2,4-difluorophenyl |
| 700. | ethyl | 3-(pyrrolidin-1-yl)-2,4-difluorophenyl |
| 701. | ethyl | 3-(2-fluoropyrrolidin-1-yl)-phenyl |
| 702. | ethyl | 3-((S)-2-fluoropyrrolidin-1-yl)-phenyl |
| 703. | ethyl | 3-((R)-2-fluoropyrrolidin-1-yl)-phenyl |
| 704. | ethyl | 3-(3-fluoropyrrolidin-1-yl)-phenyl |
| 705. | ethyl | 3-((S)-3-fluoropyrrolidin-1-yl)-phenyl |
| 706. | ethyl | 3-((R)-3-fluoropyrrolidin-1-yl)-phenyl |
| 707. | ethyl | 3-(2,2-difluoropyrrolidin-1-yl)-phenyl |
| 708. | ethyl | 3-(3,3-difluoropyrrolidin-1-yl)-phenyl |
| 709. | ethyl | 3-(2-methylpyrrolidin-1-yl)-phenyl |
| 710. | ethyl | 3-((S)-2-methylpyrrolidin-1-yl)-phenyl |
| 711. | ethyl | 3-((R)-2-methylpyrrolidin-1-yl)-phenyl |
| 712. | ethyl | 3-(3-methylpyrrolidin-1-yl)-phenyl |
| 713. | ethyl | 3-((S)-3-methylpyrrolidin-1-yl)-phenyl |
| 714. | ethyl | 3-((R)-3-methylpyrrolidin-1-yl)-phenyl |
| 715. | ethyl | 3-(1-methylpyrrolidin-2-yl)-phenyl |
| 716. | ethyl | 3-((S)-1-methylpyrrolidin-2-yl)-phenyl |
| 717. | ethyl | 3-((R)-1-methylpyrrolidin-2-yl)-phenyl |
| 718. | ethyl | 3-(1-methylpyrrolidin-3-yl)-phenyl |
| 719. | ethyl | 3-((S)-1-methylpyrrolidin-3-yl)-phenyl |
| 720. | ethyl | 3-((R)-1-methylpyrrolidin-3-yl)-phenyl |
| 721. | ethyl | 3-(2,2-dimethylpyrrolidin-1-yl)-phenyl |
| 722. | ethyl | 3-(3,3-dimethylpyrrolidin-1-yl)-phenyl |
| 723. | ethyl | 3-(2-trifluoromethylpyrrolidin-1-yl)-phenyl |
| 724. | ethyl | 3-((S)-2-trifluoromethylpyrrolidin-1-yl)-phenyl |
| 725. | ethyl | 3-((R)-2-trifluoromethylpyrrolidin-1-yl)-phenyl |
| 726. | ethyl | 3-(3-trifluoromethylpyrrolidin-1-yl)-phenyl |
| 727. | ethyl | 3-((S)-3-trifluoromethylpyrrolidin-1-yl)-phenyl |
| 728. | ethyl | 3-((R)-3-trifluoromethylpyrrolidin-1-yl)-phenyl |
| 729. | ethyl | 3-(2-oxopyrrolidin-1-yl)-phenyl |
| 730. | ethyl | 3-(2-oxo-oxazolidin-3-yl)-phenyl |
| 731. | ethyl | 3-(piperidin-1-yl)-phenyl |
| 732. | ethyl | 3-(2-methylpiperidin-1-yl)-phenyl |
| 733. | ethyl | 3-((S)-2-methylpiperidin-1-yl)-phenyl |
| 734. | ethyl | 3-((R)-2-methylpiperidin-1-yl)-phenyl |
| 735. | ethyl | 3-(2-fluoropiperidin-1-yl)-phenyl |
| 736. | ethyl | 3-((S)-2-fluoropiperidin-1-yl)-phenyl |
| 737. | ethyl | 3-((R)-2-fluoropiperidin-1-yl)-phenyl |
| 738. | ethyl | 3-(2,2-difluoropiperidin-1-yl)-phenyl |
| 739. | ethyl | 3-(piperazin-1-yl)-phenyl |
| 740. | ethyl | 3-(4-methylpiperazin-1-yl)-phenyl |
| 741. | ethyl | 3-(morpholin-4-yl)-phenyl |
| 742. | ethyl | 3-(morpholin-4-yl)-5-(trifluoromethyl)-phenyl |
| 743. | ethyl | 5-(morpholin-4-yl)-2-methoxyphenyl |
| 744. | ethyl | 3-(morpholin-4-yl)-4-methoxyphenyl |
| 745. | ethyl | 5-(morpholin-4-yl)-2,4-difluorophenyl |
| 746. | ethyl | 3-(morpholin-4-yl)-2,4-difluorophenyl |
| 747. | ethyl | 3-(thiomorpholin-4-yl)-phenyl |
| 748. | ethyl | 3-(1-oxo-thiomorpholin-4-yl)-phenyl |
| 749. | ethyl | 3-(1,1-dioxo-thiomorpholin-4-yl)-phenyl |
| 750. | ethyl | 3-(pyrrol-1-yl)-phenyl |
| 751. | ethyl | 3-(pyrrol-2-yl)-phenyl |
| 752. | ethyl | 3-(pyrrol-3-yl)-phenyl |
| 753. | ethyl | 3-(1-methylpyrrol-2-yl)-phenyl |
| 754. | ethyl | 3-(1-methylpyrrol-3-yl)-phenyl |
| 755. | ethyl | 3-(furan-2-yl)-phenyl |
| 756. | ethyl | 3-(furan-3-yl)-phenyl |
| 757. | ethyl | 3-(thiophen-2-yl)-phenyl |
| 758. | ethyl | 3-(thiophen-3-yl)-phenyl |
| 759. | ethyl | 3-(5-propylthien-2-yl)-phenyl |
| 760. | ethyl | 3-(pyrazol-1-yl)-phenyl |
| 761. | ethyl | 3-(pyrazol-3-yl)-phenyl |
| 762. | ethyl | 3-(pyrazol-4-yl)-phenyl |
| 763. | ethyl | 3-(4-fluoropyrazol-1-yl)-phenyl |
| 764. | ethyl | 3-(1-methyl-1H-pyrazol-4-yl)-phenyl |
| 765. | ethyl | 3-(1-ethyl-1H-pyrazol-4-yl)-phenyl |
| 766. | ethyl | 3-(1-methyl-1H-pyrazol-5-yl)-phenyl |
| 767. | ethyl | 3-(1H-imidazol-2-yl)-phenyl |
| 768. | ethyl | 3-(imidazol-1-yl)-phenyl |
| 769. | ethyl | 3-(1-methylimidazol-2-yl)-phenyl |

TABLE A-continued

| No. | R¹ | Ar |
|---|---|---|
| 770. | ethyl | 3-(oxazol-2-yl)-phenyl |
| 771. | ethyl | 3-(oxazol-4-yl)-phenyl |
| 772. | ethyl | 3-(oxazol-5-yl)-phenyl |
| 773. | ethyl | 3-(isoxazol-3-yl)-phenyl |
| 774. | ethyl | 3-(isoxazol-4-yl)-phenyl |
| 775. | ethyl | 3-(isoxazol-5-yl)-phenyl |
| 776. | ethyl | 3-(thiazol-2-yl)-phenyl |
| 777. | ethyl | 3-(thiazol-4-yl)-phenyl |
| 778. | ethyl | 3-(thiazol-5-yl)-phenyl |
| 779. | ethyl | 3-(2-methylthiazol-4-yl)-phenyl |
| 780. | ethyl | 3-(2-methylthiazol-5-yl)-phenyl |
| 781. | ethyl | 3-([1,2,3]-triazol-1-yl)-phenyl |
| 782. | ethyl | 3-([1,2,4]-triazol-1-yl)-phenyl |
| 783. | ethyl | 3-([1,2,3]-triazol-2-yl)-phenyl |
| 784. | ethyl | 3-(4H-[1,2,4]-triazol-3-yl)-phenyl |
| 785. | ethyl | 3-([1,2,4]-triazol-4-yl)-phenyl |
| 786. | ethyl | 3-(2H-[1,2,3]-triazol-4-yl)-phenyl |
| 787. | ethyl | 3-(4-methyl-4H-[1,2,4]-triazol-3-yl)-phenyl |
| 788. | ethyl | 3-(2-methyl-2H-[1,2,3]-triazol-4-yl)-phenyl |
| 789. | ethyl | 3-([1,3,4]-oxadiazol-2-yl)-phenyl |
| 790. | ethyl | 3-(5-methyl-[1,3,4]-oxadiazol-2-yl)-phenyl |
| 791. | ethyl | 3-([1,2,4]-oxadiazol-3-yl)-phenyl |
| 792. | ethyl | 3-(5-methyl-[1,2,4]-oxadiazol-3-yl)-phenyl |
| 793. | ethyl | 3-([1,2,4]-oxadiazol-5-yl)-phenyl |
| 794. | ethyl | 3-([1,2,3]-oxadiazol-4-yl)-phenyl |
| 795. | ethyl | 3-([1,2,3]-oxadiazol-5-yl)-phenyl |
| 796. | ethyl | 3-([1,2,3]-thiadiazol-4-yl)-phenyl |
| 797. | ethyl | 3-(1H-tetrazol-5-yl)-phenyl |
| 798. | ethyl | 3-(tetrazol-1-yl)-phenyl |
| 799. | ethyl | 3-(2-methyl-2H-tetrazol-5-yl)-phenyl |
| 800. | ethyl | 3-(1-methyl-1H-tetrazol-5-yl)-phenyl |
| 801. | ethyl | 3-furazan-3-yl-phenyl |
| 802. | ethyl | 3-(pyrid-2-yl)-phenyl |
| 803. | ethyl | 3-(pyrid-3-yl)-phenyl |
| 804. | ethyl | 3-(pyrid-4-yl)-phenyl |
| 805. | ethyl | 3-(pyrimidin-2-yl)-phenyl |
| 806. | ethyl | 3-(2-methylpyrimidin-4-yl)-phenyl |
| 807. | ethyl | 3-(pyrimidin-4-yl)-phenyl |
| 808. | ethyl | 3-(pyrimidin-5-yl)-phenyl |
| 809. | ethyl | 5-bromopyridin-3-yl |
| 810. | ethyl | 3-bromo-2-chloropyridin-5-yl |
| 811. | ethyl | 4-methylpyridin-2-yl |
| 812. | ethyl | 6-methylpyridin-2-yl |
| 813. | ethyl | 4-(trifluoromethyl)-pyridin-2-yl |
| 814. | ethyl | 6-(trifluoromethyl)-pyridin-2-yl |
| 815. | ethyl | 5-(trifluoromethyl)-pyridin-3-yl |
| 816. | ethyl | 5-(pyrrolidin-1-yl)-pyridin-3-yl |
| 817. | ethyl | 3-(pyrrolidin-1-yl)-2-chloropyridin-5-yl |
| 818. | ethyl | 3-(morpholin-4-yl)-2-chloropyridin-5-yl |
| 819. | ethyl | 2-(morpholin-4-yl)-pyridin-5-yl |
| 820. | ethyl | 2-phenoxypyridin-5-yl |
| 821. | ethyl | 4-methylphenyl |
| 822. | ethyl | 4-ethylphenyl |
| 823. | ethyl | 4-propylphenyl |
| 824. | ethyl | 4-isopropylphenyl |
| 825. | ethyl | 4-sec-butylphenyl |
| 826. | ethyl | 4-tert-butylphenyl |
| 827. | ethyl | 4-isobutylphenyl |
| 828. | ethyl | 4-(1,1-dimethylpropyl)-phenyl |
| 829. | ethyl | 4-vinylphenyl |
| 830. | ethyl | 4-isopropenylphenyl |
| 831. | ethyl | 4-fluorophenyl |
| 832. | ethyl | 4-chlorophenyl |
| 833. | ethyl | 4-bromophenyl |
| 834. | ethyl | 4-iodophenyl |
| 835. | ethyl | 4-(fluoromethyl)phenyl |
| 836. | ethyl | 4-(difluoromethyl)phenyl |
| 837. | ethyl | 4-(trifluoromethyl)phenyl |
| 838. | ethyl | 2,4-bis(trifluoromethyl)phenyl |
| 839. | ethyl | 4-(1-fluoroethyl)-phenyl |
| 840. | ethyl | 4-((S)-1-fluoroethyl)-phenyl |
| 841. | ethyl | 4-((R)-1-fluoroethyl)-phenyl |
| 842. | ethyl | 4-(2-fluoroethyl)-phenyl |
| 843. | ethyl | 4-(1,1-difluoroethyl)-phenyl |
| 844. | ethyl | 4-(2,2-difluoroethyl)-phenyl |
| 845. | ethyl | 4-(2,2,2-trifluoroethyl)-phenyl |
| 846. | ethyl | 4-(3-fluoropropyl)-phenyl |
| 847. | ethyl | 4-(2-fluoropropyl)-phenyl |

TABLE A-continued

| No. | R¹ | Ar |
|---|---|---|
| 848. | ethyl | 4-((S)-2-fluoropropyl)-phenyl |
| 849. | ethyl | 4-((R)-2-fluoropropyl)-phenyl |
| 850. | ethyl | 4-(3,3-difluoropropyl)-phenyl |
| 851. | ethyl | 4-(3,3,3-trifluoropropyl)-phenyl |
| 852. | ethyl | 4-(1-fluoro-1-methylethyl)-phenyl |
| 853. | ethyl | 4-(2-fluoro-1-methylethyl)-phenyl |
| 854. | ethyl | 4-((S)-2-fluoro-1-methylethyl)-phenyl |
| 855. | ethyl | 4-((R)-2-fluoro-1-methylethyl)-phenyl |
| 856. | ethyl | 4-(2,2-difluoro-1-methylethyl)-phenyl |
| 857. | ethyl | 4-((S)-2,2-difluoro-1-methylethyl)-phenyl |
| 858. | ethyl | 4-((R)-2,2-difluoro-1-methylethyl)-phenyl |
| 859. | ethyl | 4-(2,2,2-trifluoro-1-methylethyl)-phenyl |
| 860. | ethyl | 4-((S)-2,2,2-trifluoro-1-methylethyl)-phenyl |
| 861. | ethyl | 4-((R)-2,2,2-trifluoro-1-methylethyl)-phenyl |
| 862. | ethyl | 4-(2-fluoro-1-fluoromethylethyl)-phenyl |
| 863. | ethyl | 4-(1-difluoromethyl-2,2-difluoroethyl)-phenyl |
| 864. | ethyl | 4-(1,1-dimethyl-2-fluoroethyl)-phenyl |
| 865. | ethyl | 4-methoxyphenyl |
| 866. | ethyl | 4-ethoxyphenyl |
| 867. | ethyl | 4-propoxyphenyl |
| 868. | ethyl | 4-isopropoxyphenyl |
| 869. | ethyl | 4-butoxyphenyl |
| 870. | ethyl | 4-(fluoromethoxy)-phenyl |
| 871. | ethyl | 4-(difluoromethoxy)-phenyl |
| 872. | ethyl | 4-(trifluoromethoxy)-phenyl |
| 873. | ethyl | 4-(2-fluoroethoxy)-phenyl |
| 874. | ethyl | 4-(2,2-difluoroethoxy)-phenyl |
| 875. | ethyl | 4-(2,2,2-trifluoroethoxy)-phenyl |
| 876. | ethyl | 4-(1,1,2,2-tetrafluoroethoxy)-phenyl |
| 877. | ethyl | 4-cyclopropylphenyl |
| 878. | ethyl | 4-cyclobutylphenyl |
| 879. | ethyl | 4-cyclopentylphenyl |
| 880. | ethyl | 4-(2,2-difluorocyclopropyl)-phenyl |
| 881. | ethyl | 3,4-difluorophenyl |
| 882. | ethyl | 4-bromo-2-fluorophenyl |
| 883. | ethyl | 2-bromo-4-fluorophenyl |
| 884. | ethyl | 4-bromo-2,5-difluorophenyl |
| 885. | ethyl | 5-bromo-2,4-difluorophenyl |
| 886. | ethyl | 3-bromo-2,4-difluorophenyl |
| 887. | ethyl | 3-chloro-4-(trifluoromethyl)-phenyl |
| 888. | ethyl | 4-fluoro-3-(trifluoromethyl)-phenyl |
| 889. | ethyl | 3-fluoro-5-(trifluoromethyl)-phenyl |
| 890. | ethyl | 3-bromo-4-(trifluoromethyl)-phenyl |
| 891. | ethyl | 5-bromo-3-(trifluoromethyl)-phenyl |
| 892. | ethyl | 5-bromo-2-(trifluoromethyl)-phenyl |
| 893. | ethyl | 2-bromo-5-methoxyphenyl |
| 894. | ethyl | 4-bromo-3-methoxyphenyl |
| 895. | ethyl | 3-fluoro-2-isopropylphenyl |
| 896. | ethyl | 3-fluoro-4-isopropylphenyl |
| 897. | ethyl | 4-(1-hydroxy-1-methylethyl)-phenyl |
| 898. | ethyl | 4-(2-hydroxy-2-methylpropyl)-phenyl |
| 899. | ethyl | 4-acetylphenyl |
| 900. | ethyl | 4-acetylaminophenyl |
| 901. | ethyl | 4-carboxyphenyl |
| 902. | ethyl | 4-cyanophenyl |
| 903. | ethyl | 4-nitrophenyl |
| 904. | ethyl | 4-hydroxyphenyl |
| 905. | ethyl | 4-(O-benzyl)-phenyl |
| 906. | ethyl | 4-(2-methoxyethoxy)-phenyl |
| 907. | ethyl | 4-(CH₂—N(CH₃)₂)-phenyl |
| 908. | ethyl | 4-(NH—CO—NH₂)-phenyl |
| 909. | ethyl | 4-(methylsulfanyl)-phenyl |
| 910. | ethyl | 4-(fluoromethylsulfanyl)-phenyl |
| 911. | ethyl | 4-(difluoromethylsulfanyl)-phenyl |
| 912. | ethyl | 4-(trifluoromethylsulfanyl)-phenyl |
| 913. | ethyl | 4-(methylsulfonyl)-phenyl |
| 914. | ethyl | 4-(N-methoxy-N-methyl-amino)-phenyl |
| 915. | ethyl | 4-(methoxyamino)-phenyl |
| 916. | ethyl | 4-(ethoxyamino)-phenyl |
| 917. | ethyl | 4-(N-methylaminooxy)-phenyl |
| 918. | ethyl | 4-(N,N-dimethylaminooxy)-phenyl |
| 919. | ethyl | 4-(azetidin-1-yl)-phenyl |
| 920. | ethyl | 4-(2-methylazetidin-1-yl)-phenyl |
| 921. | ethyl | 4-((S)-2-methylazetidin-1-yl)-phenyl |
| 922. | ethyl | 4-((R)-2-methylazetidin-1-yl)-phenyl |
| 923. | ethyl | 4-(3-fluoroazetidin-1-yl)-phenyl |
| 924. | ethyl | 4-(2,2-difluoroazetidin-1-yl)-phenyl |
| 925. | ethyl | 4-(3-methoxyazetidin-1-yl)-phenyl |

TABLE A-continued

| No. | R¹ | Ar |
|---|---|---|
| 926. | ethyl | 4-(3-hydroxyazetidin-1-yl)-phenyl |
| 927. | ethyl | 4-(pyrrolidin-1-yl)-phenyl |
| 928. | ethyl | 4-(pyrrolidin-2-yl)-phenyl |
| 929. | ethyl | 4-((S)-pyrrolidin-2-yl)-phenyl |
| 930. | ethyl | 4-((R)-pyrrolidin-2-yl)-phenyl |
| 931. | ethyl | 4-(pyrrolidin-3-yl)-phenyl |
| 932. | ethyl | 4-((S)-pyrrolidin-3-yl)-phenyl |
| 933. | ethyl | 4-((R)-pyrrolidin-3-yl)-phenyl |
| 934. | ethyl | 4-(pyrrolidin-1-yl)-5-(trifluoromethyl)-phenyl |
| 935. | ethyl | 4-(pyrrolidin-1-yl)-2-methoxyphenyl |
| 936. | ethyl | 4-(pyrrolidin-1-yl)-34-methoxyphenyl |
| 937. | ethyl | 4-(pyrrolidin-1-yl)-2,5-difluorophenyl |
| 938. | ethyl | 4-(pyrrolidin-1-yl)-2,6-difluorophenyl |
| 939. | ethyl | 4-(2-fluoropyrrolidin-1-yl)-phenyl |
| 940. | ethyl | 4-((S)-2-fluoropyrrolidin-1-yl)-phenyl |
| 941. | ethyl | 4-((R)-2-fluoropyrrolidin-1-yl)-phenyl |
| 942. | ethyl | 4-(3-fluoropyrrolidin-1-yl)-phenyl |
| 943. | ethyl | 4-((S)-3-fluoropyrrolidin-1-yl)-phenyl |
| 944. | ethyl | 4-((R)-3-fluoropyrrolidin-1-yl)-phenyl |
| 945. | ethyl | 4-(2,2-difluoropyrrolidin-1-yl)-phenyl |
| 946. | ethyl | 4-(3,3-difluoropyrrolidin-1-yl)-phenyl |
| 947. | ethyl | 4-(2-methylpyrrolidin-1-yl)-phenyl |
| 948. | ethyl | 4-((S)-2-methylpyrrolidin-1-yl)-phenyl |
| 949. | ethyl | 4-((R)-2-methylpyrrolidin-1-yl)-phenyl |
| 950. | ethyl | 4-(3-methylpyrrolidin-1-yl)-phenyl |
| 951. | ethyl | 4-((S)-3-methylpyrrolidin-1-yl)-phenyl |
| 952. | ethyl | 4-((R)-3-methylpyrrolidin-1-yl)-phenyl |
| 953. | ethyl | 4-(1-methylpyrrolidin-2-yl)-phenyl |
| 954. | ethyl | 4-((S)-1-methylpyrrolidin-2-yl)-phenyl |
| 955. | ethyl | 4-((R)-1-methylpyrrolidin-2-yl)-phenyl |
| 956. | ethyl | 4-(1-methylpyrrolidin-3-yl)-phenyl |
| 957. | ethyl | 4-((S)-1-methylpyrrolidin-3-yl)-phenyl |
| 958. | ethyl | 4-((R)-1-methylpyrrolidin-3-yl)-phenyl |
| 959. | ethyl | 4-(2,2-dimethylpyrrolidin-1-yl)-phenyl |
| 960. | ethyl | 4-(3,3-dimethylpyrrolidin-1-yl)-phenyl |
| 961. | ethyl | 4-(2-trifluoromethylpyrrolidin-1-yl)-phenyl |
| 962. | ethyl | 4-((S)-2-trifluoromethylpyrrolidin-1-yl)-phenyl |
| 963. | ethyl | 4-((R)-2-trifluoromethylpyrrolidin-1-yl)-phenyl |
| 964. | ethyl | 4-(3-trifluoromethylpyrrolidin-1-yl)-phenyl |
| 965. | ethyl | 4-((S)-3-trifluoromethylpyrrolidin-1-yl)-phenyl |
| 966. | ethyl | 4-((R)-3-trifluoromethylpyrrolidin-1-yl)-phenyl |
| 967. | ethyl | 4-(2-oxopyrrolidin-1-yl)-phenyl |
| 968. | ethyl | 4-(2-oxo-oxazolidin-3-yl)-phenyl |
| 969. | ethyl | 4-(piperidin-1-yl)-phenyl |
| 970. | ethyl | 4-(2-methylpiperidin-1-yl)-phenyl |
| 971. | ethyl | 4-((S)-2-methylpiperidin-1-yl)-phenyl |
| 972. | ethyl | 4-((R)-2-methylpiperidin-1-yl)-phenyl |
| 973. | ethyl | 4-(2-fluoropiperidin-1-yl)-phenyl |
| 974. | ethyl | 4-((S)-2-fluoropiperidin-1-yl)-phenyl |
| 975. | ethyl | 4-((R)-2-fluoropiperidin-1-yl)-phenyl |
| 976. | ethyl | 4-(2,2-difluoropiperidin-1-yl)-phenyl |
| 977. | ethyl | 4-(piperazin-1-yl)-phenyl |
| 978. | ethyl | 4-(4-methylpiperazin-1-yl)-phenyl |
| 979. | ethyl | 4-(morpholin-4-yl)-phenyl |
| 980. | ethyl | 4-(morpholin-4-yl)-5-(trifluoromethyl)-phenyl |
| 981. | ethyl | 4-(morpholin-4-yl)-2-methoxyphenyl |
| 982. | ethyl | 4-(morpholin-4-yl)-3-methoxyphenyl |
| 983. | ethyl | 4-(morpholin-4-yl)-2,5-difluorophenyl |
| 984. | ethyl | 4-(morpholin-4-yl)-2,6-difluorophenyl |
| 985. | ethyl | 4-(thiomorpholin-4-yl)-phenyl |
| 986. | ethyl | 4-(1-oxo-thiomorpholin-4-yl)-phenyl |
| 987. | ethyl | 4-(1,1-dioxo-thiomorpholin-4-yl)-phenyl |
| 988. | ethyl | 4-(pyrrol-1-yl)-phenyl |
| 989. | ethyl | 4-(pyrrol-2-yl)-phenyl |
| 990. | ethyl | 4-(pyrrol-3-yl)-phenyl |
| 991. | ethyl | 4-(1-methylpyrrol-2-yl)-phenyl |
| 992. | ethyl | 4-(1-methylpyrrol-3-yl)-phenyl |
| 993. | ethyl | 4-(furan-2-yl)-phenyl |
| 994. | ethyl | 4-(furan-3-yl)-phenyl |
| 995. | ethyl | 4-(thiophen-2-yl)-phenyl |
| 996. | ethyl | 4-(thiophen-3-yl)-phenyl |
| 997. | ethyl | 4-(5-propylthien-2-yl)-phenyl |
| 998. | ethyl | 4-(pyrazol-1-yl)-phenyl |
| 999. | ethyl | 4-(pyrazol-3-yl)-phenyl |
| 1000. | ethyl | 4-(pyrazol-4-yl)-phenyl |
| 1001. | ethyl | 4-(4-fluoropyrazol-1-yl)-phenyl |
| 1002. | ethyl | 4-(1-methyl-1H-pyrazol-4-yl)-phenyl |
| 1003. | ethyl | 4-(1-ethyl-1H-pyrazol-4-yl)-phenyl |

TABLE A-continued

| No. | R¹ | Ar |
|---|---|---|
| 1004. | ethyl | 4-(1-methyl-1H-pyrazol-5-yl)-phenyl |
| 1005. | ethyl | 4-(1H-imidazol-2-yl)-phenyl |
| 1006. | ethyl | 4-(imidazol-1-yl)-phenyl |
| 1007. | ethyl | 4-(1-methylimidazol-2-yl)-phenyl |
| 1008. | ethyl | 4-(oxazol-2-yl)-phenyl |
| 1009. | ethyl | 4-(oxazol-4-yl)-phenyl |
| 1010. | ethyl | 4-(oxazol-5-yl)-phenyl |
| 1011. | ethyl | 4-(isoxazol-3-yl)-phenyl |
| 1012. | ethyl | 4-(isoxazol-4-yl)-phenyl |
| 1013. | ethyl | 4-(isoxazol-5-yl)-phenyl |
| 1014. | ethyl | 4-(thiazol-2-yl)-phenyl |
| 1015. | ethyl | 4-(thiazol-4-yl)-phenyl |
| 1016. | ethyl | 4-(thiazol-5-yl)-phenyl |
| 1017. | ethyl | 4-(2-methylthiazol-4-yl)-phenyl |
| 1018. | ethyl | 4-(2-methylthiazol-5-yl)-phenyl |
| 1019. | ethyl | 4-([1,2,3]-triazol-1-yl)-phenyl |
| 1020. | ethyl | 4-([1,2,4]-triazol-1-yl)-phenyl |
| 1021. | ethyl | 4-([1,2,3]-triazol-2-yl)-phenyl |
| 1022. | ethyl | 4-(4H-[1,2,4]-triazol-3-yl)-phenyl |
| 1023. | ethyl | 4-([1,2,4]-triazol-4-yl)-phenyl |
| 1024. | ethyl | 4-(2H-[1,2,3]-triazol-4-yl)-phenyl |
| 1025. | ethyl | 4-(4-methyl-4H-[1,2,4]-triazol-3-yl)-phenyl |
| 1026. | ethyl | 4-(2-methyl-2H-[1,2,3]-triazol-4-yl)-phenyl |
| 1027. | ethyl | 4-([1,3,4]-oxadiazol-2-yl)-phenyl |
| 1028. | ethyl | 4-(5-methyl-[1,3,4]-oxadiazol-2-yl)-phenyl |
| 1029. | ethyl | 4-([1,2,4]-oxadiazol-3-yl)-phenyl |
| 1030. | ethyl | 4-(5-methyl-[1,2,4]-oxadiazol-3-yl)-phenyl |
| 1031. | ethyl | 4-([1,2,4]-oxadiazol-5-yl)-phenyl |
| 1032. | ethyl | 4-([1,2,3]-oxadiazol-4-yl)-phenyl |
| 1033. | ethyl | 4-([1,2,3]-oxadiazol-5-yl)-phenyl |
| 1034. | ethyl | 4-([1,2,3]-thiadiazol-4-yl)-phenyl |
| 1035. | ethyl | 4-(1H-tetrazol-5-yl)-phenyl |
| 1036. | ethyl | 4-(tetrazol-1-yl)-phenyl |
| 1037. | ethyl | 4-(2-methyl-2H-tetrazol-5-yl)-phenyl |
| 1038. | ethyl | 4-(1-methyl-1H-tetrazol-5-yl)-phenyl |
| 1039. | ethyl | 4-furazan-3-yl-phenyl |
| 1040. | ethyl | 4-(pyrid-2-yl)-phenyl |
| 1041. | ethyl | 4-(pyrid-3-yl)-phenyl |
| 1042. | ethyl | 4-(pyrid-4-yl)-phenyl |
| 1043. | ethyl | 4-(pyrimidin-2-yl)-phenyl |
| 1044. | ethyl | 4-(2-methylpyrimidin-4-yl)-phenyl |
| 1045. | ethyl | 4-(pyrimidin-4-yl)-phenyl |
| 1046. | ethyl | 4-(pyrimidin-5-yl)-phenyl |
| 1047. | ethyl | 5-bromopyridin-3-yl |
| 1048. | ethyl | 4-bromo-2-chloropyridin-5-yl |
| 1049. | ethyl | 4-methylpyridin-2-yl |
| 1050. | ethyl | 5-methylpyridin-2-yl |
| 1051. | ethyl | 4-(trifluoromethyl)-pyridin-2-yl |
| 1052. | ethyl | 6-(trifluoromethyl)-pyridin-2-yl |
| 1053. | ethyl | 5-(trifluoromethyl)-pyridin-3-yl |
| 1054. | ethyl | 5-(pyrrolidin-1-yl)-pyridin-3-yl |
| 1055. | ethyl | 4-(pyrrolidin-1-yl)-2-chloropyridin-5-yl |
| 1056. | ethyl | 4-(morpholin-4-yl)-2-chloropyridin-5-yl |
| 1057. | ethyl | 2-(morpholin-4-yl)-pyridin-5-yl |
| 1058. | ethyl | 5-(morpholin-4-yl)-pyridin-2-yl |
| 1059. | ethyl | 2-phenoxypyridin-5-yl |
| 1060. | ethyl | 2,3-dichlorophenyl |
| 1061. | ethyl | 2,5-dichlorophenyl |
| 1062. | ethyl | 3,5-dichlorophenyl |
| 1063. | ethyl | 3-chloro-4-fluorophenyl |
| 1064. | ethyl | 4-bromo-2,5-dichlorophenyl |
| 1065. | ethyl | 3-bromo-4-(trifluoromethoxy)phenyl |
| 1066. | ethyl | 3,5-dibromo-4-(2-fluoroethoxy)-phenyl |
| 1067. | ethyl | 2,5-dimethylphenyl |
| 1068. | ethyl | 2,5-di-(trifluoromethyl)-phenyl |
| 1069. | ethyl | 3,5-di-(trifluoromethyl)-phenyl |
| 1070. | ethyl | 2,5-dimethoxyphenyl |
| 1071. | ethyl | 2-methoxy-5-methylphenyl |
| 1072. | ethyl | 2-methoxy-5-(trifluoromethyl)-phenyl |
| 1073. | ethyl | 4-fluoro-3-(oxazol-4-yl)-phenyl |
| 1074. | ethyl | thien-2-yl |
| 1075. | ethyl | thien-3-yl |
| 1076. | ethyl | 3-chlorothien-2-yl |
| 1077. | ethyl | 4-chlorothien-2-yl |
| 1078. | ethyl | 5-chlorothien-2-yl |
| 1079. | ethyl | 3-bromothien-2-yl |
| 1080. | ethyl | 4-bromothien-2-yl |
| 1081. | ethyl | 5-bromothien-2-yl |

TABLE A-continued

| No. | R¹ | Ar |
|---|---|---|
| 1082. | ethyl | 4,5-dichlorothien-2-yl |
| 1083. | ethyl | 4,5-dibromothien-2-yl |
| 1084. | ethyl | 4-bromo-5-chlorothien-2-yl |
| 1085. | ethyl | 3-bromo-5-chlorothien-2-yl |
| 1086. | ethyl | 5-methylthien-2-yl |
| 1087. | ethyl | 5-ethylthien-2-yl |
| 1088. | ethyl | 5-propylthien-2-yl |
| 1089. | ethyl | 5-trifluoromethylthien-2-yl |
| 1090. | ethyl | 5-phenylthien-2-yl |
| 1091. | ethyl | 5-(pyrid-2-yl)-thien-2-yl |
| 1092. | ethyl | 5-(phenylsulfonyl)-thien-2-yl |
| 1093. | ethyl | 4-(phenylsulfonyl)-thien-2-yl |
| 1094. | ethyl | 5-(pyrid-2-ylsulfonyl)-thien-2-yl |
| 1095. | ethyl | 5-(3-chloro-5-trifluoro-pyrid-2-ylsulfonyl)-thien-2-yl |
| 1096. | ethyl | 5-(benzoylaminomethyl)-thien-2-yl |
| 1097. | ethyl | 5-((4-chlorobenzoyl)aminomethyl)-thien-2-yl |
| 1098. | ethyl | 5-(acetylaminomethyl)-thien-2-yl |
| 1099. | ethyl | 5-(pyrazol-1-yl)-thien-2-yl |
| 1100. | ethyl | 5-(pyrazol-3-yl)-thien-2-yl |
| 1101. | ethyl | 5-(pyrazol-4-yl)-thien-2-yl |
| 1102. | ethyl | 5-(pyrazol-5-yl)-thien-2-yl |
| 1103. | ethyl | 5-(4-fluoropyrazol-1-yl)-thien-2-yl |
| 1104. | ethyl | 5-(1-methyl-5-trifluoromethyl-(1H)-pyrazol-3-yl)-thien-2-yl |
| 1105. | ethyl | 5-(1-methyl-3-trifluoromethyl-(1H)-pyrazol-5-yl)-thien-2-yl |
| 1106. | ethyl | 5-(4-carboxy-1-methyl-5-methylthio-(1H)-pyrazol-3-yl)-thien-2-yl |
| 1107. | ethyl | 5-(4-aminomethyl-1-methyl-5-methylthio-(1H)-pyrazol-3-yl)-thien-2-yl |
| 1108. | ethyl | 5-(isoxazol-3-yl)-thien-2-yl |
| 1109. | ethyl | 5-(isoxazol-4-yl)-thien-2-yl |
| 1110. | ethyl | 5-(isoxazol-5-yl)-thien-2-yl |
| 1111. | ethyl | 5-(5-trifluoromethylisoxazol-3-yl)-thien-2-yl |
| 1112. | ethyl | 5-(oxazol-2-yl)-thien-2-yl |
| 1113. | ethyl | 5-(oxazol-4-yl)-thien-2-yl |
| 1114. | ethyl | 5-(oxazol-5-yl)-thien-2-yl |
| 1115. | ethyl | 5-(2-methyloxazol-4-yl)-thien-2-yl |
| 1116. | ethyl | 5-(2-methyloxazol-5-yl)-thien-2-yl |
| 1117. | ethyl | 5-(isothiazol-3-yl)-thien-2-yl |
| 1118. | ethyl | 5-(isothiazol-4-yl)-thien-2-yl |
| 1119. | ethyl | 5-(isothiazol-5-yl)-thien-2-yl |
| 1120. | ethyl | 5-(5-trifluoromethylisothiazol-3-yl)-thien-2-yl |
| 1121. | ethyl | 5-(thiazol-2-yl)-thien-2-yl |
| 1122. | ethyl | 5-(thiazol-4-yl)-thien-2-yl |
| 1123. | ethyl | 5-(thiazol-5-yl)-thien-2-yl |
| 1124. | ethyl | 5-(2-methylthiazol-4-yl)-thien-2-yl |
| 1125. | ethyl | 5-(2-methylthiazol-5-yl)-thien-2-yl |
| 1126. | ethyl | 5-([1,2,3]-oxadiazol-4-yl)-thien-2-yl |
| 1127. | ethyl | 5-([1,2,3]-thiadiazol-4-yl)-thien-2-yl |
| 1128. | ethyl | 5-(pyrimidin-2-yl)-thien-2-yl |
| 1129. | ethyl | 5-(pyrimidin-4-yl)-thien-2-yl |
| 1130. | ethyl | 5-(pyrimidin-5-yl)-thien-2-yl |
| 1131. | ethyl | 5-(2-methylthiopyrimidin-4-yl)-thien-2-yl |
| 1132. | ethyl | 5-([1,3]-dioxolan-2-yl)-thien-2-yl |
| 1133. | ethyl | 3-([1,3]-dioxolan-2-yl)-thien-2-yl thien-2-yl |
| 1134. | ethyl | 5-((3-chloro-5-(trifluoromethyl)-pyridin-2-yl)-methyl)-thien-2-yl |
| 1135. | ethyl | 5-[3-chloro-5-(trifluoromethyl)-pyrid-2-ylsulfonyl]-thien-2-yl |
| 1136. | ethyl | 2-chlorothien-3-yl |
| 1137. | ethyl | 4-chlorothien-3-yl |
| 1138. | ethyl | 5-chlorothien-3-yl |
| 1139. | ethyl | 2-bromothien-3-yl |
| 1140. | ethyl | 4-bromothien-3-yl |
| 1141. | ethyl | 5-bromothien-3-yl |
| 1142. | ethyl | 2,5-dichlorothien-3-yl |
| 1143. | ethyl | 2,5-dibromothien-3-yl |
| 1144. | ethyl | 2,4,5-trichlorothien-3-yl |
| 1145. | ethyl | 4-bromo-2,5-dichlorothien-3-yl |
| 1146. | ethyl | 2-chloro-5-methylsulfonylthien-3-yl |
| 1147. | ethyl | 2,5-dimethylthien-3-yl |
| 1148. | ethyl | 4-hydroxythien-3-yl |
| 1149. | ethyl | 2-phenylthien-3-yl |
| 1150. | ethyl | 4-phenyl-5-(trofluoromethyl)-thien-3-yl |
| 1151. | ethyl | 2-methoxycarbonyl-4-phenyl-5-(trifluoromethyl)-thien-3-yl |

TABLE A-continued

| No. | R¹ | Ar |
|---|---|---|
| 1152. | ethyl | benzo[b]thiophen-2-yl |
| 1153. | ethyl | benzo[b]thiophen-3-yl |
| 1154. | ethyl | 3-methyl-benzo[b]thiophen-2-yl |
| 1155. | ethyl | 5-methyl-benzo[b]thiophen-2-yl |
| 1156. | ethyl | 5-fluoro-3-methyl-benzo[b]thiophen-2-yl |
| 1157. | ethyl | 5-chloro-3-methyl-benzo[b]thiophen-2-yl |
| 1158. | ethyl | 5-bromo-3-methyl-benzo[b]thiophen-2-yl |
| 1159. | methyl | 3-methylphenyl |
| 1160. | methyl | 3-ethylphenyl |
| 1161. | methyl | 3-propylphenyl |
| 1162. | methyl | 3-isopropylphenyl |
| 1163. | methyl | 3-sec-butylphenyl |
| 1164. | methyl | 3-tert-butylphenyl |
| 1165. | methyl | 3-isobutylphenyl |
| 1166. | methyl | 3-(1,1-dimethylpropyl)-phenyl |
| 1167. | methyl | 3-vinylphenyl |
| 1168. | methyl | 3-isopropenylphenyl |
| 1169. | methyl | 3-fluorophenyl |
| 1170. | methyl | 2-fluorophenyl |
| 1171. | methyl | 3-chlorophenyl |
| 1172. | methyl | 3-bromophenyl |
| 1173. | methyl | 3-iodophenyl |
| 1174. | methyl | 3-(fluoromethyl)phenyl |
| 1175. | methyl | 3-(difluoromethyl)phenyl |
| 1176. | methyl | 3-(trifluoromethyl)phenyl |
| 1177. | methyl | 3,5-bis(trifluoromethyl)phenyl |
| 1178. | methyl | 3-(1-fluoroethyl)-phenyl |
| 1179. | methyl | 3-((S)-1-fluoroethyl)-phenyl |
| 1180. | methyl | 3-((R)-1-fluoroethyl)-phenyl |
| 1181. | methyl | 3-(2-fluoroethyl)-phenyl |
| 1182. | methyl | 3-(1,1-difluoroethyl)-phenyl |
| 1183. | methyl | 3-(2,2-difluoroethyl)-phenyl |
| 1184. | methyl | 3-(2,2,2-trifluoroethyl)-phenyl |
| 1185. | methyl | 3-(3-fluoropropyl)-phenyl |
| 1186. | methyl | 3-(2-fluoropropyl)-phenyl |
| 1187. | methyl | 3-((S)-2-fluoropropyl)-phenyl |
| 1188. | methyl | 3-((R)-2-fluoropropyl)-phenyl |
| 1189. | methyl | 3-(3,3-difluoropropyl)-phenyl |
| 1190. | methyl | 3-(3,3,3-trifluoropropyl)-phenyl |
| 1191. | methyl | 3-(1-fluoro-1-methylethyl)-phenyl |
| 1192. | methyl | 3-(2-fluoro-1-methylethyl)-phenyl |
| 1193. | methyl | 3-((S)-2-fluoro-1-methylethyl)-phenyl |
| 1194. | methyl | 3-((R)-2-fluoro-1-methylethyl)-phenyl |
| 1195. | methyl | 3-(2,2-difluoro-1-methylethyl)-phenyl |
| 1196. | methyl | 3-((S)-2,2-difluoro-1-methylethyl)-phenyl |
| 1197. | methyl | 3-((R)-2,2-difluoro-1-methylethyl)-phenyl |
| 1198. | methyl | 3-(2,2,2-trifluoro-1-methylethyl)-phenyl |
| 1199. | methyl | 3-((S)-2,2,2-trifluoro-1-methylethyl)-phenyl |
| 1200. | methyl | 3-((R)-2,2,2-trifluoro-1-methylethyl)-phenyl |
| 1201. | methyl | 3-(2-fluoro-1-fluoromethylethyl)-phenyl |
| 1202. | methyl | 3-(1-difluoromethyl-2,2-difluoroethyl)-phenyl |
| 1203. | methyl | 3-(1,1-dimethyl-2-fluoroethyl)-phenyl |
| 1204. | methyl | 3-methoxyphenyl |
| 1205. | methyl | 3-ethoxyphenyl |
| 1206. | methyl | 3-propoxyphenyl |
| 1207. | methyl | 3-isopropoxyphenyl |
| 1208. | methyl | 3-butoxyphenyl |
| 1209. | methyl | 3-(fluoromethoxy)-phenyl |
| 1210. | methyl | 3-(difluoromethoxy)-phenyl |
| 1211. | methyl | 3-(trifluoromethoxy)-phenyl |
| 1212. | methyl | 3-(2-fluoroethoxy)-phenyl |
| 1213. | methyl | 3-(2,2-difluoroethoxy)-phenyl |
| 1214. | methyl | 3-(2,2,2-trifluoroethoxy)-phenyl |
| 1215. | methyl | 3-(1,1,2,2-tetrafluoroethoxy)-phenyl |
| 1216. | methyl | 3-cyclopropylphenyl |
| 1217. | methyl | 3-cyclobutylphenyl |
| 1218. | methyl | 3-cyclopentylphenyl |
| 1219. | methyl | 3-(2,2-difluorocyclopropyl)-phenyl |
| 1220. | methyl | 3,4-difluorophenyl |
| 1221. | methyl | 3-bromo-2-fluorophenyl |
| 1222. | methyl | 2-bromo-3-fluorophenyl |
| 1223. | methyl | 3-bromo-2,5-difluorophenyl |
| 1224. | methyl | 5-bromo-2,4-difluorophenyl |
| 1225. | methyl | 3-bromo-2,4-difluorophenyl |
| 1226. | methyl | 4-chloro-3-(trifluoromethyl)-phenyl |
| 1227. | methyl | 2-chloro-5-(trifluoromethyl)-phenyl |
| 1228. | methyl | 2-fluoro-5-(trifluoromethyl)-phenyl |
| 1229. | methyl | 4-fluoro-3-(trifluoromethyl)-phenyl |

TABLE A-continued

| No. | R¹ | Ar |
|---|---|---|
| 1230. | methyl | 3-fluoro-5-(trifluoromethyl)-phenyl |
| 1231. | methyl | 4-bromo-3-(trifluoromethyl)-phenyl |
| 1232. | methyl | 3-bromo-5-(trifluoromethyl)-phenyl |
| 1233. | methyl | 2-bromo-5-(trifluoromethyl)-phenyl |
| 1234. | methyl | 5-bromo-2-methoxyphenyl |
| 1235. | methyl | 3-bromo-4-methoxyphenyl |
| 1236. | methyl | 2-fluoro-3-isopropylphenyl |
| 1237. | methyl | 4-fluoro-3-isopropylphenyl |
| 1238. | methyl | 3-(1-hydroxy-1-methylethyl)-phenyl |
| 1239. | methyl | 3-(2-hydroxy-2-methylpropyl)-phenyl |
| 1240. | methyl | 3-acetylphenyl |
| 1241. | methyl | 3-acetylaminophenyl |
| 1242. | methyl | 3-carboxyphenyl |
| 1243. | methyl | 3-cyanophenyl |
| 1244. | methyl | 3-nitrophenyl |
| 1245. | methyl | 3-hydroxyphenyl |
| 1246. | methyl | 3-(O-benzyl)-phenyl |
| 1247. | methyl | 3-(2-methoxyethoxy)-phenyl |
| 1248. | methyl | 3-(CH₂—N(CH₃)₂)-phenyl |
| 1249. | methyl | 3-(NH—CO—NH₂)-phenyl |
| 1250. | methyl | 3-(methylsulfanyl)-phenyl |
| 1251. | methyl | 3-(fluoromethylsulfanyl)-phenyl |
| 1252. | methyl | 3-(difluoromethylsulfanyl)-phenyl |
| 1253. | methyl | 3-(trifluoromethylsulfanyl)-phenyl |
| 1254. | methyl | 3-(methylsulfonyl)-phenyl |
| 1255. | methyl | 3-(N-methoxy-N-methyl-amino)-phenyl |
| 1256. | methyl | 3-(methoxyamino)-phenyl |
| 1257. | methyl | 3-(ethoxyamino)-phenyl |
| 1258. | methyl | 3-(N-methylaminooxy)-phenyl |
| 1259. | methyl | 3-(N,N-dimethylaminooxy)-phenyl |
| 1260. | methyl | 3-(azetidin-1-yl)-phenyl |
| 1261. | methyl | 3-(2-methylazetidin-1-yl)-phenyl |
| 1262. | methyl | 3-((S)-2-methylazetidin-1-yl)-phenyl |
| 1263. | methyl | 3-((R)-2-methylazetidin-1-yl)-phenyl |
| 1264. | methyl | 3-(3-fluoroazetidin-1-yl)-phenyl |
| 1265. | methyl | 3-(2,2-difluoroazetidin-1-yl)-phenyl |
| 1266. | methyl | 3-(3-methoxyazetidin-1-yl)-phenyl |
| 1267. | methyl | 3-(3-hydroxyazetidin-1-yl)-phenyl |
| 1268. | methyl | 3-(pyrrolidin-1-yl)-phenyl |
| 1269. | methyl | 3-(pyrrolidin-2-yl)-phenyl |
| 1270. | methyl | 3-((S)-pyrrolidin-2-yl)-phenyl |
| 1271. | methyl | 3-((R)-pyrrolidin-2-yl)-phenyl |
| 1272. | methyl | 3-(pyrrolidin-3-yl)-phenyl |
| 1273. | methyl | 3-((S)-pyrrolidin-3-yl)-phenyl |
| 1274. | methyl | 3-((R)-pyrrolidin-3-yl)-phenyl |
| 1275. | methyl | 3-(pyrrolidin-1-yl)-5-(trifluoromethyl)-phenyl |
| 1276. | methyl | 5-(pyrrolidin-1-yl)-2-methoxyphenyl |
| 1277. | methyl | 3-(pyrrolidin-1-yl)-4-methoxyphenyl |
| 1278. | methyl | 5-(pyrrolidin-1-yl)-2,4-difluorophenyl |
| 1279. | methyl | 3-(pyrrolidin-1-yl)-2,4-difluorophenyl |
| 1280. | methyl | 3-(2-fluoropyrrolidin-1-yl)-phenyl |
| 1281. | methyl | 3-((S)-2-fluoropyrrolidin-1-yl)-phenyl |
| 1282. | methyl | 3-((R)-2-fluoropyrrolidin-1-yl)-phenyl |
| 1283. | methyl | 3-(3-fluoropyrrolidin-1-yl)-phenyl |
| 1284. | methyl | 3-((S)-3-fluoropyrrolidin-1-yl)-phenyl |
| 1285. | methyl | 3-((R)-3-fluoropyrrolidin-1-yl)-phenyl |
| 1286. | methyl | 3-(2,2-difluoropyrrolidin-1-yl)-phenyl |
| 1287. | methyl | 3-(3,3-difluoropyrrolidin-1-yl)-phenyl |
| 1288. | methyl | 3-(2-methylpyrrolidin-1-yl)-phenyl |
| 1289. | methyl | 3-((S)-2-methylpyrrolidin-1-yl)-phenyl |
| 1290. | methyl | 3-((R)-2-methylpyrrolidin-1-yl)-phenyl |
| 1291. | methyl | 3-(3-methylpyrrolidin-1-yl)-phenyl |
| 1292. | methyl | 3-((S)-3-methylpyrrolidin-1-yl)-phenyl |
| 1293. | methyl | 3-((R)-3-methylpyrrolidin-1-yl)-phenyl |
| 1294. | methyl | 3-(1-methylpyrrolidin-2-yl)-phenyl |
| 1295. | methyl | 3-((S)-1-methylpyrrolidin-2-yl)-phenyl |
| 1296. | methyl | 3-((R)-1-methylpyrrolidin-2-yl)-phenyl |
| 1297. | methyl | 3-(1-methylpyrrolidin-3-yl)-phenyl |
| 1298. | methyl | 3-((S)-1-methylpyrrolidin-3-yl)-phenyl |
| 1299. | methyl | 3-((R)-1-methylpyrrolidin-3-yl)-phenyl |
| 1300. | methyl | 3-(2,2-dimethylpyrrolidin-1-yl)-phenyl |
| 1301. | methyl | 3-(3,3-dimethylpyrrolidin-1-yl)-phenyl |
| 1302. | methyl | 3-(2-trifluoromethylpyrrolidin-1-yl)-phenyl |
| 1303. | methyl | 3-((S)-2-trifluoromethylpyrrolidin-1-yl)-phenyl |
| 1304. | methyl | 3-((R)-2-trifluoromethylpyrrolidin-1-yl)-phenyl |
| 1305. | methyl | 3-(3-trifluoromethylpyrrolidin-1-yl)-phenyl |
| 1306. | methyl | 3-((S)-3-trifluoromethylpyrrolidin-1-yl)-phenyl |
| 1307. | methyl | 3-((R)-3-trifluoromethylpyrrolidin-1-yl)-phenyl |

TABLE A-continued

| No. | R¹ | Ar |
|---|---|---|
| 1308. | methyl | 3-(2-oxopyrrolidin-1-yl)-phenyl |
| 1309. | methyl | 3-(2-oxo-oxazolidin-3-yl)-phenyl |
| 1310. | methyl | 3-(piperidin-1-yl)-phenyl |
| 1311. | methyl | 3-(2-methylpiperidin-1-yl)-phenyl |
| 1312. | methyl | 3-((S)-2-methylpiperidin-1-yl)-phenyl |
| 1313. | methyl | 3-((R)-2-methylpiperidin-1-yl)-phenyl |
| 1314. | methyl | 3-(2-fluoropiperidin-1-yl)-phenyl |
| 1315. | methyl | 3-((S)-2-fluoropiperidin-1-yl)-phenyl |
| 1316. | methyl | 3-((R)-2-fluoropiperidin-1-yl)-phenyl |
| 1317. | methyl | 3-(2,2-difluoropiperidin-1-yl)-phenyl |
| 1318. | methyl | 3-(piperazin-1-yl)-phenyl |
| 1319. | methyl | 3-(4-methylpiperazin-1-yl)-phenyl |
| 1320. | methyl | 3-(morpholin-4-yl)-phenyl |
| 1321. | methyl | 3-(morpholin-4-yl)-5-(trifluoromethyl)-phenyl |
| 1322. | methyl | 5-(morpholin-4-yl)-2-methoxyphenyl |
| 1323. | methyl | 3-(morpholin-4-yl)-4-methoxyphenyl |
| 1324. | methyl | 5-(morpholin-4-yl)-2,4-difluorophenyl |
| 1325. | methyl | 3-(morpholin-4-yl)-2,4-difluorophenyl |
| 1326. | methyl | 3-(thiomorpholin-4-yl)-phenyl |
| 1327. | methyl | 3-(1-oxo-thiomorpholin-4-yl)-phenyl |
| 1328. | methyl | 3-(1,1-dioxo-thiomorpholin-4-yl)-phenyl |
| 1329. | methyl | 3-(pyrrol-1-yl)-phenyl |
| 1330. | methyl | 3-(pyrrol-2-yl)-phenyl |
| 1331. | methyl | 3-(pyrrol-3-yl)-phenyl |
| 1332. | methyl | 3-(1-methylpyrrol-2-yl)-phenyl |
| 1333. | methyl | 3-(1-methylpyrrol-3-yl)-phenyl |
| 1334. | methyl | 3-(furan-2-yl)-phenyl |
| 1335. | methyl | 3-(furan-3-yl)-phenyl |
| 1336. | methyl | 3-(thiophen-2-yl)-phenyl |
| 1337. | methyl | 3-(thiophen-3-yl)-phenyl |
| 1338. | methyl | 3-(5-propylthien-2-yl)-phenyl |
| 1339. | methyl | 3-(pyrazol-1-yl)-phenyl |
| 1340. | methyl | 3-(pyrazol-3-yl)-phenyl |
| 1341. | methyl | 3-(pyrazol-4-yl)-phenyl |
| 1342. | methyl | 3-(4-fluoropyrazol-1-yl)-phenyl |
| 1343. | methyl | 3-(1-methyl-1H-pyrazol-4-yl)-phenyl |
| 1344. | methyl | 3-(1-ethyl-1H-pyrazol-4-yl)-phenyl |
| 1345. | methyl | 3-(1-methyl-1H-pyrazol-5-yl)-phenyl |
| 1346. | methyl | 3-(1H-imidazol-2-yl)-phenyl |
| 1347. | methyl | 3-(imidazol-1-yl)-phenyl |
| 1348. | methyl | 3-(1-methylimidazol-2-yl)-phenyl |
| 1349. | methyl | 3-(oxazol-2-yl)-phenyl |
| 1350. | methyl | 3-(oxazol-4-yl)-phenyl |
| 1351. | methyl | 3-(oxazol-5-yl)-phenyl |
| 1352. | methyl | 3-(isoxazol-3-yl)-phenyl |
| 1353. | methyl | 3-(isoxazol-4-yl)-phenyl |
| 1354. | methyl | 3-(isoxazol-5-yl)-phenyl |
| 1355. | methyl | 3-(thiazol-2-yl)-phenyl |
| 1356. | methyl | 3-(thiazol-4-yl)-phenyl |
| 1357. | methyl | 3-(thiazol-5-yl)-phenyl |
| 1358. | methyl | 3-(2-methylthiazol-4-yl)-phenyl |
| 1359. | methyl | 3-(2-methylthiazol-5-yl)-phenyl |
| 1360. | methyl | 3-([1,2,3]-triazol-1-yl)-phenyl |
| 1361. | methyl | 3-([1,2,4]-triazol-1-yl)-phenyl |
| 1362. | methyl | 3-([1,2,3]-triazol-2-yl)-phenyl |
| 1363. | methyl | 3-(4H-[1,2,4]-triazol-3-yl)-phenyl |
| 1364. | methyl | 3-([1,2,4]-triazol-4-yl)-phenyl |
| 1365. | methyl | 3-(2H-[1,2,3]-triazol-4-yl)-phenyl |
| 1366. | methyl | 3-(4-methyl-4H-[1,2,4]-triazol-3-yl)-phenyl |
| 1367. | methyl | 3-(2-methyl-2H-[1,2,3]-triazol-4-yl)-phenyl |
| 1368. | methyl | 3-([1,3,4]-oxadiazol-2-yl)-phenyl |
| 1369. | methyl | 3-(5-methyl-[1,3,4]-oxadiazol-2-yl)-phenyl |
| 1370. | methyl | 3-([1,2,4]-oxadiazol-3-yl)-phenyl |
| 1371. | methyl | 3-(5-methyl-[1,2,4]-oxadiazol-3-yl)-phenyl |
| 1372. | methyl | 3-([1,2,4]-oxadiazol-5-yl)-phenyl |
| 1373. | methyl | 3-([1,2,3]-oxadiazol-4-yl)-phenyl |
| 1374. | methyl | 3-([1,2,3]-oxadiazol-5-yl)-phenyl |
| 1375. | methyl | 3-([1,2,3]-thiadiazol-4-yl)-phenyl |
| 1376. | methyl | 3-(1H-tetrazol-5-yl)-phenyl |
| 1377. | methyl | 3-(tetrazol-1-yl)-phenyl |
| 1378. | methyl | 3-(2-methyl-2H-tetrazol-5-yl)-phenyl |
| 1379. | methyl | 3-(1-methyl-1H-tetrazol-5-yl)-phenyl |
| 1380. | methyl | 3-furazan-3-yl-phenyl |
| 1381. | methyl | 3-(pyrid-2-yl)-phenyl |
| 1382. | methyl | 3-(pyrid-3-yl)-phenyl |
| 1383. | methyl | 3-(pyrid-4-yl)-phenyl |
| 1384. | methyl | 3-(pyrimidin-2-yl)-phenyl |
| 1385. | methyl | 3-(2-methylpyrimidin-4-yl)-phenyl |

TABLE A-continued

| No. | R¹ | Ar |
|---|---|---|
| 1386. | methyl | 3-(pyrimidin-4-yl)-phenyl |
| 1387. | methyl | 3-(pyrimidin-5-yl)-phenyl |
| 1388. | methyl | 5-bromopyridin-3-yl |
| 1389. | methyl | 3-bromo-2-chloropyridin-5-yl |
| 1390. | methyl | 4-methylpyridin-2-yl |
| 1391. | methyl | 6-methylpyridin-2-yl |
| 1392. | methyl | 4-(trifluoromethyl)-pyridin-2-yl |
| 1393. | methyl | 6-(trifluoromethyl)-pyridin-2-yl |
| 1394. | methyl | 5-(trifluoromethyl)-pyridin-3-yl |
| 1395. | methyl | 5-(pyrrolidin-1-yl)-pyridin-3-yl |
| 1396. | methyl | 3-(pyrrolidin-1-yl)-2-chloropyridin-5-yl |
| 1397. | methyl | 3-(morpholin-4-yl)-2-chloropyridin-5-yl |
| 1398. | methyl | 2-(morpholin-4-yl)-pyridin-5-yl |
| 1399. | methyl | 2-phenoxypyridin-5-yl |
| 1400. | methyl | 4-methylphenyl |
| 1401. | methyl | 4-ethylphenyl |
| 1402. | methyl | 4-propylphenyl |
| 1403. | methyl | 4-isopropylphenyl |
| 1404. | methyl | 4-sec-butylphenyl |
| 1405. | methyl | 4-tert-butylphenyl |
| 1406. | methyl | 4-isobutylphenyl |
| 1407. | methyl | 4-(1,1-dimethylpropyl)-phenyl |
| 1408. | methyl | 4-vinylphenyl |
| 1409. | methyl | 4-isopropenylphenyl |
| 1410. | methyl | 4-fluorophenyl |
| 1411. | methyl | 4-chlorophenyl |
| 1412. | methyl | 4-bromophenyl |
| 1413. | methyl | 4-iodophenyl |
| 1414. | methyl | 4-(fluoromethyl)phenyl |
| 1415. | methyl | 4-(difluoromethyl)phenyl |
| 1416. | methyl | 4-(trifluoromethyl)phenyl |
| 1417. | methyl | 2,4-bis(trifluoromethyl)phenyl |
| 1418. | methyl | 4-(1-fluoroethyl)-phenyl |
| 1419. | methyl | 4-((S)-1-fluoroethyl)-phenyl |
| 1420. | methyl | 4-((R)-1-fluoroethyl)-phenyl |
| 1421. | methyl | 4-(2-fluoroethyl)-phenyl |
| 1422. | methyl | 4-(1,1-difluoroethyl)-phenyl |
| 1423. | methyl | 4-(2,2-difluoroethyl)-phenyl |
| 1424. | methyl | 4-(2,2,2-trifluoroethyl)-phenyl |
| 1425. | methyl | 4-(3-fluoropropyl)-phenyl |
| 1426. | methyl | 4-(2-fluoropropyl)-phenyl |
| 1427. | methyl | 4-((S)-2-fluoropropyl)-phenyl |
| 1428. | methyl | 4-((R)-2-fluoropropyl)-phenyl |
| 1429. | methyl | 4-(3,3-difluoropropyl)-phenyl |
| 1430. | methyl | 4-(3,3,3-trifluoropropyl)-phenyl |
| 1431. | methyl | 4-(1-fluoro-1-methylethyl)-phenyl |
| 1432. | methyl | 4-(2-fluoro-1-methylethyl)-phenyl |
| 1433. | methyl | 4-((S)-2-fluoro-1-methylethyl)-phenyl |
| 1434. | methyl | 4-((R)-2-fluoro-1-methylethyl)-phenyl |
| 1435. | methyl | 4-(2,2-difluoro-1-methylethyl)-phenyl |
| 1436. | methyl | 4-((S)-2,2-difluoro-1-methylethyl)-phenyl |
| 1437. | methyl | 4-((R)-2,2-difluoro-1-methylethyl)-phenyl |
| 1438. | methyl | 4-(2,2,2-trifluoro-1-methylethyl)-phenyl |
| 1439. | methyl | 4-((S)-2,2,2-trifluoro-1-methylethyl)-phenyl |
| 1440. | methyl | 4-((R)-2,2,2-trifluoro-1-methylethyl)-phenyl |
| 1441. | methyl | 4-(2-fluoro-1-fluoromethylethyl)-phenyl |
| 1442. | methyl | 4-(1-difluoromethyl-2,2-difluoroethyl)-phenyl |
| 1443. | methyl | 4-(1,1-dimethyl-2-fluoroethyl)-phenyl |
| 1444. | methyl | 4-methoxyphenyl |
| 1445. | methyl | 4-ethoxyphenyl |
| 1446. | methyl | 4-propoxyphenyl |
| 1447. | methyl | 4-isopropoxyphenyl |
| 1448. | methyl | 4-butoxyphenyl |
| 1449. | methyl | 4-(fluoromethoxy)-phenyl |
| 1450. | methyl | 4-(difluoromethoxy)-phenyl |
| 1451. | methyl | 4-(trifluoromethoxy)-phenyl |
| 1452. | methyl | 4-(2-fluoroethoxy)-phenyl |
| 1453. | methyl | 4-(2,2-difluoroethoxy)-phenyl |
| 1454. | methyl | 4-(2,2,2-trifluoroethoxy)-phenyl |
| 1455. | methyl | 4-(1,1,2,2-tetrafluoroethoxy)-phenyl |
| 1456. | methyl | 4-cyclopropylphenyl |
| 1457. | methyl | 4-cyclobutylphenyl |
| 1458. | methyl | 4-cyclopentylphenyl |
| 1459. | methyl | 4-(2,2-difluorocyclopropyl)-phenyl |
| 1460. | methyl | 3,4-difluorophenyl |
| 1461. | methyl | 4-bromo-2-fluorophenyl |
| 1462. | methyl | 2-bromo-4-fluorophenyl |
| 1463. | methyl | 4-bromo-2,5-difluorophenyl |

TABLE A-continued

| No. | R¹ | Ar |
|---|---|---|
| 1464. | methyl | 5-bromo-2,4-difluorophenyl |
| 1465. | methyl | 3-bromo-2,4-difluorophenyl |
| 1466. | methyl | 3-chloro-4-(trifluoromethyl)-phenyl |
| 1467. | methyl | 4-fluoro-3-(trifluoromethyl)-phenyl |
| 1468. | methyl | 3-fluoro-5-(trifluoromethyl)-phenyl |
| 1469. | methyl | 3-bromo-4-(trifluoromethyl)-phenyl |
| 1470. | methyl | 5-bromo-3-(trifluoromethyl)-phenyl |
| 1471. | methyl | 5-bromo-2-(trifluoromethyl)-phenyl |
| 1472. | methyl | 2-bromo-5-methoxyphenyl |
| 1473. | methyl | 4-bromo-3-methoxyphenyl |
| 1474. | methyl | 3-fluoro-2-isopropylphenyl |
| 1475. | methyl | 3-fluoro-4-isopropylphenyl |
| 1476. | methyl | 4-(1-hydroxy-1-methylethyl)-phenyl |
| 1477. | methyl | 4-(2-hydroxy-2-methylpropyl)-phenyl |
| 1478. | methyl | 4-acetylphenyl |
| 1479. | methyl | 4-acetylaminophenyl |
| 1480. | methyl | 4-carboxyphenyl |
| 1481. | methyl | 4-cyanophenyl |
| 1482. | methyl | 4-nitrophenyl |
| 1483. | methyl | 4-hydroxyphenyl |
| 1484. | methyl | 4-(O-benzyl)-phenyl |
| 1485. | methyl | 4-(2-methoxyethoxy)-phenyl |
| 1486. | methyl | 4-(CH$_2$—N(CH$_3$)$_2$)-phenyl |
| 1487. | methyl | 4-(NH—CO—NH$_2$)-phenyl |
| 1488. | methyl | 4-(methylsulfanyl)-phenyl |
| 1489. | methyl | 4-(fluoromethylsulfanyl)-phenyl |
| 1490. | methyl | 4-(difluoromethylsulfanyl)-phenyl |
| 1491. | methyl | 4-(trifluoromethylsulfanyl)-phenyl |
| 1492. | methyl | 4-(methylsulfonyl)-phenyl |
| 1493. | methyl | 4-(N-methoxy-N-methyl-amino)-phenyl |
| 1494. | methyl | 4-(methoxyamino)-phenyl |
| 1495. | methyl | 4-(ethoxyamino)-phenyl |
| 1496. | methyl | 4-(N-methylaminooxy)-phenyl |
| 1497. | methyl | 4-(N,N-dimethylaminooxy)-phenyl |
| 1498. | methyl | 4-(azetidin-1-yl)-phenyl |
| 1499. | methyl | 4-(2-methylazetidin-1-yl)-phenyl |
| 1500. | methyl | 4-((S)-2-methylazetidin-1-yl)-phenyl |
| 1501. | methyl | 4-((R)-2-methylazetidin-1-yl)-phenyl |
| 1502. | methyl | 4-(3-fluoroazetidin-1-yl)-phenyl |
| 1503. | methyl | 4-(2,2-difluoroazetidin-1-yl)-phenyl |
| 1504. | methyl | 4-(3-methoxyazetidin-1-yl)-phenyl |
| 1505. | methyl | 4-(3-hydroxyazetidin-1-yl)-phenyl |
| 1506. | methyl | 4-(pyrrolidin-1-yl)-phenyl |
| 1507. | methyl | 4-(pyrrolidin-2-yl)-phenyl |
| 1508. | methyl | 4-((S)-pyrrolidin-2-yl)-phenyl |
| 1509. | methyl | 4-((R)-pyrrolidin-2-yl)-phenyl |
| 1510. | methyl | 4-(pyrrolidin-3-yl)-phenyl |
| 1511. | methyl | 4-((S)-pyrrolidin-3-yl)-phenyl |
| 1512. | methyl | 4-((R)-pyrrolidin-3-yl)-phenyl |
| 1513. | methyl | 4-(pyrrolidin-1-yl)-5-(trifluoromethyl)-phenyl |
| 1514. | methyl | 4-(pyrrolidin-1-yl)-2-methoxyphenyl |
| 1515. | methyl | 4-(pyrrolidin-1-yl)-34-methoxyphenyl |
| 1516. | methyl | 4-(pyrrolidin-1-yl)-2,5-difluorophenyl |
| 1517. | methyl | 4-(pyrrolidin-1-yl)-2,6-difluorophenyl |
| 1518. | methyl | 4-(2-fluoropyrrolidin-1-yl)-phenyl |
| 1519. | methyl | 4-((S)-2-fluoropyrrolidin-1-yl)-phenyl |
| 1520. | methyl | 4-((R)-2-fluoropyrrolidin-1-yl)-phenyl |
| 1521. | methyl | 4-(3-fluoropyrrolidin-1-yl)-phenyl |
| 1522. | methyl | 4-((S)-3-fluoropyrrolidin-1-yl)-phenyl |
| 1523. | methyl | 4-((R)-3-fluoropyrrolidin-1-yl)-phenyl |
| 1524. | methyl | 4-(2,2-difluoropyrrolidin-1-yl)-phenyl |
| 1525. | methyl | 4-(3,3-difluoropyrrolidin-1-yl)-phenyl |
| 1526. | methyl | 4-(2-methylpyrrolidin-1-yl)-phenyl |
| 1527. | methyl | 4-((S)-2-methylpyrrolidin-1-yl)-phenyl |
| 1528. | methyl | 4-((R)-2-methylpyrrolidin-1-yl)-phenyl |
| 1529. | methyl | 4-(3-methylpyrrolidin-1-yl)-phenyl |
| 1530. | methyl | 4-((S)-3-methylpyrrolidin-1-yl)-phenyl |
| 1531. | methyl | 4-((R)-3-methylpyrrolidin-1-yl)-phenyl |
| 1532. | methyl | 4-(1-methylpyrrolidin-2-yl)-phenyl |
| 1533. | methyl | 4-((S)-1-methylpyrrolidin-2-yl)-phenyl |
| 1534. | methyl | 4-((R)-1-methylpyrrolidin-2-yl)-phenyl |
| 1535. | methyl | 4-(1-methylpyrrolidin-3-yl)-phenyl |
| 1536. | methyl | 4-((S)-1-methylpyrrolidin-3-yl)-phenyl |
| 1537. | methyl | 4-((R)-1-methylpyrrolidin-3-yl)-phenyl |
| 1538. | methyl | 4-(2,2-dimethylpyrrolidin-1-yl)-phenyl |
| 1539. | methyl | 4-(3,3-dimethylpyrrolidin-1-yl)-phenyl |
| 1540. | methyl | 4-(2-trifluoromethylpyrrolidin-1-yl)-phenyl |
| 1541. | methyl | 4-((S)-2-trifluoromethylpyrrolidin-1-yl)-phenyl |

TABLE A-continued

| No. | R¹ | Ar |
|---|---|---|
| 1542. | methyl | 4-((R)-2-trifluoromethylpyrrolidin-1-yl)-phenyl |
| 1543. | methyl | 4-(3-trifluoromethylpyrrolidin-1-yl)-phenyl |
| 1544. | methyl | 4-((S)-3-trifluoromethylpyrrolidin-1-yl)-phenyl |
| 1545. | methyl | 4-((R)-3-trifluoromethylpyrrolidin-1-yl)-phenyl |
| 1546. | methyl | 4-(2-oxopyrrolidin-1-yl)-phenyl |
| 1547. | methyl | 4-(2-oxo-oxazolidin-3-yl)-phenyl |
| 1548. | methyl | 4-(piperidin-1-yl)-phenyl |
| 1549. | methyl | 4-(2-methylpiperidin-1-yl)-phenyl |
| 1550. | methyl | 4-((S)-2-methylpiperidin-1-yl)-phenyl |
| 1551. | methyl | 4-((R)-2-methylpiperidin-1-yl)-phenyl |
| 1552. | methyl | 4-(2-fluoropiperidin-1-yl)-phenyl |
| 1553. | methyl | 4-((S)-2-fluoropiperidin-1-yl)-phenyl |
| 1554. | methyl | 4-((R)-2-fluoropiperidin-1-yl)-phenyl |
| 1555. | methyl | 4-(2,2-difluoropiperidin-1-yl)-phenyl |
| 1556. | methyl | 4-(piperazin-1-yl)-phenyl |
| 1557. | methyl | 4-(4-methylpiperazin-1-yl)-phenyl |
| 1558. | methyl | 4-(morpholin-4-yl)-phenyl |
| 1559. | methyl | 4-(morpholin-4-yl)-5-(trifluoromethyl)-phenyl |
| 1560. | methyl | 4-(morpholin-4-yl)-2-methoxyphenyl |
| 1561. | methyl | 4-(morpholin-4-yl)-3-methoxyphenyl |
| 1562. | methyl | 4-(morpholin-4-yl)-2,5-difluorophenyl |
| 1563. | methyl | 4-(morpholin-4-yl)-2,6-difluorophenyl |
| 1564. | methyl | 4-(thiomorpholin-4-yl)-phenyl |
| 1565. | methyl | 4-(1-oxo-thiomorpholin-4-yl)-phenyl |
| 1566. | methyl | 4-(1,1-dioxo-thiomorpholin-4-yl)-phenyl |
| 1567. | methyl | 4-(pyrrol-1-yl)-phenyl |
| 1568. | methyl | 4-(pyrrol-2-yl)-phenyl |
| 1569. | methyl | 4-(pyrrol-3-yl)-phenyl |
| 1570. | methyl | 4-(1-methylpyrrol-2-yl)-phenyl |
| 1571. | methyl | 4-(1-methylpyrrol-3-yl)-phenyl |
| 1572. | methyl | 4-(furan-2-yl)-phenyl |
| 1573. | methyl | 4-(furan-3-yl)-phenyl |
| 1574. | methyl | 4-(thiophen-2-yl)-phenyl |
| 1575. | methyl | 4-(thiophen-3-yl)-phenyl |
| 1576. | methyl | 4-(5-propylthien-2-yl)-phenyl |
| 1577. | methyl | 4-(pyrazol-1-yl)-phenyl |
| 1578. | methyl | 4-(pyrazol-3-yl)-phenyl |
| 1579. | methyl | 4-(pyrazol-4-yl)-phenyl |
| 1580. | methyl | 4-(4-fluoropyrazol-1-yl)-phenyl |
| 1581. | methyl | 4-(1-methyl-1H-pyrazol-4-yl)-phenyl |
| 1582. | methyl | 4-(1-ethyl-1H-pyrazol-4-yl)-phenyl |
| 1583. | methyl | 4-(1-methyl-1H-pyrazol-5-yl)-phenyl |
| 1584. | methyl | 4-(1H-imidazol-2-yl)-phenyl |
| 1585. | methyl | 4-(imidazol-1-yl)-phenyl |
| 1586. | methyl | 4-(1-methylimidazol-2-yl)-phenyl |
| 1587. | methyl | 4-(oxazol-2-yl)-phenyl |
| 1588. | methyl | 4-(oxazol-4-yl)-phenyl |
| 1589. | methyl | 4-(oxazol-5-yl)-phenyl |
| 1590. | methyl | 4-(isoxazol-3-yl)-phenyl |
| 1591. | methyl | 4-(isoxazol-4-yl)-phenyl |
| 1592. | methyl | 4-(isoxazol-5-yl)-phenyl |
| 1593. | methyl | 4-(thiazol-2-yl)-phenyl |
| 1594. | methyl | 4-(thiazol-4-yl)-phenyl |
| 1595. | methyl | 4-(thiazol-5-yl)-phenyl |
| 1596. | methyl | 4-(2-methylthiazol-4-yl)-phenyl |
| 1597. | methyl | 4-(2-methylthiazol-5-yl)-phenyl |
| 1598. | methyl | 4-([1,2,3]-triazol-1-yl)-phenyl |
| 1599. | methyl | 4-([1,2,4]-triazol-1-yl)-phenyl |
| 1600. | methyl | 4-([1,2,3]-triazol-2-yl)-phenyl |
| 1601. | methyl | 4-(4H-[1,2,4]-triazol-3-yl)-phenyl |
| 1602. | methyl | 4-([1,2,4]-triazol-4-yl)-phenyl |
| 1603. | methyl | 4-(2H-[1,2,3]-triazol-4-yl)-phenyl |
| 1604. | methyl | 4-(4-methyl-4H-[1,2,4]-triazol-3-yl)-phenyl |
| 1605. | methyl | 4-(2-methyl-2H-[1,2,3]-triazol-4-yl)-phenyl |
| 1606. | methyl | 4-([1,3,4]-oxadiazol-2-yl)-phenyl |
| 1607. | methyl | 4-(5-methyl-[1,3,4]-oxadiazol-2-yl)-phenyl |
| 1608. | methyl | 4-([1,2,4]-oxadiazol-3-yl)-phenyl |
| 1609. | methyl | 4-(5-methyl-[1,2,4]-oxadiazol-3-yl)-phenyl |
| 1610. | methyl | 4-([1,2,4]-oxadiazol-5-yl)-phenyl |
| 1611. | methyl | 4-([1,2,3]-oxadiazol-4-yl)-phenyl |
| 1612. | methyl | 4-([1,2,3]-oxadiazol-5-yl)-phenyl |
| 1613. | methyl | 4-([1,2,3]-thiadiazol-4-yl)-phenyl |
| 1614. | methyl | 4-(1H-tetrazol-5-yl)-phenyl |
| 1615. | methyl | 4-(tetrazol-1-yl)-phenyl |
| 1616. | methyl | 4-(2-methyl-2H-tetrazol-5-yl)-phenyl |
| 1617. | methyl | 4-(1-methyl-1H-tetrazol-5-yl)-phenyl |
| 1618. | methyl | 4-furazan-3-yl-phenyl |
| 1619. | methyl | 4-(pyrid-2-yl)-phenyl |

TABLE A-continued

| No. | R¹ | Ar |
|---|---|---|
| 1620. | methyl | 4-(pyrid-3-yl)-phenyl |
| 1621. | methyl | 4-(pyrid-4-yl)-phenyl |
| 1622. | methyl | 4-(pyrimidin-2-yl)-phenyl |
| 1623. | methyl | 4-(2-methylpyrimidin-4-yl)-phenyl |
| 1624. | methyl | 4-(pyrimidin-4-yl)-phenyl |
| 1625. | methyl | 4-(pyrimidin-5-yl)-phenyl |
| 1626. | methyl | 4-bromo-2-chloropyridin-5-yl |
| 1627. | methyl | 4-methylpyridin-2-yl |
| 1628. | methyl | 5-methylpyridin-2-yl |
| 1629. | methyl | 4-(pyrrolidin-1-yl)-2-chloropyridin-5-yl |
| 1630. | methyl | 4-(morpholin-4-yl)-2-chloropyridin-5-yl |
| 1631. | methyl | 2-(morpholin-4-yl)-pyridin-5-yl |
| 1632. | methyl | 5-(morpholin-4-yl)-pyridin-2-yl |
| 1633. | methyl | 2-phenoxypyridin-5-yl |
| 1634. | methyl | 2,3-dichlorophenyl |
| 1635. | methyl | 2,5-dichlorophenyl |
| 1636. | methyl | 3,5-dichlorophenyl |
| 1637. | methyl | 3-chloro-4-fluorophenyl |
| 1638. | methyl | 4-bromo-2,5-dichlorophenyl |
| 1639. | methyl | 3-bromo-4-(trifluoromethoxy)phenyl |
| 1640. | methyl | 3,5-dibromo-4-(2-fluoroethoxy)-phenyl |
| 1641. | methyl | 2,5-dimethylphenyl |
| 1642. | methyl | 2,5-di-(trifluoromethyl)-phenyl |
| 1643. | methyl | 3,5-di-(trifluoromethyl)-phenyl |
| 1644. | methyl | 2,5-dimethoxyphenyl |
| 1645. | methyl | 2-methoxy-5-methylphenyl |
| 1646. | methyl | 2-methoxy-5-(trifluoromethyl)-phenyl |
| 1647. | methyl | 4-fluoro-3-(oxazol-4-yl)-phenyl |
| 1648. | methyl | thien-2-yl |
| 1649. | methyl | thien-3-yl |
| 1650. | methyl | 3-chlorothien-2-yl |
| 1651. | methyl | 4-chlorothien-2-yl |
| 1652. | methyl | 5-chlorothien-2-yl |
| 1653. | methyl | 3-bromothien-2-yl |
| 1654. | methyl | 4-bromothien-2-yl |
| 1655. | methyl | 5-bromothien-2-yl |
| 1656. | methyl | 4,5-dichlorothien-2-yl |
| 1657. | methyl | 4,5-dibromothien-2-yl |
| 1658. | methyl | 4-bromo-5-chlorothien-2-yl |
| 1659. | methyl | 3-bromo-5-chlorothien-2-yl |
| 1660. | methyl | 5-methylthien-2-yl |
| 1661. | methyl | 5-ethylthien-2-yl |
| 1662. | methyl | 5-propylthien-2-yl |
| 1663. | methyl | 5-trifluoromethylthien-2-yl |
| 1664. | methyl | 5-phenylthien-2-yl |
| 1665. | methyl | 5-(pyrid-2-yl)-thien-2-yl |
| 1666. | methyl | 5-(phenylsulfonyl)-thien-2-yl |
| 1667. | methyl | 4-(phenylsulfonyl)-thien-2-yl |
| 1668. | methyl | 5-(pyrid-2-ylsulfonyl)-thien-2-yl |
| 1669. | methyl | 5-(3-chloro-5-trifluoro-pyrid-2-ylsulfonyl)-thien-2-yl |
| 1670. | methyl | 5-(benzoylaminomethyl)-thien-2-yl |
| 1671. | methyl | 5-((4-chlorobenzoyl)aminomethyl)-thien-2-yl |
| 1672. | methyl | 5-(acetylaminomethyl)-thien-2-yl |
| 1673. | methyl | 5-(pyrazol-1-yl)-thien-2-yl |
| 1674. | methyl | 5-(pyrazol-3-yl)-thien-2-yl |
| 1675. | methyl | 5-(pyrazol-4-yl)-thien-2-yl |
| 1676. | methyl | 5-(pyrazol-5-yl)-thien-2-yl |
| 1677. | methyl | 5-(4-fluoropyrazol-1-yl)-thien-2-yl |
| 1678. | methyl | 5-(1-methyl-5-trifluoromethyl-(1H)-pyrazol-3-yl)-thien-2-yl |
| 1679. | methyl | 5-(1-methyl-3-trifluoromethyl-(1H)-pyrazol-5-yl)-thien-2-yl |
| 1680. | methyl | 5-(4-carboxy-1-methyl-5-methylthio-(1H)-pyrazol-3-yl)-thien-2-yl |
| 1681. | methyl | 5-(4-aminomethyl-1-methyl-5-methylthio-(1H)-pyrazol-3-yl)-thien-2-yl |
| 1682. | methyl | 5-(isoxazol-3-yl)-thien-2-yl |
| 1683. | methyl | 5-(isoxazol-4-yl)-thien-2-yl |
| 1684. | methyl | 5-(isoxazol-5-yl)-thien-2-yl |
| 1685. | methyl | 5-(5-trifluoromethylisoxazol-3-yl)-thien-2-yl |
| 1686. | methyl | 5-(oxazol-2-yl)-thien-2-yl |
| 1687. | methyl | 5-(oxazol-4-yl)-thien-2-yl |
| 1688. | methyl | 5-(oxazol-5-yl)-thien-2-yl |
| 1689. | methyl | 5-(2-methyloxazol-4-yl)-thien-2-yl |
| 1690. | methyl | 5-(2-methyloxazol-5-yl)-thien-2-yl |
| 1691. | methyl | 5-(isothiazol-3-yl)-thien-2-yl |
| 1692. | methyl | 5-(isothiazol-4-yl)-thien-2-yl |

TABLE A-continued

| No. | R¹ | Ar |
|---|---|---|
| 1693. | methyl | 5-(isothiazol-5-yl)-thien-2-yl |
| 1694. | methyl | 5-(5-trifluoromethylisothiazol-3-yl)-thien-2-yl |
| 1695. | methyl | 5-(thiazol-2-yl)-thien-2-yl |
| 1696. | methyl | 5-(thiazol-4-yl)-thien-2-yl |
| 1697. | methyl | 5-(thiazol-5-yl)-thien-2-yl |
| 1698. | methyl | 5-(2-methylthiazol-4-yl)-thien-2-yl |
| 1699. | methyl | 5-(2-methylthiazol-5-yl)-thien-2-yl |
| 1700. | methyl | 5-([1,2,3]-oxadiazol-4-yl)-thien-2-yl |
| 1701. | methyl | 5-([1,2,3]-thiadiazol-4-yl)-thien-2-yl |
| 1702. | methyl | 5-(pyrimidin-2-yl)-thien-2-yl |
| 1703. | methyl | 5-(pyrimidin-4-yl)-thien-2-yl |
| 1704. | methyl | 5-(pyrimidin-5-yl)-thien-2-yl |
| 1705. | methyl | 5-(2-methylthiopyrimidin-4-yl)-thien-2-yl |
| 1706. | methyl | 5-([1,3]-dioxolan-2-yl)-thien-2-yl |
| 1707. | methyl | 3-([1,3]-dioxolan-2-yl)-thien 2-yl |
| 1708. | methyl | 5-((3-chloro-5-(trifluoromethyl-pyridin-2-yl)-methyl)-thien-2-yl |
| 1709. | methyl | 5-[3-chloro-5-(trifluoromethyl)-pyrid-2-ylsulfonyl]-thien-2-yl |
| 1710. | methyl | 2-chlorothien-3-yl |
| 1711. | methyl | 4-chlorothien-3-yl |
| 1712. | methyl | 5-chlorothien-3-yl |
| 1713. | methyl | 2-bromothien-3-yl |
| 1714. | methyl | 4-bromothien-3-yl |
| 1715. | methyl | 5-bromothien-3-yl |
| 1716. | methyl | 2,5-dichlorothien-3-yl |
| 1717. | methyl | 2,5-dibromothien-3-yl |
| 1718. | methyl | 2,4,5-trichlorothien-3-yl |
| 1719. | methyl | 4-bromo-2,5-dichlorothien-3-yl |
| 1720. | methyl | 2-chloro-5-methylsulfonylthien-3-yl |
| 1721. | methyl | 2,5-dimethylthien-3-yl |
| 1722. | methyl | 4-hydroxythien-3-yl |
| 1723. | methyl | 2-phenylthien-3-yl |
| 1724. | methyl | 4-phenyl-5-(trofluoromethyl)-thien-3-yl |
| 1725. | methyl | 2-methoxycarbonyl-4-phenyl-5-(trifluoromethyl)-thien-3-yl |
| 1726. | methyl | benzo[b]thiophen-2-yl |
| 1727. | methyl | benzo[b]thiophen-3-yl |
| 1728. | methyl | 3-methyl-benzo[b]thiophen-2-yl |
| 1729. | methyl | 5-methyl-benzo[b]thiophen-2-yl |
| 1730. | methyl | 5-fluoro-3-methyl-benzo[b]thiophen-2-yl |
| 1731. | methyl | 5-chloro-3-methyl-benzo[b]thiophen-2-yl |
| 1732. | methyl | 5-bromo-3-methyl-benzo[b]thiophen-2-yl |
| 1733. | H | 3-methylphenyl |
| 1734. | H | 3-ethylphenyl |
| 1735. | H | 3-propylphenyl |
| 1736. | H | 3-isopropylphenyl |
| 1737. | H | 3-sec-butylphenyl |
| 1738. | H | 3-tert-butylphenyl |
| 1739. | H | 3-isobutylphenyl |
| 1740. | H | 3-(1,1-dimethylpropyl)-phenyl |
| 1741. | H | 3-vinylphenyl |
| 1742. | H | 3-isopropenylphenyl |
| 1743. | H | 3-fluorophenyl |
| 1744. | H | 2-fluorophenyl |
| 1745. | H | 3-chlorophenyl |
| 1746. | H | 3-bromophenyl |
| 1747. | H | 3-iodophenyl |
| 1748. | H | 3-(fluoromethyl)phenyl |
| 1749. | H | 3-(difluoromethyl)phenyl |
| 1750. | H | 3-(trifluoromethyl)phenyl |
| 1751. | H | 3,5-bis(trifluoromethyl)phenyl |
| 1752. | H | 3-(1-fluoroethyl)-phenyl |
| 1753. | H | 3-((S)-1-fluoroethyl)-phenyl |
| 1754. | H | 3-((R)-1-fluoroethyl)-phenyl |
| 1755. | H | 3-(2-fluoroethyl)-phenyl |
| 1756. | H | 3-(1,1-difluoroethyl)-phenyl |
| 1757. | H | 3-(2,2-difluoroethyl)-phenyl |
| 1758. | H | 3-(2,2,2-trifluoroethyl)-phenyl |
| 1759. | H | 3-(3-fluoropropyl)-phenyl |
| 1760. | H | 3-(2-fluoropropyl)-phenyl |
| 1761. | H | 3-((S)-2-fluoropropyl)-phenyl |
| 1762. | H | 3-((R)-2-fluoropropyl)-phenyl |
| 1763. | H | 3-(3,3-difluoropropyl)-phenyl |
| 1764. | H | 3-(3,3,3-trifluoropropyl)-phenyl |
| 1765. | H | 3-(1-fluoro-1-methylethyl)-phenyl |
| 1766. | H | 3-(2-fluoro-1-methylethyl)-phenyl |
| 1767. | H | 3-((S)-2-fluoro-1-methylethyl)-phenyl |

TABLE A-continued

| No. | R¹ | Ar |
|---|---|---|
| 1768. | H | 3-((R)-2-fluoro-1-methylethyl)-phenyl |
| 1769. | H | 3-(2,2-difluoro-1-methylethyl)-phenyl |
| 1770. | H | 3-((S)-2,2-difluoro-1-methylethyl)-phenyl |
| 1771. | H | 3-((R)-2,2-difluoro-1-methylethyl)-phenyl |
| 1772. | H | 3-(2,2,2-trifluoro-1-methylethyl)-phenyl |
| 1773. | H | 3-((S)-2,2,2-trifluoro-1-methylethyl)-phenyl |
| 1774. | H | 3-((R)-2,2,2-trifluoro-1-methylethyl)-phenyl |
| 1775. | H | 3-(2-fluoro-1-fluoromethylethyl)-phenyl |
| 1776. | H | 3-(1-difluoromethyl-2,2-difluoroethyl)-phenyl |
| 1777. | H | 3-(1,1-dimethyl-2-fluoroethyl)-phenyl |
| 1778. | H | 3-methoxyphenyl |
| 1779. | H | 3-ethoxyphenyl |
| 1780. | H | 3-propoxyphenyl |
| 1781. | H | 3-isopropoxyphenyl |
| 1782. | H | 3-butoxyphenyl |
| 1783. | H | 3-(fluoromethoxy)-phenyl |
| 1784. | H | 3-(difluoromethoxy)-phenyl |
| 1785. | H | 3-(trifluoromethoxy)-phenyl |
| 1786. | H | 3-(2-fluoroethoxy)-phenyl |
| 1787. | H | 3-(2,2-difluoroethoxy)-phenyl |
| 1788. | H | 3-(2,2,2-trifluoroethoxy)-phenyl |
| 1789. | H | 3-(1,1,2,2-tetrafluoroethoxy)-phenyl |
| 1790. | H | 3-cyclopropylphenyl |
| 1791. | H | 3-cyclobutylphenyl |
| 1792. | H | 3-cyclopentylphenyl |
| 1793. | H | 3-(2,2-difluorocyclopropyl)-phenyl |
| 1794. | H | 3,4-difluorophenyl |
| 1795. | H | 3-bromo-2-fluorophenyl |
| 1796. | H | 2-bromo-3-fluorophenyl |
| 1797. | H | 3-bromo-2,5-difluorophenyl |
| 1798. | H | 5-bromo-2,4-difluorophenyl |
| 1799. | H | 3-bromo-2,4-difluorophenyl |
| 1800. | H | 4-chloro-3-(trifluoromethyl)-phenyl |
| 1801. | H | 2-chloro-5-(trifluoromethyl)-phenyl |
| 1802. | H | 2-fluoro-5-(trifluoromethyl)-phenyl |
| 1803. | H | 4-fluoro-3-(trifluoromethyl)-phenyl |
| 1804. | H | 3-fluoro-5-(trifluoromethyl)-phenyl |
| 1805. | H | 4-bromo-3-(trifluoromethyl)-phenyl |
| 1806. | H | 3-bromo-5-(trifluoromethyl)-phenyl |
| 1807. | H | 2-bromo-5-(trifluoromethyl)-phenyl |
| 1808. | H | 5-bromo-2-methoxyphenyl |
| 1809. | H | 3-bromo-4-methoxyphenyl |
| 1810. | H | 2-fluoro-3-isopropylphenyl |
| 1811. | H | 4-fluoro-3-isopropylphenyl |
| 1812. | H | 3-(1-hydroxy-1-methylethyl)-phenyl |
| 1813. | H | 3-(2-hydroxy-2-methylpropyl)-phenyl |
| 1814. | H | 3-acetylphenyl |
| 1815. | H | 3-acetylaminophenyl |
| 1816. | H | 3-carboxyphenyl |
| 1817. | H | 3-cyanophenyl |
| 1818. | H | 3-nitrophenyl |
| 1819. | H | 3-hydroxyphenyl |
| 1820. | H | 3-(O-benzyl)-phenyl |
| 1821. | H | 3-(2-methoxyethoxy)-phenyl |
| 1822. | H | 3-(CH₂—N(CH₃)₂)-phenyl |
| 1823. | H | 3-(NH—CO—NH₂)-phenyl |
| 1824. | H | 3-(methylsulfanyl)-phenyl |
| 1825. | H | 3-(fluoromethylsulfanyl)-phenyl |
| 1826. | H | 3-(difluoromethylsulfanyl)-phenyl |
| 1827. | H | 3-(trifluoromethylsulfanyl)-phenyl |
| 1828. | H | 3-(methylsulfonyl)-phenyl |
| 1829. | H | 3-(N-methoxy-N-methyl-amino)-phenyl |
| 1830. | H | 3-(methoxyamino)-phenyl |
| 1831. | H | 3-(ethoxyamino)-phenyl |
| 1832. | H | 3-(N-methylaminooxy)-phenyl |
| 1833. | H | 3-(N,N-dimethylaminooxy)-phenyl |
| 1834. | H | 3-(azetidin-1-yl)-phenyl |
| 1835. | H | 3-(2-methylazetidin-1-yl)-phenyl |
| 1836. | H | 3-((S)-2-methylazetidin-1-yl)-phenyl |
| 1837. | H | 3-((R)-2-methylazetidin-1-yl)-phenyl |
| 1838. | H | 3-(3-fluoroazetidin-1-yl)-phenyl |
| 1839. | H | 3-(2,2-difluoroazetidin-1-yl)-phenyl |
| 1840. | H | 3-(3-methoxyazetidin-1-yl)-phenyl |
| 1841. | H | 3-(3-hydroxyazetidin-1-yl)-phenyl |
| 1842. | H | 3-(pyrrolidin-1-yl)-phenyl |
| 1843. | H | 3-(pyrrolidin-2-yl)-phenyl |
| 1844. | H | 3-((S)-pyrrolidin-2-yl)-phenyl |
| 1845. | H | 3-((R)-pyrrolidin-2-yl)-phenyl |

TABLE A-continued

| No. | R¹ | Ar |
|---|---|---|
| 1846. | H | 3-(pyrrolidin-3-yl)-phenyl |
| 1847. | H | 3-((S)-pyrrolidin-3-yl)-phenyl |
| 1848. | H | 3-((R)-pyrrolidin-3-yl)-phenyl |
| 1849. | H | 3-(pyrrolidin-1-yl)-5-(trifluoromethyl)-phenyl |
| 1850. | H | 5-(pyrrolidin-1-yl)-2-methoxyphenyl |
| 1851. | H | 3-(pyrrolidin-1-yl)-4-methoxyphenyl |
| 1852. | H | 5-(pyrrolidin-1-yl)-2,4-difluorophenyl |
| 1853. | H | 3-(pyrrolidin-1-yl)-2,4-difluorophenyl |
| 1854. | H | 3-(2-fluoropyrrolidin-1-yl)-phenyl |
| 1855. | H | 3-((S)-2-fluoropyrrolidin-1-yl)-phenyl |
| 1856. | H | 3-((R)-2-fluoropyrrolidin-1-yl)-phenyl |
| 1857. | H | 3-(3-fluoropyrrolidin-1-yl)-phenyl |
| 1858. | H | 3-((S)-3-fluoropyrrolidin-1-yl)-phenyl |
| 1859. | H | 3-((R)-3-fluoropyrrolidin-1-yl)-phenyl |
| 1860. | H | 3-(2,2-difluoropyrrolidin-1-yl)-phenyl |
| 1861. | H | 3-(3,3-difluoropyrrolidin-1-yl)-phenyl |
| 1862. | H | 3-(2-methylpyrrolidin-1-yl)-phenyl |
| 1863. | H | 3-((S)-2-methylpyrrolidin-1-yl)-phenyl |
| 1864. | H | 3-((R)-2-methylpyrrolidin-1-yl)-phenyl |
| 1865. | H | 3-(3-methylpyrrolidin-1-yl)-phenyl |
| 1866. | H | 3-((S)-3-methylpyrrolidin-1-yl)-phenyl |
| 1867. | H | 3-((R)-3-methylpyrrolidin-1-yl)-phenyl |
| 1868. | H | 3-(1-methylpyrrolidin-2-yl)-phenyl |
| 1869. | H | 3-((S)-1-methylpyrrolidin-2-yl)-phenyl |
| 1870. | H | 3-((R)-1-methylpyrrolidin-2-yl)-phenyl |
| 1871. | H | 3-(1-methylpyrrolidin-3-yl)-phenyl |
| 1872. | H | 3-((S)-1-methylpyrrolidin-3-yl)-phenyl |
| 1873. | H | 3-((R)-1-methylpyrrolidin-3-yl)-phenyl |
| 1874. | H | 3-(2,2-dimethylpyrrolidin-1-yl)-phenyl |
| 1875. | H | 3-(3,3-dimethylpyrrolidin-1-yl)-phenyl |
| 1876. | H | 3-(2-trifluoromethylpyrrolidin-1-yl)-phenyl |
| 1877. | H | 3-((S)-2-trifluoromethylpyrrolidin-1-yl)-phenyl |
| 1878. | H | 3-((R)-2-trifluoromethylpyrrolidin-1-yl)-phenyl |
| 1879. | H | 3-(3-trifluoromethylpyrrolidin-1-yl)-phenyl |
| 1880. | H | 3-((S)-3-trifluoromethylpyrrolidin-1-yl)-phenyl |
| 1881. | H | 3-((R)-3-trifluoromethylpyrrolidin-1-yl)-phenyl |
| 1882. | H | 3-(2-oxopyrrolidin-1-yl)-phenyl |
| 1883. | H | 3-(2-oxo-oxazolidin-3-yl)-phenyl |
| 1884. | H | 3-(piperidin-1-yl)-phenyl |
| 1885. | H | 3-(2-methylpiperidin-1-yl)-phenyl |
| 1886. | H | 3-((S)-2-methylpiperidin-1-yl)-phenyl |
| 1887. | H | 3-((R)-2-methylpiperidin-1-yl)-phenyl |
| 1888. | H | 3-(2-fluoropiperidin-1-yl)-phenyl |
| 1889. | H | 3-((S)-2-fluoropiperidin-1-yl)-phenyl |
| 1890. | H | 3-((R)-2-fluoropiperidin-1-yl)-phenyl |
| 1891. | H | 3-(2,2-difluoropiperidin-1-yl)-phenyl |
| 1892. | H | 3-(piperazin-1-yl)-phenyl |
| 1893. | H | 3-(4-methylpiperazin-1-yl)-phenyl |
| 1894. | H | 3-(morpholin-4-yl)-phenyl |
| 1895. | H | 3-(morpholin-4-yl)-5-(trifluoromethyl)-phenyl |
| 1896. | H | 5-(morpholin-4-yl)-2-methoxyphenyl |
| 1897. | H | 3-(morpholin-4-yl)-4-methoxyphenyl |
| 1898. | H | 5-(morpholin-4-yl)-2,4-difluorophenyl |
| 1899. | H | 3-(morpholin-4-yl)-2,4-difluorophenyl |
| 1900. | H | 3-(thiomorpholin-4-yl)-phenyl |
| 1901. | H | 3-(1-oxo-thiomorpholin-4-yl)-phenyl |
| 1902. | H | 3-(1,1-dioxo-thiomorpholin-4-yl)-phenyl |
| 1903. | H | 3-(pyrrol-1-yl)-phenyl |
| 1904. | H | 3-(pyrrol-2-yl)-phenyl |
| 1905. | H | 3-(pyrrol-3-yl)-phenyl |
| 1906. | H | 3-(1-methylpyrrol-2-yl)-phenyl |
| 1907. | H | 3-(1-methylpyrrol-3-yl)-phenyl |
| 1908. | H | 3-(furan-2-yl)-phenyl |
| 1909. | H | 3-(furan-3-yl)-phenyl |
| 1910. | H | 3-(thiophen-2-yl)-phenyl |
| 1911. | H | 3-(thiophen-3-yl)-phenyl |
| 1912. | H | 3-(5-propylthien-2-yl)-phenyl |
| 1913. | H | 3-(pyrazol-1-yl)-phenyl |
| 1914. | H | 3-(pyrazol-3-yl)-phenyl |
| 1915. | H | 3-(pyrazol-4-yl)-phenyl |
| 1916. | H | 3-(4-fluoropyrazol-1-yl)-phenyl |
| 1917. | H | 3-(1-methyl-1H-pyrazol-4-yl)-phenyl |
| 1918. | H | 3-(1-ethyl-1H-pyrazol-4-yl)-phenyl |
| 1919. | H | 3-(1-methyl-1H-pyrazol-5-yl)-phenyl |
| 1920. | H | 3-(1H-imidazol-2-yl)-phenyl |
| 1921. | H | 3-(imidazol-1-yl)-phenyl |
| 1922. | H | 3-(1-methylimidazol-2-yl)-phenyl |
| 1923. | H | 3-(oxazol-2-yl)-phenyl |

TABLE A-continued

| No. | R¹ | Ar |
|---|---|---|
| 1924. | H | 3-(oxazol-4-yl)-phenyl |
| 1925. | H | 3-(oxazol-5-yl)-phenyl |
| 1926. | H | 3-(isoxazol-3-yl)-phenyl |
| 1927. | H | 3-(isoxazol-4-yl)-phenyl |
| 1928. | H | 3-(isoxazol-5-yl)-phenyl |
| 1929. | H | 3-(thiazol-2-yl)-phenyl |
| 1930. | H | 3-(thiazol-4-yl)-phenyl |
| 1931. | H | 3-(thiazol-5-yl)-phenyl |
| 1932. | H | 3-(2-methylthiazol-4-yl)-phenyl |
| 1933. | H | 3-(2-methylthiazol-5-yl)-phenyl |
| 1934. | H | 3-([1,2,3]-triazol-1-yl)-phenyl |
| 1935. | H | 3-([1,2,4]-triazol-1-yl)-phenyl |
| 1936. | H | 3-([1,2,3]-triazol-2-yl)-phenyl |
| 1937. | H | 3-(4H-[1,2,4]-triazol-3-yl)-phenyl |
| 1938. | H | 3-([1,2,4]-triazol-4-yl)-phenyl |
| 1939. | H | 3-(2H-[1,2,3]-triazol-4-yl)-phenyl |
| 1940. | H | 3-(4-methyl-4H-[1,2,4]-triazol-3-yl)-phenyl |
| 1941. | H | 3-(2-methyl-2H-[1,2,3]-triazol-4-yl)-phenyl |
| 1942. | H | 3-([1,3,4]-oxadiazol-2-yl)-phenyl |
| 1943. | H | 3-(5-methyl-[1,3,4]-oxadiazol-2-yl)-phenyl |
| 1944. | H | 3-([1,2,4]-oxadiazol-3-yl)-phenyl |
| 1945. | H | 3-(5-methyl-[1,2,4]-oxadiazol-3-yl)-phenyl |
| 1946. | H | 3-([1,2,4]-oxadiazol-5-yl)-phenyl |
| 1947. | H | 3-([1,2,3]-oxadiazol-4-yl)-phenyl |
| 1948. | H | 3-([1,2,3]-oxadiazol-5-yl)-phenyl |
| 1949. | H | 3-([1,2,3]-thiadiazol-4-yl)-phenyl |
| 1950. | H | 3-(1H-tetrazol-5-yl)-phenyl |
| 1951. | H | 3-(tetrazol-1-yl)-phenyl |
| 1952. | H | 3-(2-methyl-2H-tetrazol-5-yl)-phenyl |
| 1953. | H | 3-(1-methyl-1H-tetrazol-5-yl)-phenyl |
| 1954. | H | 3-furazan-3-yl-phenyl |
| 1955. | H | 3-(pyrid-2-yl)-phenyl |
| 1956. | H | 3-(pyrid-3-yl)-phenyl |
| 1957. | H | 3-(pyrid-4-yl)-phenyl |
| 1958. | H | 3-(pyrimidin-2-yl)-phenyl |
| 1959. | H | 3-(2-methylpyrimidin-4-yl)-phenyl |
| 1960. | H | 3-(pyrimidin-4-yl)-phenyl |
| 1961. | H | 3-(pyrimidin-5-yl)-phenyl |
| 1962. | H | 5-bromopyridin-3-yl |
| 1963. | H | 3-bromo-2-chloropyridin-5-yl |
| 1964. | H | 4-methylpyridin-2-yl |
| 1965. | H | 6-methylpyridin-2-yl |
| 1966. | H | 4-(trifluoromethyl)-pyridin-2-yl |
| 1967. | H | 6-(trifluoromethyl)-pyridin-2-yl |
| 1968. | H | 5-(trifluoromethyl)-pyridin-3-yl |
| 1969. | H | 5-(pyrrolidin-1-yl)-pyridin-3-yl |
| 1970. | H | 3-(pyrrolidin-1-yl)-2-chloropyridin-5-yl |
| 1971. | H | 3-(morpholin-4-yl)-2-chloropyridin-5-yl |
| 1972. | H | 2-(morpholin-4-yl)-pyridin-5-yl |
| 1973. | H | 2-phenoxypyridin-5-yl |
| 1974. | H | 4-methylphenyl |
| 1975. | H | 4-ethylphenyl |
| 1976. | H | 4-propylphenyl |
| 1977. | H | 4-isopropylphenyl |
| 1978. | H | 4-sec-butylphenyl |
| 1979. | H | 4-tert-butylphenyl |
| 1980. | H | 4-isobutylphenyl |
| 1981. | H | 4-(1,1-dimethylpropyl)-phenyl |
| 1982. | H | 4-vinylphenyl |
| 1983. | H | 4-isopropenylphenyl |
| 1984. | H | 4-fluorophenyl |
| 1985. | H | 4-chlorophenyl |
| 1986. | H | 4-bromophenyl |
| 1987. | H | 4-iodophenyl |
| 1988. | H | 4-(fluoromethyl)phenyl |
| 1989. | H | 4-(difluoromethyl)phenyl |
| 1990. | H | 4-(trifluoromethyl)phenyl |
| 1991. | H | 2,4-bis(trifluoromethyl)phenyl |
| 1992. | H | 4-(1-fluoroethyl)-phenyl |
| 1993. | H | 4-((S)-1-fluoroethyl)-phenyl |
| 1994. | H | 4-((R)-1-fluoroethyl)-phenyl |
| 1995. | H | 4-(2-fluoroethyl)-phenyl |
| 1996. | H | 4-(1,1-difluoroethyl)-phenyl |
| 1997. | H | 4-(2,2-difluoroethyl)-phenyl |
| 1998. | H | 4-(2,2,2-trifluoroethyl)-phenyl |
| 1999. | H | 4-(3-fluoropropyl)-phenyl |
| 2000. | H | 4-(2-fluoropropyl)-phenyl |
| 2001. | H | 4-((S)-2-fluoropropyl)-phenyl |

TABLE A-continued

| No. | R¹ | Ar |
|---|---|---|
| 2002. | H | 4-((R)-2-fluoropropyl)-phenyl |
| 2003. | H | 4-(3,3-difluoropropyl)-phenyl |
| 2004. | H | 4-(3,3,3-trifluoropropyl)-phenyl |
| 2005. | H | 4-(1-fluoro-1-methylethyl)-phenyl |
| 2006. | H | 4-(2-fluoro-1-methylethyl)-phenyl |
| 2007. | H | 4-((S)-2-fluoro-1-methylethyl)-phenyl |
| 2008. | H | 4-((R)-2-fluoro-1-methylethyl)-phenyl |
| 2009. | H | 4-(2,2-difluoro-1-methylethyl)-phenyl |
| 2010. | H | 4-((S)-2,2-difluoro-1-methylethyl)-phenyl |
| 2011. | H | 4-((R)-2,2-difluoro-1-methylethyl)-phenyl |
| 2012. | H | 4-(2,2,2-trifluoro-1-methylethyl)-phenyl |
| 2013. | H | 4-((S)-2,2,2-trifluoro-1-methylethyl)-phenyl |
| 2014. | H | 4-((R)-2,2,2-trifluoro-1-methylethyl)-phenyl |
| 2015. | H | 4-(2-fluoro-1-fluoromethylethyl)-phenyl |
| 2016. | H | 4-(1-difluoromethyl-2,2-difluoroethyl)-phenyl |
| 2017. | H | 4-(1,1-dimethyl-2-fluoroethyl)-phenyl |
| 2018. | H | 4-methoxyphenyl |
| 2019. | H | 4-ethoxyphenyl |
| 2020. | H | 4-propoxyphenyl |
| 2021. | H | 4-isopropoxyphenyl |
| 2022. | H | 4-butoxyphenyl |
| 2023. | H | 4-(fluoromethoxy)-phenyl |
| 2024. | H | 4-(difluoromethoxy)-phenyl |
| 2025. | H | 4-(trifluoromethoxy)-phenyl |
| 2026. | H | 4-(2-fluoroethoxy)-phenyl |
| 2027. | H | 4-(2,2-difluoroethoxy)-phenyl |
| 2028. | H | 4-(2,2,2-trifluoroethoxy)-phenyl |
| 2029. | H | 4-(1,1,2,2-tetrafluoroethoxy)-phenyl |
| 2030. | H | 4-cyclopropylphenyl |
| 2031. | H | 4-cyclobutylphenyl |
| 2032. | H | 4-cyclopentylphenyl |
| 2033. | H | 4-(2,2-difluorocyclopropyl)-phenyl |
| 2034. | H | 3,4-difluorophenyl |
| 2035. | H | 4-bromo-2-fluorophenyl |
| 2036. | H | 2-bromo-4-fluorophenyl |
| 2037. | H | 4-bromo-2,5-difluorophenyl |
| 2038. | H | 5-bromo-2,4-difluorophenyl |
| 2039. | H | 3-bromo-2,4-difluorophenyl |
| 2040. | H | 3-chloro-4-(trifluoromethyl)-phenyl |
| 2041. | H | 4-fluoro-3-(trifluoromethyl)-phenyl |
| 2042. | H | 3-fluoro-5-(trifluoromethyl)-phenyl |
| 2043. | H | 3-bromo-4-(trifluoromethyl)-phenyl |
| 2044. | H | 5-bromo-3-(trifluoromethyl)-phenyl |
| 2045. | H | 5-bromo-2-(trifluoromethyl)-phenyl |
| 2046. | H | 2-bromo-5-methoxyphenyl |
| 2047. | H | 4-bromo-3-methoxyphenyl |
| 2048. | H | 3-fluoro-2-isopropylphenyl |
| 2049. | H | 3-fluoro-4-isopropylphenyl |
| 2050. | H | 4-(1-hydroxy-1-methylethyl)-phenyl |
| 2051. | H | 4-(2-hydroxy-2-methylpropyl)-phenyl |
| 2052. | H | 4-acetylphenyl |
| 2053. | H | 4-acetylaminophenyl |
| 2054. | H | 4-carboxyphenyl |
| 2055. | H | 4-cyanophenyl |
| 2056. | H | 4-nitrophenyl |
| 2057. | H | 4-hydroxyphenyl |
| 2058. | H | 4-(O-benzyl)-phenyl |
| 2059. | H | 4-(2-methoxyethoxy)-phenyl |
| 2060. | H | 4-(CH$_2$—N(CH$_3$)$_2$)-phenyl |
| 2061. | H | 4-(NH—CO—NH$_2$)-phenyl |
| 2062. | H | 4-(methylsulfanyl)-phenyl |
| 2063. | H | 4-(fluoromethylsulfanyl)-phenyl |
| 2064. | H | 4-(difluoromethylsulfanyl)-phenyl |
| 2065. | H | 4-(trifluoromethylsulfanyl)-phenyl |
| 2066. | H | 4-(methylsulfonyl)-phenyl |
| 2067. | H | 4-(N-methoxy-N-methyl-amino)-phenyl |
| 2068. | H | 4-(methoxyamino)-phenyl |
| 2069. | H | 4-(ethoxyamino)-phenyl |
| 2070. | H | 4-(N-methylaminooxy)-phenyl |
| 2071. | H | 4-(N,N-dimethylaminooxy)-phenyl |
| 2072. | H | 4-(azetidin-1-yl)-phenyl |
| 2073. | H | 4-(2-methylazetidin-1-yl)-phenyl |
| 2074. | H | 4-((S)-2-methylazetidin-1-yl)-phenyl |
| 2075. | H | 4-((R)-2-methylazetidin-1-yl)-phenyl |
| 2076. | H | 4-(3-fluoroazetidin-1-yl)-phenyl |
| 2077. | H | 4-(2,2-difluoroazetidin-1-yl)-phenyl |
| 2078. | H | 4-(3-methoxyazetidin-1-yl)-phenyl |
| 2079. | H | 4-(3-hydroxyazetidin-1-yl)-phenyl |

TABLE A-continued

| No. | R¹ | Ar |
|---|---|---|
| 2080. | H | 4-(pyrrolidin-1-yl)-phenyl |
| 2081. | H | 4-(pyrrolidin-2-yl)-phenyl |
| 2082. | H | 4-((S)-pyrrolidin-2-yl)-phenyl |
| 2083. | H | 4-((R)-pyrrolidin-2-yl)-phenyl |
| 2084. | H | 4-(pyrrolidin-3-yl)-phenyl |
| 2085. | H | 4-((S)-pyrrolidin-3-yl)-phenyl |
| 2086. | H | 4-((R)-pyrrolidin-3-yl)-phenyl |
| 2087. | H | 4-(pyrrolidin-1-yl)-5-(trifluoromethyl)-phenyl |
| 2088. | H | 4-(pyrrolidin-1-yl)-2-methoxyphenyl |
| 2089. | H | 4-(pyrrolidin-1-yl)-34-methoxyphenyl |
| 2090. | H | 4-(pyrrolidin-1-yl)-2,5-difluorophenyl |
| 2091. | H | 4-(pyrrolidin-1-yl)-2,6-difluorophenyl |
| 2092. | H | 4-(2-fluoropyrrolidin-1-yl)-phenyl |
| 2093. | H | 4-((S)-2-fluoropyrrolidin-1-yl)-phenyl |
| 2094. | H | 4-((R)-2-fluoropyrrolidin-1-yl)-phenyl |
| 2095. | H | 4-(3-fluoropyrrolidin-1-yl)-phenyl |
| 2096. | H | 4-((S)-3-fluoropyrrolidin-1-yl)-phenyl |
| 2097. | H | 4-((R)-3-fluoropyrrolidin-1-yl)-phenyl |
| 2098. | H | 4-(2,2-difluoropyrrolidin-1-yl)-phenyl |
| 2099. | H | 4-(3,3-difluoropyrrolidin-1-yl)-phenyl |
| 2100. | H | 4-(2-methylpyrrolidin-1-yl)-phenyl |
| 2101. | H | 4-((S)-2-methylpyrrolidin-1-yl)-phenyl |
| 2102. | H | 4-((R)-2-methylpyrrolidin-1-yl)-phenyl |
| 2103. | H | 4-(3-methylpyrrolidin-1-yl)-phenyl |
| 2104. | H | 4-((S)-3-methylpyrrolidin-1-yl)-phenyl |
| 2105. | H | 4-((R)-3-methylpyrrolidin-1-yl)-phenyl |
| 2106. | H | 4-(1-methylpyrrolidin-2-yl)-phenyl |
| 2107. | H | 4-((S)-1-methylpyrrolidin-2-yl)-phenyl |
| 2108. | H | 4-((R)-1-methylpyrrolidin-2-yl)-phenyl |
| 2109. | H | 4-(1-methylpyrrolidin-3-yl)-phenyl |
| 2110. | H | 4-((S)-1-methylpyrrolidin-3-yl)-phenyl |
| 2111. | H | 4-((R)-1-methylpyrrolidin-3-yl)-phenyl |
| 2112. | H | 4-(2,2-dimethylpyrrolidin-1-yl)-phenyl |
| 2113. | H | 4-(3,3-dimethylpyrrolidin-1-yl)-phenyl |
| 2114. | H | 4-(2-trifluoromethylpyrrolidin-1-yl)-phenyl |
| 2115. | H | 4-((S)-2-trifluoromethylpyrrolidin-1-yl)-phenyl |
| 2116. | H | 4-((R)-2-trifluoromethylpyrrolidin-1-yl)-phenyl |
| 2117. | H | 4-(3-trifluoromethylpyrrolidin-1-yl)-phenyl |
| 2118. | H | 4-((S)-3-trifluoromethylpyrrolidin-1-yl)-phenyl |
| 2119. | H | 4-((R)-3-trifluoromethylpyrrolidin-1-yl)-phenyl |
| 2120. | H | 4-(2-oxopyrrolidin-1-yl)-phenyl |
| 2121. | H | 4-(2-oxo-oxazolidin-3-yl)-phenyl |
| 2122. | H | 4-(piperidin-1-yl)-phenyl |
| 2123. | H | 4-(2-methylpiperidin-1-yl)-phenyl |
| 2124. | H | 4-((S)-2-methylpiperidin-1-yl)-phenyl |
| 2125. | H | 4-((R)-2-methylpiperidin-1-yl)-phenyl |
| 2126. | H | 4-(2-fluoropiperidin-1-yl)-phenyl |
| 2127. | H | 4-((S)-2-fluoropiperidin-1-yl)-phenyl |
| 2128. | H | 4-((R)-2-fluoropiperidin-1-yl)-phenyl |
| 2129. | H | 4-(2,2-difluoropiperidin-1-yl)-phenyl |
| 2130. | H | 4-(piperazin-1-yl)-phenyl |
| 2131. | H | 4-(4-methylpiperazin-1-yl)-phenyl |
| 2132. | H | 4-(morpholin-4-yl)-phenyl |
| 2133. | H | 4-(morpholin-4-yl)-5-(trifluoromethyl)-phenyl |
| 2134. | H | 4-(morpholin-4-yl)-2-methoxyphenyl |
| 2135. | H | 4-(morpholin-4-yl)-3-methoxyphenyl |
| 2136. | H | 4-(morpholin-4-yl)-2,5-difluorophenyl |
| 2137. | H | 4-(morpholin-4-yl)-2,6-difluorophenyl |
| 2138. | H | 4-(thiomorpholin-4-yl)-phenyl |
| 2139. | H | 4-(1-oxo-thiomorpholin-4-yl)-phenyl |
| 2140. | H | 4-(1,1-dioxo-thiomorpholin-4-yl)-phenyl |
| 2141. | H | 4-(pyrrol-1-yl)-phenyl |
| 2142. | H | 4-(pyrrol-2-yl)-phenyl |
| 2143. | H | 4-(pyrrol-3-yl)-phenyl |
| 2144. | H | 4-(1-methylpyrrol-2-yl)-phenyl |
| 2145. | H | 4-(1-methylpyrrol-3-yl)-phenyl |
| 2146. | H | 4-(furan-2-yl)-phenyl |
| 2147. | H | 4-(furan-3-yl)-phenyl |
| 2148. | H | 4-(thiophen-2-yl)-phenyl |
| 2149. | H | 4-(thiophen-3-yl)-phenyl |
| 2150. | H | 4-(5-propylthien-2-yl)-phenyl |
| 2151. | H | 4-(pyrazol-1-yl)-phenyl |
| 2152. | H | 4-(pyrazol-3-yl)-phenyl |
| 2153. | H | 4-(pyrazol-4-yl)-phenyl |
| 2154. | H | 4-(1-methyl-1H-pyrazol-4-yl)-phenyl |
| 2155. | H | 4-(1-ethyl-1H-pyrazol-4-yl)-phenyl |
| 2156. | H | 4-(1-methyl-1H-pyrazol-5-yl)-phenyl |
| 2157. | H | 4-(1H-imidazol-2-yl)-phenyl |

TABLE A-continued

| No. | R¹ | Ar |
|---|---|---|
| 2158. | H | 4-(imidazol-1-yl)-phenyl |
| 2159. | H | 4-(1-methylimidazol-2-yl)-phenyl |
| 2160. | H | 4-(oxazol-2-yl)-phenyl |
| 2161. | H | 4-(oxazol-4-yl)-phenyl |
| 2162. | H | 4-(oxazol-5-yl)-phenyl |
| 2163. | H | 4-(isoxazol-3-yl)-phenyl |
| 2164. | H | 4-(isoxazol-4-yl)-phenyl |
| 2165. | H | 4-(isoxazol-5-yl)-phenyl |
| 2166. | H | 4-(thiazol-2-yl)-phenyl |
| 2167. | H | 4-(thiazol-4-yl)-phenyl |
| 2168. | H | 4-(thiazol-5-yl)-phenyl |
| 2169. | H | 4-(2-methylthiazol-4-yl)-phenyl |
| 2170. | H | 4-(4-fluoropyrazol-1-yl)-phenyl |
| 2171. | H | 4-([1,2,3]-triazol-1-yl)-phenyl |
| 2172. | H | 4-([1,2,4]-triazol-1-yl)-phenyl |
| 2173. | H | 4-([1,2,3]-triazol-2-yl)-phenyl |
| 2174. | H | 4-(4H-[1,2,4]-triazol-3-yl)-phenyl |
| 2175. | H | 4-([1,2,4]-triazol-4-yl)-phenyl |
| 2176. | H | 4-(2H-[1,2,3]-triazol-4-yl)-phenyl |
| 2177. | H | 4-(4-methyl-4H-[1,2,4]-triazol-3-yl)-phenyl |
| 2178. | H | 4-(2-methyl-2H-[1,2,3]-triazol-4-yl)-phenyl |
| 2179. | H | 4-([1,3,4]-oxadiazol-2-yl)-phenyl |
| 2180. | H | 4-(5-methyl-[1,3,4]-oxadiazol-2-yl)-phenyl |
| 2181. | H | 4-([1,2,4]-oxadiazol-3-yl)-phenyl |
| 2182. | H | 4-(5-methyl-[1,2,4]-oxadiazol-3-yl)-phenyl |
| 2183. | H | 4-([1,2,4]-oxadiazol-5-yl)-phenyl |
| 2184. | H | 4-([1,2,3]-oxadiazol-4-yl)-phenyl |
| 2185. | H | 4-([1,2,3]-oxadiazol-5-yl)-phenyl |
| 2186. | H | 4-([1,2,3]-thiadiazol-4-yl)-phenyl |
| 2187. | H | 4-(1H-tetrazol-5-yl)-phenyl |
| 2188. | H | 4-(tetrazol-1-yl)-phenyl |
| 2189. | H | 4-(2-methyl-2H-tetrazol-5-yl)-phenyl |
| 2190. | H | 4-(1-methyl-1H-tetrazol-5-yl)-phenyl |
| 2191. | H | 4-furazan-3-yl-phenyl |
| 2192. | H | 4-(pyrid-2-yl)-phenyl |
| 2193. | H | 4-(pyrid-3-yl)-phenyl |
| 2194. | H | 4-(pyrid-4-yl)-phenyl |
| 2195. | H | 4-(pyrimidin-2-yl)-phenyl |
| 2196. | H | 4-(2-methylpyrimidin-4-yl)-phenyl |
| 2197. | H | 4-(pyrimidin-4-yl)-phenyl |
| 2198. | H | 4-(pyrimidin-5-yl)-phenyl |
| 2199. | H | 4-bromo-2-chloropyridin-5-yl |
| 2200. | H | 4-methylpyridin-2-yl |
| 2201. | H | 5-methylpyridin-2-yl |
| 2202. | H | 4-(pyrrolidin-1-yl)-2-chloropyridin-5-yl |
| 2203. | H | 4-(morpholin-4-yl)-2-chloropyridin-5-yl |
| 2204. | H | 2-(morpholin-4-yl)-pyridin-5-yl |
| 2205. | H | 5-(morpholin-4-yl)-pyridin-2-yl |
| 2206. | H | 2-phenoxypyridin-5-yl |
| 2207. | H | 2,3-dichlorophenyl |
| 2208. | H | 2,5-dichlorophenyl |
| 2209. | H | 3,5-dichlorophenyl |
| 2210. | H | 3-chloro-4-fluorophenyl |
| 2211. | H | 4-bromo-2,5-dichlorophenyl |
| 2212. | H | 3-bromo-4-(trifluoromethoxy)phenyl |
| 2213. | H | 3,5-dibromo-4-(2-fluoroethoxy)-phenyl |
| 2214. | H | 2,5-dimethylphenyl |
| 2215. | H | 2,5-di-(trifluoromethyl)-phenyl |
| 2216. | H | 3,5-di-(trifluoromethyl)-phenyl |
| 2217. | H | 2,5-dimethoxyphenyl |
| 2218. | H | 2-methoxy-5-methylphenyl |
| 2219. | H | 2-methoxy-5-(trifluoromethyl)-phenyl |
| 2220. | H | 4-fluoro-3-(oxazol-4-yl)-phenyl |
| 2221. | H | thien-2-yl |
| 2222. | H | thien-3-yl |
| 2223. | H | 3-chlorothien-2-yl |
| 2224. | H | 4-chlorothien-2-yl |
| 2225. | H | 5-chlorothien-2-yl |
| 2226. | H | 3-bromothien-2-yl |
| 2227. | H | 4-bromothien-2-yl |
| 2228. | H | 5-bromothien-2-yl |
| 2229. | H | 4,5-dichlorothien-2-yl |
| 2230. | H | 4,5-dibromothien-2-yl |
| 2231. | H | 4-bromo-5-chlorothien-2-yl |
| 2232. | H | 3-bromo-5-chlorothien-2-yl |
| 2233. | H | 5-methylthien-2-yl |
| 2234. | H | 5-ethylthien-2-yl |
| 2235. | H | 5-propylthien-2-yl |

TABLE A-continued

| No. | R¹ | Ar |
|---|---|---|
| 2236. | H | 5-trifluoromethylthien-2-yl |
| 2237. | H | 5-phenylthien-2-yl |
| 2238. | H | 5-(pyrid-2-yl)-thien-2-yl |
| 2239. | H | 5-(phenylsulfonyl)-thien-2-yl |
| 2240. | H | 4-(phenylsulfonyl)-thien-2-yl |
| 2241. | H | 5-(pyrid-2-ylsulfonyl)-thien-2-yl |
| 2242. | H | 5-(3-chloro-5-trifluoro-pyrid-2-ylsulfonyl)-thien-2-yl |
| 2243. | H | 5-(benzoylaminomethyl)-thien-2-yl |
| 2244. | H | 5-((4-chlorobenzoyl)aminomethyl)-thien-2-yl |
| 2245. | H | 5-(acetylaminomethyl)-thien-2-yl |
| 2246. | H | 5-(pyrazol-1-yl)-thien-2-yl |
| 2247. | H | 5-(pyrazol-3-yl)-thien-2-yl |
| 2248. | H | 5-(pyrazol-4-yl)-thien-2-yl |
| 2249. | H | 5-(pyrazol-5-yl)-thien-2-yl |
| 2250. | H | 5-(4-fluoropyrazol-1-yl)-thien-2-yl |
| 2251. | H | 5-(1-methyl-5-trifluoromethyl-(1H)-pyrazol-3-yl)-thien-2-yl |
| 2252. | H | 5-(1-methyl-3-trifluoromethyl-(1H)-pyrazol-5-yl)-thien-2-yl |
| 2253. | H | 5-(4-carboxy-1-methyl-5-methylthio-(1H)-pyrazol-3-yl)-thien-2-yl |
| 2254. | H | 5-(4-aminomethyl-1-methyl-5-methylthio-(1H)-pyrazol-3-yl)-thien-2-yl |
| 2255. | H | 5-(isoxazol-3-yl)-thien-2-yl |
| 2256. | H | 5-(isoxazol-4-yl)-thien-2-yl |
| 2257. | H | 5-(isoxazol-5-yl)-thien-2-yl |
| 2258. | H | 5-(5-trifluoromethylisoxazol-3-yl)-thien-2-yl |
| 2259. | H | 5-(oxazol-2-yl)-thien-2-yl |
| 2260. | H | 5-(oxazol-4-yl)-thien-2-yl |
| 2261. | H | 5-(oxazol-5-yl)-thien-2-yl |
| 2262. | H | 5-(2-methyloxazol-4-yl)-thien-2-yl |
| 2263. | H | 5-(2-methyloxazol-5-yl)-thien-2-yl |
| 2264. | H | 5-(isothiazol-3-yl)-thien-2-yl |
| 2265. | H | 5-(isothiazol-4-yl)-thien-2-yl |
| 2266. | H | 5-(isothiazol-5-yl)-thien-2-yl |
| 2267. | H | 5-(5-trifluoromethylisothiazol-3-yl)-thien-2-yl |
| 2268. | H | 5-(thiazol-2-yl)-thien-2-yl |
| 2269. | H | 5-(thiazol-4-yl)-thien-2-yl |
| 2270. | H | 5-(thiazol-5-yl)-thien-2-yl |
| 2271. | H | 5-(2-methylthiazol-4-yl)-thien-2-yl |
| 2272. | H | 5-(2-methylthiazol-5-yl)-thien-2-yl |
| 2273. | H | 5-([1,2,3]-oxadiazol-4-yl)-thien-2-yl |
| 2274. | H | 5-([1,2,3]-thiadiazol-4-yl)-thien-2-yl |
| 2275. | H | 5-(pyrimidin-2-yl)-thien-2-yl |
| 2276. | H | 5-(pyrimidin-4-yl)-thien-2-yl |
| 2277. | H | 5-(pyrimidin-5-yl)-thien-2-yl |
| 2278. | H | 5-(2-methylthiopyrimidin-4-yl)-thien-2-yl |
| 2279. | H | 5-([1,3]-dioxolan-2-yl)-thien-2-yl |
| 2280. | H | 3-([1,3]-dioxolan-2-yl)-thien-2-yl thien-2-yl |
| 2281. | H | 5-((3-chloro-5-(trifluoromethyl)-pyridin-2-yl)-methyl)-thien-2-yl |
| 2282. | H | 5-[3-chloro-5-(trifluoromethyl)-pyrid-2-ylsulfonyl]-thien-2-yl |
| 2283. | H | 2-chlorothien-3-yl |
| 2284. | H | 4-chlorothien-3-yl |
| 2285. | H | 5-chlorothien-3-yl |
| 2286. | H | 2-bromothien-3-yl |
| 2287. | H | 4-bromothien-3-yl |
| 2288. | H | 5-bromothien-3-yl |
| 2289. | H | 2,5-dichlorothien-3-yl |
| 2290. | H | 2,5-dibromothien-3-yl |
| 2291. | H | 2,4,5-trichlorothien-3-yl |
| 2292. | H | 4-bromo-2,5-dichlorothien-3-yl |
| 2293. | H | 2-chloro-5-methylsulfonylthien-3-yl |
| 2294. | H | 2,5-dimethylthien-3-yl |
| 2295. | H | 4-hydroxythien-3-yl |
| 2296. | H | 2-phenylthien-3-yl |
| 2297. | H | 4-phenyl-5-(trofluoromethyl)-thien-3-yl |
| 2298. | H | 2-methoxycarbonyl-4-phenyl-5-(trifluoromethyl)-thien-3-yl |
| 2299. | H | benzo[b]thiophen-2-yl |
| 2300. | H | benzo[b]thiophen-3-yl |
| 2301. | H | 3-methyl-benzo[b]thiophen-2-yl |
| 2302. | H | 5-methyl-benzo[b]thiophen-2-yl |
| 2303. | H | 5-fluoro-3-methyl-benzo[b]thiophen-2-yl |
| 2304. | H | 5-chloro-3-methyl-benzo[b]thiophen-2-yl |
| 2305. | H | 5-bromo-3-methyl-benzo[b]thiophen-2-yl |
| 2306. | 3-fluoropropyl | 3-methylphenyl |

TABLE A-continued

| No. | R¹ | Ar |
|---|---|---|
| 2307. | 3-fluoropropyl | 3-ethylphenyl |
| 2308. | 3-fluoropropyl | 3-propylphenyl |
| 2309. | 3-fluoropropyl | 3-isopropylphenyl |
| 2310. | 3-fluoropropyl | 3-sec-butylphenyl |
| 2311. | 3-fluoropropyl | 3-tert-butylphenyl |
| 2312. | 3-fluoropropyl | 3-isobutylphenyl |
| 2313. | 3-fluoropropyl | 3-(1,1-dimethylpropyl)-phenyl |
| 2314. | 3-fluoropropyl | 3-vinylphenyl |
| 2315. | 3-fluoropropyl | 3-isopropenylphenyl |
| 2316. | 3-fluoropropyl | 3-fluorophenyl |
| 2317. | 3-fluoropropyl | 2-fluorophenyl |
| 2318. | 3-fluoropropyl | 3-chlorophenyl |
| 2319. | 3-fluoropropyl | 3-bromophenyl |
| 2320. | 3-fluoropropyl | 3-iodophenyl |
| 2321. | 3-fluoropropyl | 3-(fluoromethyl)phenyl |
| 2322. | 3-fluoropropyl | 3-(difluoromethyl)phenyl |
| 2323. | 3-fluoropropyl | 3-(trifluoromethyl)phenyl |
| 2324. | 3-fluoropropyl | 3,5-bis(trifluoromethyl)phenyl |
| 2325. | 3-fluoropropyl | 3-(1-fluoroethyl)-phenyl |
| 2326. | 3-fluoropropyl | 3-((S)-1-fluoroethyl)-phenyl |
| 2327. | 3-fluoropropyl | 3-((R)-1-fluoroethyl)-phenyl |
| 2328. | 3-fluoropropyl | 3-(2-fluoroethyl)-phenyl |
| 2329. | 3-fluoropropyl | 3-(1,1-difluoroethyl)-phenyl |
| 2330. | 3-fluoropropyl | 3-(2,2-difluoroethyl)-phenyl |
| 2331. | 3-fluoropropyl | 3-(2,2,2-trifluoroethyl)-phenyl |
| 2332. | 3-fluoropropyl | 3-(3-fluoropropyl)-phenyl |
| 2333. | 3-fluoropropyl | 3-(2-fluoropropyl)-phenyl |
| 2334. | 3-fluoropropyl | 3-((S)-2-fluoropropyl)-phenyl |
| 2335. | 3-fluoropropyl | 3-((R)-2-fluoropropyl)-phenyl |
| 2336. | 3-fluoropropyl | 3-(3,3-difluoropropyl)-phenyl |
| 2337. | 3-fluoropropyl | 3-(3,3,3-trifluoropropyl)-phenyl |
| 2338. | 3-fluoropropyl | 3-(1-fluoro-1-methylethyl)-phenyl |
| 2339. | 3-fluoropropyl | 3-(2-fluoro-1-methylethyl)-phenyl |
| 2340. | 3-fluoropropyl | 3-((S)-2-fluoro-1-methylethyl)-phenyl |
| 2341. | 3-fluoropropyl | 3-((R)-2-fluoro-1-methylethyl)-phenyl |
| 2342. | 3-fluoropropyl | 3-(2,2-difluoro-1-methylethyl)-phenyl |
| 2343. | 3-fluoropropyl | 3-((S)-2,2-difluoro-1-methylethyl)-phenyl |
| 2344. | 3-fluoropropyl | 3-((R)-2,2-difluoro-1-methylethyl)-phenyl |
| 2345. | 3-fluoropropyl | 3-(2,2,2-trifluoro-1-methylethyl)-phenyl |
| 2346. | 3-fluoropropyl | 3-((S)-2,2,2-trifluoro-1-methylethyl)-phenyl |
| 2347. | 3-fluoropropyl | 3-((R)-2,2,2-trifluoro-1-methylethyl)-phenyl |
| 2348. | 3-fluoropropyl | 3-(2-fluoro-1-fluoromethylethyl)-phenyl |
| 2349. | 3-fluoropropyl | 3-(1-difluoromethyl-2,2-difluoroethyl)-phenyl |
| 2350. | 3-fluoropropyl | 3-(1,1-dimethyl-2-fluoroethyl)-phenyl |
| 2351. | 3-fluoropropyl | 3-methoxyphenyl |
| 2352. | 3-fluoropropyl | 3-ethoxyphenyl |
| 2353. | 3-fluoropropyl | 3-propoxyphenyl |
| 2354. | 3-fluoropropyl | 3-isopropoxyphenyl |
| 2355. | 3-fluoropropyl | 3-butoxyphenyl |
| 2356. | 3-fluoropropyl | 3-(fluoromethoxy)-phenyl |
| 2357. | 3-fluoropropyl | 3-(difluoromethoxy)-phenyl |
| 2358. | 3-fluoropropyl | 3-(trifluoromethoxy)-phenyl |
| 2359. | 3-fluoropropyl | 3-(2-fluoroethoxy)-phenyl |
| 2360. | 3-fluoropropyl | 3-(2,2-difluoroethoxy)-phenyl |
| 2361. | 3-fluoropropyl | 3-(2,2,2-trifluoroethoxy)-phenyl |
| 2362. | 3-fluoropropyl | 3-(1,1,2,2-tetrafluoroethoxy)-phenyl |
| 2363. | 3-fluoropropyl | 3-cyclopropylphenyl |
| 2364. | 3-fluoropropyl | 3-cyclobutylphenyl |
| 2365. | 3-fluoropropyl | 3-cyclopentylphenyl |
| 2366. | 3-fluoropropyl | 3-(2,2-difluorocyclopropyl)-phenyl |
| 2367. | 3-fluoropropyl | 3,4-difluorophenyl |
| 2368. | 3-fluoropropyl | 3-bromo-2-fluorophenyl |
| 2369. | 3-fluoropropyl | 2-bromo-3-fluorophenyl |
| 2370. | 3-fluoropropyl | 3-bromo-2,5-difluorophenyl |
| 2371. | 3-fluoropropyl | 5-bromo-2,4-difluorophenyl |
| 2372. | 3-fluoropropyl | 3-bromo-2,4-difluorophenyl |
| 2373. | 3-fluoropropyl | 4-chloro-3-(trifluoromethyl)-phenyl |
| 2374. | 3-fluoropropyl | 2-chloro-5-(trifluoromethyl)-phenyl |
| 2375. | 3-fluoropropyl | 2-fluoro-5-(trifluoromethyl)-phenyl |
| 2376. | 3-fluoropropyl | 4-fluoro-3-(trifluoromethyl)-phenyl |
| 2377. | 3-fluoropropyl | 3-fluoro-5-(trifluoromethyl)-phenyl |
| 2378. | 3-fluoropropyl | 4-bromo-3-(trifluoromethyl)-phenyl |
| 2379. | 3-fluoropropyl | 3-bromo-5-(trifluoromethyl)-phenyl |
| 2380. | 3-fluoropropyl | 2-bromo-5-(trifluoromethyl)-phenyl |
| 2381. | 3-fluoropropyl | 5-bromo-2-methoxyphenyl |
| 2382. | 3-fluoropropyl | 3-bromo-4-methoxyphenyl |
| 2383. | 3-fluoropropyl | 2-fluoro-3-isopropylphenyl |
| 2384. | 3-fluoropropyl | 4-fluoro-3-isopropylphenyl |

TABLE A-continued

| No. | R¹ | Ar |
|---|---|---|
| 2385. | 3-fluoropropyl | 3-(1-hydroxy-1-methylethyl)-phenyl |
| 2386. | 3-fluoropropyl | 3-(2-hydroxy-2-methylpropyl)-phenyl |
| 2387. | 3-fluoropropyl | 3-acetylphenyl |
| 2388. | 3-fluoropropyl | 3-acetylaminophenyl |
| 2389. | 3-fluoropropyl | 3-carboxyphenyl |
| 2390. | 3-fluoropropyl | 3-cyanophenyl |
| 2391. | 3-fluoropropyl | 3-nitrophenyl |
| 2392. | 3-fluoropropyl | 3-hydroxyphenyl |
| 2393. | 3-fluoropropyl | 3-(O-benzyl)-phenyl |
| 2394. | 3-fluoropropyl | 3-(2-methoxyethoxy)-phenyl |
| 2395. | 3-fluoropropyl | 3-(CH$_2$—N(CH$_3$)$_2$)-phenyl |
| 2396. | 3-fluoropropyl | 3-(NH—CO—NH$_2$)-phenyl |
| 2397. | 3-fluoropropyl | 3-(methylsulfanyl)-phenyl |
| 2398. | 3-fluoropropyl | 3-(fluoromethylsulfanyl)-phenyl |
| 2399. | 3-fluoropropyl | 3-(difluoromethylsulfanyl)-phenyl |
| 2400. | 3-fluoropropyl | 3-(trifluoromethylsulfanyl)-phenyl |
| 2401. | 3-fluoropropyl | 3-(methylsulfonyl)-phenyl |
| 2402. | 3-fluoropropyl | 3-(N-methoxy-N-methyl-amino)-phenyl |
| 2403. | 3-fluoropropyl | 3-(methoxyamino)-phenyl |
| 2404. | 3-fluoropropyl | 3-(ethoxyamino)-phenyl |
| 2405. | 3-fluoropropyl | 3-(N-methylaminooxy)-phenyl |
| 2406. | 3-fluoropropyl | 3-(N,N-dimethylaminooxy)-phenyl |
| 2407. | 3-fluoropropyl | 3-(azetidin-1-yl)-phenyl |
| 2408. | 3-fluoropropyl | 3-(2-methylazetidin-1-yl)-phenyl |
| 2409. | 3-fluoropropyl | 3-((S)-2-methylazetidin-1-yl)-phenyl |
| 2410. | 3-fluoropropyl | 3-((R)-2-methylazetidin-1-yl)-phenyl |
| 2411. | 3-fluoropropyl | 3-(3-fluoroazetidin-1-yl)-phenyl |
| 2412. | 3-fluoropropyl | 3-(2,2-difluoroazetidin-1-yl)-phenyl |
| 2413. | 3-fluoropropyl | 3-(3-methoxyazetidin-1-yl)-phenyl |
| 2414. | 3-fluoropropyl | 3-(3-hydroxyazetidin-1-yl)-phenyl |
| 2415. | 3-fluoropropyl | 3-(pyrrolidin-1-yl)-phenyl |
| 2416. | 3-fluoropropyl | 3-(pyrrolidin-2-yl)-phenyl |
| 2417. | 3-fluoropropyl | 3-((S)-pyrrolidin-2-yl)-phenyl |
| 2418. | 3-fluoropropyl | 3-((R)-pyrrolidin-2-yl)-phenyl |
| 2419. | 3-fluoropropyl | 3-(pyrrolidin-3-yl)-phenyl |
| 2420. | 3-fluoropropyl | 3-((S)-pyrrolidin-3-yl)-phenyl |
| 2421. | 3-fluoropropyl | 3-((R)-pyrrolidin-3-yl)-phenyl |
| 2422. | 3-fluoropropyl | 3-(pyrrolidin-1-yl)-5-(trifluoromethyl)-phenyl |
| 2423. | 3-fluoropropyl | 5-(pyrrolidin-1-yl)-2-methoxyphenyl |
| 2424. | 3-fluoropropyl | 3-(pyrrolidin-1-yl)-4-methoxyphenyl |
| 2425. | 3-fluoropropyl | 5-(pyrrolidin-1-yl)-2,4-difluorophenyl |
| 2426. | 3-fluoropropyl | 3-(pyrrolidin-1-yl)-2,4-difluorophenyl |
| 2427. | 3-fluoropropyl | 3-(2-fluoropyrrolidin-1-yl)-phenyl |
| 2428. | 3-fluoropropyl | 3-((S)-2-fluoropyrrolidin-1-yl)-phenyl |
| 2429. | 3-fluoropropyl | 3-((R)-2-fluoropyrrolidin-1-yl)-phenyl |
| 2430. | 3-fluoropropyl | 3-(3-fluoropyrrolidin-1-yl)-phenyl |
| 2431. | 3-fluoropropyl | 3-((S)-3-fluoropyrrolidin-1-yl)-phenyl |
| 2432. | 3-fluoropropyl | 3-((R)-3-fluoropyrrolidin-1-yl)-phenyl |
| 2433. | 3-fluoropropyl | 3-(2,2-difluoropyrrolidin-1-yl)-phenyl |
| 2434. | 3-fluoropropyl | 3-(3,3-difluoropyrrolidin-1-yl)-phenyl |
| 2435. | 3-fluoropropyl | 3-(2-methylpyrrolidin-1-yl)-phenyl |
| 2436. | 3-fluoropropyl | 3-((S)-2-methylpyrrolidin-1-yl)-phenyl |
| 2437. | 3-fluoropropyl | 3-((R)-2-methylpyrrolidin-1-yl)-phenyl |
| 2438. | 3-fluoropropyl | 3-(3-methylpyrrolidin-1-yl)-phenyl |
| 2439. | 3-fluoropropyl | 3-((S)-3-methylpyrrolidin-1-yl)-phenyl |
| 2440. | 3-fluoropropyl | 3-((R)-3-methylpyrrolidin-1-yl)-phenyl |
| 2441. | 3-fluoropropyl | 3-(1-methylpyrrolidin-2-yl)-phenyl |
| 2442. | 3-fluoropropyl | 3-((S)-1-methylpyrrolidin-2-yl)-phenyl |
| 2443. | 3-fluoropropyl | 3-((R)-1-methylpyrrolidin-2-yl)-phenyl |
| 2444. | 3-fluoropropyl | 3-(1-methylpyrrolidin-3-yl)-phenyl |
| 2445. | 3-fluoropropyl | 3-((S)-1-methylpyrrolidin-3-yl)-phenyl |
| 2446. | 3-fluoropropyl | 3-((R)-1-methylpyrrolidin-3-yl)-phenyl |
| 2447. | 3-fluoropropyl | 3-(2,2-dimethylpyrrolidin-1-yl)-phenyl |
| 2448. | 3-fluoropropyl | 3-(3,3-dimethylpyrrolidin-1-yl)-phenyl |
| 2449. | 3-fluoropropyl | 3-(2-trifluoromethylpyrrolidin-1-yl)-phenyl |
| 2450. | 3-fluoropropyl | 3-((S)-2-trifluoromethylpyrrolidin-1-yl)-phenyl |
| 2451. | 3-fluoropropyl | 3-((R)-2-trifluoromethylpyrrolidin-1-yl)-phenyl |
| 2452. | 3-fluoropropyl | 3-(3-trifluoromethylpyrrolidin-1-yl)-phenyl |
| 2453. | 3-fluoropropyl | 3-((S)-3-trifluoromethylpyrrolidin-1-yl)-phenyl |
| 2454. | 3-fluoropropyl | 3-((R)-3-trifluoromethylpyrrolidin-1-yl)-phenyl |
| 2455. | 3-fluoropropyl | 3-(2-oxopyrrolidin-1-yl)-phenyl |
| 2456. | 3-fluoropropyl | 3-(2-oxo-oxazolidin-3-yl)-phenyl |
| 2457. | 3-fluoropropyl | 3-(piperidin-1-yl)-phenyl |
| 2458. | 3-fluoropropyl | 3-(2-methylpiperidin-1-yl)-phenyl |
| 2459. | 3-fluoropropyl | 3-((S)-2-methylpiperidin-1-yl)-phenyl |
| 2460. | 3-fluoropropyl | 3-((R)-2-methylpiperidin-1-yl)-phenyl |
| 2461. | 3-fluoropropyl | 3-(2-fluoropiperidin-1-yl)-phenyl |
| 2462. | 3-fluoropropyl | 3-((S)-2-fluoropiperidin-1-yl)-phenyl |

TABLE A-continued

| No. | R¹ | Ar |
|---|---|---|
| 2463. | 3-fluoropropyl | 3-((R)-2-fluoropiperidin-1-yl)-phenyl |
| 2464. | 3-fluoropropyl | 3-(2,2-difluoropiperidin-1-yl)-phenyl |
| 2465. | 3-fluoropropyl | 3-(piperazin-1-yl)-phenyl |
| 2466. | 3-fluoropropyl | 3-(4-methylpiperazin-1-yl)-phenyl |
| 2467. | 3-fluoropropyl | 3-(morpholin-4-yl)-phenyl |
| 2468. | 3-fluoropropyl | 3-(morpholin-4-yl)-5-(trifluoromethyl)-phenyl |
| 2469. | 3-fluoropropyl | 5-(morpholin-4-yl)-2-methoxyphenyl |
| 2470. | 3-fluoropropyl | 3-(morpholin-4-yl)-4-methoxyphenyl |
| 2471. | 3-fluoropropyl | 5-(morpholin-4-yl)-2,4-difluorophenyl |
| 2472. | 3-fluoropropyl | 3-(morpholin-4-yl)-2,4-difluorophenyl |
| 2473. | 3-fluoropropyl | 3-(thiomorpholin-4-yl)-phenyl |
| 2474. | 3-fluoropropyl | 3-(1-oxo-thiomorpholin-4-yl)-phenyl |
| 2475. | 3-fluoropropyl | 3-(1,1-dioxo-thiomorpholin-4-yl)-phenyl |
| 2476. | 3-fluoropropyl | 3-(pyrrol-1-yl)-phenyl |
| 2477. | 3-fluoropropyl | 3-(pyrrol-2-yl)-phenyl |
| 2478. | 3-fluoropropyl | 3-(pyrrol-3-yl)-phenyl |
| 2479. | 3-fluoropropyl | 3-(1-methylpyrrol-2-yl)-phenyl |
| 2480. | 3-fluoropropyl | 3-(1-methylpyrrol-3-yl)-phenyl |
| 2481. | 3-fluoropropyl | 3-(furan-2-yl)-phenyl |
| 2482. | 3-fluoropropyl | 3-(furan-3-yl)-phenyl |
| 2483. | 3-fluoropropyl | 3-(thiophen-2-yl)-phenyl |
| 2484. | 3-fluoropropyl | 3-(thiophen-3-yl)-phenyl |
| 2485. | 3-fluoropropyl | 3-(5-propylthien-2-yl)-phenyl |
| 2486. | 3-fluoropropyl | 3-(pyrazol-1-yl)-phenyl |
| 2487. | 3-fluoropropyl | 3-(pyrazol-3-yl)-phenyl |
| 2488. | 3-fluoropropyl | 3-(pyrazol-4-yl)-phenyl |
| 2489. | 3-fluoropropyl | 3-(4-fluoropyrazol-1-yl)-phenyl |
| 2490. | 3-fluoropropyl | 3-(1-methyl-1H-pyrazol-4-yl)-phenyl |
| 2491. | 3-fluoropropyl | 3-(1-ethyl-1H-pyrazol-4-yl)-phenyl |
| 2492. | 3-fluoropropyl | 3-(1-methyl-1H-pyrazol-5-yl)-phenyl |
| 2493. | 3-fluoropropyl | 3-(1H-imidazol-2-yl)-phenyl |
| 2494. | 3-fluoropropyl | 3-(imidazol-1-yl)-phenyl |
| 2495. | 3-fluoropropyl | 3-(1-methylimidazol-2-yl)-phenyl |
| 2496. | 3-fluoropropyl | 3-(oxazol-2-yl)-phenyl |
| 2497. | 3-fluoropropyl | 3-(oxazol-4-yl)-phenyl |
| 2498. | 3-fluoropropyl | 3-(oxazol-5-yl)-phenyl |
| 2499. | 3-fluoropropyl | 3-(isoxazol-3-yl)-phenyl |
| 2500. | 3-fluoropropyl | 3-(isoxazol-4-yl)-phenyl |
| 2501. | 3-fluoropropyl | 3-(isoxazol-5-yl)-phenyl |
| 2502. | 3-fluoropropyl | 3-(thiazol-2-yl)-phenyl |
| 2503. | 3-fluoropropyl | 3-(thiazol-4-yl)-phenyl |
| 2504. | 3-fluoropropyl | 3-(thiazol-5-yl)-phenyl |
| 2505. | 3-fluoropropyl | 3-(2-methylthiazol-4-yl)-phenyl |
| 2506. | 3-fluoropropyl | 3-(2-methylthiazol-5-yl)-phenyl |
| 2507. | 3-fluoropropyl | 3-([1,2,3]-triazol-1-yl)-phenyl |
| 2508. | 3-fluoropropyl | 3-([1,2,4]-triazol-1-yl)-phenyl |
| 2509. | 3-fluoropropyl | 3-([1,2,3]-triazol-2-yl)-phenyl |
| 2510. | 3-fluoropropyl | 3-(4H-[1,2,4]-triazol-3-yl)-phenyl |
| 2511. | 3-fluoropropyl | 3-([1,2,4]-triazol-4-yl)-phenyl |
| 2512. | 3-fluoropropyl | 3-(2H-[1,2,3]-triazol-4-yl)-phenyl |
| 2513. | 3-fluoropropyl | 3-(4-methyl-4H-[1,2,4]-triazol-3-yl)-phenyl |
| 2514. | 3-fluoropropyl | 3-(2-methyl-2H-[1,2,3]-triazol-4-yl)-phenyl |
| 2515. | 3-fluoropropyl | 3-([1,3,4]-oxadiazol-2-yl)-phenyl |
| 2516. | 3-fluoropropyl | 3-(5-methyl-[1,3,4]-oxadiazol-2-yl)-phenyl |
| 2517. | 3-fluoropropyl | 3-([1,2,4]-oxadiazol-3-yl)-phenyl |
| 2518. | 3-fluoropropyl | 3-(5-methyl-[1,2,4]-oxadiazol-3-yl)-phenyl |
| 2519. | 3-fluoropropyl | 3-([1,2,4]-oxadiazol-5-yl)-phenyl |
| 2520. | 3-fluoropropyl | 3-([1,2,3]-oxadiazol-4-yl)-phenyl |
| 2521. | 3-fluoropropyl | 3-([1,2,3]-oxadiazol-5-yl)-phenyl |
| 2522. | 3-fluoropropyl | 3-([1,2,3]-thiadiazol-4-yl)-phenyl |
| 2523. | 3-fluoropropyl | 3-(1H-tetrazol-5-yl)-phenyl |
| 2524. | 3-fluoropropyl | 3-(tetrazol-1-yl)-phenyl |
| 2525. | 3-fluoropropyl | 3-(2-methyl-2H-tetrazol-5-yl)-phenyl |
| 2526. | 3-fluoropropyl | 3-(1-methyl-1H-tetrazol-5-yl)-phenyl |
| 2527. | 3-fluoropropyl | 3-furazan-3-yl-phenyl |
| 2528. | 3-fluoropropyl | 3-(pyrid-2-yl)-phenyl |
| 2529. | 3-fluoropropyl | 3-(pyrid-3-yl)-phenyl |
| 2530. | 3-fluoropropyl | 3-(pyrid-4-yl)-phenyl |
| 2531. | 3-fluoropropyl | 3-(pyrimidin-2-yl)-phenyl |
| 2532. | 3-fluoropropyl | 3-(2-methylpyrimidin-4-yl)-phenyl |
| 2533. | 3-fluoropropyl | 3-(pyrimidin-4-yl)-phenyl |
| 2534. | 3-fluoropropyl | 3-(pyrimidin-5-yl)-phenyl |
| 2535. | 3-fluoropropyl | 5-bromopyridin-3-yl |
| 2536. | 3-fluoropropyl | 3-bromo-2-chloropyridin-5-yl |
| 2537. | 3-fluoropropyl | 4-methylpyridin-2-yl |
| 2538. | 3-fluoropropyl | 6-methylpyridin-2-yl |
| 2539. | 3-fluoropropyl | 4-(trifluoromethyl)-pyridin-2-yl |
| 2540. | 3-fluoropropyl | 6-(trifluoromethyl)-pyridin-2-yl |

TABLE A-continued

| No. | R¹ | Ar |
|---|---|---|
| 2541. | 3-fluoropropyl | 5-(trifluoromethyl)-pyridin-3-yl |
| 2542. | 3-fluoropropyl | 5-(pyrrolidin-1-yl)-pyridin-3-yl |
| 2543. | 3-fluoropropyl | 3-(pyrrolidin-1-yl)-2-chloropyridin-5-yl |
| 2544. | 3-fluoropropyl | 3-(morpholin-4-yl)-2-chloropyridin-5-yl |
| 2545. | 3-fluoropropyl | 2-(morpholin-4-yl)-pyridin-5-yl |
| 2546. | 3-fluoropropyl | 2-phenoxypyridin-5-yl |
| 2547. | 3-fluoropropyl | 4-methylphenyl |
| 2548. | 3-fluoropropyl | 4-ethylphenyl |
| 2549. | 3-fluoropropyl | 4-propylphenyl |
| 2550. | 3-fluoropropyl | 4-isopropylphenyl |
| 2551. | 3-fluoropropyl | 4-sec-butylphenyl |
| 2552. | 3-fluoropropyl | 4-tert-butylphenyl |
| 2553. | 3-fluoropropyl | 4-isobutylphenyl |
| 2554. | 3-fluoropropyl | 4-(1,1-dimethylpropyl)-phenyl |
| 2555. | 3-fluoropropyl | 4-vinylphenyl |
| 2556. | 3-fluoropropyl | 4-isopropenylphenyl |
| 2557. | 3-fluoropropyl | 4-fluorophenyl |
| 2558. | 3-fluoropropyl | 4-chlorophenyl |
| 2559. | 3-fluoropropyl | 4-bromophenyl |
| 2560. | 3-fluoropropyl | 4-iodophenyl |
| 2561. | 3-fluoropropyl | 4-(fluoromethyl)phenyl |
| 2562. | 3-fluoropropyl | 4-(difluoromethyl)phenyl |
| 2563. | 3-fluoropropyl | 4-(trifluoromethyl)phenyl |
| 2564. | 3-fluoropropyl | 2,4-bis(trifluoromethyl)phenyl |
| 2565. | 3-fluoropropyl | 4-(1-fluoroethyl)-phenyl |
| 2566. | 3-fluoropropyl | 4-((S)-1-fluoroethyl)-phenyl |
| 2567. | 3-fluoropropyl | 4-((R)-1-fluoroethyl)-phenyl |
| 2568. | 3-fluoropropyl | 4-(2-fluoroethyl)-phenyl |
| 2569. | 3-fluoropropyl | 4-(1,1-difluoroethyl)-phenyl |
| 2570. | 3-fluoropropyl | 4-(2,2-difluoroethyl)-phenyl |
| 2571. | 3-fluoropropyl | 4-(2,2,2-trifluoroethyl)-phenyl |
| 2572. | 3-fluoropropyl | 4-(3-fluoropropyl)-phenyl |
| 2573. | 3-fluoropropyl | 4-(2-fluoropropyl)-phenyl |
| 2574. | 3-fluoropropyl | 4-((S)-2-fluoropropyl)-phenyl |
| 2575. | 3-fluoropropyl | 4-((R)-2-fluoropropyl)-phenyl |
| 2576. | 3-fluoropropyl | 4-(3,3-difluoropropyl)-phenyl |
| 2577. | 3-fluoropropyl | 4-(3,3,3-trifluoropropyl)-phenyl |
| 2578. | 3-fluoropropyl | 4-(1-fluoro-1-methylethyl)-phenyl |
| 2579. | 3-fluoropropyl | 4-(2-fluoro-1-methylethyl)-phenyl |
| 2580. | 3-fluoropropyl | 4-((S)-2-fluoro-1-methylethyl)-phenyl |
| 2581. | 3-fluoropropyl | 4-((R)-2-fluoro-1-methylethyl)-phenyl |
| 2582. | 3-fluoropropyl | 4-(2,2-difluoro-1-methylethyl)-phenyl |
| 2583. | 3-fluoropropyl | 4-((S)-2,2-difluoro-1-methylethyl)-phenyl |
| 2584. | 3-fluoropropyl | 4-((R)-2,2-difluoro-1-methylethyl)-phenyl |
| 2585. | 3-fluoropropyl | 4-(2,2,2-trifluoro-1-methylethyl)-phenyl |
| 2586. | 3-fluoropropyl | 4-((S)-2,2,2-trifluoro-1-methylethyl)-phenyl |
| 2587. | 3-fluoropropyl | 4-((R)-2,2,2-trifluoro-1-methylethyl)-phenyl |
| 2588. | 3-fluoropropyl | 4-(2-fluoro-1-fluoromethylethyl)-phenyl |
| 2589. | 3-fluoropropyl | 4-(1-difluoromethyl-2,2-difluoroethyl)-phenyl |
| 2590. | 3-fluoropropyl | 4-(1,1-dimethyl-2-fluoroethyl)-phenyl |
| 2591. | 3-fluoropropyl | 4-methoxyphenyl |
| 2592. | 3-fluoropropyl | 4-ethoxyphenyl |
| 2593. | 3-fluoropropyl | 4-propoxyphenyl |
| 2594. | 3-fluoropropyl | 4-isopropoxyphenyl |
| 2595. | 3-fluoropropyl | 4-butoxyphenyl |
| 2596. | 3-fluoropropyl | 4-(fluoromethoxy)-phenyl |
| 2597. | 3-fluoropropyl | 4-(difluoromethoxy)-phenyl |
| 2598. | 3-fluoropropyl | 4-(trifluoromethoxy)-phenyl |
| 2599. | 3-fluoropropyl | 4-(2-fluoroethoxy)-phenyl |
| 2600. | 3-fluoropropyl | 4-(2,2-difluoroethoxy)-phenyl |
| 2601. | 3-fluoropropyl | 4-(2,2,2-trifluoroethoxy)-phenyl |
| 2602. | 3-fluoropropyl | 4-(1,1,2,2-tetrafluoroethoxy)-phenyl |
| 2603. | 3-fluoropropyl | 4-cyclopropylphenyl |
| 2604. | 3-fluoropropyl | 4-cyclobutylphenyl |
| 2605. | 3-fluoropropyl | 4-cyclopentylphenyl |
| 2606. | 3-fluoropropyl | 4-(2,2-difluorocyclopropyl)-phenyl |
| 2607. | 3-fluoropropyl | 3,4-difluorophenyl |
| 2608. | 3-fluoropropyl | 4-bromo-2-fluorophenyl |
| 2609. | 3-fluoropropyl | 2-bromo-4-fluorophenyl |
| 2610. | 3-fluoropropyl | 4-bromo-2,5-difluorophenyl |
| 2611. | 3-fluoropropyl | 5-bromo-2,4-difluorophenyl |
| 2612. | 3-fluoropropyl | 3-bromo-2,4-difluorophenyl |
| 2613. | 3-fluoropropyl | 3-chloro-4-(trifluoromethyl)-phenyl |
| 2614. | 3-fluoropropyl | 4-fluoro-3-(trifluoromethyl)-phenyl |
| 2615. | 3-fluoropropyl | 3-fluoro-5-(trifluoromethyl)-phenyl |
| 2616. | 3-fluoropropyl | 3-bromo-4-(trifluoromethyl)-phenyl |
| 2617. | 3-fluoropropyl | 5-bromo-3-(trifluoromethyl)-phenyl |
| 2618. | 3-fluoropropyl | 5-bromo-2-(trifluoromethyl)-phenyl |

TABLE A-continued

| No. | R¹ | Ar |
|---|---|---|
| 2619. | 3-fluoropropyl | 2-bromo-5-methoxyphenyl |
| 2620. | 3-fluoropropyl | 4-bromo-3-methoxyphenyl |
| 2621. | 3-fluoropropyl | 3-fluoro-2-isopropylphenyl |
| 2622. | 3-fluoropropyl | 3-fluoro-4-isopropylphenyl |
| 2623. | 3-fluoropropyl | 4-(1-hydroxy-1-methylethyl)-phenyl |
| 2624. | 3-fluoropropyl | 4-(2-hydroxy-2-methylpropyl)-phenyl |
| 2625. | 3-fluoropropyl | 4-acetylphenyl |
| 2626. | 3-fluoropropyl | 4-acetylaminophenyl |
| 2627. | 3-fluoropropyl | 4-carboxyphenyl |
| 2628. | 3-fluoropropyl | 4-cyanophenyl |
| 2629. | 3-fluoropropyl | 4-nitrophenyl |
| 2630. | 3-fluoropropyl | 4-hydroxyphenyl |
| 2631. | 3-fluoropropyl | 4-(O-benzyl)-phenyl |
| 2632. | 3-fluoropropyl | 4-(2-methoxyethoxy)-phenyl |
| 2633. | 3-fluoropropyl | 4-($CH_2$—$N(CH_3)_2$)-phenyl |
| 2634. | 3-fluoropropyl | 4-(NH—CO—$NH_2$)-phenyl |
| 2635. | 3-fluoropropyl | 4-(methylsulfanyl)-phenyl |
| 2636. | 3-fluoropropyl | 4-(fluoromethylsulfanyl)-phenyl |
| 2637. | 3-fluoropropyl | 4-(difluoromethylsulfanyl)-phenyl |
| 2638. | 3-fluoropropyl | 4-(trifluoromethylsulfanyl)-phenyl |
| 2639. | 3-fluoropropyl | 4-(methylsulfonyl)-phenyl |
| 2640. | 3-fluoropropyl | 4-(N-methoxy-N-methyl-amino)-phenyl |
| 2641. | 3-fluoropropyl | 4-(methoxyamino)-phenyl |
| 2642. | 3-fluoropropyl | 4-(ethoxyamino)-phenyl |
| 2643. | 3-fluoropropyl | 4-(N-methylaminooxy)-phenyl |
| 2644. | 3-fluoropropyl | 4-(N,N-dimethylaminooxy)-phenyl |
| 2645. | 3-fluoropropyl | 4-(azetidin-1-yl)-phenyl |
| 2646. | 3-fluoropropyl | 4-(2-methylazetidin-1-yl)-phenyl |
| 2647. | 3-fluoropropyl | 4-((S)-2-methylazetidin-1-yl)-phenyl |
| 2648. | 3-fluoropropyl | 4-((R)-2-methylazetidin-1-yl)-phenyl |
| 2649. | 3-fluoropropyl | 4-(3-fluoroazetidin-1-yl)-phenyl |
| 2650. | 3-fluoropropyl | 4-(2,2-difluoroazetidin-1-yl)-phenyl |
| 2651. | 3-fluoropropyl | 4-(3-methoxyazetidin-1-yl)-phenyl |
| 2652. | 3-fluoropropyl | 4-(3-hydroxyazetidin-1-yl)-phenyl |
| 2653. | 3-fluoropropyl | 4-(pyrrolidin-1-yl)-phenyl |
| 2654. | 3-fluoropropyl | 4-(pyrrolidin-2-yl)-phenyl |
| 2655. | 3-fluoropropyl | 4-((S)-pyrrolidin-2-yl)-phenyl |
| 2656. | 3-fluoropropyl | 4-((R)-pyrrolidin-2-yl)-phenyl |
| 2657. | 3-fluoropropyl | 4-(pyrrolidin-3-yl)-phenyl |
| 2658. | 3-fluoropropyl | 4-((S)-pyrrolidin-3-yl)-phenyl |
| 2659. | 3-fluoropropyl | 4-((R)-pyrrolidin-3-yl)-phenyl |
| 2660. | 3-fluoropropyl | 4-(pyrrolidin-1-yl)-5-(trifluoromethyl)-phenyl |
| 2661. | 3-fluoropropyl | 4-(pyrrolidin-1-yl)-2-methoxyphenyl |
| 2662. | 3-fluoropropyl | 4-(pyrrolidin-1-yl)-34-methoxyphenyl |
| 2663. | 3-fluoropropyl | 4-(pyrrolidin-1-yl)-2,5-difluorophenyl |
| 2664. | 3-fluoropropyl | 4-(pyrrolidin-1-yl)-2,6-difluorophenyl |
| 2665. | 3-fluoropropyl | 4-(2-fluoropyrrolidin-1-yl)-phenyl |
| 2666. | 3-fluoropropyl | 4-((S)-2-fluoropyrrolidin-1-yl)-phenyl |
| 2667. | 3-fluoropropyl | 4-((R)-2-fluoropyrrolidin-1-yl)-phenyl |
| 2668. | 3-fluoropropyl | 4-(3-fluoropyrrolidin-1-yl)-phenyl |
| 2669. | 3-fluoropropyl | 4-((S)-3-fluoropyrrolidin-1-yl)-phenyl |
| 2670. | 3-fluoropropyl | 4-((R)-3-fluoropyrrolidin-1-yl)-phenyl |
| 2671. | 3-fluoropropyl | 4-(2,2-difluoropyrrolidin-1-yl)-phenyl |
| 2672. | 3-fluoropropyl | 4-(3,3-difluoropyrrolidin-1-yl)-phenyl |
| 2673. | 3-fluoropropyl | 4-(2-methylpyrrolidin-1-yl)-phenyl |
| 2674. | 3-fluoropropyl | 4-((S)-2-methylpyrrolidin-1-yl)-phenyl |
| 2675. | 3-fluoropropyl | 4-((R)-2-methylpyrrolidin-1-yl)-phenyl |
| 2676. | 3-fluoropropyl | 4-(3-methylpyrrolidin-1-yl)-phenyl |
| 2677. | 3-fluoropropyl | 4-((S)-3-methylpyrrolidin-1-yl)-phenyl |
| 2678. | 3-fluoropropyl | 4-((R)-3-methylpyrrolidin-1-yl)-phenyl |
| 2679. | 3-fluoropropyl | 4-(1-methylpyrrolidin-2-yl)-phenyl |
| 2680. | 3-fluoropropyl | 4-((S)-1-methylpyrrolidin-2-yl)-phenyl |
| 2681. | 3-fluoropropyl | 4-((R)-1-methylpyrrolidin-2-yl)-phenyl |
| 2682. | 3-fluoropropyl | 4-(1-methylpyrrolidin-3-yl)-phenyl |
| 2683. | 3-fluoropropyl | 4-((S)-1-methylpyrrolidin-3-yl)-phenyl |
| 2684. | 3-fluoropropyl | 4-((R)-1-methylpyrrolidin-3-yl)-phenyl |
| 2685. | 3-fluoropropyl | 4-(2,2-dimethylpyrrolidin-1-yl)-phenyl |
| 2686. | 3-fluoropropyl | 4-(3,3-dimethylpyrrolidin-1-yl)-phenyl |
| 2687. | 3-fluoropropyl | 4-(2-trifluoromethylpyrrolidin-1-yl)-phenyl |
| 2688. | 3-fluoropropyl | 4-((S)-2-trifluoromethylpyrrolidin-1-yl)-phenyl |
| 2689. | 3-fluoropropyl | 4-((R)-2-trifluoromethylpyrrolidin-1-yl)-phenyl |
| 2690. | 3-fluoropropyl | 4-(3-trifluoromethylpyrrolidin-1-yl)-phenyl |
| 2691. | 3-fluoropropyl | 4-((S)-3-trifluoromethylpyrrolidin-1-yl)-phenyl |
| 2692. | 3-fluoropropyl | 4-((R)-3-trifluoromethylpyrrolidin-1-yl)-phenyl |
| 2693. | 3-fluoropropyl | 4-(2-oxopyrrolidin-1-yl)-phenyl |
| 2694. | 3-fluoropropyl | 4-(2-oxo-oxazolidin-3-yl)-phenyl |
| 2695. | 3-fluoropropyl | 4-(piperidin-1-yl)-phenyl |
| 2696. | 3-fluoropropyl | 4-(2-methylpiperidin-1-yl)-phenyl |

TABLE A-continued

| No. | R¹ | Ar |
|---|---|---|
| 2697. | 3-fluoropropyl | 4-((S)-2-methylpiperidin-1-yl)-phenyl |
| 2698. | 3-fluoropropyl | 4-((R)-2-methylpiperidin-1-yl)-phenyl |
| 2699. | 3-fluoropropyl | 4-(2-fluoropiperidin-1-yl)-phenyl |
| 2700. | 3-fluoropropyl | 4-((S)-2-fluoropiperidin-1-yl)-phenyl |
| 2701. | 3-fluoropropyl | 4-((R)-2-fluoropiperidin-1-yl)-phenyl |
| 2702. | 3-fluoropropyl | 4-(2,2-difluoropiperidin-1-yl)-phenyl |
| 2703. | 3-fluoropropyl | 4-(piperazin-1-yl)-phenyl |
| 2704. | 3-fluoropropyl | 4-(4-methylpiperazin-1-yl)-phenyl |
| 2705. | 3-fluoropropyl | 4-(morpholin-4-yl)-phenyl |
| 2706. | 3-fluoropropyl | 4-(morpholin-4-yl)-5-(trifluoromethyl)-phenyl |
| 2707. | 3-fluoropropyl | 4-(morpholin-4-yl)-2-methoxyphenyl |
| 2708. | 3-fluoropropyl | 4-(morpholin-4-yl)-3-methoxyphenyl |
| 2709. | 3-fluoropropyl | 4-(morpholin-4-yl)-2,5-difluorophenyl |
| 2710. | 3-fluoropropyl | 4-(morpholin-4-yl)-2,6-difluorophenyl |
| 2711. | 3-fluoropropyl | 4-(thiomorpholin-4-yl)-phenyl |
| 2712. | 3-fluoropropyl | 4-(1-oxo-thiomorpholin-4-yl)-phenyl |
| 2713. | 3-fluoropropyl | 4-(1,1-dioxo-thiomorpholin-4-yl)-phenyl |
| 2714. | 3-fluoropropyl | 4-(pyrrol-1-yl)-phenyl |
| 2715. | 3-fluoropropyl | 4-(pyrrol-2-yl)-phenyl |
| 2716. | 3-fluoropropyl | 4-(pyrrol-3-yl)-phenyl |
| 2717. | 3-fluoropropyl | 4-(1-methylpyrrol-2-yl)-phenyl |
| 2718. | 3-fluoropropyl | 4-(1-methylpyrrol-3-yl)-phenyl |
| 2719. | 3-fluoropropyl | 4-(furan-2-yl)-phenyl |
| 2720. | 3-fluoropropyl | 4-(furan-3-yl)-phenyl |
| 2721. | 3-fluoropropyl | 4-(thiophen-2-yl)-phenyl |
| 2722. | 3-fluoropropyl | 4-(thiophen-3-yl)-phenyl |
| 2723. | 3-fluoropropyl | 4-(5-propylthien-2-yl)-phenyl |
| 2724. | 3-fluoropropyl | 4-(pyrazol-1-yl)-phenyl |
| 2725. | 3-fluoropropyl | 4-(pyrazol-3-yl)-phenyl |
| 2726. | 3-fluoropropyl | 4-(pyrazol-4-yl)-phenyl |
| 2727. | 3-fluoropropyl | 4-(4-fluoropyrazol-1-yl)-phenyl |
| 2728. | 3-fluoropropyl | 4-(1-methyl-1H-pyrazol-4-yl)-phenyl |
| 2729. | 3-fluoropropyl | 4-(1-ethyl-1H-pyrazol-4-yl)-phenyl |
| 2730. | 3-fluoropropyl | 4-(1-methyl-1H-pyrazol-5-yl)-phenyl |
| 2731. | 3-fluoropropyl | 4-(1H-imidazol-2-yl)-phenyl |
| 2732. | 3-fluoropropyl | 4-(imidazol-1-yl)-phenyl |
| 2733. | 3-fluoropropyl | 4-(1-methylimidazol-2-yl)-phenyl |
| 2734. | 3-fluoropropyl | 4-(oxazol-2-yl)-phenyl |
| 2735. | 3-fluoropropyl | 4-(oxazol-4-yl)-phenyl |
| 2736. | 3-fluoropropyl | 4-(oxazol-5-yl)-phenyl |
| 2737. | 3-fluoropropyl | 4-(isoxazol-3-yl)-phenyl |
| 2738. | 3-fluoropropyl | 4-(isoxazol-4-yl)-phenyl |
| 2739. | 3-fluoropropyl | 4-(isoxazol-5-yl)-phenyl |
| 2740. | 3-fluoropropyl | 4-(thiazol-2-yl)-phenyl |
| 2741. | 3-fluoropropyl | 4-(thiazol-4-yl)-phenyl |
| 2742. | 3-fluoropropyl | 4-(thiazol-5-yl)-phenyl |
| 2743. | 3-fluoropropyl | 4-(2-methylthiazol-4-yl)-phenyl |
| 2744. | 3-fluoropropyl | 4-(2-methylthiazol-5-yl)-phenyl |
| 2745. | 3-fluoropropyl | 4-([1,2,3]-triazol-1-yl)-phenyl |
| 2746. | 3-fluoropropyl | 4-([1,2,4]-triazol-1-yl)-phenyl |
| 2747. | 3-fluoropropyl | 4-([1,2,3]-triazol-2-yl)-phenyl |
| 2748. | 3-fluoropropyl | 4-(4H-[1,2,4]-triazol-3-yl)-phenyl |
| 2749. | 3-fluoropropyl | 4-([1,2,4]-triazol-4-yl)-phenyl |
| 2750. | 3-fluoropropyl | 4-(2H-[1,2,3]-triazol-4-yl)-phenyl |
| 2751. | 3-fluoropropyl | 4-(4-methyl-4H-[1,2,4]-triazol-3-yl)-phenyl |
| 2752. | 3-fluoropropyl | 4-(2-methyl-2H-[1,2,3]-triazol-4-yl)-phenyl |
| 2753. | 3-fluoropropyl | 4-([1,3,4]-oxadiazol-2-yl)-phenyl |
| 2754. | 3-fluoropropyl | 4-(5-methyl-[1,3,4]-oxadiazol-2-yl)-phenyl |
| 2755. | 3-fluoropropyl | 4-([1,2,4]-oxadiazol-3-yl)-phenyl |
| 2756. | 3-fluoropropyl | 4-(5-methyl-[1,2,4]-oxadiazol-3-yl)-phenyl |
| 2757. | 3-fluoropropyl | 4-([1,2,4]-oxadiazol-5-yl)-phenyl |
| 2758. | 3-fluoropropyl | 4-([1,2,3]-oxadiazol-4-yl)-phenyl |
| 2759. | 3-fluoropropyl | 4-([1,2,3]-oxadiazol-5-yl)-phenyl |
| 2760. | 3-fluoropropyl | 4-([1,2,3]-thiadiazol-4-yl)-phenyl |
| 2761. | 3-fluoropropyl | 4-(1H-tetrazol-5-yl)-phenyl |
| 2762. | 3-fluoropropyl | 4-(tetrazol-1-yl)-phenyl |
| 2763. | 3-fluoropropyl | 4-(2-methyl-2H-tetrazol-5-yl)-phenyl |
| 2764. | 3-fluoropropyl | 4-(1-methyl-1H-tetrazol-5-yl)-phenyl |
| 2765. | 3-fluoropropyl | 4-furazan-3-yl-phenyl |
| 2766. | 3-fluoropropyl | 4-(pyrid-2-yl)-phenyl |
| 2767. | 3-fluoropropyl | 4-(pyrid-3-yl)-phenyl |
| 2768. | 3-fluoropropyl | 4-(pyrid-4-yl)-phenyl |
| 2769. | 3-fluoropropyl | 4-(pyrimidin-2-yl)-phenyl |
| 2770. | 3-fluoropropyl | 4-(2-methylpyrimidin-4-yl)-phenyl |
| 2771. | 3-fluoropropyl | 4-(pyrimidin-4-yl)-phenyl |
| 2772. | 3-fluoropropyl | 4-(pyrimidin-5-yl)-phenyl |
| 2773. | 3-fluoropropyl | 4-bromo-2-chloropyridin-5-yl |
| 2774. | 3-fluoropropyl | 4-methylpyridin-2-yl |

TABLE A-continued

| No. | R¹ | Ar |
|---|---|---|
| 2775. | 3-fluoropropyl | 5-methylpyridin-2-yl |
| 2776. | 3-fluoropropyl | 4-(pyrrolidin-1-yl)-2-chloropyridin-5-yl |
| 2777. | 3-fluoropropyl | 4-(morpholin-4-yl)-2-chloropyridin-5-yl |
| 2778. | 3-fluoropropyl | 2-(morpholin-4-yl)-pyridin-5-yl |
| 2779. | 3-fluoropropyl | 5-(morpholin-4-yl)-pyridin-2-yl |
| 2780. | 3-fluoropropyl | 2-phenoxypyridin-5-yl |
| 2781. | 3-fluoropropyl | 2,3-dichlorophenyl |
| 2782. | 3-fluoropropyl | 2,5-dichlorophenyl |
| 2783. | 3-fluoropropyl | 3,5-dichlorophenyl |
| 2784. | 3-fluoropropyl | 3-chloro-4-fluorophenyl |
| 2785. | 3-fluoropropyl | 4-bromo-2,5-dichlorophenyl |
| 2786. | 3-fluoropropyl | 3-bromo-4-(trifluoromethoxy)phenyl |
| 2787. | 3-fluoropropyl | 3,5-dibromo-4-(2-fluoroethoxy)-phenyl |
| 2788. | 3-fluoropropyl | 2,5-dimethylphenyl |
| 2789. | 3-fluoropropyl | 2,5-di-(trifluoromethyl)-phenyl |
| 2790. | 3-fluoropropyl | 3,5-di-(trifluoromethyl)-phenyl |
| 2791. | 3-fluoropropyl | 2,5-dimethoxyphenyl |
| 2792. | 3-fluoropropyl | 2-methoxy-5-methylphenyl |
| 2793. | 3-fluoropropyl | 2-methoxy-5-(trifluoromethyl)-phenyl |
| 2794. | 3-fluoropropyl | 4-fluoro-3-(oxazol-4-yl)-phenyl |
| 2795. | 3-fluoropropyl | thien-2-yl |
| 2796. | 3-fluoropropyl | thien-3-yl |
| 2797. | 3-fluoropropyl | 3-chlorothien-2-yl |
| 2798. | 3-fluoropropyl | 4-chlorothien-2-yl |
| 2799. | 3-fluoropropyl | 5-chlorothien-2-yl |
| 2800. | 3-fluoropropyl | 3-bromothien-2-yl |
| 2801. | 3-fluoropropyl | 4-bromothien-2-yl |
| 2802. | 3-fluoropropyl | 5-bromothien-2-yl |
| 2803. | 3-fluoropropyl | 4,5-dichlorothien-2-yl |
| 2804. | 3-fluoropropyl | 4,5-dibromothien-2-yl |
| 2805. | 3-fluoropropyl | 4-bromo-5-chlorothien-2-yl |
| 2806. | 3-fluoropropyl | 3-bromo-5-chlorothien-2-yl |
| 2807. | 3-fluoropropyl | 5-methylthien-2-yl |
| 2808. | 3-fluoropropyl | 5-ethylthien-2-yl |
| 2809. | 3-fluoropropyl | 5-propylthien-2-yl |
| 2810. | 3-fluoropropyl | 5-trifluoromethylthien-2-yl |
| 2811. | 3-fluoropropyl | 5-phenylthien-2-yl |
| 2812. | 3-fluoropropyl | 5-(pyrid-2-yl)-thien-2-yl |
| 2813. | 3-fluoropropyl | 5-(phenylsulfonyl)-thien-2-yl |
| 2814. | 3-fluoropropyl | 4-(phenylsulfonyl)-thien-2-yl |
| 2815. | 3-fluoropropyl | 5-(pyrid-2-ylsulfonyl)-thien-2-yl |
| 2816. | 3-fluoropropyl | 5-(3-chloro-5-trifluoro-pyrid-2-ylsulfonyl)-thien-2-yl |
| 2817. | 3-fluoropropyl | 5-(benzoylaminomethyl)-thien-2-yl |
| 2818. | 3-fluoropropyl | 5-((4-chlorobenzoyl)aminomethyl)-thien-2-yl |
| 2819. | 3-fluoropropyl | 5-(acetylaminomethyl)-thien-2-yl |
| 2820. | 3-fluoropropyl | 5-(pyrazol-1-yl)-thien-2-yl |
| 2821. | 3-fluoropropyl | 5-(pyrazol-3-yl)-thien-2-yl |
| 2822. | 3-fluoropropyl | 5-(pyrazol-4-yl)-thien-2-yl |
| 2823. | 3-fluoropropyl | 5-(pyrazol-5-yl)-thien-2-yl |
| 2824. | 3-fluoropropyl | 5-(4-fluoropyrazol-1-yl)-thien-2-yl |
| 2825. | 3-fluoropropyl | 5-(1-methyl-5-trifluoromethyl-(1H)-pyrazol-3-yl)-thien-2-yl |
| 2826. | 3-fluoropropyl | 5-(1-methyl-3-trifluoromethyl-(1H)-pyrazol-5-yl)-thien-2-yl |
| 2827. | 3-fluoropropyl | 5-(4-carboxy-1-methyl-5-methylthio-(1H)-pyrazol-3-yl)-thien-2-yl |
| 2828. | 3-fluoropropyl | 5-(4-aminomethyl-1-methyl-5-methylthio-(1H)-pyrazol-3-yl)-thien-2-yl |
| 2829. | 3-fluoropropyl | 5-(isoxazol-3-yl)-thien-2-yl |
| 2830. | 3-fluoropropyl | 5-(isoxazol-4-yl)-thien-2-yl |
| 2831. | 3-fluoropropyl | 5-(isoxazol-5-yl)-thien-2-yl |
| 2832. | 3-fluoropropyl | 5-(5-trifluoromethylisoxazol-3-yl)-thien-2-yl |
| 2833. | 3-fluoropropyl | 5-(oxazol-2-yl)-thien-2-yl |
| 2834. | 3-fluoropropyl | 5-(oxazol-4-yl)-thien-2-yl |
| 2835. | 3-fluoropropyl | 5-(oxazol-5-yl)-thien-2-yl |
| 2836. | 3-fluoropropyl | 5-(2-methyloxazol-4-yl)-thien-2-yl |
| 2837. | 3-fluoropropyl | 5-(2-methyloxazol-5-yl)-thien-2-yl |
| 2838. | 3-fluoropropyl | 5-(isothiazol-3-yl)-thien-2-yl |
| 2839. | 3-fluoropropyl | 5-(isothiazol-4-yl)-thien-2-yl |
| 2840. | 3-fluoropropyl | 5-(isothiazol-5-yl)-thien-2-yl |
| 2841. | 3-fluoropropyl | 5-(5-trifluoromethylisothiazol-3-yl)-thien-2-yl |
| 2842. | 3-fluoropropyl | 5-(thiazol-2-yl)-thien-2-yl |
| 2843. | 3-fluoropropyl | 5-(thiazol-4-yl)-thien-2-yl |
| 2844. | 3-fluoropropyl | 5-(thiazol-5-yl)-thien-2-yl |
| 2845. | 3-fluoropropyl | 5-(2-methylthiazol-4-yl)-thien-2-yl |
| 2846. | 3-fluoropropyl | 5-(2-methylthiazol-5-yl)-thien-2-yl |
| 2847. | 3-fluoropropyl | 5-([1,2,3]-oxadiazol-4-yl)-thien-2-yl |

TABLE A-continued

| No. | R¹ | Ar |
|---|---|---|
| 2848. | 3-fluoropropyl | 5-([1,2,3]-thiadiazol-4-yl)-thien-2-yl |
| 2849. | 3-fluoropropyl | 5-(pyrimidin-2-yl)-thien-2-yl |
| 2850. | 3-fluoropropyl | 5-(pyrimidin-4-yl)-thien-2-yl |
| 2851. | 3-fluoropropyl | 5-(pyrimidin-5-yl)-thien-2-yl |
| 2852. | 3-fluoropropyl | 5-(2-methylthiopyrimidin-4-yl)-thien-2-yl |
| 2853. | 3-fluoropropyl | 5-([1,3]-dioxolan-2-yl)-thien-2-yl |
| 2854. | 3-fluoropropyl | 3-([1,3]-dioxolan-2-yl)-thien-2-yl thien-2-yl |
| 2855. | 3-fluoropropyl | 5-((3-chloro-5-(trifluoromethyl)-pyridin-2-yl)-methyl)-thien-2-yl |
| 2856. | 3-fluoropropyl | 5-[3-chloro-5-(trifluoromethyl)-pyrid-2-ylsulfonyl]-thien-2-yl |
| 2857. | 3-fluoropropyl | 2-chlorothien-3-yl |
| 2858. | 3-fluoropropyl | 4-chlorothien-3-yl |
| 2859. | 3-fluoropropyl | 5-chlorothien-3-yl |
| 2860. | 3-fluoropropyl | 2-bromothien-3-yl |
| 2861. | 3-fluoropropyl | 4-bromothien-3-yl |
| 2862. | 3-fluoropropyl | 5-bromothien-3-yl |
| 2863. | 3-fluoropropyl | 2,5-dichlorothien-3-yl |
| 2864. | 3-fluoropropyl | 2,5-dibromothien-3-yl |
| 2865. | 3-fluoropropyl | 2,4,5-trichlorothien-3-yl |
| 2866. | 3-fluoropropyl | 4-bromo-2,5-dichlorothien-3-yl |
| 2867. | 3-fluoropropyl | 2-chloro-5-methylsulfonylthien-3-yl |
| 2868. | 3-fluoropropyl | 2,5-dimethylthien-3-yl |
| 2869. | 3-fluoropropyl | 4-hydroxythien-3-yl |
| 2870. | 3-fluoropropyl | 2-phenylthien-3-yl |
| 2871. | 3-fluoropropyl | 4-phenyl-5-(trofluoromethyl)-thien-3-yl |
| 2872. | 3-fluoropropyl | 2-methoxycarbonyl-4-phenyl-5-(trifluoromethyl)-thien-3-yl |
| 2873. | 3-fluoropropyl | benzo[b]thiophen-2-yl |
| 2874. | 3-fluoropropyl | benzo[b]thiophen-3-yl |
| 2875. | 3-fluoropropyl | 3-methyl-benzo[b]thiophen-2-yl |
| 2876. | 3-fluoropropyl | 5-methyl-benzo[b]thiophen-2-yl |
| 2877. | 3-fluoropropyl | 5-fluoro-3-methyl-benzo[b]thiophen-2-yl |
| 2878. | 3-fluoropropyl | 5-chloro-3-methyl-benzo[b]thiophen-2-yl |
| 2879. | 3-fluoropropyl | 5-bromo-3-methyl-benzo[b]thiophen-2-yl |
| 2880. | 2-fluoroethyl | 3-methylphenyl |
| 2881. | 2-fluoroethyl | 3-ethylphenyl |
| 2882. | 2-fluoroethyl | 3-propylphenyl |
| 2883. | 2-fluoroethyl | 3-isopropylphenyl |
| 2884. | 2-fluoroethyl | 3-sec-butylphenyl |
| 2885. | 2-fluoroethyl | 3-tert-butylphenyl |
| 2886. | 2-fluoroethyl | 3-isobutylphenyl |
| 2887. | 2-fluoroethyl | 3-(1,1-dimethylpropyl)-phenyl |
| 2888. | 2-fluoroethyl | 3-vinylphenyl |
| 2889. | 2-fluoroethyl | 3-isopropenylphenyl |
| 2890. | 2-fluoroethyl | 3-fluorophenyl |
| 2891. | 2-fluoroethyl | 2-fluorophenyl |
| 2892. | 2-fluoroethyl | 3-chlorophenyl |
| 2893. | 2-fluoroethyl | 3-bromophenyl |
| 2894. | 2-fluoroethyl | 3-iodophenyl |
| 2895. | 2-fluoroethyl | 3-(fluoromethyl)phenyl |
| 2896. | 2-fluoroethyl | 3-(difluoromethyl)phenyl |
| 2897. | 2-fluoroethyl | 3-(trifluoromethyl)phenyl |
| 2898. | 2-fluoroethyl | 3,5-bis(trifluoromethyl)phenyl |
| 2899. | 2-fluoroethyl | 3-(1-fluoroethyl)-phenyl |
| 2900. | 2-fluoroethyl | 3-((S)-1-fluoroethyl)-phenyl |
| 2901. | 2-fluoroethyl | 3-((R)-1-fluoroethyl)-phenyl |
| 2902. | 2-fluoroethyl | 3-(2-fluoroethyl)-phenyl |
| 2903. | 2-fluoroethyl | 3-(1,1-difluoroethyl)-phenyl |
| 2904. | 2-fluoroethyl | 3-(2,2-difluoroethyl)-phenyl |
| 2905. | 2-fluoroethyl | 3-(2,2,2-trifluoroethyl)-phenyl |
| 2906. | 2-fluoroethyl | 3-(3-fluoropropyl)-phenyl |
| 2907. | 2-fluoroethyl | 3-(2-fluoropropyl)-phenyl |
| 2908. | 2-fluoroethyl | 3-((S)-2-fluoropropyl)-phenyl |
| 2909. | 2-fluoroethyl | 3-((R)-2-fluoropropyl)-phenyl |
| 2910. | 2-fluoroethyl | 3-(3,3-difluoropropyl)-phenyl |
| 2911. | 2-fluoroethyl | 3-(3,3,3-trifluoropropyl)-phenyl |
| 2912. | 2-fluoroethyl | 3-(1-fluoro-1-methylethyl)-phenyl |
| 2913. | 2-fluoroethyl | 3-(2-fluoro-1-methylethyl)-phenyl |
| 2914. | 2-fluoroethyl | 3-((S)-2-fluoro-1-methylethyl)-phenyl |
| 2915. | 2-fluoroethyl | 3-((R)-2-fluoro-1-methylethyl)-phenyl |
| 2916. | 2-fluoroethyl | 3-(2,2-difluoro-1-methylethyl)-phenyl |
| 2917. | 2-fluoroethyl | 3-((S)-2,2-difluoro-1-methylethyl)-phenyl |
| 2918. | 2-fluoroethyl | 3-((R)-2,2-difluoro-1-methylethyl)-phenyl |
| 2919. | 2-fluoroethyl | 3-(2,2,2-trifluoro-1-methylethyl)-phenyl |
| 2920. | 2-fluoroethyl | 3-((S)-2,2,2-trifluoro-1-methylethyl)-phenyl |
| 2921. | 2-fluoroethyl | 3-((R)-2,2,2-trifluoro-1-methylethyl)-phenyl |
| 2922. | 2-fluoroethyl | 3-(2-fluoro-1-fluoromethylethyl)-phenyl |

TABLE A-continued

| No. | R¹ | Ar |
|---|---|---|
| 2923. | 2-fluoroethyl | 3-(1-difluoromethyl-2,2-difluoroethyl)-phenyl |
| 2924. | 2-fluoroethyl | 3-(1,1-dimethyl-2-fluoroethyl)-phenyl |
| 2925. | 2-fluoroethyl | 3-methoxyphenyl |
| 2926. | 2-fluoroethyl | 3-ethoxyphenyl |
| 2927. | 2-fluoroethyl | 3-propoxyphenyl |
| 2928. | 2-fluoroethyl | 3-isopropoxyphenyl |
| 2929. | 2-fluoroethyl | 3-butoxyphenyl |
| 2930. | 2-fluoroethyl | 3-(fluoromethoxy)-phenyl |
| 2931. | 2-fluoroethyl | 3-(difluoromethoxy)-phenyl |
| 2932. | 2-fluoroethyl | 3-(trifluoromethoxy)-phenyl |
| 2933. | 2-fluoroethyl | 3-(2-fluoroethoxy)-phenyl |
| 2934. | 2-fluoroethyl | 3-(2,2-difluoroethoxy)-phenyl |
| 2935. | 2-fluoroethyl | 3-(2,2,2-trifluoroethoxy)-phenyl |
| 2936. | 2-fluoroethyl | 3-(1,1,2,2-tetrafluoroethoxy)-phenyl |
| 2937. | 2-fluoroethyl | 3-cyclopropylphenyl |
| 2938. | 2-fluoroethyl | 3-cyclobutylphenyl |
| 2939. | 2-fluoroethyl | 3-cyclopentylphenyl |
| 2940. | 2-fluoroethyl | 3-(2,2-difluorocyclopropyl)-phenyl |
| 2941. | 2-fluoroethyl | 3,4-difluorophenyl |
| 2942. | 2-fluoroethyl | 3-bromo-2-fluorophenyl |
| 2943. | 2-fluoroethyl | 2-bromo-3-fluorophenyl |
| 2944. | 2-fluoroethyl | 3-bromo-2,5-difluorophenyl |
| 2945. | 2-fluoroethyl | 5-bromo-2,4-difluorophenyl |
| 2946. | 2-fluoroethyl | 3-bromo-2,4-difluorophenyl |
| 2947. | 2-fluoroethyl | 4-chloro-3-(trifluoromethyl)-phenyl |
| 2948. | 2-fluoroethyl | 2-chloro-5-(trifluoromethyl)-phenyl |
| 2949. | 2-fluoroethyl | 2-fluoro-5-(trifluoromethyl)-phenyl |
| 2950. | 2-fluoroethyl | 4-fluoro-3-(trifluoromethyl)-phenyl |
| 2951. | 2-fluoroethyl | 3-fluoro-5-(trifluoromethyl)-phenyl |
| 2952. | 2-fluoroethyl | 4-bromo-3-(trifluoromethyl)-phenyl |
| 2953. | 2-fluoroethyl | 3-bromo-5-(trifluoromethyl)-phenyl |
| 2954. | 2-fluoroethyl | 2-bromo-5-(trifluoromethyl)-phenyl |
| 2955. | 2-fluoroethyl | 5-bromo-2-methoxyphenyl |
| 2956. | 2-fluoroethyl | 3-bromo-4-methoxyphenyl |
| 2957. | 2-fluoroethyl | 2-fluoro-3-isopropylphenyl |
| 2958. | 2-fluoroethyl | 4-fluoro-3-isopropylphenyl |
| 2959. | 2-fluoroethyl | 3-(1-hydroxy-1-methylethyl)-phenyl |
| 2960. | 2-fluoroethyl | 3-(2-hydroxy-2-methylpropyl)-phenyl |
| 2961. | 2-fluoroethyl | 3-acetylphenyl |
| 2962. | 2-fluoroethyl | 3-acetylaminophenyl |
| 2963. | 2-fluoroethyl | 3-carboxyphenyl |
| 2964. | 2-fluoroethyl | 3-cyanophenyl |
| 2965. | 2-fluoroethyl | 3-nitrophenyl |
| 2966. | 2-fluoroethyl | 3-hydroxyphenyl |
| 2967. | 2-fluoroethyl | 3-(O-benzyl)-phenyl |
| 2968. | 2-fluoroethyl | 3-(2-methoxyethoxy)-phenyl |
| 2969. | 2-fluoroethyl | 3-($CH_2$—$N(CH_3)_2$)-phenyl |
| 2970. | 2-fluoroethyl | 3-(NH—CO—$NH_2$)-phenyl |
| 2971. | 2-fluoroethyl | 3-(methylsulfanyl)-phenyl |
| 2972. | 2-fluoroethyl | 3-(fluoromethylsulfanyl)-phenyl |
| 2973. | 2-fluoroethyl | 3-(difluoromethylsulfanyl)-phenyl |
| 2974. | 2-fluoroethyl | 3-(trifluoromethylsulfanyl)-phenyl |
| 2975. | 2-fluoroethyl | 3-(methylsulfonyl)-phenyl |
| 2976. | 2-fluoroethyl | 3-(N-methoxy-N-methyl-amino)-phenyl |
| 2977. | 2-fluoroethyl | 3-(methoxyamino)-phenyl |
| 2978. | 2-fluoroethyl | 3-(ethoxyamino)-phenyl |
| 2979. | 2-fluoroethyl | 3-(N-methylaminooxy)-phenyl |
| 2980. | 2-fluoroethyl | 3-(N,N-dimethylaminooxy)-phenyl |
| 2981. | 2-fluoroethyl | 3-(azetidin-1-yl)-phenyl |
| 2982. | 2-fluoroethyl | 3-(2-methylazetidin-1-yl)-phenyl |
| 2983. | 2-fluoroethyl | 3-((S)-2-methylazetidin-1-yl)-phenyl |
| 2984. | 2-fluoroethyl | 3-((R)-2-methylazetidin-1-yl)-phenyl |
| 2985. | 2-fluoroethyl | 3-(3-fluoroazetidin-1-yl)-phenyl |
| 2986. | 2-fluoroethyl | 3-(2,2-difluoroazetidin-1-yl)-phenyl |
| 2987. | 2-fluoroethyl | 3-(3-methoxyazetidin-1-yl)-phenyl |
| 2988. | 2-fluoroethyl | 3-(3-hydroxyazetidin-1-yl)-phenyl |
| 2989. | 2-fluoroethyl | 3-(pyrrolidin-1-yl)-phenyl |
| 2990. | 2-fluoroethyl | 3-(pyrrolidin-2-yl)-phenyl |
| 2991. | 2-fluoroethyl | 3-((S)-pyrrolidin-2-yl)-phenyl |
| 2992. | 2-fluoroethyl | 3-((R)-pyrrolidin-2-yl)-phenyl |
| 2993. | 2-fluoroethyl | 3-(pyrrolidin-3-yl)-phenyl |
| 2994. | 2-fluoroethyl | 3-((S)-pyrrolidin-3-yl)-phenyl |
| 2995. | 2-fluoroethyl | 3-((R)-pyrrolidin-3-yl)-phenyl |
| 2996. | 2-fluoroethyl | 3-(pyrrolidin-1-yl)-5-(trifluoromethyl)-phenyl |
| 2997. | 2-fluoroethyl | 5-(pyrrolidin-1-yl)-2-methoxyphenyl |
| 2998. | 2-fluoroethyl | 3-(pyrrolidin-1-yl)-4-methoxyphenyl |
| 2999. | 2-fluoroethyl | 5-(pyrrolidin-1-yl)-2,4-difluorophenyl |
| 3000. | 2-fluoroethyl | 3-(pyrrolidin-1-yl)-2,4-difluorophenyl |

TABLE A-continued

| No. | R¹ | Ar |
|---|---|---|
| 3001. | 2-fluoroethyl | 3-(2-fluoropyrrolidin-1-yl)-phenyl |
| 3002. | 2-fluoroethyl | 3-((S)-2-fluoropyrrolidin-1-yl)-phenyl |
| 3003. | 2-fluoroethyl | 3-((R)-2-fluoropyrrolidin-1-yl)-phenyl |
| 3004. | 2-fluoroethyl | 3-(3-fluoropyrrolidin-1-yl)-phenyl |
| 3005. | 2-fluoroethyl | 3-((S)-3-fluoropyrrolidin-1-yl)-phenyl |
| 3006. | 2-fluoroethyl | 3-((R)-3-fluoropyrrolidin-1-yl)-phenyl |
| 3007. | 2-fluoroethyl | 3-(2,2-difluoropyrrolidin-1-yl)-phenyl |
| 3008. | 2-fluoroethyl | 3-(3,3-difluoropyrrolidin-1-yl)-phenyl |
| 3009. | 2-fluoroethyl | 3-(2-methylpyrrolidin-1-yl)-phenyl |
| 3010. | 2-fluoroethyl | 3-((S)-2-methylpyrrolidin-1-yl)-phenyl |
| 3011. | 2-fluoroethyl | 3-((R)-2-methylpyrrolidin-1-yl)-phenyl |
| 3012. | 2-fluoroethyl | 3-(3-methylpyrrolidin-1-yl)-phenyl |
| 3013. | 2-fluoroethyl | 3-((S)-3-methylpyrrolidin-1-yl)-phenyl |
| 3014. | 2-fluoroethyl | 3-((R)-3-methylpyrrolidin-1-yl)-phenyl |
| 3015. | 2-fluoroethyl | 3-(1-methylpyrrolidin-2-yl)-phenyl |
| 3016. | 2-fluoroethyl | 3-((S)-1-methylpyrrolidin-2-yl)-phenyl |
| 3017. | 2-fluoroethyl | 3-((R)-1-methylpyrrolidin-2-yl)-phenyl |
| 3018. | 2-fluoroethyl | 3-(1-methylpyrrolidin-3-yl)-phenyl |
| 3019. | 2-fluoroethyl | 3-((S)-1-methylpyrrolidin-3-yl)-phenyl |
| 3020. | 2-fluoroethyl | 3-((R)-1-methylpyrrolidin-3-yl)-phenyl |
| 3021. | 2-fluoroethyl | 3-(2,2-dimethylpyrrolidin-1-yl)-phenyl |
| 3022. | 2-fluoroethyl | 3-(3,3-dimethylpyrrolidin-1-yl)-phenyl |
| 3023. | 2-fluoroethyl | 3-(2-trifluoromethylpyrrolidin-1-yl)-phenyl |
| 3024. | 2-fluoroethyl | 3-((S)-2-trifluoromethylpyrrolidin-1-yl)-phenyl |
| 3025. | 2-fluoroethyl | 3-((R)-2-trifluoromethylpyrrolidin-1-yl)-phenyl |
| 3026. | 2-fluoroethyl | 3-(3-trifluoromethylpyrrolidin-1-yl)-phenyl |
| 3027. | 2-fluoroethyl | 3-((S)-3-trifluoromethylpyrrolidin-1-yl)-phenyl |
| 3028. | 2-fluoroethyl | 3-((R)-3-trifluoromethylpyrrolidin-1-yl)-phenyl |
| 3029. | 2-fluoroethyl | 3-(2-oxopyrrolidin-1-yl)-phenyl |
| 3030. | 2-fluoroethyl | 3-(2-oxo-oxazolidin-3-yl)-phenyl |
| 3031. | 2-fluoroethyl | 3-(piperidin-1-yl)-phenyl |
| 3032. | 2-fluoroethyl | 3-(2-methylpiperidin-1-yl)-phenyl |
| 3033. | 2-fluoroethyl | 3-((S)-2-methylpiperidin-1-yl)-phenyl |
| 3034. | 2-fluoroethyl | 3-((R)-2-methylpiperidin-1-yl)-phenyl |
| 3035. | 2-fluoroethyl | 3-(2-fluoropiperidin-1-yl)-phenyl |
| 3036. | 2-fluoroethyl | 3-((S)-2-fluoropiperidin-1-yl)-phenyl |
| 3037. | 2-fluoroethyl | 3-((R)-2-fluoropiperidin-1-yl)-phenyl |
| 3038. | 2-fluoroethyl | 3-(2,2-difluoropiperidin-1-yl)-phenyl |
| 3039. | 2-fluoroethyl | 3-(piperazin-1-yl)-phenyl |
| 3040. | 2-fluoroethyl | 3-(4-methylpiperazin-1-yl)-phenyl |
| 3041. | 2-fluoroethyl | 3-(morpholin-4-yl)-phenyl |
| 3042. | 2-fluoroethyl | 3-(morpholin-4-yl)-5-(trifluoromethyl)-phenyl |
| 3043. | 2-fluoroethyl | 5-(morpholin-4-yl)-2-methoxyphenyl |
| 3044. | 2-fluoroethyl | 3-(morpholin-4-yl)-4-methoxyphenyl |
| 3045. | 2-fluoroethyl | 5-(morpholin-4-yl)-2,4-difluorophenyl |
| 3046. | 2-fluoroethyl | 3-(morpholin-4-yl)-2,4-difluorophenyl |
| 3047. | 2-fluoroethyl | 3-(thiomorpholin-4-yl)-phenyl |
| 3048. | 2-fluoroethyl | 3-(1-oxo-thiomorpholin-4-yl)-phenyl |
| 3049. | 2-fluoroethyl | 3-(1,1-dioxo-thiomorpholin-4-yl)-phenyl |
| 3050. | 2-fluoroethyl | 3-(pyrrol-1-yl)-phenyl |
| 3051. | 2-fluoroethyl | 3-(pyrrol-2-yl)-phenyl |
| 3052. | 2-fluoroethyl | 3-(pyrrol-3-yl)-phenyl |
| 3053. | 2-fluoroethyl | 3-(1-methylpyrrol-2-yl)-phenyl |
| 3054. | 2-fluoroethyl | 3-(1-methylpyrrol-3-yl)-phenyl |
| 3055. | 2-fluoroethyl | 3-(furan-2-yl)-phenyl |
| 3056. | 2-fluoroethyl | 3-(furan-3-yl)-phenyl |
| 3057. | 2-fluoroethyl | 3-(thiophen-2-yl)-phenyl |
| 3058. | 2-fluoroethyl | 3-(thiophen-3-yl)-phenyl |
| 3059. | 2-fluoroethyl | 3-(5-propylthien-2-yl)-phenyl |
| 3060. | 2-fluoroethyl | 3-(pyrazol-1-yl)-phenyl |
| 3061. | 2-fluoroethyl | 3-(pyrazol-3-yl)-phenyl |
| 3062. | 2-fluoroethyl | 3-(pyrazol-4-yl)-phenyl |
| 3063. | 2-fluoroethyl | 3-(4-fluoropyrazol-1-yl)-phenyl |
| 3064. | 2-fluoroethyl | 3-(1-methyl-1H-pyrazol-4-yl)-phenyl |
| 3065. | 2-fluoroethyl | 3-(1-ethyl-1H-pyrazol-4-yl)-phenyl |
| 3066. | 2-fluoroethyl | 3-(1-methyl-1H-pyrazol-5-yl)-phenyl |
| 3067. | 2-fluoroethyl | 3-(1H-imidazol-2-yl)-phenyl |
| 3068. | 2-fluoroethyl | 3-(imidazol-1-yl)-phenyl |
| 3069. | 2-fluoroethyl | 3-(1-methylimidazol-2-yl)-phenyl |
| 3070. | 2-fluoroethyl | 3-(oxazol-2-yl)-phenyl |
| 3071. | 2-fluoroethyl | 3-(oxazol-4-yl)-phenyl |
| 3072. | 2-fluoroethyl | 3-(oxazol-5-yl)-phenyl |
| 3073. | 2-fluoroethyl | 3-(isoxazol-3-yl)-phenyl |
| 3074. | 2-fluoroethyl | 3-(isoxazol-4-yl)-phenyl |
| 3075. | 2-fluoroethyl | 3-(isoxazol-5-yl)-phenyl |
| 3076. | 2-fluoroethyl | 3-(thiazol-2-yl)-phenyl |
| 3077. | 2-fluoroethyl | 3-(thiazol-4-yl)-phenyl |
| 3078. | 2-fluoroethyl | 3-(thiazol-5-yl)-phenyl |

TABLE A-continued

| No. | R¹ | Ar |
|---|---|---|
| 3079. | 2-fluoroethyl | 3-(2-methylthiazol-4-yl)-phenyl |
| 3080. | 2-fluoroethyl | 3-(2-methylthiazol-5-yl)-phenyl |
| 3081. | 2-fluoroethyl | 3-([1,2,3]-triazol-1-yl)-phenyl |
| 3082. | 2-fluoroethyl | 3-([1,2,4]-triazol-1-yl)-phenyl |
| 3083. | 2-fluoroethyl | 3-([1,2,3]-triazol-2-yl)-phenyl |
| 3084. | 2-fluoroethyl | 3-(4H-[1,2,4]-triazol-3-yl)-phenyl |
| 3085. | 2-fluoroethyl | 3-([1,2,4]-triazol-4-yl)-phenyl |
| 3086. | 2-fluoroethyl | 3-(2H-[1,2,3]-triazol-4-yl)-phenyl |
| 3087. | 2-fluoroethyl | 3-(4-methyl-4H-[1,2,4]-triazol-3-yl)-phenyl |
| 3088. | 2-fluoroethyl | 3-(2-methyl-2H-[1,2,3]-triazol-4-yl)-phenyl |
| 3089. | 2-fluoroethyl | 3-([1,3,4]-oxadiazol-2-yl)-phenyl |
| 3090. | 2-fluoroethyl | 3-(5-methyl-[1,3,4]-oxadiazol-2-yl)-phenyl |
| 3091. | 2-fluoroethyl | 3-([1,2,4]-oxadiazol-3-yl)-phenyl |
| 3092. | 2-fluoroethyl | 3-(5-methyl-[1,2,4]-oxadiazol-3-yl)-phenyl |
| 3093. | 2-fluoroethyl | 3-([1,2,4]-oxadiazol-5-yl)-phenyl |
| 3094. | 2-fluoroethyl | 3-([1,2,3]-oxadiazol-4-yl)-phenyl |
| 3095. | 2-fluoroethyl | 3-([1,2,3]-oxadiazol-5-yl)-phenyl |
| 3096. | 2-fluoroethyl | 3-([1,2,3]-thiadiazol-4-yl)-phenyl |
| 3097. | 2-fluoroethyl | 3-(1H-tetrazol-5-yl)-phenyl |
| 3098. | 2-fluoroethyl | 3-(tetrazol-1-yl)-phenyl |
| 3099. | 2-fluoroethyl | 3-(2-methyl-2H-tetrazol-5-yl)-phenyl |
| 3100. | 2-fluoroethyl | 3-(1-methyl-1H-tetrazol-5-yl)-phenyl |
| 3101. | 2-fluoroethyl | 3-furazan-3-yl-phenyl |
| 3102. | 2-fluoroethyl | 3-(pyrid-2-yl)-phenyl |
| 3103. | 2-fluoroethyl | 3-(pyrid-3-yl)-phenyl |
| 3104. | 2-fluoroethyl | 3-(pyrid-4-yl)-phenyl |
| 3105. | 2-fluoroethyl | 3-(pyrimidin-2-yl)-phenyl |
| 3106. | 2-fluoroethyl | 3-(2-methylpyrimidin-4-yl)-phenyl |
| 3107. | 2-fluoroethyl | 3-(pyrimidin-4-yl)-phenyl |
| 3108. | 2-fluoroethyl | 3-(pyrimidin-5-yl)-phenyl |
| 3109. | 2-fluoroethyl | 5-bromopyridin-3-yl |
| 3110. | 2-fluoroethyl | 3-bromo-2-chloropyridin-5-yl |
| 3111. | 2-fluoroethyl | 4-methylpyridin-2-yl |
| 3112. | 2-fluoroethyl | 6-methylpyridin-2-yl |
| 3113. | 2-fluoroethyl | 4-(trifluoromethyl)-pyridin-2-yl |
| 3114. | 2-fluoroethyl | 6-(trifluoromethyl)-pyridin-2-yl |
| 3115. | 2-fluoroethyl | 5-(trifluoromethyl)-pyridin-3-yl |
| 3116. | 2-fluoroethyl | 5-(pyrrolidin-1-yl)-pyridin-3-yl |
| 3117. | 2-fluoroethyl | 3-(pyrrolidin-1-yl)-2-chloropyridin-5-yl |
| 3118. | 2-fluoroethyl | 3-(morpholin-4-yl)-2-chloropyridin-5-yl |
| 3119. | 2-fluoroethyl | 2-(morpholin-4-yl)-pyridin-5-yl |
| 3120. | 2-fluoroethyl | 2-phenoxypyridin-5-yl |
| 3121. | 2-fluoroethyl | 4-methylphenyl |
| 3122. | 2-fluoroethyl | 4-ethylphenyl |
| 3123. | 2-fluoroethyl | 4-propylphenyl |
| 3124. | 2-fluoroethyl | 4-isopropylphenyl |
| 3125. | 2-fluoroethyl | 4-sec-butylphenyl |
| 3126. | 2-fluoroethyl | 4-tert-butylphenyl |
| 3127. | 2-fluoroethyl | 4-isobutylphenyl |
| 3128. | 2-fluoroethyl | 4-(1,1-dimethylpropyl)-phenyl |
| 3129. | 2-fluoroethyl | 4-vinylphenyl |
| 3130. | 2-fluoroethyl | 4-isopropenylphenyl |
| 3131. | 2-fluoroethyl | 4-fluorophenyl |
| 3132. | 2-fluoroethyl | 4-chlorophenyl |
| 3133. | 2-fluoroethyl | 4-bromophenyl |
| 3134. | 2-fluoroethyl | 4-iodophenyl |
| 3135. | 2-fluoroethyl | 4-(fluoromethyl)phenyl |
| 3136. | 2-fluoroethyl | 4-(difluoromethyl)phenyl |
| 3137. | 2-fluoroethyl | 4-(trifluoromethyl)phenyl |
| 3138. | 2-fluoroethyl | 2,4-bis(trifluoromethyl)phenyl |
| 3139. | 2-fluoroethyl | 4-(1-fluoroethyl)-phenyl |
| 3140. | 2-fluoroethyl | 4-((S)-1-fluoroethyl)-phenyl |
| 3141. | 2-fluoroethyl | 4-((R)-1-fluoroethyl)-phenyl |
| 3142. | 2-fluoroethyl | 4-(2-fluoroethyl)-phenyl |
| 3143. | 2-fluoroethyl | 4-(1,1-difluoroethyl)-phenyl |
| 3144. | 2-fluoroethyl | 4-(2,2-difluoroethyl)-phenyl |
| 3145. | 2-fluoroethyl | 4-(2,2,2-trifluoroethyl)-phenyl |
| 3146. | 2-fluoroethyl | 4-(3-fluoropropyl)-phenyl |
| 3147. | 2-fluoroethyl | 4-(2-fluoropropyl)-phenyl |
| 3148. | 2-fluoroethyl | 4-((S)-2-fluoropropyl)-phenyl |
| 3149. | 2-fluoroethyl | 4-((R)-2-fluoropropyl)-phenyl |
| 3150. | 2-fluoroethyl | 4-(3,3-difluoropropyl)-phenyl |
| 3151. | 2-fluoroethyl | 4-(3,3,3-trifluoropropyl)-phenyl |
| 3152. | 2-fluoroethyl | 4-(1-fluoro-1-methylethyl)-phenyl |
| 3153. | 2-fluoroethyl | 4-(2-fluoro-1-methylethyl)-phenyl |
| 3154. | 2-fluoroethyl | 4-((S)-2-fluoro-1-methylethyl)-phenyl |
| 3155. | 2-fluoroethyl | 4-((R)-2-fluoro-1-methylethyl)-phenyl |
| 3156. | 2-fluoroethyl | 4-(2,2-difluoro-1-methylethyl)-phenyl |

TABLE A-continued

| No. | R¹ | Ar |
|---|---|---|
| 3157. | 2-fluoroethyl | 4-((S)-2,2-difluoro-1-methylethyl)-phenyl |
| 3158. | 2-fluoroethyl | 4-((R)-2,2-difluoro-1-methylethyl)-phenyl |
| 3159. | 2-fluoroethyl | 4-(2,2,2-trifluoro-1-methylethyl)-phenyl |
| 3160. | 2-fluoroethyl | 4-((S)-2,2,2-trifluoro-1-methylethyl)-phenyl |
| 3161. | 2-fluoroethyl | 4-((R)-2,2,2-trifluoro-1-methylethyl)-phenyl |
| 3162. | 2-fluoroethyl | 4-(2-fluoro-1-fluoromethylethyl)-phenyl |
| 3163. | 2-fluoroethyl | 4-(1-difluoromethyl-2,2-difluoroethyl)-phenyl |
| 3164. | 2-fluoroethyl | 4-(1,1-dimethyl-2-fluoroethyl)-phenyl |
| 3165. | 2-fluoroethyl | 4-methoxyphenyl |
| 3166. | 2-fluoroethyl | 4-ethoxyphenyl |
| 3167. | 2-fluoroethyl | 4-propoxyphenyl |
| 3168. | 2-fluoroethyl | 4-isopropoxyphenyl |
| 3169. | 2-fluoroethyl | 4-butoxyphenyl |
| 3170. | 2-fluoroethyl | 4-(fluoromethoxy)-phenyl |
| 3171. | 2-fluoroethyl | 4-(difluoromethoxy)-phenyl |
| 3172. | 2-fluoroethyl | 4-(trifluoromethoxy)-phenyl |
| 3173. | 2-fluoroethyl | 4-(2-fluoroethoxy)-phenyl |
| 3174. | 2-fluoroethyl | 4-(2,2-difluoroethoxy)-phenyl |
| 3175. | 2-fluoroethyl | 4-(2,2,2-trifluoroethoxy)-phenyl |
| 3176. | 2-fluoroethyl | 4-(1,1,2,2-tetrafluoroethoxy)-phenyl |
| 3177. | 2-fluoroethyl | 4-cyclopropylphenyl |
| 3178. | 2-fluoroethyl | 4-cyclobutylphenyl |
| 3179. | 2-fluoroethyl | 4-cyclopentylphenyl |
| 3180. | 2-fluoroethyl | 4-(2,2-difluorocyclopropyl)-phenyl |
| 3181. | 2-fluoroethyl | 3,4-difluorophenyl |
| 3182. | 2-fluoroethyl | 4-bromo-2-fluorophenyl |
| 3183. | 2-fluoroethyl | 2-bromo-4-fluorophenyl |
| 3184. | 2-fluoroethyl | 4-bromo-2,5-difluorophenyl |
| 3185. | 2-fluoroethyl | 5-bromo-2,4-difluorophenyl |
| 3186. | 2-fluoroethyl | 3-bromo-2,4-difluorophenyl |
| 3187. | 2-fluoroethyl | 3-chloro-4-(trifluoromethyl)-phenyl |
| 3188. | 2-fluoroethyl | 4-fluoro-3-(trifluoromethyl)-phenyl |
| 3189. | 2-fluoroethyl | 3-fluoro-5-(trifluoromethyl)-phenyl |
| 3190. | 2-fluoroethyl | 3-bromo-4-(trifluoromethyl)-phenyl |
| 3191. | 2-fluoroethyl | 5-bromo-3-(trifluoromethyl)-phenyl |
| 3192. | 2-fluoroethyl | 5-bromo-2-(trifluoromethyl)-phenyl |
| 3193. | 2-fluoroethyl | 2-bromo-5-methoxyphenyl |
| 3194. | 2-fluoroethyl | 4-bromo-3-methoxyphenyl |
| 3195. | 2-fluoroethyl | 3-fluoro-2-isopropylphenyl |
| 3196. | 2-fluoroethyl | 3-fluoro-4-isopropylphenyl |
| 3197. | 2-fluoroethyl | 4-(1-hydroxy-1-methylethyl)-phenyl |
| 3198. | 2-fluoroethyl | 4-(2-hydroxy-2-methylpropyl)-phenyl |
| 3199. | 2-fluoroethyl | 4-acetylphenyl |
| 3200. | 2-fluoroethyl | 4-acetylaminophenyl |
| 3201. | 2-fluoroethyl | 4-carboxyphenyl |
| 3202. | 2-fluoroethyl | 4-cyanophenyl |
| 3203. | 2-fluoroethyl | 4-nitrophenyl |
| 3204. | 2-fluoroethyl | 4-hydroxyphenyl |
| 3205. | 2-fluoroethyl | 4-(O-benzyl)-phenyl |
| 3206. | 2-fluoroethyl | 4-(2-methoxyethoxy)-phenyl |
| 3207. | 2-fluoroethyl | 4-(CH$_2$—N(CH$_3$)$_2$)-phenyl |
| 3208. | 2-fluoroethyl | 4-(NH—CO—NH$_2$)-phenyl |
| 3209. | 2-fluoroethyl | 4-(methylsulfanyl)-phenyl |
| 3210. | 2-fluoroethyl | 4-(fluoromethylsulfanyl)-phenyl |
| 3211. | 2-fluoroethyl | 4-(difluoromethylsulfanyl)-phenyl |
| 3212. | 2-fluoroethyl | 4-(trifluoromethylsulfanyl)-phenyl |
| 3213. | 2-fluoroethyl | 4-(methylsulfonyl)-phenyl |
| 3214. | 2-fluoroethyl | 4-(N-methoxy-N-methyl-amino)-phenyl |
| 3215. | 2-fluoroethyl | 4-(methoxyamino)-phenyl |
| 3216. | 2-fluoroethyl | 4-(ethoxyamino)-phenyl |
| 3217. | 2-fluoroethyl | 4-(N-methylaminooxy)-phenyl |
| 3218. | 2-fluoroethyl | 4-(N,N-dimethylaminooxy)-phenyl |
| 3219. | 2-fluoroethyl | 4-(azetidin-1-yl)-phenyl |
| 3220. | 2-fluoroethyl | 4-(2-methylazetidin-1-yl)-phenyl |
| 3221. | 2-fluoroethyl | 4-((S)-2-methylazetidin-1-yl)-phenyl |
| 3222. | 2-fluoroethyl | 4-((R)-2-methylazetidin-1-yl)-phenyl |
| 3223. | 2-fluoroethyl | 4-(3-fluoroazetidin-1-yl)-phenyl |
| 3224. | 2-fluoroethyl | 4-(2,2-difluoroazetidin-1-yl)-phenyl |
| 3225. | 2-fluoroethyl | 4-(3-methoxyazetidin-1-yl)-phenyl |
| 3226. | 2-fluoroethyl | 4-(3-hydroxyazetidin-1-yl)-phenyl |
| 3227. | 2-fluoroethyl | 4-(pyrrolidin-1-yl)-phenyl |
| 3228. | 2-fluoroethyl | 4-(pyrrolidin-2-yl)-phenyl |
| 3229. | 2-fluoroethyl | 4-((S)-pyrrolidin-2-yl)-phenyl |
| 3230. | 2-fluoroethyl | 4-((R)-pyrrolidin-2-yl)-phenyl |
| 3231. | 2-fluoroethyl | 4-(pyrrolidin-3-yl)-phenyl |
| 3232. | 2-fluoroethyl | 4-((S)-pyrrolidin-3-yl)-phenyl |
| 3233. | 2-fluoroethyl | 4-((R)-pyrrolidin-3-yl)-phenyl |
| 3234. | 2-fluoroethyl | 4-(pyrrolidin-1-yl)-5-(trifluoromethyl)-phenyl |

TABLE A-continued

| No. | R¹ | Ar |
|---|---|---|
| 3235. | 2-fluoroethyl | 4-(pyrrolidin-1-yl)-2-methoxyphenyl |
| 3236. | 2-fluoroethyl | 4-(pyrrolidin-1-yl)-34-methoxyphenyl |
| 3237. | 2-fluoroethyl | 4-(pyrrolidin-1-yl)-2,5-difluorophenyl |
| 3238. | 2-fluoroethyl | 4-(pyrrolidin-1-yl)-2,6-difluorophenyl |
| 3239. | 2-fluoroethyl | 4-(2-fluoropyrrolidin-1-yl)-phenyl |
| 3240. | 2-fluoroethyl | 4-((S)-2-fluoropyrrolidin-1-yl)-phenyl |
| 3241. | 2-fluoroethyl | 4-((R)-2-fluoropyrrolidin-1-yl)-phenyl |
| 3242. | 2-fluoroethyl | 4-(3-fluoropyrrolidin-1-yl)-phenyl |
| 3243. | 2-fluoroethyl | 4-((S)-3-fluoropyrrolidin-1-yl)-phenyl |
| 3244. | 2-fluoroethyl | 4-((R)-3-fluoropyrrolidin-1-yl)-phenyl |
| 3245. | 2-fluoroethyl | 4-(2,2-difluoropyrrolidin-1-yl)-phenyl |
| 3246. | 2-fluoroethyl | 4-(3,3-difluoropyrrolidin-1-yl)-phenyl |
| 3247. | 2-fluoroethyl | 4-(2-methylpyrrolidin-1-yl)-phenyl |
| 3248. | 2-fluoroethyl | 4-((S)-2-methylpyrrolidin-1-yl)-phenyl |
| 3249. | 2-fluoroethyl | 4-((R)-2-methylpyrrolidin-1-yl)-phenyl |
| 3250. | 2-fluoroethyl | 4-(3-methylpyrrolidin-1-yl)-phenyl |
| 3251. | 2-fluoroethyl | 4-((S)-3-methylpyrrolidin-1-yl)-phenyl |
| 3252. | 2-fluoroethyl | 4-((R)-3-methylpyrrolidin-1-yl)-phenyl |
| 3253. | 2-fluoroethyl | 4-(1-methylpyrrolidin-2-yl)-phenyl |
| 3254. | 2-fluoroethyl | 4-((S)-1-methylpyrrolidin-2-yl)-phenyl |
| 3255. | 2-fluoroethyl | 4-((R)-1-methylpyrrolidin-2-yl)-phenyl |
| 3256. | 2-fluoroethyl | 4-(1-methylpyrrolidin-3-yl)-phenyl |
| 3257. | 2-fluoroethyl | 4-((S)-1-methylpyrrolidin-3-yl)-phenyl |
| 3258. | 2-fluoroethyl | 4-((R)-1-methylpyrrolidin-3-yl)-phenyl |
| 3259. | 2-fluoroethyl | 4-(2,2-dimethylpyrrolidin-1-yl)-phenyl |
| 3260. | 2-fluoroethyl | 4-(3,3-dimethylpyrrolidin-1-yl)-phenyl |
| 3261. | 2-fluoroethyl | 4-(2-trifluoromethylpyrrolidin-1-yl)-phenyl |
| 3262. | 2-fluoroethyl | 4-((S)-2-trifluoromethylpyrrolidin-1-yl)-phenyl |
| 3263. | 2-fluoroethyl | 4-((R)-2-trifluoromethylpyrrolidin-1-yl)-phenyl |
| 3264. | 2-fluoroethyl | 4-(3-trifluoromethylpyrrolidin-1-yl)-phenyl |
| 3265. | 2-fluoroethyl | 4-((S)-3-trifluoromethylpyrrolidin-1-yl)-phenyl |
| 3266. | 2-fluoroethyl | 4-((R)-3-trifluoromethylpyrrolidin-1-yl)-phenyl |
| 3267. | 2-fluoroethyl | 4-(2-oxopyrrolidin-1-yl)-phenyl |
| 3268. | 2-fluoroethyl | 4-(2-oxo-oxazolidin-3-yl)-phenyl |
| 3269. | 2-fluoroethyl | 4-(piperidin-1-yl)-phenyl |
| 3270. | 2-fluoroethyl | 4-(2-methylpiperidin-1-yl)-phenyl |
| 3271. | 2-fluoroethyl | 4-((S)-2-methylpiperidin-1-yl)-phenyl |
| 3272. | 2-fluoroethyl | 4-((R)-2-methylpiperidin-1-yl)-phenyl |
| 3273. | 2-fluoroethyl | 4-(2-fluoropiperidin-1-yl)-phenyl |
| 3274. | 2-fluoroethyl | 4-((S)-2-fluoropiperidin-1-yl)-phenyl |
| 3275. | 2-fluoroethyl | 4-((R)-2-fluoropiperidin-1-yl)-phenyl |
| 3276. | 2-fluoroethyl | 4-(2,2-difluoropiperidin-1-yl)-phenyl |
| 3277. | 2-fluoroethyl | 4-(piperazin-1-yl)-phenyl |
| 3278. | 2-fluoroethyl | 4-(4-methylpiperazin-1-yl)-phenyl |
| 3279. | 2-fluoroethyl | 4-(morpholin-4-yl)-phenyl |
| 3280. | 2-fluoroethyl | 4-(morpholin-4-yl)-5-(trifluoromethyl)-phenyl |
| 3281. | 2-fluoroethyl | 4-(morpholin-4-yl)-2-methoxyphenyl |
| 3282. | 2-fluoroethyl | 4-(morpholin-4-yl)-3-methoxyphenyl |
| 3283. | 2-fluoroethyl | 4-(morpholin-4-yl)-2,5-difluorophenyl |
| 3284. | 2-fluoroethyl | 4-(morpholin-4-yl)-2,6-difluorophenyl |
| 3285. | 2-fluoroethyl | 4-(thiomorpholin-4-yl)-phenyl |
| 3286. | 2-fluoroethyl | 4-(1-oxo-thiomorpholin-4-yl)-phenyl |
| 3287. | 2-fluoroethyl | 4-(1,1-dioxo-thiomorpholin-4-yl)-phenyl |
| 3288. | 2-fluoroethyl | 4-(pyrrol-1-yl)-phenyl |
| 3289. | 2-fluoroethyl | 4-(pyrrol-2-yl)-phenyl |
| 3290. | 2-fluoroethyl | 4-(pyrrol-3-yl)-phenyl |
| 3291. | 2-fluoroethyl | 4-(1-methylpyrrol-2-yl)-phenyl |
| 3292. | 2-fluoroethyl | 4-(1-methylpyrrol-3-yl)-phenyl |
| 3293. | 2-fluoroethyl | 4-(furan-2-yl)-phenyl |
| 3294. | 2-fluoroethyl | 4-(furan-3-yl)-phenyl |
| 3295. | 2-fluoroethyl | 4-(thiophen-2-yl)-phenyl |
| 3296. | 2-fluoroethyl | 4-(thiophen-3-yl)-phenyl |
| 3297. | 2-fluoroethyl | 4-(5-propylthien-2-yl)-phenyl |
| 3298. | 2-fluoroethyl | 4-(pyrazol-1-yl)-phenyl |
| 3299. | 2-fluoroethyl | 4-(pyrazol-3-yl)-phenyl |
| 3300. | 2-fluoroethyl | 4-(pyrazol-4-yl)-phenyl |
| 3301. | 2-fluoroethyl | 4-(4-fluoropyrazol-1-yl)-phenyl |
| 3302. | 2-fluoroethyl | 4-(1-methyl-1H-pyrazol-4-yl)-phenyl |
| 3303. | 2-fluoroethyl | 4-(1-ethyl-1H-pyrazol-4-yl)-phenyl |
| 3304. | 2-fluoroethyl | 4-(1-methyl-1H-pyrazol-5-yl)-phenyl |
| 3305. | 2-fluoroethyl | 4-(1H-imidazol-2-yl)-phenyl |
| 3306. | 2-fluoroethyl | 4-(imidazol-1-yl)-phenyl |
| 3307. | 2-fluoroethyl | 4-(1-methylimidazol-2-yl)-phenyl |
| 3308. | 2-fluoroethyl | 4-(oxazol-2-yl)-phenyl |
| 3309. | 2-fluoroethyl | 4-(oxazol-4-yl)-phenyl |
| 3310. | 2-fluoroethyl | 4-(oxazol-5-yl)-phenyl |
| 3311. | 2-fluoroethyl | 4-(isoxazol-3-yl)-phenyl |
| 3312. | 2-fluoroethyl | 4-(isoxazol-4-yl)-phenyl |

TABLE A-continued

| No. | R¹ | Ar |
|---|---|---|
| 3313. | 2-fluoroethyl | 4-(isoxazol-5-yl)-phenyl |
| 3314. | 2-fluoroethyl | 4-(thiazol-2-yl)-phenyl |
| 3315. | 2-fluoroethyl | 4-(thiazol-4-yl)-phenyl |
| 3316. | 2-fluoroethyl | 4-(thiazol-5-yl)-phenyl |
| 3317. | 2-fluoroethyl | 4-(2-methylthiazol-4-yl)-phenyl |
| 3318. | 2-fluoroethyl | 4-(2-methylthiazol-5-yl)-phenyl |
| 3319. | 2-fluoroethyl | 4-([1,2,3]-triazol-1-yl)-phenyl |
| 3320. | 2-fluoroethyl | 4-([1,2,4]-triazol-1-yl)-phenyl |
| 3321. | 2-fluoroethyl | 4-([1,2,3]-triazol-2-yl)-phenyl |
| 3322. | 2-fluoroethyl | 4-(4H-[1,2,4]-triazol-3-yl)-phenyl |
| 3323. | 2-fluoroethyl | 4-([1,2,4]-triazol-4-yl)-phenyl |
| 3324. | 2-fluoroethyl | 4-(2H-[1,2,3]-triazol-4-yl)-phenyl |
| 3325. | 2-fluoroethyl | 4-(4-methyl-4H-[1,2,4]-triazol-3-yl)-phenyl |
| 3326. | 2-fluoroethyl | 4-(2-methyl-2H-[1,2,3]-triazol-4-yl)-phenyl |
| 3327. | 2-fluoroethyl | 4-([1,3,4]-oxadiazol-2-yl)-phenyl |
| 3328. | 2-fluoroethyl | 4-(5-methyl-[1,3,4]-oxadiazol-2-yl)-phenyl |
| 3329. | 2-fluoroethyl | 4-([1,2,4]-oxadiazol-3-yl)-phenyl |
| 3330. | 2-fluoroethyl | 4-(5-methyl-[1,2,4]-oxadiazol-3-yl)-phenyl |
| 3331. | 2-fluoroethyl | 4-([1,2,4]-oxadiazol-5-yl)-phenyl |
| 3332. | 2-fluoroethyl | 4-([1,2,3]-oxadiazol-4-yl)-phenyl |
| 3333. | 2-fluoroethyl | 4-([1,2,3]-oxadiazol-5-yl)-phenyl |
| 3334. | 2-fluoroethyl | 4-([1,2,3]-thiadiazol-4-yl)-phenyl |
| 3335. | 2-fluoroethyl | 4-(1H-tetrazol-5-yl)-phenyl |
| 3336. | 2-fluoroethyl | 4-(tetrazol-1-yl)-phenyl |
| 3337. | 2-fluoroethyl | 4-(2-methyl-2H-tetrazol-5-yl)-phenyl |
| 3338. | 2-fluoroethyl | 4-(1-methyl-1H-tetrazol-5-yl)-phenyl |
| 3339. | 2-fluoroethyl | 4-furazan-3-yl-phenyl |
| 3340. | 2-fluoroethyl | 4-(pyrid-2-yl)-phenyl |
| 3341. | 2-fluoroethyl | 4-(pyrid-3-yl)-phenyl |
| 3342. | 2-fluoroethyl | 4-(pyrid-4-yl)-phenyl |
| 3343. | 2-fluoroethyl | 4-(pyrimidin-2-yl)-phenyl |
| 3344. | 2-fluoroethyl | 4-(2-methylpyrimidin-4-yl)-phenyl |
| 3345. | 2-fluoroethyl | 4-(pyrimidin-4-yl)-phenyl |
| 3346. | 2-fluoroethyl | 4-(pyrimidin-5-yl)-phenyl |
| 3347. | 2-fluoroethyl | 4-bromo-2-chloropyridin-5-yl |
| 3348. | 2-fluoroethyl | 4-methylpyridin-2-yl |
| 3349. | 2-fluoroethyl | 5-methylpyridin-2-yl |
| 3350. | 2-fluoroethyl | 4-(pyrrolidin-1-yl)-2-chloropyridin-5-yl |
| 3351. | 2-fluoroethyl | 4-(morpholin-4-yl)-2-chloropyridin-5-yl |
| 3352. | 2-fluoroethyl | 2-(morpholin-4-yl)-pyridin-5-yl |
| 3353. | 2-fluoroethyl | 5-(morpholin-4-yl)-pyridin-2-yl |
| 3354. | 2-fluoroethyl | 2-phenoxypyridin-5-yl |
| 3355. | 2-fluoroethyl | 2,3-dichlorophenyl |
| 3356. | 2-fluoroethyl | 2,5-dichlorophenyl |
| 3357. | 2-fluoroethyl | 3,5-dichlorophenyl |
| 3358. | 2-fluoroethyl | 3-chloro-4-fluorophenyl |
| 3359. | 2-fluoroethyl | 4-bromo-2,5-dichlorophenyl |
| 3360. | 2-fluoroethyl | 3-bromo-4-(trifluoromethoxy)phenyl |
| 3361. | 2-fluoroethyl | 3,5-dibromo-4-(2-fluoroethoxy)-phenyl |
| 3362. | 2-fluoroethyl | 2,5-dimethylphenyl |
| 3363. | 2-fluoroethyl | 2,5-di-(trifluoromethyl)-phenyl |
| 3364. | 2-fluoroethyl | 3,5-di-(trifluoromethyl)-phenyl |
| 3365. | 2-fluoroethyl | 2,5-dimethoxyphenyl |
| 3366. | 2-fluoroethyl | 2-methoxy-5-methylphenyl |
| 3367. | 2-fluoroethyl | 2-methoxy-5-(trifluoromethyl)-phenyl |
| 3368. | 2-fluoroethyl | 4-fluoro-3-(oxazol-4-yl)-phenyl |
| 3369. | 2-fluoroethyl | thien-2-yl |
| 3370. | 2-fluoroethyl | thien-3-yl |
| 3371. | 2-fluoroethyl | 3-chlorothien-2-yl |
| 3372. | 2-fluoroethyl | 4-chlorothien-2-yl |
| 3373. | 2-fluoroethyl | 5-chlorothien-2-yl |
| 3374. | 2-fluoroethyl | 3-bromothien-2-yl |
| 3375. | 2-fluoroethyl | 4-bromothien-2-yl |
| 3376. | 2-fluoroethyl | 5-bromothien-2-yl |
| 3377. | 2-fluoroethyl | 4,5-dichlorothien-2-yl |
| 3378. | 2-fluoroethyl | 4,5-dibromothien-2-yl |
| 3379. | 2-fluoroethyl | 4-bromo-5-chlorothien-2-yl |
| 3380. | 2-fluoroethyl | 3-bromo-5-chlorothien-2-yl |
| 3381. | 2-fluoroethyl | 5-methylthien-2-yl |
| 3382. | 2-fluoroethyl | 5-ethylthien-2-yl |
| 3383. | 2-fluoroethyl | 5-propylthien-2-yl |
| 3384. | 2-fluoroethyl | 5-trifluoromethylthien-2-yl |
| 3385. | 2-fluoroethyl | 5-phenylthien-2-yl |
| 3386. | 2-fluoroethyl | 5-(pyrid-2-yl)-thien-2-yl |
| 3387. | 2-fluoroethyl | 5-(phenylsulfonyl)-thien-2-yl |
| 3388. | 2-fluoroethyl | 4-(phenylsulfonyl)-thien-2-yl |
| 3389. | 2-fluoroethyl | 5-(pyrid-2-ylsulfonyl)-thien-2-yl |

TABLE A-continued

| No. | R¹ | Ar |
|---|---|---|
| 3390. | 2-fluoroethyl | 5-(3-chloro-5-trifluoro-pyrid-2-ylsulfonyl)-thien-2-yl |
| 3391. | 2-fluoroethyl | 5-(benzoylaminomethyl)-thien-2-yl |
| 3392. | 2-fluoroethyl | 5-((4-chlorobenzoyl)aminomethyl)-thien-2-yl |
| 3393. | 2-fluoroethyl | 5-(acetylaminomethyl)-thien-2-yl |
| 3394. | 2-fluoroethyl | 5-(pyrazol-1-yl)-thien-2-yl |
| 3395. | 2-fluoroethyl | 5-(pyrazol-3-yl)-thien-2-yl |
| 3396. | 2-fluoroethyl | 5-(pyrazol-4-yl)-thien-2-yl |
| 3397. | 2-fluoroethyl | 5-(pyrazol-5-yl)-thien-2-yl |
| 3398. | 2-fluoroethyl | 5-(4-fluoropyrazol-1-yl)-thien-2-yl |
| 3399. | 2-fluoroethyl | 5-(1-methyl-5-trifluoromethyl-(1H)-pyrazol-3-yl)-thien-2-yl |
| 3400. | 2-fluoroethyl | 5-(1-methyl-3-trifluoromethyl-(1H)-pyrazol-5-yl)-thien-2-yl |
| 3401. | 2-fluoroethyl | 5-(4-carboxy-1-methyl-5-methylthio-(1H)-pyrazol-3-yl)-thien-2-yl |
| 3402. | 2-fluoroethyl | 5-(4-aminomethyl-1-methyl-5-methylthio-(1H)-pyrazol-3-yl)-thien-2-yl |
| 3403. | 2-fluoroethyl | 5-(isoxazol-3-yl)-thien-2-yl |
| 3404. | 2-fluoroethyl | 5-(isoxazol-4-yl)-thien-2-yl |
| 3405. | 2-fluoroethyl | 5-(isoxazol-5-yl)-thien-2-yl |
| 3406. | 2-fluoroethyl | 5-(5-trifluoromethylisoxazol-3-yl)-thien-2-yl |
| 3407. | 2-fluoroethyl | 5-(oxazol-2-yl)-thien-2-yl |
| 3408. | 2-fluoroethyl | 5-(oxazol-4-yl)-thien-2-yl |
| 3409. | 2-fluoroethyl | 5-(oxazol-5-yl)-thien-2-yl |
| 3410. | 2-fluoroethyl | 5-(2-methyloxazol-4-yl)-thien-2-yl |
| 3411. | 2-fluoroethyl | 5-(2-methyloxazol-5-yl)-thien-2-yl |
| 3412. | 2-fluoroethyl | 5-(isothiazol-3-yl)-thien-2-yl |
| 3413. | 2-fluoroethyl | 5-(isothiazol-4-yl)-thien-2-yl |
| 3414. | 2-fluoroethyl | 5-(isothiazol-5-yl)-thien-2-yl |
| 3415. | 2-fluoroethyl | 5-(5-trifluoromethylisothiazol-3-yl)-thien-2-yl |
| 3416. | 2-fluoroethyl | 5-(thiazol-2-yl)-thien-2-yl |
| 3417. | 2-fluoroethyl | 5-(thiazol-4-yl)-thien-2-yl |
| 3418. | 2-fluoroethyl | 5-(thiazol-5-yl)-thien-2-yl |
| 3419. | 2-fluoroethyl | 5-(2-methylthiazol-4-yl)-thien-2-yl |
| 3420. | 2-fluoroethyl | 5-(2-methylthiazol-5-yl)-thien-2-yl |
| 3421. | 2-fluoroethyl | 5-([1,2,3]-oxadiazol-4-yl)-thien-2-yl |
| 3422. | 2-fluoroethyl | 5-([1,2,3]-thiadiazol-4-yl)-thien-2-yl |
| 3423. | 2-fluoroethyl | 5-(pyrimidin-2-yl)-thien-2-yl |
| 3424. | 2-fluoroethyl | 5-(pyrimidin-4-yl)-thien-2-yl |
| 3425. | 2-fluoroethyl | 5-(pyrimidin-5-yl)-thien-2-yl |
| 3426. | 2-fluoroethyl | 5-(2-methylthiopyrimidin-4-yl)-thien-2-yl |
| 3427. | 2-fluoroethyl | 5-([1,3]-dioxolan-2-yl)-thien-2-yl |
| 3428. | 2-fluoroethyl | 3-([1,3]-dioxolan-2-yl)-thien-2-yl thien-2-yl |
| 3429. | 2-fluoroethyl | 5-((3-chloro-5-(trifluoromethyl)-pyridin-2-yl)-methyl)-thien-2-yl |
| 3430. | 2-fluoroethyl | 5-[3-chloro-5-(trifluoromethyl)-pyrid-2-ylsulfonyl]-thien-2-yl |
| 3431. | 2-fluoroethyl | 2-chlorothien-3-yl |
| 3432. | 2-fluoroethyl | 4-chlorothien-3-yl |
| 3433. | 2-fluoroethyl | 5-chlorothien-3-yl |
| 3434. | 2-fluoroethyl | 2-bromothien-3-yl |
| 3435. | 2-fluoroethyl | 4-bromothien-3-yl |
| 3436. | 2-fluoroethyl | 5-bromothien-3-yl |
| 3437. | 2-fluoroethyl | 2,5-dichlorothien-3-yl |
| 3438. | 2-fluoroethyl | 2,5-dibromothien-3-yl |
| 3439. | 2-fluoroethyl | 2,4,5-trichlorothien-3-yl |
| 3440. | 2-fluoroethyl | 4-bromo-2,5-dichlorothien-3-yl |
| 3441. | 2-fluoroethyl | 2-chloro-5-methylsulfonylthien-3-yl |
| 3442. | 2-fluoroethyl | 2,5-dimethylthien-3-yl |
| 3443. | 2-fluoroethyl | 4-hydroxythien-3-yl |
| 3444. | 2-fluoroethyl | 2-phenylthien-3-yl |
| 3445. | 2-fluoroethyl | 4-phenyl-5-(trofluoromethyl)-thien-3-yl |
| 3446. | 2-fluoroethyl | 2-methoxycarbonyl-4-phenyl-5-(trifluoromethyl)-thien-3-yl |
| 3447. | 2-fluoroethyl | benzo[b]thiophen-2-yl |
| 3448. | 2-fluoroethyl | benzo[b]thiophen-3-yl |
| 3449. | 2-fluoroethyl | 3-methyl-benzo[b]thiophen-2-yl |
| 3450. | 2-fluoroethyl | 5-methyl-benzo[b]thiophen-2-yl |
| 3451. | 2-fluoroethyl | 5-fluoro-3-methyl-benzo[b]thiophen-2-yl |
| 3452. | 2-fluoroethyl | 5-chloro-3-methyl-benzo[b]thiophen-2-yl |
| 3453. | 2-fluoroethyl | 5-bromo-3-methyl-benzo[b]thiophen-2-yl |
| 3454. | cyclopropylmethyl | 3-methylphenyl |
| 3455. | cyclopropylmethyl | 3-ethylphenyl |
| 3456. | cyclopropylmethyl | 3-propylphenyl |
| 3457. | cyclopropylmethyl | 3-isopropylphenyl |
| 3458. | cyclopropylmethyl | 3-sec-butylphenyl |
| 3459. | cyclopropylmethyl | 3-tert-butylphenyl |

TABLE A-continued

| No. | R¹ | Ar |
|---|---|---|
| 3460. | cyclopropylmethyl | 3-isobutylphenyl |
| 3461. | cyclopropylmethyl | 3-(1,1-dimethylpropyl)-phenyl |
| 3462. | cyclopropylmethyl | 3-vinylphenyl |
| 3463. | cyclopropylmethyl | 3-isopropenylphenyl |
| 3464. | cyclopropylmethyl | 3-fluorophenyl |
| 3465. | cyclopropylmethyl | 2-fluorophenyl |
| 3466. | cyclopropylmethyl | 3-chlorophenyl |
| 3467. | cyclopropylmethyl | 3-bromophenyl |
| 3468. | cyclopropylmethyl | 3-iodophenyl |
| 3469. | cyclopropylmethyl | 3-(fluoromethyl)phenyl |
| 3470. | cyclopropylmethyl | 3-(difluoromethyl)phenyl |
| 3471. | cyclopropylmethyl | 3-(trifluoromethyl)phenyl |
| 3472. | cyclopropylmethyl | 3,5-bis(trifluoromethyl)phenyl |
| 3473. | cyclopropylmethyl | 3-(1-fluoroethyl)-phenyl |
| 3474. | cyclopropylmethyl | 3-((S)-1-fluoroethyl)-phenyl |
| 3475. | cyclopropylmethyl | 3-((R)-1-fluoroethyl)-phenyl |
| 3476. | cyclopropylmethyl | 3-(2-fluoroethyl)-phenyl |
| 3477. | cyclopropylmethyl | 3-(1,1-difluoroethyl)-phenyl |
| 3478. | cyclopropylmethyl | 3-(2,2-difluoroethyl)-phenyl |
| 3479. | cyclopropylmethyl | 3-(2,2,2-trifluoroethyl)-phenyl |
| 3480. | cyclopropylmethyl | 3-(3-fluoropropyl)-phenyl |
| 3481. | cyclopropylmethyl | 3-(2-fluoropropyl)-phenyl |
| 3482. | cyclopropylmethyl | 3-((S)-2-fluoropropyl)-phenyl |
| 3483. | cyclopropylmethyl | 3-((R)-2-fluoropropyl)-phenyl |
| 3484. | cyclopropylmethyl | 3-(3,3-difluoropropyl)-phenyl |
| 3485. | cyclopropylmethyl | 3-(3,3,3-trifluoropropyl)-phenyl |
| 3486. | cyclopropylmethyl | 3-(1-fluoro-1-methylethyl)-phenyl |
| 3487. | cyclopropylmethyl | 3-(2-fluoro-1-methylethyl)-phenyl |
| 3488. | cyclopropylmethyl | 3-((S)-2-fluoro-1-methylethyl)-phenyl |
| 3489. | cyclopropylmethyl | 3-((R)-2-fluoro-1-methylethyl)-phenyl |
| 3490. | cyclopropylmethyl | 3-(2,2-difluoro-1-methylethyl)-phenyl |
| 3491. | cyclopropylmethyl | 3-((S)-2,2-difluoro-1-methylethyl)-phenyl |
| 3492. | cyclopropylmethyl | 3-((R)-2,2-difluoro-1-methylethyl)-phenyl |
| 3493. | cyclopropylmethyl | 3-(2,2,2-trifluoro-1-methylethyl)-phenyl |
| 3494. | cyclopropylmethyl | 3-((S)-2,2,2-trifluoro-1-methylethyl)-phenyl |
| 3495. | cyclopropylmethyl | 3-((R)-2,2,2-trifluoro-1-methylethyl)-phenyl |
| 3496. | cyclopropylmethyl | 3-(2-fluoro-1-fluoromethylethyl)-phenyl |
| 3497. | cyclopropylmethyl | 3-(1-difluoromethyl-2,2-difluoroethyl)-phenyl |
| 3498. | cyclopropylmethyl | 3-(1,1-dimethyl-2-fluoroethyl)-phenyl |
| 3499. | cyclopropylmethyl | 3-methoxyphenyl |
| 3500. | cyclopropylmethyl | 3-ethoxyphenyl |
| 3501. | cyclopropylmethyl | 3-propoxyphenyl |
| 3502. | cyclopropylmethyl | 3-isopropoxyphenyl |
| 3503. | cyclopropylmethyl | 3-butoxyphenyl |
| 3504. | cyclopropylmethyl | 3-(fluoromethoxy)-phenyl |
| 3505. | cyclopropylmethyl | 3-(difluoromethoxy)-phenyl |
| 3506. | cyclopropylmethyl | 3-(trifluoromethoxy)-phenyl |
| 3507. | cyclopropylmethyl | 3-(2-fluoroethoxy)-phenyl |
| 3508. | cyclopropylmethyl | 3-(2,2-difluoroethoxy)-phenyl |
| 3509. | cyclopropylmethyl | 3-(2,2,2-trifluoroethoxy)-phenyl |
| 3510. | cyclopropylmethyl | 3-(1,1,2,2-tetrafluoroethoxy)-phenyl |
| 3511. | cyclopropylmethyl | 3-cyclopropylphenyl |
| 3512. | cyclopropylmethyl | 3-cyclobutylphenyl |
| 3513. | cyclopropylmethyl | 3-cyclopentylphenyl |
| 3514. | cyclopropylmethyl | 3-(2,2-difluorocyclopropyl)-phenyl |
| 3515. | cyclopropylmethyl | 3,4-difluorophenyl |
| 3516. | cyclopropylmethyl | 3-bromo-2-fluorophenyl |
| 3517. | cyclopropylmethyl | 2-bromo-3-fluorophenyl |
| 3518. | cyclopropylmethyl | 3-bromo-2,5-difluorophenyl |
| 3519. | cyclopropylmethyl | 5-bromo-2,4-difluorophenyl |
| 3520. | cyclopropylmethyl | 3-bromo-2,4-difluorophenyl |
| 3521. | cyclopropylmethyl | 4-chloro-3-(trifluoromethyl)-phenyl |
| 3522. | cyclopropylmethyl | 2-chloro-5-(trifluoromethyl)-phenyl |
| 3523. | cyclopropylmethyl | 2-fluoro-5-(trifluoromethyl)-phenyl |
| 3524. | cyclopropylmethyl | 4-fluoro-3-(trifluoromethyl)-phenyl |
| 3525. | cyclopropylmethyl | 3-fluoro-5-(trifluoromethyl)-phenyl |
| 3526. | cyclopropylmethyl | 4-bromo-3-(trifluoromethyl)-phenyl |
| 3527. | cyclopropylmethyl | 3-bromo-5-(trifluoromethyl)-phenyl |
| 3528. | cyclopropylmethyl | 2-bromo-5-(trifluoromethyl)-phenyl |
| 3529. | cyclopropylmethyl | 5-bromo-2-methoxyphenyl |
| 3530. | cyclopropylmethyl | 3-bromo-4-methoxyphenyl |
| 3531. | cyclopropylmethyl | 2-fluoro-3-isopropylphenyl |
| 3532. | cyclopropylmethyl | 4-fluoro-3-isopropylphenyl |
| 3533. | cyclopropylmethyl | 3-(1-hydroxy-1-methylethyl)-phenyl |
| 3534. | cyclopropylmethyl | 3-(2-hydroxy-2-methylpropyl)-phenyl |
| 3535. | cyclopropylmethyl | 3-acetylphenyl |
| 3536. | cyclopropylmethyl | 3-acetylaminophenyl |
| 3537. | cyclopropylmethyl | 3-carboxyphenyl |

TABLE A-continued

| No. | R¹ | Ar |
|---|---|---|
| 3538. | cyclopropylmethyl | 3-cyanophenyl |
| 3539. | cyclopropylmethyl | 3-nitrophenyl |
| 3540. | cyclopropylmethyl | 3-hydroxyphenyl |
| 3541. | cyclopropylmethyl | 3-(O-benzyl)-phenyl |
| 3542. | cyclopropylmethyl | 3-(2-methoxyethoxy)-phenyl |
| 3543. | cyclopropylmethyl | 3-($CH_2$—$N(CH_3)_2$)-phenyl |
| 3544. | cyclopropylmethyl | 3-(NH—CO—$NH_2$)-phenyl |
| 3545. | cyclopropylmethyl | 3-(methylsulfanyl)-phenyl |
| 3546. | cyclopropylmethyl | 3-(fluoromethylsulfanyl)-phenyl |
| 3547. | cyclopropylmethyl | 3-(difluoromethylsulfanyl)-phenyl |
| 3548. | cyclopropylmethyl | 3-(trifluoromethylsulfanyl)-phenyl |
| 3549. | cyclopropylmethyl | 3-(methylsulfonyl)-phenyl |
| 3550. | cyclopropylmethyl | 3-(N-methoxy-N-methyl-amino)-phenyl |
| 3551. | cyclopropylmethyl | 3-(methoxyamino)-phenyl |
| 3552. | cyclopropylmethyl | 3-(ethoxyamino)-phenyl |
| 3553. | cyclopropylmethyl | 3-(N-methylaminooxy)-phenyl |
| 3554. | cyclopropylmethyl | 3-(N,N-dimethylaminooxy)-phenyl |
| 3555. | cyclopropylmethyl | 3-(azetidin-1-yl)-phenyl |
| 3556. | cyclopropylmethyl | 3-(2-methylazetidin-1-yl)-phenyl |
| 3557. | cyclopropylmethyl | 3-((S)-2-methylazetidin-1-yl)-phenyl |
| 3558. | cyclopropylmethyl | 3-((R)-2-methylazetidin-1-yl)-phenyl |
| 3559. | cyclopropylmethyl | 3-(3-fluoroazetidin-1-yl)-phenyl |
| 3560. | cyclopropylmethyl | 3-(2,2-difluoroazetidin-1-yl)-phenyl |
| 3561. | cyclopropylmethyl | 3-(3-methoxyazetidin-1-yl)-phenyl |
| 3562. | cyclopropylmethyl | 3-(3-hydroxyazetidin-1-yl)-phenyl |
| 3563. | cyclopropylmethyl | 3-(pyrrolidin-1-yl)-phenyl |
| 3564. | cyclopropylmethyl | 3-(pyrrolidin-2-yl)-phenyl |
| 3565. | cyclopropylmethyl | 3-((S)-pyrrolidin-2-yl)-phenyl |
| 3566. | cyclopropylmethyl | 3-((R)-pyrrolidin-2-yl)-phenyl |
| 3567. | cyclopropylmethyl | 3-(pyrrolidin-3-yl)-phenyl |
| 3568. | cyclopropylmethyl | 3-((S)-pyrrolidin-3-yl)-phenyl |
| 3569. | cyclopropylmethyl | 3-((R)-pyrrolidin-3-yl)-phenyl |
| 3570. | cyclopropylmethyl | 3-(pyrrolidin-1-yl)-5-(trifluoromethyl)-phenyl |
| 3571. | cyclopropylmethyl | 5-(pyrrolidin-1-yl)-2-methoxyphenyl |
| 3572. | cyclopropylmethyl | 3-(pyrrolidin-1-yl)-4-methoxyphenyl |
| 3573. | cyclopropylmethyl | 5-(pyrrolidin-1-yl)-2,4-difluorophenyl |
| 3574. | cyclopropylmethyl | 3-(pyrrolidin-1-yl)-2,4-difluorophenyl |
| 3575. | cyclopropylmethyl | 3-(2-fluoropyrrolidin-1-yl)-phenyl |
| 3576. | cyclopropylmethyl | 3-((S)-2-fluoropyrrolidin-1-yl)-phenyl |
| 3577. | cyclopropylmethyl | 3-((R)-2-fluoropyrrolidin-1-yl)-phenyl |
| 3578. | cyclopropylmethyl | 3-(3-fluoropyrrolidin-1-yl)-phenyl |
| 3579. | cyclopropylmethyl | 3-((S)-3-fluoropyrrolidin-1-yl)-phenyl |
| 3580. | cyclopropylmethyl | 3-((R)-3-fluoropyrrolidin-1-yl)-phenyl |
| 3581. | cyclopropylmethyl | 3-(2,2-difluoropyrrolidin-1-yl)-phenyl |
| 3582. | cyclopropylmethyl | 3-(3,3-difluoropyrrolidin-1-yl)-phenyl |
| 3583. | cyclopropylmethyl | 3-(2-methylpyrrolidin-1-yl)-phenyl |
| 3584. | cyclopropylmethyl | 3-((S)-2-methylpyrrolidin-1-yl)-phenyl |
| 3585. | cyclopropylmethyl | 3-((R)-2-methylpyrrolidin-1-yl)-phenyl |
| 3586. | cyclopropylmethyl | 3-(3-methylpyrrolidin-1-yl)-phenyl |
| 3587. | cyclopropylmethyl | 3-((S)-3-methylpyrrolidin-1-yl)-phenyl |
| 3588. | cyclopropylmethyl | 3-((R)-3-methylpyrrolidin-1-yl)-phenyl |
| 3589. | cyclopropylmethyl | 3-(1-methylpyrrolidin-2-yl)-phenyl |
| 3590. | cyclopropylmethyl | 3-((S)-1-methylpyrrolidin-2-yl)-phenyl |
| 3591. | cyclopropylmethyl | 3-((R)-1-methylpyrrolidin-2-yl)-phenyl |
| 3592. | cyclopropylmethyl | 3-(1-methylpyrrolidin-3-yl)-phenyl |
| 3593. | cyclopropylmethyl | 3-((S)-1-methylpyrrolidin-3-yl)-phenyl |
| 3594. | cyclopropylmethyl | 3-((R)-1-methylpyrrolidin-3-yl)-phenyl |
| 3595. | cyclopropylmethyl | 3-(2,2-dimethylpyrrolidin-1-yl)-phenyl |
| 3596. | cyclopropylmethyl | 3-(3,3-dimethylpyrrolidin-1-yl)-phenyl |
| 3597. | cyclopropylmethyl | 3-(2-trifluoromethylpyrrolidin-1-yl)-phenyl |
| 3598. | cyclopropylmethyl | 3-((S)-2-trifluoromethylpyrrolidin-1-yl)-phenyl |
| 3599. | cyclopropylmethyl | 3-((R)-2-trifluoromethylpyrrolidin-1-yl)-phenyl |
| 3600. | cyclopropylmethyl | 3-(3-trifluoromethylpyrrolidin-1-yl)-phenyl |
| 3601. | cyclopropylmethyl | 3-((S)-3-trifluoromethylpyrrolidin-1-yl)-phenyl |
| 3602. | cyclopropylmethyl | 3-((R)-3-trifluoromethylpyrrolidin-1-yl)-phenyl |
| 3603. | cyclopropylmethyl | 3-(2-oxopyrrolidin-1-yl)-phenyl |
| 3604. | cyclopropylmethyl | 3-(2-oxo-oxazolidin-3-yl)-phenyl |
| 3605. | cyclopropylmethyl | 3-(piperidin-1-yl)-phenyl |
| 3606. | cyclopropylmethyl | 3-(2-methylpiperidin-1-yl)-phenyl |
| 3607. | cyclopropylmethyl | 3-((S)-2-methylpiperidin-1-yl)-phenyl |
| 3608. | cyclopropylmethyl | 3-((R)-2-methylpiperidin-1-yl)-phenyl |
| 3609. | cyclopropylmethyl | 3-(2-fluoropiperidin-1-yl)-phenyl |
| 3610. | cyclopropylmethyl | 3-((S)-2-fluoropiperidin-1-yl)-phenyl |
| 3611. | cyclopropylmethyl | 3-((R)-2-fluoropiperidin-1-yl)-phenyl |
| 3612. | cyclopropylmethyl | 3-(2,2-difluoropiperidin-1-yl)-phenyl |
| 3613. | cyclopropylmethyl | 3-(piperazin-1-yl)-phenyl |
| 3614. | cyclopropylmethyl | 3-(4-methylpiperazin-1-yl)-phenyl |
| 3615. | cyclopropylmethyl | 3-(morpholin-4-yl)-phenyl |

TABLE A-continued

| No. | R¹ | Ar |
|---|---|---|
| 3616. | cyclopropylmethyl | 3-(morpholin-4-yl)-5-(trifluoromethyl)-phenyl |
| 3617. | cyclopropylmethyl | 5-(morpholin-4-yl)-2-methoxyphenyl |
| 3618. | cyclopropylmethyl | 3-(morpholin-4-yl)-4-methoxyphenyl |
| 3619. | cyclopropylmethyl | 5-(morpholin-4-yl)-2,4-difluorophenyl |
| 3620. | cyclopropylmethyl | 3-(morpholin-4-yl)-2,4-difluorophenyl |
| 3621. | cyclopropylmethyl | 3-(thiomorpholin-4-yl)-phenyl |
| 3622. | cyclopropylmethyl | 3-(1-oxo-thiomorpholin-4-yl)-phenyl |
| 3623. | cyclopropylmethyl | 3-(1,1-dioxo-thiomorpholin-4-yl)-phenyl |
| 3624. | cyclopropylmethyl | 3-(pyrrol-1-yl)-phenyl |
| 3625. | cyclopropylmethyl | 3-(pyrrol-2-yl)-phenyl |
| 3626. | cyclopropylmethyl | 3-(pyrrol-3-yl)-phenyl |
| 3627. | cyclopropylmethyl | 3-(1-methylpyrrol-2-yl)-phenyl |
| 3628. | cyclopropylmethyl | 3-(1-methylpyrrol-3-yl)-phenyl |
| 3629. | cyclopropylmethyl | 3-(furan-2-yl)-phenyl |
| 3630. | cyclopropylmethyl | 3-(furan-3-yl)-phenyl |
| 3631. | cyclopropylmethyl | 3-(thiophen-2-yl)-phenyl |
| 3632. | cyclopropylmethyl | 3-(thiophen-3-yl)-phenyl |
| 3633. | cyclopropylmethyl | 3-(5-propylthien-2-yl)-phenyl |
| 3634. | cyclopropylmethyl | 3-(pyrazol-1-yl)-phenyl |
| 3635. | cyclopropylmethyl | 3-(pyrazol-3-yl)-phenyl |
| 3636. | cyclopropylmethyl | 3-(pyrazol-4-yl)-phenyl |
| 3637. | cyclopropylmethyl | 3-(4-fluoropyrazol-1-yl)-phenyl |
| 3638. | cyclopropylmethyl | 3-(1-methyl-1H-pyrazol-4-yl)-phenyl |
| 3639. | cyclopropylmethyl | 3-(1-ethyl-1H-pyrazol-4-yl)-phenyl |
| 3640. | cyclopropylmethyl | 3-(1-methyl-1H-pyrazol-5-yl)-phenyl |
| 3641. | cyclopropylmethyl | 3-(1H-imidazol-2-yl)-phenyl |
| 3642. | cyclopropylmethyl | 3-(imidazol-1-yl)-phenyl |
| 3643. | cyclopropylmethyl | 3-(1-methylimidazol-2-yl)-phenyl |
| 3644. | cyclopropylmethyl | 3-(oxazol-2-yl)-phenyl |
| 3645. | cyclopropylmethyl | 3-(oxazol-4-yl)-phenyl |
| 3646. | cyclopropylmethyl | 3-(oxazol-5-yl)-phenyl |
| 3647. | cyclopropylmethyl | 3-(isoxazol-3-yl)-phenyl |
| 3648. | cyclopropylmethyl | 3-(isoxazol-4-yl)-phenyl |
| 3649. | cyclopropylmethyl | 3-(isoxazol-5-yl)-phenyl |
| 3650. | cyclopropylmethyl | 3-(thiazol-2-yl)-phenyl |
| 3651. | cyclopropylmethyl | 3-(thiazol-4-yl)-phenyl |
| 3652. | cyclopropylmethyl | 3-(thiazol-5-yl)-phenyl |
| 3653. | cyclopropylmethyl | 3-(2-methylthiazol-4-yl)-phenyl |
| 3654. | cyclopropylmethyl | 3-(2-methylthiazol-5-yl)-phenyl |
| 3655. | cyclopropylmethyl | 3-([1,2,3]-triazol-1-yl)-phenyl |
| 3656. | cyclopropylmethyl | 3-([1,2,4]-triazol-1-yl)-phenyl |
| 3657. | cyclopropylmethyl | 3-([1,2,3]-triazol-2-yl)-phenyl |
| 3658. | cyclopropylmethyl | 3-(4H-[1,2,4]-triazol-3-yl)-phenyl |
| 3659. | cyclopropylmethyl | 3-([1,2,4]-triazol-4-yl)-phenyl |
| 3660. | cyclopropylmethyl | 3-(2H-[1,2,3]-triazol-4-yl)-phenyl |
| 3661. | cyclopropylmethyl | 3-(4-methyl-4H-[1,2,4]-triazol-3-yl)-phenyl |
| 3662. | cyclopropylmethyl | 3-(2-methyl-2H-[1,2,3]-triazol-4-yl)-phenyl |
| 3663. | cyclopropylmethyl | 3-([1,3,4]-oxadiazol-2-yl)-phenyl |
| 3664. | cyclopropylmethyl | 3-(5-methyl-[1,3,4]-oxadiazol-2-yl)-phenyl |
| 3665. | cyclopropylmethyl | 3-([1,2,4]-oxadiazol-3-yl)-phenyl |
| 3666. | cyclopropylmethyl | 3-(5-methyl-[1,2,4]-oxadiazol-3-yl)-phenyl |
| 3667. | cyclopropylmethyl | 3-([1,2,4]-oxadiazol-5-yl)-phenyl |
| 3668. | cyclopropylmethyl | 3-([1,2,3]-oxadiazol-4-yl)-phenyl |
| 3669. | cyclopropylmethyl | 3-([1,2,3]-oxadiazol-5-yl)-phenyl |
| 3670. | cyclopropylmethyl | 3-([1,2,3]-thiadiazol-4-yl)-phenyl |
| 3671. | cyclopropylmethyl | 3-(1H-tetrazol-5-yl)-phenyl |
| 3672. | cyclopropylmethyl | 3-(tetrazol-1-yl)-phenyl |
| 3673. | cyclopropylmethyl | 3-(2-methyl-2H-tetrazol-5-yl)-phenyl |
| 3674. | cyclopropylmethyl | 3-(1-methyl-1H-tetrazol-5-yl)-phenyl |
| 3675. | cyclopropylmethyl | 3-furazan-3-yl-phenyl |
| 3676. | cyclopropylmethyl | 3-(pyrid-2-yl)-phenyl |
| 3677. | cyclopropylmethyl | 3-(pyrid-3-yl)-phenyl |
| 3678. | cyclopropylmethyl | 3-(pyrid-4-yl)-phenyl |
| 3679. | cyclopropylmethyl | 3-(pyrimidin-2-yl)-phenyl |
| 3680. | cyclopropylmethyl | 3-(2-methylpyrimidin-4-yl)-phenyl |
| 3681. | cyclopropylmethyl | 3-(pyrimidin-4-yl)-phenyl |
| 3682. | cyclopropylmethyl | 3-(pyrimidin-5-yl)-phenyl |
| 3683. | cyclopropylmethyl | 5-bromopyridin-3-yl |
| 3684. | cyclopropylmethyl | 3-bromo-2-chloropyridin-5-yl |
| 3685. | cyclopropylmethyl | 4-methylpyridin-2-yl |
| 3686. | cyclopropylmethyl | 6-methylpyridin-2-yl |
| 3687. | cyclopropylmethyl | 4-(trifluoromethyl)-pyridin-2-yl |
| 3688. | cyclopropylmethyl | 6-(trifluoromethyl)-pyridin-2-yl |
| 3689. | cyclopropylmethyl | 5-(trifluoromethyl)-pyridin-3-yl |
| 3690. | cyclopropylmethyl | 5-(pyrrolidin-1-yl)-pyridin-3-yl |
| 3691. | cyclopropylmethyl | 3-(pyrrolidin-1-yl)-2-chloropyridin-5-yl |
| 3692. | cyclopropylmethyl | 3-(morpholin-4-yl)-2-chloropyridin-5-yl |
| 3693. | cyclopropylmethyl | 2-(morpholin-4-yl)-pyridin-5-yl |

TABLE A-continued

| No. | R¹ | Ar |
|---|---|---|
| 3694. | cyclopropylmethyl | 2-phenoxypyridin-5-yl |
| 3695. | cyclopropylmethyl | 4-methylphenyl |
| 3696. | cyclopropylmethyl | 4-ethylphenyl |
| 3697. | cyclopropylmethyl | 4-propylphenyl |
| 3698. | cyclopropylmethyl | 4-isopropylphenyl |
| 3699. | cyclopropylmethyl | 4-sec-butylphenyl |
| 3700. | cyclopropylmethyl | 4-tert-butylphenyl |
| 3701. | cyclopropylmethyl | 4-isobutylphenyl |
| 3702. | cyclopropylmethyl | 4-(1,1-dimethylpropyl)-phenyl |
| 3703. | cyclopropylmethyl | 4-vinylphenyl |
| 3704. | cyclopropylmethyl | 4-isopropenylphenyl |
| 3705. | cyclopropylmethyl | 4-fluorophenyl |
| 3706. | cyclopropylmethyl | 4-chlorophenyl |
| 3707. | cyclopropylmethyl | 4-bromophenyl |
| 3708. | cyclopropylmethyl | 4-iodophenyl |
| 3709. | cyclopropylmethyl | 4-(fluoromethyl)phenyl |
| 3710. | cyclopropylmethyl | 4-(difluoromethyl)phenyl |
| 3711. | cyclopropylmethyl | 4-(trifluoromethyl)phenyl |
| 3712. | cyclopropylmethyl | 2,4-bis(trifluoromethyl)phenyl |
| 3713. | cyclopropylmethyl | 4-(1-fluoroethyl)-phenyl |
| 3714. | cyclopropylmethyl | 4-((S)-1-fluoroethyl)-phenyl |
| 3715. | cyclopropylmethyl | 4-((R)-1-fluoroethyl)-phenyl |
| 3716. | cyclopropylmethyl | 4-(2-fluoroethyl)-phenyl |
| 3717. | cyclopropylmethyl | 4-(1,1-difluoroethyl)-phenyl |
| 3718. | cyclopropylmethyl | 4-(2,2-difluoroethyl)-phenyl |
| 3719. | cyclopropylmethyl | 4-(2,2,2-trifluoroethyl)-phenyl |
| 3720. | cyclopropylmethyl | 4-(3-fluoropropyl)-phenyl |
| 3721. | cyclopropylmethyl | 4-(2-fluoropropyl)-phenyl |
| 3722. | cyclopropylmethyl | 4-((S)-2-fluoropropyl)-phenyl |
| 3723. | cyclopropylmethyl | 4-((R)-2-fluoropropyl)-phenyl |
| 3724. | cyclopropylmethyl | 4-(3,3-difluoropropyl)-phenyl |
| 3725. | cyclopropylmethyl | 4-(3,3,3-trifluoropropyl)-phenyl |
| 3726. | cyclopropylmethyl | 4-(1-fluoro-1-methylethyl)-phenyl |
| 3727. | cyclopropylmethyl | 4-(2-fluoro-1-methylethyl)-phenyl |
| 3728. | cyclopropylmethyl | 4-((S)-2-fluoro-1-methylethyl)-phenyl |
| 3729. | cyclopropylmethyl | 4-((R)-2-fluoro-1-methylethyl)-phenyl |
| 3730. | cyclopropylmethyl | 4-(2,2-difluoro-1-methylethyl)-phenyl |
| 3731. | cyclopropylmethyl | 4-((S)-2,2-difluoro-1-methylethyl)-phenyl |
| 3732. | cyclopropylmethyl | 4-((R)-2,2-difluoro-1-methylethyl)-phenyl |
| 3733. | cyclopropylmethyl | 4-(2,2,2-trifluoro-1-methylethyl)-phenyl |
| 3734. | cyclopropylmethyl | 4-((S)-2,2,2-trifluoro-1-methylethyl)-phenyl |
| 3735. | cyclopropylmethyl | 4-((R)-2,2,2-trifluoro-1-methylethyl)-phenyl |
| 3736. | cyclopropylmethyl | 4-(2-fluoro-1-fluoromethylethyl)-phenyl |
| 3737. | cyclopropylmethyl | 4-(1-difluoromethyl-2,2-difluoroethyl)-phenyl |
| 3738. | cyclopropylmethyl | 4-(1,1-dimethyl-2-fluoroethyl)-phenyl |
| 3739. | cyclopropylmethyl | 4-methoxyphenyl |
| 3740. | cyclopropylmethyl | 4-ethoxyphenyl |
| 3741. | cyclopropylmethyl | 4-propoxyphenyl |
| 3742. | cyclopropylmethyl | 4-isopropoxyphenyl |
| 3743. | cyclopropylmethyl | 4-butoxyphenyl |
| 3744. | cyclopropylmethyl | 4-(fluoromethoxy)-phenyl |
| 3745. | cyclopropylmethyl | 4-(difluoromethoxy)-phenyl |
| 3746. | cyclopropylmethyl | 4-(trifluoromethoxy)-phenyl |
| 3747. | cyclopropylmethyl | 4-(2-fluoroethoxy)-phenyl |
| 3748. | cyclopropylmethyl | 4-(2,2-difluoroethoxy)-phenyl |
| 3749. | cyclopropylmethyl | 4-(2,2,2-trifluoroethoxy)-phenyl |
| 3750. | cyclopropylmethyl | 4-(1,1,2,2-tetrafluoroethoxy)-phenyl |
| 3751. | cyclopropylmethyl | 4-cyclopropylphenyl |
| 3752. | cyclopropylmethyl | 4-cyclobutylphenyl |
| 3753. | cyclopropylmethyl | 4-cyclopentylphenyl |
| 3754. | cyclopropylmethyl | 4-(2,2-difluorocyclopropyl)-phenyl |
| 3755. | cyclopropylmethyl | 3,4-difluorophenyl |
| 3756. | cyclopropylmethyl | 4-bromo-2-fluorophenyl |
| 3757. | cyclopropylmethyl | 2-bromo-4-fluorophenyl |
| 3758. | cyclopropylmethyl | 4-bromo-2,5-difluorophenyl |
| 3759. | cyclopropylmethyl | 5-bromo-2,4-difluorophenyl |
| 3760. | cyclopropylmethyl | 3-bromo-2,4-difluorophenyl |
| 3761. | cyclopropylmethyl | 3-chloro-4-(trifluoromethyl)-phenyl |
| 3762. | cyclopropylmethyl | 4-fluoro-3-(trifluoromethyl)-phenyl |
| 3763. | cyclopropylmethyl | 3-fluoro-5-(trifluoromethyl)-phenyl |
| 3764. | cyclopropylmethyl | 3-bromo-4-(trifluoromethyl)-phenyl |
| 3765. | cyclopropylmethyl | 5-bromo-3-(trifluoromethyl)-phenyl |
| 3766. | cyclopropylmethyl | 5-bromo-2-(trifluoromethyl)-phenyl |
| 3767. | cyclopropylmethyl | 2-bromo-5-methoxyphenyl |
| 3768. | cyclopropylmethyl | 4-bromo-3-methoxyphenyl |
| 3769. | cyclopropylmethyl | 3-fluoro-2-isopropylphenyl |
| 3770. | cyclopropylmethyl | 3-fluoro-4-isopropylphenyl |
| 3771. | cyclopropylmethyl | 4-(1-hydroxy-1-methylethyl)-phenyl |

TABLE A-continued

| No. | R¹ | Ar |
|---|---|---|
| 3772. | cyclopropylmethyl | 4-(2-hydroxy-2-methylpropyl)-phenyl |
| 3773. | cyclopropylmethyl | 4-acetylphenyl |
| 3774. | cyclopropylmethyl | 4-acetylaminophenyl |
| 3775. | cyclopropylmethyl | 4-carboxyphenyl |
| 3776. | cyclopropylmethyl | 4-cyanophenyl |
| 3777. | cyclopropylmethyl | 4-nitrophenyl |
| 3778. | cyclopropylmethyl | 4-hydroxyphenyl |
| 3779. | cyclopropylmethyl | 4-(O-benzyl)-phenyl |
| 3780. | cyclopropylmethyl | 4-(2-methoxyethoxy)-phenyl |
| 3781. | cyclopropylmethyl | 4-($CH_2$—$N(CH_3)_2$)-phenyl |
| 3782. | cyclopropylmethyl | 4-(NH—CO—$NH_2$)-phenyl |
| 3783. | cyclopropylmethyl | 4-(methylsulfanyl)-phenyl |
| 3784. | cyclopropylmethyl | 4-(fluoromethylsulfanyl)-phenyl |
| 3785. | cyclopropylmethyl | 4-(difluoromethylsulfanyl)-phenyl |
| 3786. | cyclopropylmethyl | 4-(trifluoromethylsulfanyl)-phenyl |
| 3787. | cyclopropylmethyl | 4-(methylsulfonyl)-phenyl |
| 3788. | cyclopropylmethyl | 4-(N-methoxy-N-methyl-amino)-phenyl |
| 3789. | cyclopropylmethyl | 4-(methoxyamino)-phenyl |
| 3790. | cyclopropylmethyl | 4-(ethoxyamino)-phenyl |
| 3791. | cyclopropylmethyl | 4-(N-methylaminooxy)-phenyl |
| 3792. | cyclopropylmethyl | 4-(N,N-dimethylaminooxy)-phenyl |
| 3793. | cyclopropylmethyl | 4-(azetidin-1-yl)-phenyl |
| 3794. | cyclopropylmethyl | 4-(2-methylazetidin-1-yl)-phenyl |
| 3795. | cyclopropylmethyl | 4-((S)-2-methylazetidin-1-yl)-phenyl |
| 3796. | cyclopropylmethyl | 4-((R)-2-methylazetidin-1-yl)-phenyl |
| 3797. | cyclopropylmethyl | 4-(3-fluoroazetidin-1-yl)-phenyl |
| 3798. | cyclopropylmethyl | 4-(2,2-difluoroazetidin-1-yl)-phenyl |
| 3799. | cyclopropylmethyl | 4-(3-methoxyazetidin-1-yl)-phenyl |
| 3800. | cyclopropylmethyl | 4-(3-hydroxyazetidin-1-yl)-phenyl |
| 3801. | cyclopropylmethyl | 4-(pyrrolidin-1-yl)-phenyl |
| 3802. | cyclopropylmethyl | 4-(pyrrolidin-2-yl)-phenyl |
| 3803. | cyclopropylmethyl | 4-((S)-pyrrolidin-2-yl)-phenyl |
| 3804. | cyclopropylmethyl | 4-((R)-pyrrolidin-2-yl)-phenyl |
| 3805. | cyclopropylmethyl | 4-(pyrrolidin-3-yl)-phenyl |
| 3806. | cyclopropylmethyl | 4-((S)-pyrrolidin-3-yl)-phenyl |
| 3807. | cyclopropylmethyl | 4-((R)-pyrrolidin-3-yl)-phenyl |
| 3808. | cyclopropylmethyl | 4-(pyrrolidin-1-yl)-5-(trifluoromethyl)-phenyl |
| 3809. | cyclopropylmethyl | 4-(pyrrolidin-1-yl)-2-methoxyphenyl |
| 3810. | cyclopropylmethyl | 4-(pyrrolidin-1-yl)-34-methoxyphenyl |
| 3811. | cyclopropylmethyl | 4-(pyrrolidin-1-yl)-2,5-difluorophenyl |
| 3812. | cyclopropylmethyl | 4-(pyrrolidin-1-yl)-2,6-difluorophenyl |
| 3813. | cyclopropylmethyl | 4-(2-fluoropyrrolidin-1-yl)-phenyl |
| 3814. | cyclopropylmethyl | 4-((S)-2-fluoropyrrolidin-1-yl)-phenyl |
| 3815. | cyclopropylmethyl | 4-((R)-2-fluoropyrrolidin-1-yl)-phenyl |
| 3816. | cyclopropylmethyl | 4-(3-fluoropyrrolidin-1-yl)-phenyl |
| 3817. | cyclopropylmethyl | 4-((S)-3-fluoropyrrolidin-1-yl)-phenyl |
| 3818. | cyclopropylmethyl | 4-((R)-3-fluoropyrrolidin-1-yl)-phenyl |
| 3819. | cyclopropylmethyl | 4-(2,2-difluoropyrrolidin-1-yl)-phenyl |
| 3820. | cyclopropylmethyl | 4-(3,3-difluoropyrrolidin-1-yl)-phenyl |
| 3821. | cyclopropylmethyl | 4-(2-methylpyrrolidin-1-yl)-phenyl |
| 3822. | cyclopropylmethyl | 4-((S)-2-methylpyrrolidin-1-yl)-phenyl |
| 3823. | cyclopropylmethyl | 4-((R)-2-methylpyrrolidin-1-yl)-phenyl |
| 3824. | cyclopropylmethyl | 4-(3-methylpyrrolidin-1-yl)-phenyl |
| 3825. | cyclopropylmethyl | 4-((S)-3-methylpyrrolidin-1-yl)-phenyl |
| 3826. | cyclopropylmethyl | 4-((R)-3-methylpyrrolidin-1-yl)-phenyl |
| 3827. | cyclopropylmethyl | 4-(1-methylpyrrolidin-2-yl)-phenyl |
| 3828. | cyclopropylmethyl | 4-((S)-1-methylpyrrolidin-2-yl)-phenyl |
| 3829. | cyclopropylmethyl | 4-((R)-1-methylpyrrolidin-2-yl)-phenyl |
| 3830. | cyclopropylmethyl | 4-(1-methylpyrrolidin-3-yl)-phenyl |
| 3831. | cyclopropylmethyl | 4-((S)-1-methylpyrrolidin-3-yl)-phenyl |
| 3832. | cyclopropylmethyl | 4-((R)-1-methylpyrrolidin-3-yl)-phenyl |
| 3833. | cyclopropylmethyl | 4-(2,2-dimethylpyrrolidin-1-yl)-phenyl |
| 3834. | cyclopropylmethyl | 4-(3,3-dimethylpyrrolidin-1-yl)-phenyl |
| 3835. | cyclopropylmethyl | 4-(2-trifluoromethylpyrrolidin-1-yl)-phenyl |
| 3836. | cyclopropylmethyl | 4-((S)-2-trifluoromethylpyrrolidin-1-yl)-phenyl |
| 3837. | cyclopropylmethyl | 4-((R)-2-trifluoromethylpyrrolidin-1-yl)-phenyl |
| 3838. | cyclopropylmethyl | 4-(3-trifluoromethylpyrrolidin-1-yl)-phenyl |
| 3839. | cyclopropylmethyl | 4-((S)-3-trifluoromethylpyrrolidin-1-yl)-phenyl |
| 3840. | cyclopropylmethyl | 4-((R)-3-trifluoromethylpyrrolidin-1-yl)-phenyl |
| 3841. | cyclopropylmethyl | 4-(2-oxopyrrolidin-1-yl)-phenyl |
| 3842. | cyclopropylmethyl | 4-(2-oxo-oxazolidin-3-yl)-phenyl |
| 3843. | cyclopropylmethyl | 4-(piperidin-1-yl)-phenyl |
| 3844. | cyclopropylmethyl | 4-(2-methylpiperidin-1-yl)-phenyl |
| 3845. | cyclopropylmethyl | 4-((S)-2-methylpiperidin-1-yl)-phenyl |
| 3846. | cyclopropylmethyl | 4-((R)-2-methylpiperidin-1-yl)-phenyl |
| 3847. | cyclopropylmethyl | 4-(2-fluoropiperidin-1-yl)-phenyl |
| 3848. | cyclopropylmethyl | 4-((S)-2-fluoropiperidin-1-yl)-phenyl |
| 3849. | cyclopropylmethyl | 4-((R)-2-fluoropiperidin-1-yl)-phenyl |

TABLE A-continued

| No. | R¹ | Ar |
|---|---|---|
| 3850. | cyclopropylmethyl | 4-(2,2-difluoropiperidin-1-yl)-phenyl |
| 3851. | cyclopropylmethyl | 4-(piperazin-1-yl)-phenyl |
| 3852. | cyclopropylmethyl | 4-(4-methylpiperazin-1-yl)-phenyl |
| 3853. | cyclopropylmethyl | 4-(morpholin-4-yl)-phenyl |
| 3854. | cyclopropylmethyl | 4-(morpholin-4-yl)-5-(trifluoromethyl)-phenyl |
| 3855. | cyclopropylmethyl | 4-(morpholin-4-yl)-2-methoxyphenyl |
| 3856. | cyclopropylmethyl | 4-(morpholin-4-yl)-3-methoxyphenyl |
| 3857. | cyclopropylmethyl | 4-(morpholin-4-yl)-2,5-difluorophenyl |
| 3858. | cyclopropylmethyl | 4-(morpholin-4-yl)-2,6-difluorophenyl |
| 3859. | cyclopropylmethyl | 4-(thiomorpholin-4-yl)-phenyl |
| 3860. | cyclopropylmethyl | 4-(1-oxo-thiomorpholin-4-yl)-phenyl |
| 3861. | cyclopropylmethyl | 4-(1,1-dioxo-thiomorpholin-4-yl)-phenyl |
| 3862. | cyclopropylmethyl | 4-(pyrrol-1-yl)-phenyl |
| 3863. | cyclopropylmethyl | 4-(pyrrol-2-yl)-phenyl |
| 3864. | cyclopropylmethyl | 4-(pyrrol-3-yl)-phenyl |
| 3865. | cyclopropylmethyl | 4-(1-methylpyrrol-2-yl)-phenyl |
| 3866. | cyclopropylmethyl | 4-(1-methylpyrrol-3-yl)-phenyl |
| 3867. | cyclopropylmethyl | 4-(furan-2-yl)-phenyl |
| 3868. | cyclopropylmethyl | 4-(furan-3-yl)-phenyl |
| 3869. | cyclopropylmethyl | 4-(thiophen-2-yl)-phenyl |
| 3870. | cyclopropylmethyl | 4-(thiophen-3-yl)-phenyl |
| 3871. | cyclopropylmethyl | 4-(5-propylthien-2-yl)-phenyl |
| 3872. | cyclopropylmethyl | 4-(pyrazol-1-yl)-phenyl |
| 3873. | cyclopropylmethyl | 4-(pyrazol-3-yl)-phenyl |
| 3874. | cyclopropylmethyl | 4-(pyrazol-4-yl)-phenyl |
| 3875. | cyclopropylmethyl | 4-(4-fluoropyrazol-1-yl)-phenyl |
| 3876. | cyclopropylmethyl | 4-(1-methyl-1H-pyrazol-4-yl)-phenyl |
| 3877. | cyclopropylmethyl | 4-(1-ethyl-1H-pyrazol-4-yl)-phenyl |
| 3878. | cyclopropylmethyl | 4-(1-methyl-1H-pyrazol-5-yl)-phenyl |
| 3879. | cyclopropylmethyl | 4-(1H-imidazol-2-yl)-phenyl |
| 3880. | cyclopropylmethyl | 4-(imidazol-1-yl)-phenyl |
| 3881. | cyclopropylmethyl | 4-(1-methylimidazol-2-yl)-phenyl |
| 3882. | cyclopropylmethyl | 4-(oxazol-2-yl)-phenyl |
| 3883. | cyclopropylmethyl | 4-(oxazol-4-yl)-phenyl |
| 3884. | cyclopropylmethyl | 4-(oxazol-5-yl)-phenyl |
| 3885. | cyclopropylmethyl | 4-(isoxazol-3-yl)-phenyl |
| 3886. | cyclopropylmethyl | 4-(isoxazol-4-yl)-phenyl |
| 3887. | cyclopropylmethyl | 4-(isoxazol-5-yl)-phenyl |
| 3888. | cyclopropylmethyl | 4-(thiazol-2-yl)-phenyl |
| 3889. | cyclopropylmethyl | 4-(thiazol-4-yl)-phenyl |
| 3890. | cyclopropylmethyl | 4-(thiazol-5-yl)-phenyl |
| 3891. | cyclopropylmethyl | 4-(2-methylthiazol-4-yl)-phenyl |
| 3892. | cyclopropylmethyl | 4-(2-methylthiazol-5-yl)-phenyl |
| 3893. | cyclopropylmethyl | 4-([1,2,3]-triazol-1-yl)-phenyl |
| 3894. | cyclopropylmethyl | 4-([1,2,4]-triazol-1-yl)-phenyl |
| 3895. | cyclopropylmethyl | 4-([1,2,3]-triazol-2-yl)-phenyl |
| 3896. | cyclopropylmethyl | 4-(4H-[1,2,4]-triazol-3-yl)-phenyl |
| 3897. | cyclopropylmethyl | 4-([1,2,4]-triazol-4-yl)-phenyl |
| 3898. | cyclopropylmethyl | 4-(2H-[1,2,3]-triazol-4-yl)-phenyl |
| 3899. | cyclopropylmethyl | 4-(4-methyl-4H-[1,2,4]-triazol-3-yl)-phenyl |
| 3900. | cyclopropylmethyl | 4-(2-methyl-2H-[1,2,3]-triazol-4-yl)-phenyl |
| 3901. | cyclopropylmethyl | 4-([1,3,4]-oxadiazol-2-yl)-phenyl |
| 3902. | cyclopropylmethyl | 4-(5-methyl-[1,3,4]-oxadiazol-2-yl)-phenyl |
| 3903. | cyclopropylmethyl | 4-([1,2,4]-oxadiazol-3-yl)-phenyl |
| 3904. | cyclopropylmethyl | 4-(5-methyl-[1,2,4]-oxadiazol-3-yl)-phenyl |
| 3905. | cyclopropylmethyl | 4-([1,2,4]-oxadiazol-5-yl)-phenyl |
| 3906. | cyclopropylmethyl | 4-([1,2,3]-oxadiazol-4-yl)-phenyl |
| 3907. | cyclopropylmethyl | 4-([1,2,3]-oxadiazol-5-yl)-phenyl |
| 3908. | cyclopropylmethyl | 4-([1,2,3]-thiadiazol-4-yl)-phenyl |
| 3909. | cyclopropylmethyl | 4-(1H-tetrazol-5-yl)-phenyl |
| 3910. | cyclopropylmethyl | 4-(tetrazol-1-yl)-phenyl |
| 3911. | cyclopropylmethyl | 4-(2-methyl-2H-tetrazol-5-yl)-phenyl |
| 3912. | cyclopropylmethyl | 4-(1-methyl-1H-tetrazol-5-yl)-phenyl |
| 3913. | cyclopropylmethyl | 4-furazan-3-yl-phenyl |
| 3914. | cyclopropylmethyl | 4-(pyrid-2-yl)-phenyl |
| 3915. | cyclopropylmethyl | 4-(pyrid-3-yl)-phenyl |
| 3916. | cyclopropylmethyl | 4-(pyrid-4-yl)-phenyl |
| 3917. | cyclopropylmethyl | 4-(pyrimidin-2-yl)-phenyl |
| 3918. | cyclopropylmethyl | 4-(2-methylpyrimidin-4-yl)-phenyl |
| 3919. | cyclopropylmethyl | 4-(pyrimidin-4-yl)-phenyl |
| 3920. | cyclopropylmethyl | 4-(pyrimidin-5-yl)-phenyl |
| 3921. | cyclopropylmethyl | 4-bromo-2-chloropyridin-5-yl |
| 3922. | cyclopropylmethyl | 4-methylpyridin-2-yl |
| 3923. | cyclopropylmethyl | 5-methylpyridin-2-yl |
| 3924. | cyclopropylmethyl | 4-(pyrrolidin-1-yl)-2-chloropyridin-5-yl |
| 3925. | cyclopropylmethyl | 4-(morpholin-4-yl)-2-chloropyridin-5-yl |
| 3926. | cyclopropylmethyl | 2-(morpholin-4-yl)-pyridin-5-yl |
| 3927. | cyclopropylmethyl | 5-(morpholin-4-yl)-pyridin-2-yl |

TABLE A-continued

| No. | R¹ | Ar |
|---|---|---|
| 3928. | cyclopropylmethyl | 2-phenoxypyridin-5-yl |
| 3929. | cyclopropylmethyl | 2,3-dichlorophenyl |
| 3930. | cyclopropylmethyl | 2,5-dichlorophenyl |
| 3931. | cyclopropylmethyl | 3,5-dichlorophenyl |
| 3932. | cyclopropylmethyl | 3-chloro-4-fluorophenyl |
| 3933. | cyclopropylmethyl | 4-bromo-2,5-dichlorophenyl |
| 3934. | cyclopropylmethyl | 3-bromo-4-(trifluoromethoxy)phenyl |
| 3935. | cyclopropylmethyl | 3,5-dibromo-4-(2-fluoroethoxy)-phenyl |
| 3936. | cyclopropylmethyl | 2,5-dimethylphenyl |
| 3937. | cyclopropylmethyl | 2,5-di-(trifluoromethyl)-phenyl |
| 3938. | cyclopropylmethyl | 3,5-di-(trifluoromethyl)-phenyl |
| 3939. | cyclopropylmethyl | 2,5-dimethoxyphenyl |
| 3940. | cyclopropylmethyl | 2-methoxy-5-methylphenyl |
| 3941. | cyclopropylmethyl | 2-methoxy-5-(trifluoromethyl)-phenyl |
| 3942. | cyclopropylmethyl | 4-fluoro-3-(oxazol-4-yl)-phenyl |
| 3943. | cyclopropylmethyl | thien-2-yl |
| 3944. | cyclopropylmethyl | thien-3-yl |
| 3945. | cyclopropylmethyl | 3-chlorothien-2-yl |
| 3946. | cyclopropylmethyl | 4-chlorothien-2-yl |
| 3947. | cyclopropylmethyl | 5-chlorothien-2-yl |
| 3948. | cyclopropylmethyl | 3-bromothien-2-yl |
| 3949. | cyclopropylmethyl | 4-bromothien-2-yl |
| 3950. | cyclopropylmethyl | 5-bromothien-2-yl |
| 3951. | cyclopropylmethyl | 4,5-dichlorothien-2-yl |
| 3952. | cyclopropylmethyl | 4,5-dibromothien-2-yl |
| 3953. | cyclopropylmethyl | 4-bromo-5-chlorothien-2-yl |
| 3954. | cyclopropylmethyl | 3-bromo-5-chlorothien-2-yl |
| 3955. | cyclopropylmethyl | 5-methylthien-2-yl |
| 3956. | cyclopropylmethyl | 5-ethylthien-2-yl |
| 3957. | cyclopropylmethyl | 5-propylthien-2-yl |
| 3958. | cyclopropylmethyl | 5-trifluoromethylthien-2-yl |
| 3959. | cyclopropylmethyl | 5-phenylthien-2-yl |
| 3960. | cyclopropylmethyl | 5-(pyrid-2-yl)-thien-2-yl |
| 3961. | cyclopropylmethyl | 5-(phenylsulfonyl)-thien-2-yl |
| 3962. | cyclopropylmethyl | 4-(phenylsulfonyl)-thien-2-yl |
| 3963. | cyclopropylmethyl | 5-(pyrid-2-ylsulfonyl)-thien-2-yl |
| 3964. | cyclopropylmethyl | 5-(3-chloro-5-trifluoro-pyrid-2-ylsulfonyl)-thien-2-yl |
| 3965. | cyclopropylmethyl | 5-(benzoylaminomethyl)-thien-2-yl |
| 3966. | cyclopropylmethyl | 5-((4-chlorobenzoyl)aminomethyl)-thien-2-yl |
| 3967. | cyclopropylmethyl | 5-(acetylaminomethyl)-thien-2-yl |
| 3968. | cyclopropylmethyl | 5-(pyrazol-1-yl)-thien-2-yl |
| 3969. | cyclopropylmethyl | 5-(pyrazol-3-yl)-thien-2-yl |
| 3970. | cyclopropylmethyl | 5-(pyrazol-4-yl)-thien-2-yl |
| 3971. | cyclopropylmethyl | 5-(pyrazol-5-yl)-thien-2-yl |
| 3972. | cyclopropylmethyl | 5-(4-fluoropyrazol-1-yl)-thien-2-yl |
| 3973. | cyclopropylmethyl | 5-(1-methyl-5-trifluoromethyl-(1H)-pyrazol-3-yl)-thien-2-yl |
| 3974. | cyclopropylmethyl | 5-(1-methyl-3-trifluoromethyl-(1H)-pyrazol-5-yl)-thien-2-yl |
| 3975. | cyclopropylmethyl | 5-(4-carboxy-1-methyl-5-methylthio-(1H)-pyrazol-3-yl)-thien-2-yl |
| 3976. | cyclopropylmethyl | 5-(4-aminomethyl-1-methyl-5-methylthio-(1H)-pyrazol-3-yl)-thien-2-yl |
| 3977. | cyclopropylmethyl | 5-(isoxazol-3-yl)-thien-2-yl |
| 3978. | cyclopropylmethyl | 5-(isoxazol-4-yl)-thien-2-yl |
| 3979. | cyclopropylmethyl | 5-(isoxazol-5-yl)-thien-2-yl |
| 3980. | cyclopropylmethyl | 5-(5-trifluoromethylisoxazol-3-yl)-thien-2-yl |
| 3981. | cyclopropylmethyl | 5-(oxazol-2-yl)-thien-2-yl |
| 3982. | cyclopropylmethyl | 5-(oxazol-4-yl)-thien-2-yl |
| 3983. | cyclopropylmethyl | 5-(oxazol-5-yl)-thien-2-yl |
| 3984. | cyclopropylmethyl | 5-(2-methyloxazol-4-yl)-thien-2-yl |
| 3985. | cyclopropylmethyl | 5-(2-methyloxazol-5-yl)-thien-2-yl |
| 3986. | cyclopropylmethyl | 5-(isothiazol-3-yl)-thien-2-yl |
| 3987. | cyclopropylmethyl | 5-(isothiazol-4-yl)-thien-2-yl |
| 3988. | cyclopropylmethyl | 5-(isothiazol-5-yl)-thien-2-yl |
| 3989. | cyclopropylmethyl | 5-(5-trifluoromethylisothiazol-3-yl)-thien-2-yl |
| 3990. | cyclopropylmethyl | 5-(thiazol-2-yl)-thien-2-yl |
| 3991. | cyclopropylmethyl | 5-(thiazol-4-yl)-thien-2-yl |
| 3992. | cyclopropylmethyl | 5-(thiazol-5-yl)-thien-2-yl |
| 3993. | cyclopropylmethyl | 5-(2-methylthiazol-4-yl)-thien-2-yl |
| 3994. | cyclopropylmethyl | 5-(2-methylthiazol-5-yl)-thien-2-yl |
| 3995. | cyclopropylmethyl | 5-([1,2,3]-oxadiazol-4-yl)-thien-2-yl |
| 3996. | cyclopropylmethyl | 5-([1,2,3]-thiadiazol-4-yl)-thien-2-yl |
| 3997. | cyclopropylmethyl | 5-(pyrimidin-2-yl)-thien-2-yl |
| 3998. | cyclopropylmethyl | 5-(pyrimidin-4-yl)-thien-2-yl |
| 3999. | cyclopropylmethyl | 5-(pyrimidin-5-yl)-thien-2-yl |
| 4000. | cyclopropylmethyl | 5-(2-methylthiopyrimidin-4-yl)-thien-2-yl |

TABLE A-continued

| No. | R¹ | Ar |
|---|---|---|
| 4001. | cyclopropylmethyl | 5-([1,3]-dioxolan-2-yl)-thien-2-yl |
| 4002. | cyclopropylmethyl | 3-([1,3]-dioxolan-2-yl) thien-2-yl |
| 4003. | cyclopropylmethyl | 5-((3-chloro-5-(trifluoromethyl)-pyridin-2-yl)-methyl)-thien-2-yl |
| 4004. | cyclopropylmethyl | 5-[3-chloro-5-(trifluoromethyl)-pyrid-2-ylsulfonyl]-thien-2-yl |
| 4005. | cyclopropylmethyl | 2-chlorothien-3-yl |
| 4006. | cyclopropylmethyl | 4-chlorothien-3-yl |
| 4007. | cyclopropylmethyl | 5-chlorothien-3-yl |
| 4008. | cyclopropylmethyl | 2-bromothien-3-yl |
| 4009. | cyclopropylmethyl | 4-bromothien-3-yl |
| 4010. | cyclopropylmethyl | 5-bromothien-3-yl |
| 4011. | cyclopropylmethyl | 2,5-dichlorothien-3-yl |
| 4012. | cyclopropylmethyl | 2,5-dibromothien-3-yl |
| 4013. | cyclopropylmethyl | 2,4,5-trichlorothien-3-yl |
| 4014. | cyclopropylmethyl | 4-bromo-2,5-dichlorothien-3-yl |
| 4015. | cyclopropylmethyl | 2-chloro-5-methylsulfonylthien-3-yl |
| 4016. | cyclopropylmethyl | 2,5-dimethylthien-3-yl |
| 4017. | cyclopropylmethyl | 4-hydroxythien-3-yl |
| 4018. | cyclopropylmethyl | 2-phenylthien-3-yl |
| 4019. | cyclopropylmethyl | 4-phenyl-5-(trofluoromethyl)-thien-3-yl |
| 4020. | cyclopropylmethyl | 2-methoxycarbonyl-4-phenyl-5-(trifluoromethyl)-thien-3-yl |
| 4021. | cyclopropylmethyl | benzo[b]thiophen-2-yl |
| 4022. | cyclopropylmethyl | benzo[b]thiophen-3-yl |
| 4023. | cyclopropylmethyl | 3-methyl-benzo[b]thiophen-2-yl |
| 4024. | cyclopropylmethyl | 5-methyl-benzo[b]thiophen-2-yl |
| 4025. | cyclopropylmethyl | 5-fluoro-3-methyl-benzo[b]thiophen-2-yl |
| 4026. | cyclopropylmethyl | 5-chloro-3-methyl-benzo[b]thiophen-2-yl |
| 4027. | cyclopropylmethyl | 5-bromo-3-methyl-benzo[b]thiophen-2-yl |
| 4028. | allyl | 3-methylphenyl |
| 4029. | allyl | 3-ethylphenyl |
| 4030. | allyl | 3-propylphenyl |
| 4031. | allyl | 3-isopropylphenyl |
| 4032. | allyl | 3-sec-butylphenyl |
| 4033. | allyl | 3-tert-butylphenyl |
| 4034. | allyl | 3-isobutylphenyl |
| 4035. | allyl | 3-(1,1-dimethylpropyl)-phenyl |
| 4036. | allyl | 3-vinylphenyl |
| 4037. | allyl | 3-isopropenylphenyl |
| 4038. | allyl | 3-fluorophenyl |
| 4039. | allyl | 2-fluorophenyl |
| 4040. | allyl | 3-chlorophenyl |
| 4041. | allyl | 3-bromophenyl |
| 4042. | allyl | 3-iodophenyl |
| 4043. | allyl | 3-(fluoromethyl)phenyl |
| 4044. | allyl | 3-(difluoromethyl)phenyl |
| 4045. | allyl | 3-(trifluoromethyl)phenyl |
| 4046. | allyl | 3,5-bis(trifluoromethyl)phenyl |
| 4047. | allyl | 3-(1-fluoroethyl)-phenyl |
| 4048. | allyl | 3-((S)-1-fluoroethyl)-phenyl |
| 4049. | allyl | 3-((R)-1-fluoroethyl)-phenyl |
| 4050. | allyl | 3-(2-fluoroethyl)-phenyl |
| 4051. | allyl | 3-(1,1-difluoroethyl)-phenyl |
| 4052. | allyl | 3-(2,2-difluoroethyl)-phenyl |
| 4053. | allyl | 3-(2,2,2-trifluoroethyl)-phenyl |
| 4054. | allyl | 3-(3-fluoropropyl)-phenyl |
| 4055. | allyl | 3-(2-fluoropropyl)-phenyl |
| 4056. | allyl | 3-((S)-2-fluoropropyl)-phenyl |
| 4057. | allyl | 3-((R)-2-fluoropropyl)-phenyl |
| 4058. | allyl | 3-(3,3-difluoropropyl)-phenyl |
| 4059. | allyl | 3-(3,3,3-trifluoropropyl)-phenyl |
| 4060. | allyl | 3-(1-fluoro-1-methylethyl)-phenyl |
| 4061. | allyl | 3-(2-fluoro-1-methylethyl)-phenyl |
| 4062. | allyl | 3-((S)-2-fluoro-1-methylethyl)-phenyl |
| 4063. | allyl | 3-((R)-2-fluoro-1-methylethyl)-phenyl |
| 4064. | allyl | 3-(2,2-difluoro-1-methylethyl)-phenyl |
| 4065. | allyl | 3-((S)-2,2-difluoro-1-methylethyl)-phenyl |
| 4066. | allyl | 3-((R)-2,2-difluoro-1-methylethyl)-phenyl |
| 4067. | allyl | 3-(2,2,2-trifluoro-1-methylethyl)-phenyl |
| 4068. | allyl | 3-((S)-2,2,2-trifluoro-1-methylethyl)-phenyl |
| 4069. | allyl | 3-((R)-2,2,2-trifluoro-1-methylethyl)-phenyl |
| 4070. | allyl | 3-(2-fluoro-1-fluoromethylethyl)-phenyl |
| 4071. | allyl | 3-(1-difluoromethyl-2,2-difluoroethyl)-phenyl |
| 4072. | allyl | 3-(1,1-dimethyl-2-fluoroethyl)-phenyl |
| 4073. | allyl | 3-methoxyphenyl |
| 4074. | allyl | 3-ethoxyphenyl |
| 4075. | allyl | 3-propoxyphenyl |

TABLE A-continued

| No. | R¹ | Ar |
|---|---|---|
| 4076. | allyl | 3-isopropoxyphenyl |
| 4077. | allyl | 3-butoxyphenyl |
| 4078. | allyl | 3-(fluoromethoxy)-phenyl |
| 4079. | allyl | 3-(difluoromethoxy)-phenyl |
| 4080. | allyl | 3-(trifluoromethoxy)-phenyl |
| 4081. | allyl | 3-(2-fluoroethoxy)-phenyl |
| 4082. | allyl | 3-(2,2-difluoroethoxy)-phenyl |
| 4083. | allyl | 3-(2,2,2-trifluoroethoxy)-phenyl |
| 4084. | allyl | 3-(1,1,2,2-tetrafluoroethoxy)-phenyl |
| 4085. | allyl | 3-cyclopropylphenyl |
| 4086. | allyl | 3-cyclobutylphenyl |
| 4087. | allyl | 3-cyclopentylphenyl |
| 4088. | allyl | 3-(2,2-difluorocyclopropyl)-phenyl |
| 4089. | allyl | 3,4-difluorophenyl |
| 4090. | allyl | 3-bromo-2-fluorophenyl |
| 4091. | allyl | 2-bromo-3-fluorophenyl |
| 4092. | allyl | 3-bromo-2,5-difluorophenyl |
| 4093. | allyl | 5-bromo-2,4-difluorophenyl |
| 4094. | allyl | 3-bromo-2,4-difluorophenyl |
| 4095. | allyl | 4-chloro-3-(trifluoromethyl)-phenyl |
| 4096. | allyl | 2-chloro-5-(trifluoromethyl)-phenyl |
| 4097. | allyl | 2-fluoro-5-(trifluoromethyl)-phenyl |
| 4098. | allyl | 4-fluoro-3-(trifluoromethyl)-phenyl |
| 4099. | allyl | 3-fluoro-5-(trifluoromethyl)-phenyl |
| 4100. | allyl | 4-bromo-3-(trifluoromethyl)-phenyl |
| 4101. | allyl | 3-bromo-5-(trifluoromethyl)-phenyl |
| 4102. | allyl | 2-bromo-5-(trifluoromethyl)-phenyl |
| 4103. | allyl | 5-bromo-2-methoxyphenyl |
| 4104. | allyl | 3-bromo-4-methoxyphenyl |
| 4105. | allyl | 2-fluoro-3-isopropylphenyl |
| 4106. | allyl | 4-fluoro-3-isopropylphenyl |
| 4107. | allyl | 3-(1-hydroxy-1-methylethyl)-phenyl |
| 4108. | allyl | 3-(2-hydroxy-2-methylpropyl)-phenyl |
| 4109. | allyl | 3-acetylphenyl |
| 4110. | allyl | 3-acetylaminophenyl |
| 4111. | allyl | 3-carboxyphenyl |
| 4112. | allyl | 3-cyanophenyl |
| 4113. | allyl | 3-nitrophenyl |
| 4114. | allyl | 3-hydroxyphenyl |
| 4115. | allyl | 3-(O-benzyl)-phenyl |
| 4116. | allyl | 3-(2-methoxyethoxy)-phenyl |
| 4117. | allyl | 3-(CH₂—N(CH₃)₂)-phenyl |
| 4118. | allyl | 3-(NH—CO—NH₂)-phenyl |
| 4119. | allyl | 3-(methylsulfanyl)-phenyl |
| 4120. | allyl | 3-(fluoromethylsulfanyl)-phenyl |
| 4121. | allyl | 3-(difluoromethylsulfanyl)-phenyl |
| 4122. | allyl | 3-(trifluoromethylsulfanyl)-phenyl |
| 4123. | allyl | 3-(methylsulfonyl)-phenyl |
| 4124. | allyl | 3-(N-methoxy-N-methyl-amino)-phenyl |
| 4125. | allyl | 3-(methoxyamino)-phenyl |
| 4126. | allyl | 3-(ethoxyamino)-phenyl |
| 4127. | allyl | 3-(N-methylaminooxy)-phenyl |
| 4128. | allyl | 3-(N,N-dimethylaminooxy)-phenyl |
| 4129. | allyl | 3-(azetidin-1-yl)-phenyl |
| 4130. | allyl | 3-(2-methylazetidin-1-yl)-phenyl |
| 4131. | allyl | 3-((S)-2-methylazetidin-1-yl)-phenyl |
| 4132. | allyl | 3-((R)-2-methylazetidin-1-yl)-phenyl |
| 4133. | allyl | 3-(3-fluoroazetidin-1-yl)-phenyl |
| 4134. | allyl | 3-(2,2-difluoroazetidin-1-yl)-phenyl |
| 4135. | allyl | 3-(3-methoxyazetidin-1-yl)-phenyl |
| 4136. | allyl | 3-(3-hydroxyazetidin-1-yl)-phenyl |
| 4137. | allyl | 3-(pyrrolidin-1-yl)-phenyl |
| 4138. | allyl | 3-(pyrrolidin-2-yl)-phenyl |
| 4139. | allyl | 3-((S)-pyrrolidin-2-yl)-phenyl |
| 4140. | allyl | 3-((R)-pyrrolidin-2-yl)-phenyl |
| 4141. | allyl | 3-(pyrrolidin-3-yl)-phenyl |
| 4142. | allyl | 3-((S)-pyrrolidin-3-yl)-phenyl |
| 4143. | allyl | 3-((R)-pyrrolidin-3-yl)-phenyl |
| 4144. | allyl | 3-(pyrrolidin-1-yl)-5-(trifluoromethyl)-phenyl |
| 4145. | allyl | 5-(pyrrolidin-1-yl)-2-methoxyphenyl |
| 4146. | allyl | 3-(pyrrolidin-1-yl)-4-methoxyphenyl |
| 4147. | allyl | 5-(pyrrolidin-1-yl)-2,4-difluorophenyl |
| 4148. | allyl | 3-(pyrrolidin-1-yl)-2,4-difluorophenyl |
| 4149. | allyl | 3-(2-fluoropyrrolidin-1-yl)-phenyl |
| 4150. | allyl | 3-((S)-2-fluoropyrrolidin-1-yl)-phenyl |
| 4151. | allyl | 3-((R)-2-fluoropyrrolidin-1-yl)-phenyl |
| 4152. | allyl | 3-(3-fluoropyrrolidin-1-yl)-phenyl |
| 4153. | allyl | 3-((S)-3-fluoropyrrolidin-1-yl)-phenyl |

TABLE A-continued

| No. | R¹ | Ar |
|---|---|---|
| 4154. | allyl | 3-((R)-3-fluoropyrrolidin-1-yl)-phenyl |
| 4155. | allyl | 3-(2,2-difluoropyrrolidin-1-yl)-phenyl |
| 4156. | allyl | 3-(3,3-difluoropyrrolidin-1-yl)-phenyl |
| 4157. | allyl | 3-(2-methylpyrrolidin-1-yl)-phenyl |
| 4158. | allyl | 3-((S)-2-methylpyrrolidin-1-yl)-phenyl |
| 4159. | allyl | 3-((R)-2-methylpyrrolidin-1-yl)-phenyl |
| 4160. | allyl | 3-(3-methylpyrrolidin-1-yl)-phenyl |
| 4161. | allyl | 3-((S)-3-methylpyrrolidin-1-yl)-phenyl |
| 4162. | allyl | 3-((R)-3-methylpyrrolidin-1-yl)-phenyl |
| 4163. | allyl | 3-(1-methylpyrrolidin-2-yl)-phenyl |
| 4164. | allyl | 3-((S)-1-methylpyrrolidin-2-yl)-phenyl |
| 4165. | allyl | 3-((R)-1-methylpyrrolidin-2-yl)-phenyl |
| 4166. | allyl | 3-(1-methylpyrrolidin-3-yl)-phenyl |
| 4167. | allyl | 3-((S)-1-methylpyrrolidin-3-yl)-phenyl |
| 4168. | allyl | 3-((R)-1-methylpyrrolidin-3-yl)-phenyl |
| 4169. | allyl | 3-(2,2-dimethylpyrrolidin-1-yl)-phenyl |
| 4170. | allyl | 3-(3,3-dimethylpyrrolidin-1-yl)-phenyl |
| 4171. | allyl | 3-(2-trifluoromethylpyrrolidin-1-yl)-phenyl |
| 4172. | allyl | 3-((S)-2-trifluoromethylpyrrolidin-1-yl)-phenyl |
| 4173. | allyl | 3-((R)-2-trifluoromethylpyrrolidin-1-yl)-phenyl |
| 4174. | allyl | 3-(3-trifluoromethylpyrrolidin-1-yl)-phenyl |
| 4175. | allyl | 3-((S)-3-trifluoromethylpyrrolidin-1-yl)-phenyl |
| 4176. | allyl | 3-((R)-3-trifluoromethylpyrrolidin-1-yl)-phenyl |
| 4177. | allyl | 3-(2-oxopyrrolidin-1-yl)-phenyl |
| 4178. | allyl | 3-(2-oxo-oxazolidin-3-yl)-phenyl |
| 4179. | allyl | 3-(piperidin-1-yl)-phenyl |
| 4180. | allyl | 3-(2-methylpiperidin-1-yl)-phenyl |
| 4181. | allyl | 3-((S)-2-methylpiperidin-1-yl)-phenyl |
| 4182. | allyl | 3-((R)-2-methylpiperidin-1-yl)-phenyl |
| 4183. | allyl | 3-(2-fluoropiperidin-1-yl)-phenyl |
| 4184. | allyl | 3-((S)-2-fluoropiperidin-1-yl)-phenyl |
| 4185. | allyl | 3-((R)-2-fluoropiperidin-1-yl)-phenyl |
| 4186. | allyl | 3-(2,2-difluoropiperidin-1-yl)-phenyl |
| 4187. | allyl | 3-(piperazin-1-yl)-phenyl |
| 4188. | allyl | 3-(4-methylpiperazin-1-yl)-phenyl |
| 4189. | allyl | 3-(morpholin-4-yl)-phenyl |
| 4190. | allyl | 3-(morpholin-4-yl)-5-(trifluoromethyl)-phenyl |
| 4191. | allyl | 5-(morpholin-4-yl)-2-methoxyphenyl |
| 4192. | allyl | 3-(morpholin-4-yl)-4-methoxyphenyl |
| 4193. | allyl | 5-(morpholin-4-yl)-2,4-difluorophenyl |
| 4194. | allyl | 3-(morpholin-4-yl)-2,4-difluorophenyl |
| 4195. | allyl | 3-(thiomorpholin-4-yl)-phenyl |
| 4196. | allyl | 3-(1-oxo-thiomorpholin-4-yl)-phenyl |
| 4197. | allyl | 3-(1,1-dioxo-thiomorpholin-4-yl)-phenyl |
| 4198. | allyl | 3-(pyrrol-1-yl)-phenyl |
| 4199. | allyl | 3-(pyrrol-2-yl)-phenyl |
| 4200. | allyl | 3-(pyrrol-3-yl)-phenyl |
| 4201. | allyl | 3-(1-methylpyrrol-2-yl)-phenyl |
| 4202. | allyl | 3-(1-methylpyrrol-3-yl)-phenyl |
| 4203. | allyl | 3-(furan-2-yl)-phenyl |
| 4204. | allyl | 3-(furan-3-yl)-phenyl |
| 4205. | allyl | 3-(thiophen-2-yl)-phenyl |
| 4206. | allyl | 3-(thiophen-3-yl)-phenyl |
| 4207. | allyl | 3-(5-propylthien-2-yl)-phenyl |
| 4208. | allyl | 3-(pyrazol-1-yl)-phenyl |
| 4209. | allyl | 3-(pyrazol-3-yl)-phenyl |
| 4210. | allyl | 3-(pyrazol-4-yl)-phenyl |
| 4211. | allyl | 3-(4-fluoropyrazol-1-yl)-phenyl |
| 4212. | allyl | 3-(1-methyl-1H-pyrazol-4-yl)-phenyl |
| 4213. | allyl | 3-(1-ethyl-1H-pyrazol-4-yl)-phenyl |
| 4214. | allyl | 3-(1-methyl-1H-pyrazol-5-yl)-phenyl |
| 4215. | allyl | 3-(1H-imidazol-2-yl)-phenyl |
| 4216. | allyl | 3-(imidazol-1-yl)-phenyl |
| 4217. | allyl | 3-(1-methylimidazol-2-yl)-phenyl |
| 4218. | allyl | 3-(oxazol-2-yl)-phenyl |
| 4219. | allyl | 3-(oxazol-4-yl)-phenyl |
| 4220. | allyl | 3-(oxazol-5-yl)-phenyl |
| 4221. | allyl | 3-(isoxazol-3-yl)-phenyl |
| 4222. | allyl | 3-(isoxazol-4-yl)-phenyl |
| 4223. | allyl | 3-(isoxazol-5-yl)-phenyl |
| 4224. | allyl | 3-(thiazol-2-yl)-phenyl |
| 4225. | allyl | 3-(thiazol-4-yl)-phenyl |
| 4226. | allyl | 3-(thiazol-5-yl)-phenyl |
| 4227. | allyl | 3-(2-methylthiazol-4-yl)-phenyl |
| 4228. | allyl | 3-(2-methylthiazol-5-yl)-phenyl |
| 4229. | allyl | 3-([1,2,3]-triazol-1-yl)-phenyl |
| 4230. | allyl | 3-([1,2,4]-triazol-1-yl)-phenyl |
| 4231. | allyl | 3-([1,2,3]-triazol-2-yl)-phenyl |

TABLE A-continued

| No. | R¹ | Ar |
|---|---|---|
| 4232. | allyl | 3-(4H-[1,2,4]-triazol-3-yl)-phenyl |
| 4233. | allyl | 3-([1,2,4]-triazol-4-yl)-phenyl |
| 4234. | allyl | 3-(2H-[1,2,3]-triazol-4-yl)-phenyl |
| 4235. | allyl | 3-(4-methyl-4H-[1,2,4]-triazol-3-yl)-phenyl |
| 4236. | allyl | 3-(2-methyl-2H-[1,2,3]-triazol-4-yl)-phenyl |
| 4237. | allyl | 3-([1,3,4]-oxadiazol-2-yl)-phenyl |
| 4238. | allyl | 3-(5-methyl-[1,3,4]-oxadiazol-2-yl)-phenyl |
| 4239. | allyl | 3-([1,2,4]-oxadiazol-3-yl)-phenyl |
| 4240. | allyl | 3-(5-methyl-[1,2,4]-oxadiazol-3-yl)-phenyl |
| 4241. | allyl | 3-([1,2,4]-oxadiazol-5-yl)-phenyl |
| 4242. | allyl | 3-([1,2,3]-oxadiazol-4-yl)-phenyl |
| 4243. | allyl | 3-([1,2,3]-oxadiazol-5-yl)-phenyl |
| 4244. | allyl | 3-([1,2,3]-thiadiazol-4-yl)-phenyl |
| 4245. | allyl | 3-(1H-tetrazol-5-yl)-phenyl |
| 4246. | allyl | 3-(tetrazol-1-yl)-phenyl |
| 4247. | allyl | 3-(2-methyl-2H-tetrazol-5-yl)-phenyl |
| 4248. | allyl | 3-(1-methyl-1H-tetrazol-5-yl)-phenyl |
| 4249. | allyl | 3-furazan-3-yl-phenyl |
| 4250. | allyl | 3-(pyrid-2-yl)-phenyl |
| 4251. | allyl | 3-(pyrid-3-yl)-phenyl |
| 4252. | allyl | 3-(pyrid-4-yl)-phenyl |
| 4253. | allyl | 3-(pyrimidin-2-yl)-phenyl |
| 4254. | allyl | 3-(2-methylpyrimidin-4-yl)-phenyl |
| 4255. | allyl | 3-(pyrimidin-4-yl)-phenyl |
| 4256. | allyl | 3-(pyrimidin-5-yl)-phenyl |
| 4257. | allyl | 5-bromopyridin-3-yl |
| 4258. | allyl | 3-bromo-2-chloropyridin-5-yl |
| 4259. | allyl | 4-methylpyridin-2-yl |
| 4260. | allyl | 6-methylpyridin-2-yl |
| 4261. | allyl | 4-(trifluoromethyl)-pyridin-2-yl |
| 4262. | allyl | 6-(trifluoromethyl)-pyridin-2-yl |
| 4263. | allyl | 5-(trifluoromethyl)-pyridin-3-yl |
| 4264. | allyl | 5-(pyrrolidin-1-yl)-pyridin-3-yl |
| 4265. | allyl | 3-(pyrrolidin-1-yl)-2-chloropyridin-5-yl |
| 4266. | allyl | 3-(morpholin-4-yl)-2-chloropyridin-5-yl |
| 4267. | allyl | 2-(morpholin-4-yl)-pyridin-5-yl |
| 4268. | allyl | 2-phenoxypyridin-5-yl |
| 4269. | allyl | 4-methylphenyl |
| 4270. | allyl | 4-ethylphenyl |
| 4271. | allyl | 4-propylphenyl |
| 4272. | allyl | 4-isopropylphenyl |
| 4273. | allyl | 4-sec-butylphenyl |
| 4274. | allyl | 4-tert-butylphenyl |
| 4275. | allyl | 4-isobutylphenyl |
| 4276. | allyl | 4-(1,1-dimethylpropyl)-phenyl |
| 4277. | allyl | 4-vinylphenyl |
| 4278. | allyl | 4-isopropenylphenyl |
| 4279. | allyl | 4-fluorophenyl |
| 4280. | allyl | 4-chlorophenyl |
| 4281. | allyl | 4-bromophenyl |
| 4282. | allyl | 4-iodophenyl |
| 4283. | allyl | 4-(fluoromethyl)phenyl |
| 4284. | allyl | 4-(difluoromethyl)phenyl |
| 4285. | allyl | 4-(trifluoromethyl)phenyl |
| 4286. | allyl | 2,4-bis(trifluoromethyl)phenyl |
| 4287. | allyl | 4-(1-fluoroethyl)-phenyl |
| 4288. | allyl | 4-((S)-1-fluoroethyl)-phenyl |
| 4289. | allyl | 4-((R)-1-fluoroethyl)-phenyl |
| 4290. | allyl | 4-(2-fluoroethyl)-phenyl |
| 4291. | allyl | 4-(1,1-difluoroethyl)-phenyl |
| 4292. | allyl | 4-(2,2-difluoroethyl)-phenyl |
| 4293. | allyl | 4-(2,2,2-trifluoroethyl)-phenyl |
| 4294. | allyl | 4-(3-fluoropropyl)-phenyl |
| 4295. | allyl | 4-(2-fluoropropyl)-phenyl |
| 4296. | allyl | 4-((S)-2-fluoropropyl)-phenyl |
| 4297. | allyl | 4-((R)-2-fluoropropyl)-phenyl |
| 4298. | allyl | 4-(3,3-difluoropropyl)-phenyl |
| 4299. | allyl | 4-(3,3,3-trifluoropropyl)-phenyl |
| 4300. | allyl | 4-(1-fluoro-1-methylethyl)-phenyl |
| 4301. | allyl | 4-(2-fluoro-1-methylethyl)-phenyl |
| 4302. | allyl | 4-((S)-2-fluoro-1-methylethyl)-phenyl |
| 4303. | allyl | 4-((R)-2-fluoro-1-methylethyl)-phenyl |
| 4304. | allyl | 4-(2,2-difluoro-1-methylethyl)-phenyl |
| 4305. | allyl | 4-((S)-2,2-difluoro-1-methylethyl)-phenyl |
| 4306. | allyl | 4-((R)-2,2-difluoro-1-methylethyl)-phenyl |
| 4307. | allyl | 4-(2,2,2-trifluoro-1-methylethyl)-phenyl |
| 4308. | allyl | 4-((S)-2,2,2-trifluoro-1-methylethyl)-phenyl |
| 4309. | allyl | 4-((R)-2,2,2-trifluoro-1-methylethyl)-phenyl |

TABLE A-continued

| No. | R¹ | Ar |
|---|---|---|
| 4310. | allyl | 4-(2-fluoro-1-fluoromethylethyl)-phenyl |
| 4311. | allyl | 4-(1-difluoromethyl-2,2-difluoroethyl)-phenyl |
| 4312. | allyl | 4-(1,1-dimethyl-2-fluoroethyl)-phenyl |
| 4313. | allyl | 4-methoxyphenyl |
| 4314. | allyl | 4-ethoxyphenyl |
| 4315. | allyl | 4-propoxyphenyl |
| 4316. | allyl | 4-isopropoxyphenyl |
| 4317. | allyl | 4-butoxyphenyl |
| 4318. | allyl | 4-(fluoromethoxy)-phenyl |
| 4319. | allyl | 4-(difluoromethoxy)-phenyl |
| 4320. | allyl | 4-(trifluoromethoxy)-phenyl |
| 4321. | allyl | 4-(2-fluoroethoxy)-phenyl |
| 4322. | allyl | 4-(2,2-difluoroethoxy)-phenyl |
| 4323. | allyl | 4-(2,2,2-trifluoroethoxy)-phenyl |
| 4324. | allyl | 4-(1,1,2,2-tetrafluoroethoxy)-phenyl |
| 4325. | allyl | 4-cyclopropylphenyl |
| 4326. | allyl | 4-cyclobutylphenyl |
| 4327. | allyl | 4-cyclopentylphenyl |
| 4328. | allyl | 4-(2,2-difluorocyclopropyl)-phenyl |
| 4329. | allyl | 3,4-difluorophenyl |
| 4330. | allyl | 4-bromo-2-fluorophenyl |
| 4331. | allyl | 2-bromo-4-fluorophenyl |
| 4332. | allyl | 4-bromo-2,5-difluorophenyl |
| 4333. | allyl | 5-bromo-2,4-difluorophenyl |
| 4334. | allyl | 3-bromo-2,4-difluorophenyl |
| 4335. | allyl | 3-chloro-4-(trifluoromethyl)-phenyl |
| 4336. | allyl | 4-fluoro-3-(trifluoromethyl)-phenyl |
| 4337. | allyl | 3-fluoro-5-(trifluoromethyl)-phenyl |
| 4338. | allyl | 3-bromo-4-(trifluoromethyl)-phenyl |
| 4339. | allyl | 5-bromo-3-(trifluoromethyl)-phenyl |
| 4340. | allyl | 5-bromo-2-(trifluoromethyl)-phenyl |
| 4341. | allyl | 2-bromo-5-methoxyphenyl |
| 4342. | allyl | 4-bromo-3-methoxyphenyl |
| 4343. | allyl | 3-fluoro-2-isopropylphenyl |
| 4344. | allyl | 3-fluoro-4-isopropylphenyl |
| 4345. | allyl | 4-(1-hydroxy-1-methylethyl)-phenyl |
| 4346. | allyl | 4-(2-hydroxy-2-methylpropyl)-phenyl |
| 4347. | allyl | 4-acetylphenyl |
| 4348. | allyl | 4-acetylaminophenyl |
| 4349. | allyl | 4-carboxyphenyl |
| 4350. | allyl | 4-cyanophenyl |
| 4351. | allyl | 4-nitrophenyl |
| 4352. | allyl | 4-hydroxyphenyl |
| 4353. | allyl | 4-(O-benzyl)-phenyl |
| 4354. | allyl | 4-(2-methoxyethoxy)-phenyl |
| 4355. | allyl | 4-(CH2—N(CH3)2)-phenyl |
| 4356. | allyl | 4-(NH—CO—NH2)-phenyl |
| 4357. | allyl | 4-(methylsulfanyl)-phenyl |
| 4358. | allyl | 4-(fluoromethylsulfanyl)-phenyl |
| 4359. | allyl | 4-(difluoromethylsulfanyl)-phenyl |
| 4360. | allyl | 4-(trifluoromethylsulfanyl)-phenyl |
| 4361. | allyl | 4-(methylsulfonyl)-phenyl |
| 4362. | allyl | 4-(N-methoxy-N-methyl-amino)-phenyl |
| 4363. | allyl | 4-(methoxyamino)-phenyl |
| 4364. | allyl | 4-(ethoxyamino)-phenyl |
| 4365. | allyl | 4-(N-methylaminooxy)-phenyl |
| 4366. | allyl | 4-(N,N-dimethylaminooxy)-phenyl |
| 4367. | allyl | 4-(azetidin-1-yl)-phenyl |
| 4368. | allyl | 4-(2-methylazetidin-1-yl)-phenyl |
| 4369. | allyl | 4-((S)-2-methylazetidin-1-yl)-phenyl |
| 4370. | allyl | 4-((R)-2-methylazetidin-1-yl)-phenyl |
| 4371. | allyl | 4-(3-fluoroazetidin-1-yl)-phenyl |
| 4372. | allyl | 4-(2,2-difluoroazetidin-1-yl)-phenyl |
| 4373. | allyl | 4-(3-methoxyazetidin-1-yl)-phenyl |
| 4374. | allyl | 4-(3-hydroxyazetidin-1-yl)-phenyl |
| 4375. | allyl | 4-(pyrrolidin-1-yl)-phenyl |
| 4376. | allyl | 4-(pyrrolidin-2-yl)-phenyl |
| 4377. | allyl | 4-((S)-pyrrolidin-2-yl)-phenyl |
| 4378. | allyl | 4-((R)-pyrrolidin-2-yl)-phenyl |
| 4379. | allyl | 4-(pyrrolidin-3-yl)-phenyl |
| 4380. | allyl | 4-((S)-pyrrolidin-3-yl)-phenyl |
| 4381. | allyl | 4-((R)-pyrrolidin-3-yl)-phenyl |
| 4382. | allyl | 4-(pyrrolidin-1-yl)-5-(trifluoromethyl)-phenyl |
| 4383. | allyl | 4-(pyrrolidin-1-yl)-2-methoxyphenyl |
| 4384. | allyl | 4-(pyrrolidin-1-yl)-34-methoxyphenyl |
| 4385. | allyl | 4-(pyrrolidin-1-yl)-2,5-difluorophenyl |

TABLE A-continued

| No. | R¹ | Ar |
|---|---|---|
| 4386. | allyl | 4-(pyrrolidin-1-yl)-2,6-difluorophenyl |
| 4387. | allyl | 4-(2-fluoropyrrolidin-1-yl)-phenyl |
| 4388. | allyl | 4-((S)-2-fluoropyrrolidin-1-yl)-phenyl |
| 4389. | allyl | 4-((R)-2-fluoropyrrolidin-1-yl)-phenyl |
| 4390. | allyl | 4-(3-fluoropyrrolidin-1-yl)-phenyl |
| 4391. | allyl | 4-((S)-3-fluoropyrrolidin-1-yl)-phenyl |
| 4392. | allyl | 4-((R)-3-fluoropyrrolidin-1-yl)-phenyl |
| 4393. | allyl | 4-(2,2-difluoropyrrolidin-1-yl)-phenyl |
| 4394. | allyl | 4-(3,3-difluoropyrrolidin-1-yl)-phenyl |
| 4395. | allyl | 4-(2-methylpyrrolidin-1-yl)-phenyl |
| 4396. | allyl | 4-((S)-2-methylpyrrolidin-1-yl)-phenyl |
| 4397. | allyl | 4-((R)-2-methylpyrrolidin-1-yl)-phenyl |
| 4398. | allyl | 4-(3-methylpyrrolidin-1-yl)-phenyl |
| 4399. | allyl | 4-((S)-3-methylpyrrolidin-1-yl)-phenyl |
| 4400. | allyl | 4-((R)-3-methylpyrrolidin-1-yl)-phenyl |
| 4401. | allyl | 4-(1-methylpyrrolidin-2-yl)-phenyl |
| 4402. | allyl | 4-((S)-1-methylpyrrolidin-2-yl)-phenyl |
| 4403. | allyl | 4-((R)-1-methylpyrrolidin-2-yl)-phenyl |
| 4404. | allyl | 4-(1-methylpyrrolidin-3-yl)-phenyl |
| 4405. | allyl | 4-((S)-1-methylpyrrolidin-3-yl)-phenyl |
| 4406. | allyl | 4-((R)-1-methylpyrrolidin-3-yl)-phenyl |
| 4407. | allyl | 4-(2,2-dimethylpyrrolidin-1-yl)-phenyl |
| 4408. | allyl | 4-(3,3-dimethylpyrrolidin-1-yl)-phenyl |
| 4409. | allyl | 4-(2-trifluoromethylpyrrolidin-1-yl)-phenyl |
| 4410. | allyl | 4-((S)-2-trifluoromethylpyrrolidin-1-yl)-phenyl |
| 4411. | allyl | 4-((R)-2-trifluoromethylpyrrolidin-1-yl)-phenyl |
| 4412. | allyl | 4-(3-trifluoromethylpyrrolidin-1-yl)-phenyl |
| 4413. | allyl | 4-((S)-3-trifluoromethylpyrrolidin-1-yl)-phenyl |
| 4414. | allyl | 4-((R)-3-trifluoromethylpyrrolidin-1-yl)-phenyl |
| 4415. | allyl | 4-(2-oxopyrrolidin-1-yl)-phenyl |
| 4416. | allyl | 4-(2-oxo-oxazolidin-3-yl)-phenyl |
| 4417. | allyl | 4-(piperidin-1-yl)-phenyl |
| 4418. | allyl | 4-(2-methylpiperidin-1-yl)-phenyl |
| 4419. | allyl | 4-((S)-2-methylpiperidin-1-yl)-phenyl |
| 4420. | allyl | 4-((R)-2-methylpiperidin-1-yl)-phenyl |
| 4421. | allyl | 4-(2-fluoropiperidin-1-yl)-phenyl |
| 4422. | allyl | 4-((S)-2-fluoropiperidin-1-yl)-phenyl |
| 4423. | allyl | 4-((R)-2-fluoropiperidin-1-yl)-phenyl |
| 4424. | allyl | 4-(2,2-difluoropiperidin-1-yl)-phenyl |
| 4425. | allyl | 4-(piperazin-1-yl)-phenyl |
| 4426. | allyl | 4-(4-methylpiperazin-1-yl)-phenyl |
| 4427. | allyl | 4-(morpholin-4-yl)-phenyl |
| 4428. | allyl | 4-(morpholin-4-yl)-5-(trifluoromethyl)-phenyl |
| 4429. | allyl | 4-(morpholin-4-yl)-2-methoxyphenyl |
| 4430. | allyl | 4-(morpholin-4-yl)-3-methoxyphenyl |
| 4431. | allyl | 4-(morpholin-4-yl)-2,5-difluorophenyl |
| 4432. | allyl | 4-(morpholin-4-yl)-2,6-difluorophenyl |
| 4433. | allyl | 4-(thiomorpholin-4-yl)-phenyl |
| 4434. | allyl | 4-(1-oxo-thiomorpholin-4-yl)-phenyl |
| 4435. | allyl | 4-(1,1-dioxo-thiomorpholin-4-yl)-phenyl |
| 4436. | allyl | 4-(pyrrol-1-yl)-phenyl |
| 4437. | allyl | 4-(pyrrol-2-yl)-phenyl |
| 4438. | allyl | 4-(pyrrol-3-yl)-phenyl |
| 4439. | allyl | 4-(1-methylpyrrol-2-yl)-phenyl |
| 4440. | allyl | 4-(1-methylpyrrol-3-yl)-phenyl |
| 4441. | allyl | 4-(furan-2-yl)-phenyl |
| 4442. | allyl | 4-(furan-3-yl)-phenyl |
| 4443. | allyl | 4-(thiophen-2-yl)-phenyl |
| 4444. | allyl | 4-(thiophen-3-yl)-phenyl |
| 4445. | allyl | 4-(5-propylthien-2-yl)-phenyl |
| 4446. | allyl | 4-(pyrazol-1-yl)-phenyl |
| 4447. | allyl | 4-(pyrazol-3-yl)-phenyl |
| 4448. | allyl | 4-(pyrazol-4-yl)-phenyl |
| 4449. | allyl | 4-(4-fluoropyrazol-1-yl)-phenyl |
| 4450. | allyl | 4-(1-methyl-1H-pyrazol-4-yl)-phenyl |
| 4451. | allyl | 4-(1-ethyl-1H-pyrazol-4-yl)-phenyl |
| 4452. | allyl | 4-(1-methyl-1H-pyrazol-5-yl)-phenyl |
| 4453. | allyl | 4-(1H-imidazol-2-yl)-phenyl |
| 4454. | allyl | 4-(imidazol-1-yl)-phenyl |
| 4455. | allyl | 4-(1-methylimidazol-2-yl)-phenyl |
| 4456. | allyl | 4-(oxazol-2-yl)-phenyl |
| 4457. | allyl | 4-(oxazol-4-yl)-phenyl |
| 4458. | allyl | 4-(oxazol-5-yl)-phenyl |
| 4459. | allyl | 4-(isoxazol-3-yl)-phenyl |
| 4460. | allyl | 4-(isoxazol-4-yl)-phenyl |

TABLE A-continued

| No. | R¹ | Ar |
|---|---|---|
| 4461. | allyl | 4-(isoxazol-5-yl)-phenyl |
| 4462. | allyl | 4-(thiazol-2-yl)-phenyl |
| 4463. | allyl | 4-(thiazol-4-yl)-phenyl |
| 4464. | allyl | 4-(thiazol-5-yl)-phenyl |
| 4465. | allyl | 4-(2-methylthiazol-4-yl)-phenyl |
| 4466. | allyl | 4-(2-methylthiazol-5-yl)-phenyl |
| 4467. | allyl | 4-([1,2,3]-triazol-1-yl)-phenyl |
| 4468. | allyl | 4-([1,2,4]-triazol-1-yl)-phenyl |
| 4469. | allyl | 4-([1,2,3]-triazol-2-yl)-phenyl |
| 4470. | allyl | 4-(4H-[1,2,4]-triazol-3-yl)-phenyl |
| 4471. | allyl | 4-([1,2,4]-triazol-4-yl)-phenyl |
| 4472. | allyl | 4-(2H-[1,2,3]-triazol-4-yl)-phenyl |
| 4473. | allyl | 4-(4-methyl-4H-[1,2,4]-triazol-3-yl)-phenyl |
| 4474. | allyl | 4-(2-methyl-2H-[1,2,3]-triazol-4-yl)-phenyl |
| 4475. | allyl | 4-([1,3,4]-oxadiazol-2-yl)-phenyl |
| 4476. | allyl | 4-(5-methyl-[1,3,4]-oxadiazol-2-yl)-phenyl |
| 4477. | allyl | 4-([1,2,4]-oxadiazol-3-yl)-phenyl |
| 4478. | allyl | 4-(5-methyl-[1,2,4]-oxadiazol-3-yl)-phenyl |
| 4479. | allyl | 4-([1,2,4]-oxadiazol-5-yl)-phenyl |
| 4480. | allyl | 4-([1,2,3]-oxadiazol-4-yl)-phenyl |
| 4481. | allyl | 4-([1,2,3]-oxadiazol-5-yl)-phenyl |
| 4482. | allyl | 4-([1,2,3]-thiadiazol-4-yl)-phenyl |
| 4483. | allyl | 4-(1H-tetrazol-5-yl)-phenyl |
| 4484. | allyl | 4-(tetrazol-1-yl)-phenyl |
| 4485. | allyl | 4-(2-methyl-2H-tetrazol-5-yl)-phenyl |
| 4486. | allyl | 4-(1-methyl-1H-tetrazol-5-yl)-phenyl |
| 4487. | allyl | 4-furazan-3-yl-phenyl |
| 4488. | allyl | 4-(pyrid-2-yl)-phenyl |
| 4489. | allyl | 4-(pyrid-3-yl)-phenyl |
| 4490. | allyl | 4-(pyrid-4-yl)-phenyl |
| 4491. | allyl | 4-(pyrimidin-2-yl)-phenyl |
| 4492. | allyl | 4-(2-methylpyrimidin-4-yl)-phenyl |
| 4493. | allyl | 4-(pyrimidin-4-yl)-phenyl |
| 4494. | allyl | 4-(pyrimidin-5-yl)-phenyl |
| 4495. | allyl | 4-bromo-2-chloropyridin-5-yl |
| 4496. | allyl | 4-methylpyridin-2-yl |
| 4497. | allyl | 5-methylpyridin-2-yl |
| 4498. | allyl | 4-(pyrrolidin-1-yl)-2-chloropyridin-5-yl |
| 4499. | allyl | 4-(morpholin-4-yl)-2-chloropyridin-5-yl |
| 4500. | allyl | 2-(morpholin-4-yl)-pyridin-5-yl |
| 4501. | allyl | 5-(morpholin-4-yl)-pyridin-2-yl |
| 4502. | allyl | 2-phenoxypyridin-5-yl |
| 4503. | allyl | 2,3-dichlorophenyl |
| 4504. | allyl | 2,5-dichlorophenyl |
| 4505. | allyl | 3,5-dichlorophenyl |
| 4506. | allyl | 3-chloro-4-fluorophenyl |
| 4507. | allyl | 4-bromo-2,5-dichlorophenyl |
| 4508. | allyl | 3-bromo-4-(trifluoromethoxy)phenyl |
| 4509. | allyl | 3,5-dibromo-4-(2-fluoroethoxy)-phenyl |
| 4510. | allyl | 2,5-dimethylphenyl |
| 4511. | allyl | 2,5-di-(trifluoromethyl)-phenyl |
| 4512. | allyl | 3,5-di-(trifluoromethyl)-phenyl |
| 4513. | allyl | 2,5-dimethoxyphenyl |
| 4514. | allyl | 2-methoxy-5-methylphenyl |
| 4515. | allyl | 2-methoxy-5-(trifluoromethyl)-phenyl |
| 4516. | allyl | 4-fluoro-3-(oxazol-4-yl)-phenyl |
| 4517. | allyl | thien-2-yl |
| 4518. | allyl | thien-3-yl |
| 4519. | allyl | 3-chlorothien-2-yl |
| 4520. | allyl | 4-chlorothien-2-yl |
| 4521. | allyl | 5-chlorothien-2-yl |
| 4522. | allyl | 3-bromothien-2-yl |
| 4523. | allyl | 4-bromothien-2-yl |
| 4524. | allyl | 5-bromothien-2-yl |
| 4525. | allyl | 4,5-dichlorothien-2-yl |
| 4526. | allyl | 4,5-dibromothien-2-yl |
| 4527. | allyl | 4-bromo-5-chlorothien-2-yl |
| 4528. | allyl | 3-bromo-5-chlorothien-2-yl |
| 4529. | allyl | 5-methylthien-2-yl |
| 4530. | allyl | 5-ethylthien-2-yl |
| 4531. | allyl | 5-propylthien-2-yl |
| 4532. | allyl | 5-trifluoromethylthien-2-yl |
| 4533. | allyl | 5-phenylthien-2-yl |
| 4534. | allyl | 5-(pyrid-2-yl)-thien-2-yl |
| 4535. | allyl | 5-(phenylsulfonyl)-thien-2-yl |

TABLE A-continued

| No. | R¹ | Ar |
|---|---|---|
| 4536. | allyl | 4-(phenylsulfonyl)-thien-2-yl |
| 4537. | allyl | 5-(pyrid-2-ylsulfonyl)-thien-2-yl |
| 4538. | allyl | 5-(3-chloro-5-trifluoro-pyrid-2-ylsulfonyl)-thien-2-yl |
| 4539. | allyl | 5-(benzoylaminomethyl)-thien-2-yl |
| 4540. | allyl | 5-((4-chlorobenzoyl)aminomethyl)-thien-2-yl |
| 4541. | allyl | 5-(acetylaminomethyl)-thien-2-yl |
| 4542. | allyl | 5-(pyrazol-1-yl)-thien-2-yl |
| 4543. | allyl | 5-(pyrazol-3-yl)-thien-2-yl |
| 4544. | allyl | 5-(pyrazol-4-yl)-thien-2-yl |
| 4545. | allyl | 5-(pyrazol-5-yl)-thien-2-yl |
| 4546. | allyl | 5-(4-fluoropyrazol-1-yl)-thien-2-yl |
| 4547. | allyl | 5-(1-methyl-5-trifluoromethyl-(1H)-pyrazol-3-yl)-thien-2-yl |
| 4548. | allyl | 5-(1-methyl-3-trifluoromethyl-(1H)-pyrazol-5-yl)-thien-2-yl |
| 4549. | allyl | 5-(4-carboxy-1-methyl-5-methylthio-(1H)-pyrazol-3-yl)-thien-2-yl |
| 4550. | allyl | 5-(4-aminomethyl-1-methyl-5-methylthio-(1H)-pyrazol-3-yl)-thien-2-yl |
| 4551. | allyl | 5-(isoxazol-3-yl)-thien-2-yl |
| 4552. | allyl | 5-(isoxazol-4-yl)-thien-2-yl |
| 4553. | allyl | 5-(isoxazol-5-yl)-thien-2-yl |
| 4554. | allyl | 5-(5-trifluoromethylisoxazol-3-yl)-thien-2-yl |
| 4555. | allyl | 5-(oxazol-2-yl)-thien-2-yl |
| 4556. | allyl | 5-(oxazol-4-yl)-thien-2-yl |
| 4557. | allyl | 5-(oxazol-5-yl)-thien-2-yl |
| 4558. | allyl | 5-(2-methyloxazol-4-yl)-thien-2-yl |
| 4559. | allyl | 5-(2-methyloxazol-5-yl)-thien-2-yl |
| 4560. | allyl | 5-(isothiazol-3-yl)-thien-2-yl |
| 4561. | allyl | 5-(isothiazol-4-yl)-thien-2-yl |
| 4562. | allyl | 5-(isothiazol-5-yl)-thien-2-yl |
| 4563. | allyl | 5-(5-trifluoromethylisothiazol-3-yl)-thien-2-yl |
| 4564. | allyl | 5-(thiazol-2-yl)-thien-2-yl |
| 4565. | allyl | 5-(thiazol-4-yl)-thien-2-yl |
| 4566. | allyl | 5-(thiazol-5-yl)-thien-2-yl |
| 4567. | allyl | 5-(2-methylthiazol-4-yl)-thien-2-yl |
| 4568. | allyl | 5-(2-methylthiazol-5-yl)-thien-2-yl |
| 4569. | allyl | 5-([1,2,3]-oxadiazol-4-yl)-thien-2-yl |
| 4570. | allyl | 5-([1,2,3]-thiadiazol-4-yl)-thien-2-yl |
| 4571. | allyl | 5-(pyrimidin-2-yl)-thien-2-yl |
| 4572. | allyl | 5-(pyrimidin-4-yl)-thien-2-yl |
| 4573. | allyl | 5-(pyrimidin-5-yl)-thien-2-yl |
| 4574. | allyl | 5-(2-methylthiopyrimidin-4-yl)-thien-2-yl |
| 4575. | allyl | 5-([1,3]-dioxolan-2-yl)-thien-2-yl |
| 4576. | allyl | 3-([1,3]-dioxolan-2-yl)-thien 2-yl |
| 4577. | allyl | 5-((3-chloro-5-(trifluoromethyl)-pyridin-2-yl)-methyl)-thien-2-yl |
| 4578. | allyl | 5-[3-chloro-5-(trifluoromethyl)-pyrid-2-ylsulfonyl]-thien-2-yl |
| 4579. | allyl | 2-chlorothien-3-yl |
| 4580. | allyl | 4-chlorothien-3-yl |
| 4581. | allyl | 5-chlorothien-3-yl |
| 4582. | allyl | 2-bromothien-3-yl |
| 4583. | allyl | 4-bromothien-3-yl |
| 4584. | allyl | 5-bromothien-3-yl |
| 4585. | allyl | 2,5-dichlorothien-3-yl |
| 4586. | allyl | 2,5-dibromothien-3-yl |
| 4587. | allyl | 2,4,5-trichlorothien-3-yl |
| 4588. | allyl | 4-bromo-2,5-dichlorothien-3-yl |
| 4589. | allyl | 2-chloro-5-methylsulfonylthien-3-yl |
| 4590. | allyl | 2,5-dimethylthien-3-yl |
| 4591. | allyl | 4-hydroxythien-3-yl |
| 4592. | allyl | 2-phenylthien-3-yl |
| 4593. | allyl | 4-phenyl-5-(trofluoromethyl)-thien-3-yl |
| 4594. | allyl | 2-methoxycarbonyl-4-phenyl-5-(trifluoromethyl)-thien-3-yl |
| 4595. | allyl | benzo[b]thiophen-2-yl |
| 4596. | allyl | benzo[b]thiophen-3-yl |
| 4597. | allyl | 3-methyl-benzo[b]thiophen-2-yl |
| 4598. | allyl | 5-methyl-benzo[b]thiophen-2-yl |
| 4599. | allyl | 5-fluoro-3-methyl-benzo[b]thiophen-2-yl |
| 4600. | allyl | 5-chloro-3-methyl-benzo[b]thiophen-2-yl |
| 4601. | allyl | 5-bromo-3-methyl-benzo[b]thiophen-2-yl |

Compounds I of the present invention can be synthesized as outlined in the synthetic routes A, B and C below.

Scheme 1:

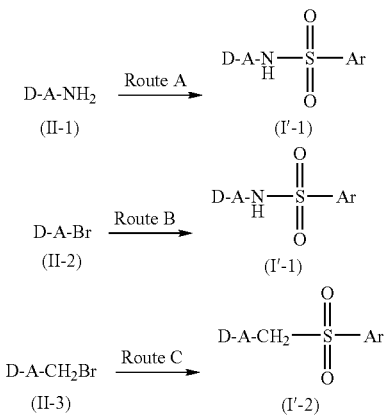

In scheme 1, A and Ar G, n, $R^2$, and $R^4$ are as defined above. D is a group of the formula A' or B'

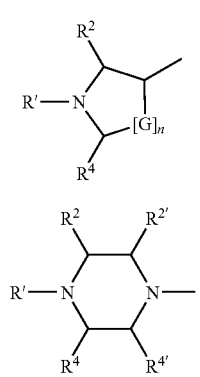

where G, n, $R^2$, $R^{2'}$, $R^4$ and $R^{4'}$ are as defined above and R' is either $R^1$ or is a precursor of $R^1$.

Route A

In route A, the amino compound (II-1) is reacted with a suitable sulfonic acid derivative to give the sulfonamide (I-1) (E=NH). A suitable sulfonic acid derivative is e.g. the sulfonyl chloride Ar—$SO_2Cl$. The sulfonation reaction is preferably carried out in the presence of a base, according to standard procedures in the art. In the reaction depicted in the above scheme 1, the sulfonation takes place under the reaction conditions which are customary for preparing arylsulfonamide compounds or arylsulfonic esters, respectively, and which are described, for example, in J. March, Advanced Organic Chemistry, 3$^{rd}$ edition, John Wiley & Sons, New York, 1985 page 444ff and the literature cited therein, European J. Org. Chem. 2002 (13), pp. 2094-2108, Tetrahedron 2001, 57 (27) pp. 5885-5895, Bioorganic and Medicinal Chemistry Letters, 2000, 10(8), pp. 835-838 and Synthesis 2000 (1), pp. 103-108. The reaction customarily takes place in an inert solvent, for example in an ether, such as diethyl ether, diisopropyl ether, methyl tert-butyl ether or tetrahydrofuran, a halohydrocarbon, such as dichloro-methane, an aliphatic or cycloaliphatic hydrocarbon, such as pentane, hexane or cyclohexane, or an aromatic hydrocarbon, such as toluene, xylene, cumene and the like, or in a mixture of the abovementioned solvents. The reaction with Cl—$SO_2$—Ar is customarily carried out in the presence of an auxiliary base. Suitable bases are inorganic bases, such as sodium carbonate or potassium carbonate, or sodium hydrogen-carbonate or potassium hydrogencarbonate, and organic bases, for example trialkylamines, such as triethylamine, or pyridine compounds, such as pyridine, lutidine and the like. The latter compounds can at the same time serve as solvents. The auxiliary base is customarily employed in at least equimolar quantities, based on the amine compound (II-1).

Prior to the sulfonation reaction, the radical $NH_2$ can be converted into a $NR^{5'}$ group, in which $R^{5'}$ has the meanings different from hydrogen which are specified for $R^5$ (not shown in scheme 1).

If in the resulting sulfonamide (I'-1) $R^1$ is not the desired radical $R^1$ but a precursor thereof, the compound can be modified as outlined below to obtain the desired substituent $R^1$. A precursor is a radical which can be easily removed and replaced by the desired group $R^1$ or which can be modified to give $R^1$. The precursor can also be an N-protective group.

If R' is allyl, the allyl group can be cleaved to obtain a compound wherein R' is hydrogen. The cleavage of the allyl group is achieved, for example, by reacting compound (I'-1) [R'=allyl] with an allyl trapping agent, such as mercaptobenzoic acid or 1,3-dimethylbarbituric acid, in the presence of catalytic quantities of palladium (0) compounds or palladium compounds which are able to form a palladium(0) compound under reaction conditions, e.g. palladium dichloride, tetrakis (triphenylphosphine)-palladium(0) or tris(dibenzylideneacetone)dipalladium(0), advantageously in combination with phosphine ligands, e.g. triarylphosphines, such as triphenylphosphine, trial-kylphosphines, such as tributylphosphine, and cycloalkylphosphines, such as tricyclo-hexylphosphine, and especially with phosphine chelate ligands, such as 2,2'-bis(diphenylphosphino)-1,1'-binaphthyl or 1,4-bis(diphenylphosphino)butane, using methods known from the literature (with regard to eliminating N-allyl in the presence of mercaptobenzoic acid, see WO 94/24088; with regard to eliminating in the presence of 1,3-dimethylbarbituric acid, see J. Am. Chem. Soc. 2001, 123 (28), pp. 6801-6808 and J. Org. Chem. 2002, 67(11) pp. 3718-3723). Alternatively, the cleavage of N-allyl can also be effected by reacting in the presence of rhodium compounds, such as tris(triphenylphosphine)chlororhodium(I), using methods known from the literature (see J. Chem. Soc., Perkin Transaction I: Organic and Bio-Organic Chemistry 1999 (21) pp. 3089-3104 and Tetrahedron Asymmetry 1997, 8(20), pp. 3387-3391).

If R' is benzyl, this substituent may also be cleaved to obtain a compound (I'-1) wherein R' is H. The reaction conditions for the cleavage are known in the art. Typically, the benzyl group is removed by a hydrogenation reaction in the presence of a suitable Pd catalyst, such as Pd on carbon or palladium hydroxide.

R' can also be a protective group. The protective group may be removed to yield a compound (I'-1) wherein R' is H. Suitable protective groups are known in the art and are, for example, selected from tert-butoxycarbonyl (boc), benzyloxycarbonyl (Cbz), 9-fluorenylmethoxycarbonyl (Fmoc), triphenylmethyl (Trt) and nitrobenzenesulfenyl (Nps). A preferred protective group is boc. The protective groups can be removed by known methods, such as treatment of the protected amine with an acid, e.g. halogen acid, such as HCl or HBr, or trifluoroacetic acid, or by hydrogenation, optionally in the presence of a Pd catalyst.

The resulting compound, wherein R' is H, can then be reacted, in a known manner, in the sense of an alkylation, with a compound $R^1$—X. In this compound, $R^1$ is $C_1$-$C_4$-alkyl, $C_3$-$C_6$-cycloalkyl, $C_1$-$C_4$-haloalkyl, $C_1$-$C_4$-alkoxy-$C_1$-$C_4$-alkyl or $C_3$-$C_6$-cycloalkyl-$C_1$-$C_4$-alkyl and X is a nucleophilically displaceable leaving group, e.g. halogen, trifluoroacetate, alkylsulfonate, arylsulfonate, alkyl sulfate and the like. The reaction conditions which are required for the alkylation have been adequately disclosed, e.g. in Bioorganic and Medicinal Chemistry Lett. 2002, 12(7), pp. 2443-2446 and also 2002, 12(5), pp. 1917-1919.

The alkylation can also be achieved, in the sense of a reductive amination, by reacting the compound (I'-1), wherein R'=H, with a suitable ketone or aldehyde in the presence of a reducing agent, e.g. in the presence of a borohydride such as sodium borohydride, sodium cyanoborohydride or sodium triacetoxyborohydride. The skilled person is familiar with the reaction conditions which are required for a reductive amination, e.g. from Bioorganic and Medicinal Chemistry Lett. 2002, 12(5), pp. 795-798 and 12(7) pp. 1269-1273.

In case R' is hydrogen, the resulting sulfonamide (I'-1) can further be reacted with an acyl halide to obtain a compound of the formula I wherein $R^1$ is $C_1$-$C_3$-alkylcarbonyl. The carbonyl group in these compounds can be reduced with diborane to obtain compounds of the general formula I, wherein $R^1$ is $C_2$-$C_4$-alkyl. The carbonyl group can also be reacted with a fluorinating agent to obtain a compound I wherein $R^1$ is 1,1-difluoroalkyl. Acylation and reduction can be achieved by standard methods, which are discussed in Jerry March, Advanced Organic Chemistry, 3rd ed. J. Wiley & Sons, New York 1985, p. 370 and 373 (acylation) and p. 1099 f. and in the literature cited in this publication (with regard to acylation, see also Synth. Commun. 1986, 16, p. 267, and with regard to reduction, see also J. Heterocycl. Chem. 1979, 16, p. 1525).

Route B

In route B, the bromo substituted compound (II-2) is reacted with an appropriate sulfonamide $ArSO_2NHR^5$ to give the sulfonamide (I'-1). The reaction is generally carried out under activating conditions, e.g. under microwave conditions. Pd, especially Pd(0), or Cu catalysts may also be used for coupling (see, e.g. Org. Lett. 2000, 2, 1101; J. Am. Chem. Soc. 2002, 124, 6043; Org. Lett. 2003, 5, 4373; Tetrahedron Lett. 2003, 44, 3385). Examples for suitable Pd(0) catalysts are tetrakis(triphenylphosphine)-palladium(0) and $Pd_2(dba)_3$ (tris(dibenzylideneacetone)-dipalladium(0)), which are customarily used in the presence of a tri(substituted)phosphine, e.g. a triarylphosphine such as triphenylphosphine, tritolylphosphine or xantphos, tri(cyclo)alkylphosphine such as tris-n-butylphosphine, tris(tert.-butyl)phosphine or tris(cyclohexylphosphine). This route is especially useful in cases where the corresponding sulfonyl chloride is not available.

Alternatively, the bromo substituent may be replaced by an amino substituent, e.g. by reacting with a benzophenone imine or with lithium bis(trimethylsilyl)amide in the presence of a palladium(0) compound such as tris(dibenzylideneacetone)dipalladium(0) in the presence of a tri(substituted) phosphine, e.g. a triarylphosphine such as triphenyl-phosphine or tritolylphosphine, tri(cyclo)alkylphosphine such as tris-n-butylphosphine, tris(tert.-butyl)phosphine or tris(cyclohexylphosphine), preferably in the presence of a base such as sodium hydride according to the method described in, e.g., J. Org. Chem., 68 (2993) pp 8274-8276, or J. Org. Chem. 2000, 65, 2612. The resulting amino compound may then be subjected to the sulfonation reaction of route A.

Route C

In route C, compound (II-3) is reacted with a mercapto compound HS—Ar in the presence of a base, such as sodium hydride or sodium alkoxide or with an alkali metal salt thereof thereby yielding a thioether compound. The thioether moiety is then oxidized to a sulfone moiety, e.g. by oxone, to yield the sulfone (I'-2).

The substituent Ar can be varied by either using different sulfonyl chlorides or by modifying the substituents of the group Ar after the formation of the sulfonamide (I'-1) or the sulfone (I'-2) by known methods. For example, a bromine substituent of the Ar group may be replaced by an N-bound pyrrolidinyl group according to the procedure described in Tetrahedron Asym. 1999, 10, 1831. This Pd-mediated coupling is generally applicable to all nitrogen-containing heterocycles such as azetidinyl, pyrazolidinyl, imidazolidinyl, piperidinyl, piperazinyl, morpholinyl and the like. The reaction is also applicable to heterocyclic compounds carrying one or more substituents such as halogen, alkyl or fluorinated alkyl. A bromine substituent of the Ar group may further be replaced by an isopropenyl group according to a Stille coupling where the bromo compound is reacted with an alkenyl tributyl stannate in the presence of an appropriate Pd coupling catalyst, e.g. tetrakistriphenylphosphine palladium(0) (see, e.g. Tetrahedron, 2003, 59(34), 6545 and Bioorg. Med. Chem. 1999, 7(5), 665). The isopropenyl group may then be converted into the isopropyl group by known hydrogenation methods.

Compounds of formula (II) (II-1, II-2 and II-3) can be synthesized by as shown below.

1. Synthesis of Compounds (II-1) Wherein D is a Group B

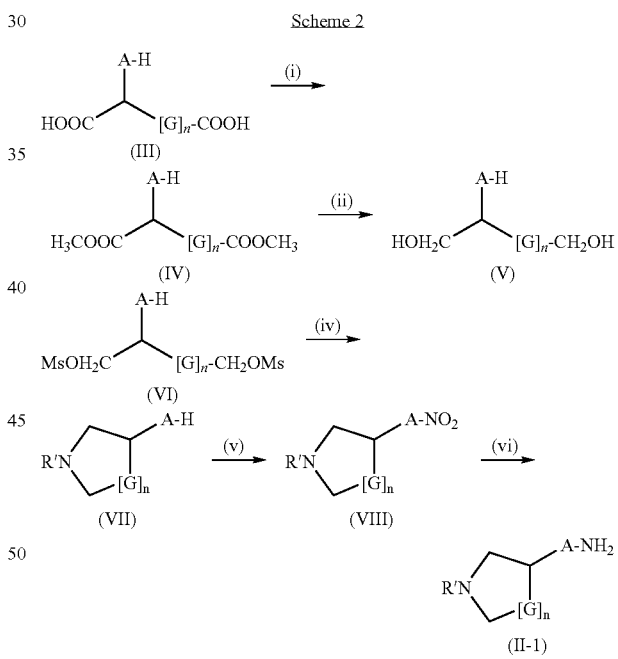

Scheme 2

In scheme 2, A, G, n and R' are as defined above.

The conversion of the acid (III) into its methyl ester (IV) is performed by standard techniques, e.g. as described in Jerry March, Advanced Organic Chemistry, John Wiley, $3^{rd}$ edition, page 348ff. For instance, the acid is transformed into the corresponding acid chloride, e.g. by reacting it with $SOCl_2$. The chloride is then converted into the ester by reaction with methanol.

The reduction in step (ii) is suitably carried out under standard conditions for the con-version of carboxylic esters into alcohols. Appropriate reaction conditions and reducing agents are described, e.g. in Jerry March, Advanced Organic Chemistry, John Wiley, 3$^{rd}$ edition, page 1093ff. Typical reducing agents are metal hydrides and complex hydrides. Examples of suitable metal hydrides include $BH_3$, 9-BBN, $AlH_3$ and $AlH(i-Bu)_2$ (DIBAL-H), suitably in the presence of complexing solvents, such as tetrahydrofuran and diethylether. Complex hydrides are e.g. $NaBH_4$, $LiAlH_4$ and $LiAlH(OR)_3$, where R is $C_1$-$C_4$-alkyl, such as methyl, ethyl, isobutyl or tert-butyl. A preferred reducing agent is $LiAlH_4$. The reduction is suitably carried out in complexing solvents, such as open-chain and cyclic ethers, e.g. tetrahydrofuran, diethyl ether, dipropyl ether, diisopropyl ether, dibutyl ether and methylbutyl ether. A preferred solvent is tetrahydrofuran.

In the mesylation step (iii), the alcohol functionality is converted into a better leaving group. The mesylation is performed under standard conditions, e.g. by reacting the alcohol with methansulfonyl chloride in the presence of a base. Suitable bases are, among others, alkyl amines, such as diethyl amine, triethyl amine and ethyldiisopropyl amine. In this step, other functionalties representing good leaving groups, such as trifluoroacetate, other alkylsulfonates, arylsulfonates, e.g. tosylates, alkyl sulfates and the like tosylate, may be introduced instead of the methansulfonyl group.

In the cyclisation step (iv), compound (VI) or a suitable derivative thereof is reacted with a primary amine $NH_2R'$. In case the primary amine is a liquid, it may also be used as solvent, no further solvent being necessary. If the amine is visquous or a solid, the reaction is advantageously carried out in a suitable solvent.

The reaction of step (v) takes place under the reaction conditions which are customary for a nitration reaction on an aromatic radical and which are described, for example, in Jerry March, Advanced Organic Chemistry, John Wiley, 3$^{rd}$ edition, page 468ff, Tetrahedron 1999, 55(33), pp. 10243-10252, J. Med. Chem. 1997, 40(22), pp. 3679-3686 and Synthetic Communications, 1993, 23(5), pp. 591-599. For example, compound (VII) is reacted with concentrated nitric acid or a nitrate, such as potassium or sodium nitrate, in the presence of concentrated sulfuric acid. The resulting product (VIII) may in the form of different regioisomers (e.g. ortho, meta or para, if A is phenyl or a 6-membered hetaryl. In the case of A being phenyl or a 6-membered hetaryl, the paranitro compound generally predominates. However, some ortho product may also be obtained, whereas the meta product is not produced at all or only in neglectable amounts. By separating ortho and para products, compounds of formula I, wherein A is 1,4-bound phenyl, are accessible via the reaction path shown in scheme 2.

In step (vi), the nitro group in (VIII) is reduced to an $NH_2$ group. Subsequently, the $NH_2$ group can be converted into a —$NR^{5'}$ group, in which $R^{5'}$ has the meanings different from hydrogen which are specified for $R^5$. The reaction conditions which are required for step (vi) correspond to the customary conditions for reducing aromatic nitro groups which have been described extensively in the literature (see, for example, J. March, Advanced Organic Chemistry, 3rd ed., J. Wiley & Sons, New-York, 1985, p. 1183 and the literature cited in this reference). The reduction is achieved, for example, by reacting the nitro compound VII with a metal such as iron, zinc or tin under acidic reaction conditions, i.e. using nascent hydrogen, or using a complex hydride such as lithium aluminum hydride or sodium borohydride, preferably in the presence of transition metal compounds of nickel or cobalt such as $NiCl_2$ $(P(phenyl)_3)_2$, or $COCl_2$, (see Ono et al. Chem. Ind. (London), 1983 p. 480), or using $NaBH_2S_3$ (see Lalancette et al. Can. J. Chem. 49, 1971, p. 2990), with it being possible to carry out these reductions, depending on the given reagent, in substance or in a solvent or diluent. Alternatively, the reduction can be carried out with hydrogen in the presence of a transition metal catalyst, e.g. using hydrogen in the presence of catalysts based on platinum, palladium, nickel, ruthenium or rhodium. The catalysts can contain the transition metal in elemental form or in the form of a complex compound, of a salt or of an oxide of the transition metal, with it being possible, for the purpose of modifying the activity, to use customary coligands, e.g. organic phosphine compounds, such as triphenylphosphine, tricyclohexyl-phosphine or tri-n-butylphosphines or phosphites. The catalyst is customarily employed in quantities of from 0.001 to 1 mol per mol of nitro compound, calculated as catalyst metal. In a preferred variant, the reduction is effected using tin(II) chloride in analogy with the methods described in Bioorganic and Medicinal Chemistry Letters, 2002, 12(15), pp. 1917-1919 and J. Med. Chem. 2002, 45(21), pp. 4679-4688. The reaction of VII with tin(II) chloride is preferably carried out in an inert organic solvent, preferably an alcohol such as methanol, ethanol, isopropanol or butanol.

The skilled person will appreciate that the synthesis described in scheme 2 is also suitable for the preparation of compounds (II) and consequently for compounds (I), wherein $R^2$, $R^3$ and $R^4$ are different from H, e.g. by starting from the correspondingly substituted compound (III). The same applies to the synthesis of enantiomerically pure (I) which can be synthesized by starting from the corresponding enantiomer (III).

2. Synthesis of Compounds (II-2)

Compounds of formula (II-2) can be synthesized by carrying out in step (v) of scheme 2 a halogenation instead of a nitration. Halogenation reactions of pyridyl groups are widespread standard methods and are, e.g., discussed in Jerry March, Advanced Organic Chemistry, John Wiley, 3$^{rd}$ edition page 476 ff.

3. Synthesis of Compounds (II-3)

The synthesis of these compounds also belongs to standard reaction methods and can be performed by monohalogenating the methyl group of a methyl-substituted pyridyl compound.

4. Synthesis of Enantiomerically Pure Compounds I

In addition to the method described in item 1., enantiomerically pure compounds (I) can also be obtained by applying standard resolution techniques to suitable precursors thereof. For instance, compound VIII (see scheme 2 above) or compounds (II-2) or (II-3) (see scheme 1 above), wherein R' is a suitable protective group, such as benzyl, may be reacted with tartric acid or a derivative thereof (e.g. diethyltartrate, dipropyltartrate, diisopropyltartrate, etc.) to afford two diastereomeric salts. These can be separated in a customary manner, e.g. by extraction or chromatographic methods or preferably by fractionated crystallization. The thus separated diastereomeric salts are then converted into enantiomerically pure compounds VIII, II-2 or II-3 by reacting the salts with a suitable base to afford the S- or R-enantiomers of compounds VIII, II-2 or II-3. Suitable bases are, e.g., alkali metal hydroxides, such as potassium hydroxide and sodium hydroxide, alkaline earth metal hydroxides, such as magnesium hydroxide and calcium hydroxide, alkali metal carbonates, such as sodium carbonate and potassium carbonate, alkaline earth metal carbonates, such as magnesium carbonate and calcium carbonate, alkali metal oxides such as sodium oxide and potassium oxide, and alkaline earth metal oxides, such as magnesium oxide and calcium oxide; organic bases, such as alkoholates, e.g. sodium methanolate, sodium ethanolate or sodium-tert-butanolate, amines, such as dimethylamine, trimethylamine, diethylamine, triethyl-amine, dipropylamine, tripropylamine, diisopropylamine, diisopropylethylamine and the like, and nitrogen-containing basic heterocyclic compounds, such as pyridine, picoline und lutidine.

5. Specific Syntheses

5.1 Synthesis of Compounds I, Wherein D is a Group B and n is 1 (Pyrrolidinyl Sulfonyl Derivatives) and Precursors Thereof

5.1.1

Scheme 3:

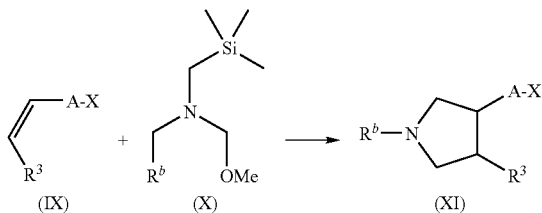

In scheme 3, A and $R^3$ are as defined above.

The pyrrolidine ring is also available by a [3+2] dipolar cycloaddition of a non-stabilized azomethine ylid to an alkenylpyridine derivative (IX) (e.g. a 2-, 3- or 4-vinyl pyridine, $R^3$=H). This procedure is generally described in J. Org. Chem. 1987, 52, 235. The precursor of the ylid, the amine $N(CH_2R^b)(CH_2SiMe_3)(CH_2OCH_3)(X)$, is commercially available or can be synthesized from $NH_2(CH_2R^b)$, $Me_3SiCH_2Cl$ and HCHO in the presence of methanol.

The alkenylpyridine compound (IX) can be synthesized e.g. by a Stille coupling of a halogeno pyridine, e.g. a bromo pyridine (2-, 3- or 4-bromo pyridine), with the corresponding alkenyl tributyl stannate, such as vinyl or isobutenyl tributyl stannate, in the presence of an appropriate Pd coupling catalyst, e.g. tetrakistriphenylphosphine palladium(0) (see, e.g. Tetrahedron, 2003, 59(34), 6545 and Bioorg. Med. Chem. 1999, 7(5), 665). By choosing a special Stille isomer (e.g. cis- or trans-isobutenyl tributyl stannate), the corresponding cis- or trans alkyl pyridyl pyrrolidine can be prepared selectively.

Alternatively, the alkenylpyridine compound (IX) can be synthesized by a Wittig reaction of the corresponding pyridyl aldehyde with a Wittig reagent such as $PPh_3$=CHR(R is H, or $C_1$-$C_3$-alkyl). Conditions for the Wittig reaction are well known in the art and are, e.g. discussed in Jerry March, Advanced Organic Chemistry, John Wiley, 3$^{rd}$ edition, page 845 ff.

Advantageously, the alkenylpyridine compound (IX) further carries a nitro group or another halogeno substituent (X=$NO_2$ or halogen), preferably in the appropriate position (a 2-alkenyl pyridine is preferably substituted by X in the 4- or 6-position, a 3-alkenyl pyridine is preferably substituted by X in the 3-position and a 4-alkenyl pyridine is preferably substituted by X in the 2-position). In this case, the subsequent reaction steps can be carried out as outlined in route A or B. If X=H, the A ring may be first nitrated as described in scheme 2, step (v) and then subjected to the reaction of scheme 2, step (vi) and scheme 1, route A; or ring A may be halogenated and then subjected to the procedure of route B.

The group $CH_2R^b$ of the precursor amine advantageously corresponds either to the desired group $R^1$ of the final compound I or is alternatively a cleavable group, such as benzyl, which can be removed to give the N-unsubstituted pyrrolidine. The latter can subsequently be functionalized as described above (see route A).

The synthesis of pyridylpyrrolidines is e.g. described in Chem. Pharm. Bull., 1985, 33, 2762-66; J. Heterocyclic Chemistry, 1996, 1995-2005; J. Heterocyclic Chemistry, 2001, 38, 1039-1044; Tetrahedron Letters, 1992, 33, 44, 6607-10; Heterocycles, 1998, 48, 12, 2535-2541.

5.1.2

Scheme 4:

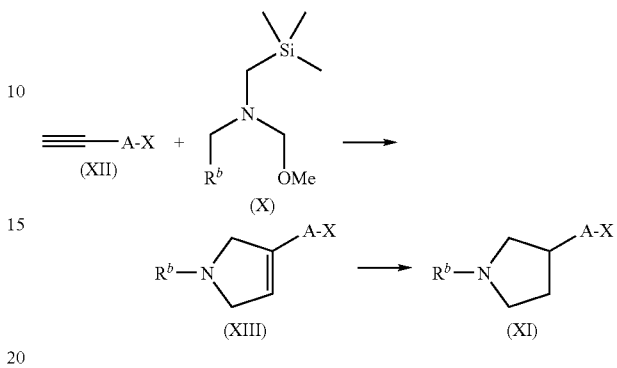

Pyridylpyrrolidines can also be prepared by a [3+2] dipolar cycloaddition of a non-stabilized azomethine ylid to a 1-alkynylbenzene (XII) (in analogy to, e.g., Tetrahedron 1996, 52, 59). The resulting pyrroline (XIII) or the final product (I') is then hydrogenated to the corresponding pyrrolidine (XI). If the hydrogenation is carried out under chiral conditions, e.g. by using chiral catalysts, the enantiomerically pure pyridylpyrrolidine compounds can be obtained. Chiral hydrogenation catalysts are well known in the art. The subsequent conversion to the desired sulfonamide can be carried out as described in route A or B.

5.1.3

Alternatively, pyridyl pyrrolidinyl compounds can be prepared from pyridyl halides which are subjected to a Pd-mediated cross coupling with an organozinc pyrrolidine compound. This process is described in further detail below in route F. In this alternative, too, the pyridyl halide advantageously carries a nitro group. In this case, the con-version to the desired sulfonamides can be carried out as described in route A. Alternatively, the pyridyl halide carries a halogen atom. In this case, the conversion to the de-sired sulfonamides can be achieved as described in route B.

5.1.4

The pyridyl pyrrolidine may be prepared by way of a Heck reaction where a protected pyrroline is reacted with the desired pyridine (e.g. 2-iodo-4-nitropyridine 2-iodo-6-nitropyridine or 3-iodo-5-nitropyridine) under typical Heck conditions. Catalytic hydrogenation of the pyrroline double bond and reduction of the nitro group according to the procedure described in scheme 2 yields the desired product.

The N-protected pyrroline can be obtained by reacting commercially available pyrroline with the desired protective group, e.g. with chloromethylfumarate, benzylchloride, Cbz-anhydride or Boc-anhydride.

The pyrroline may be synthesized in a metathesis reaction of N-protected diallylamine in the presence of a metathesis catalyst, e.g. a Grubbs catalyst.

5.1.5

The pyridyl pyrrolidine may further be prepared by reacting N-protected 3-oxopyrrolidine with a metallated nitropyridine, dehydrating the resulting alcohol and hydrogenating the double bond of the pyrroline ring. The metallated nitropyridine may be obtained by reacting a halonitropyridine, e.g. 2-bromo-4-nitropyridine or 4-bromo-2-nitropyridine or 3-bromo-5-nitropyridine, with $MgBr_2$ or preferably with n-butyllithium under standard conditions for Grignard reactions or lithiations. The N-protected 3-oxopyrrolidine can be obtained by reacting commercially available 3-oxopyrrolidine with the desired protective group, e.g. with chloromethylfumarate, benzylchloride, allyl chloride, Cbz-anhydride or Boc-anhydride.

5.2 Synthesis of compounds I, Wherein D is a Group B and n is 0 (N-(azetidin-3-yl)-sulfonamides) and Precursors Thereof.

Compounds I, wherein n is 0 (azetidine compounds) can be synthesized as follows:

Scheme 5:

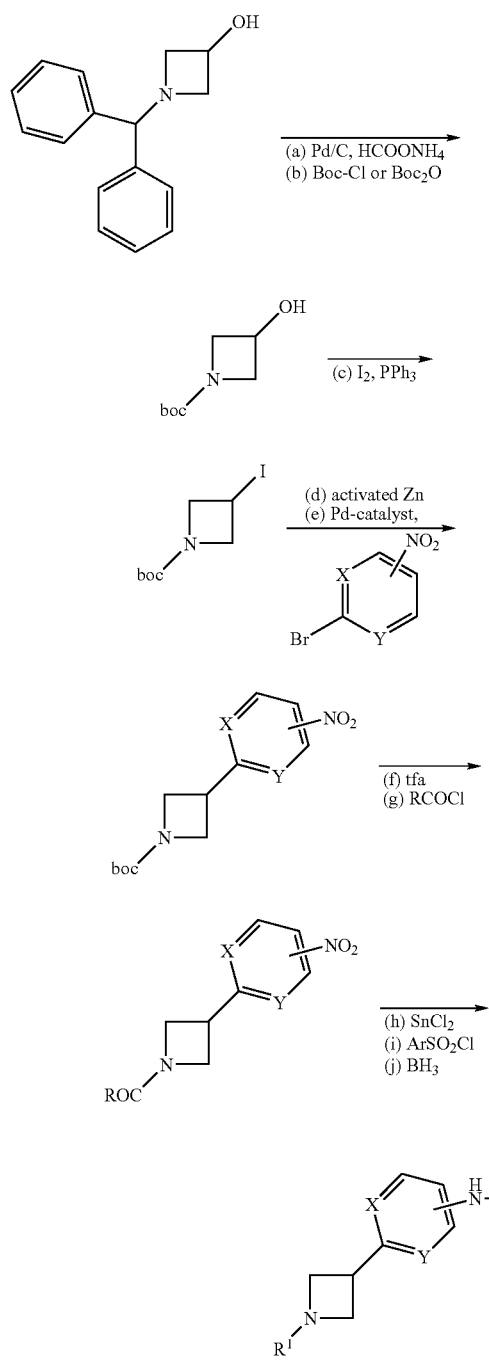

In scheme 5, Ar and $R^1$ are as defined above. X and Y are, independently of each other, CH or N.

Starting from 1-benzhydryl-azetidin-3-ol, Pd-mediated deprotection of the amine (Tetrahedron 2002, 58, 9865-9870), carbamate formation and subsequent halogenation generate an intermediate that undergoes Zn insertion (Tetrahedron 1987, 43, 2203-2212; J. Org. Chem. 1988, 53, 2390-2392). The thus obtained organozinc species can react with an appropriate 2-halo-nitro-ring (Synlett 1998, 4, 379-380; J. Am. Chem. Soc. 2003, 125, 12527-12530) to give the nitro-aryl-azetidine core. If one utilizes a 2-halo-halo-ring, there is also the possibility to realize the direct coupling between the aryl-azetidine halide and the appropriate sulfonamides (Org. Lett. 2000, 2, 1101-1104; J. Am. Chem. Soc. 2002, 124, 6043-6048; Org. Lett. 2003, 5, 4373-4376; Tetrahedron Lett. 2003, 44, 3385-3386). The amine may be regenerated by cleavage of the carbamate (e.g. with trifluoroacetic acid in the case of a Boc carbamate) and subsequently converted into an amide by reaction with the appropriate acyl chloride. The nitro group can be reduced to the amine via tin chloride or catalytic hydrogenation (e.g. Pd—C) and then converted to the desired sulfonamide by reaction with the appropriate sulfonyl chloride in the presence of a base such as pyridine. Ultimate reduction of the amide via hydroboration furnishes the final compounds.

Of course, the reaction also applies to compounds wherein the (hetero)aromatic ring bound to the azetidine group is a 5-membered heterocyclic radical, e.g. thienyl.

5.3 Synthesis of compounds I, wherein D is a Group B and n is 2 (N-(piperidin-3-yl)-sulfonamides) and Precursors Thereof Further to the above-described syntheses (routes A, B and C), compounds I, wherein n is 2 and E is $NR^5$ (piperidin-3-yl sulfonamides) may be prepared by starting from commercially available 3-aryl or 3-hetaryl piperidines. These starting compounds may then be converted into the amino-substituted or halogenated derivative and then be subjected to the synthetic path of route A or B.

5.4 Synthesis of compounds I, wherein D is a group C(N-(piperazin-4-yl)-sulfonamides) and precursors thereof.

Piperazinyl pyridine compounds I can be prepared by Pd-mediated coupling of a N-monoprotected piperazine to a halonitropyridine, e.g. to 3-bromo-5-nitropyridine, 3-bromo-2-methoxy-5-nitropyridine, 2-bromo-4-nitropyridine, 4-bromo-2-nitropyridine, or 4-bromo-5-methoxy-2-nitropyridine, to give the corresponding piperazinyl-substituted nitropyridine, reduction of the nitro group and sulfonation according to the above scheme A.

Suitable N-protective groups are those mentioned above.

A skilled person will readily appreciate that compounds of the formula I can also be obtained from structurally similar compounds by functional group interconversion. In particular N-bound radicals $R^a$ can be introduced into compounds of the formula I by reacting the corresponding halogen compound, i.e. a compound of the formula I, which instead of $R^a$ carries a halogen atom, in particular a bromine or iodine atom, with a primary or secondary amine in the presence of a base, preferably also in the presence of a palladium catalyst in terms of a Buchwald-Hartwig reaction.

If not indicated otherwise, the above-described reactions are generally carried out in a solvent at temperatures between room temperature and the boiling temperature of the solvent employed. Alternatively, the activation energy which is required for the reaction can be introduced into the reaction mixture using microwaves, something which has proved to be of value, in particular, in the case of the reactions catalyzed by transition metals (with regard to reactions using microwaves, see Tetrahedron 2001, 57, p. 9199 ff. p. 9225 ff. and also, in a general manner, "Microwaves in Organic Synthesis", André Loupy (Ed.), Wiley-VCH 2002.

The sulfonylchlorides $C_1$—$SO_2$—Ar are either commercially available or can be prepared according to standard synthetic methods. Sulfonylchlorides containing a fluorinated radical $R^a$ may be prepared by different synthetic routes, e.g. by reacting suitable hydroxy or oxo precursor (e.g. a compound $C_1$—$SO_2$—Ar, carrying a hydroxy or oxo substituted radical) with fluorinating reagents like DAST (diethylaminosulfurtrifluoride), morpholine-DAST, deoxo-fluor (bis(2-methoxyethyl)aminosulfur trifluoride), Ishikawa's re-agent (N,N-diethyl-(1,1,2,3,3,3-hexafluoropropyl)amine; Journal of Fluorine Chemistry, 1989, 43, 371-377). More conventionally, the hydroxy group of an aromatic compound which carries a hydroxy substituted radical but not a chlorosulfonyl group, is trans-formed into a leaving group which is then replace by a fluoride ion (J. Org. Chem., 1994, 59, 2898-22901; Tetrahedron Letters, 1998, 7305-6; J. Org. Chem., 1998, 63, 9587-9589, Synthesis, 1987, 920-21)). Subsequent direct chlorosulfonylation with chlorosulfonic acid (Heterocycles, 2001, 55, 9, 1789-1803; J. Org. Chem., 2000, 65, 1399-1406) or a two step process preparing first the sulfonic acid derivatives which are then transformed to the sulfonylchlorides with e.g. chlorosulfonic acid, phosphorous penta-chloride (Eur. J. Med. Chem., 2002, 36, 809-828) and the like, yields the desired sulfonylchloride (Tetrahedron Letters, 1991, 33, 50 7787-7788)) Sulfonylchlorides may also be prepared by diazotation of suitable amine precursor Ar—$NH_2$ with sodium nitrite under acidic conditions and reaction with sulfur dioxide in acetic acid (scheme (iii); J. Org. Chem., 1960, 25, 1824-26); by oxidation of suitable heteroaryl-thiols HS—Ar or heteroaryl-benzyl-thioethers $C_6H_5$—$CH_2$—S—Ar with chlorine (Synthesis, 1998, 36-38; J. Am. Chem. Soc., 1950, 74, 4890-92); directly to the corresponding sulfonyl chlorides. The further are known in the art or may be prepared by standard methods.

In the following schemes 6 to 8 several routes are shown which are suitable to prepare benzenesulfonyl chlorides carrying a fluorinated propyl radical.

The 4-(1,1-difluoropropan-2-yl)benzene-1-sulfonyl chloride intermediate can be prepared from the commercially available 2-phenylpropanoic acid. In the first step a) the 2-phenylpropanic acid is converted to the alkyl ester by esterification with an alcohol (e.g. methanol or ethanol) under acid catalysis (e.g. HCl, $SO_2Cl_2$). The ester can be reduced to the corresponding 2-phenyl propanal by a reducing agent such as DIBAL (diisobutylaluminium hydride). The aldehyde is converted to the 1,1-difluoro-2-propyl derivative by reaction with a suitable fluorinating reagent like DAST (diethylaminosulfurtrifluoride), morpholine-DAST, deoxo-fluor (bis(2-methoxyethyl)aminosulfur trifluoride), Ishikawa's reagent (N,N-diethyl-(1,1,2,3,3,3-hexafluoropropyl)amine; Journal of Fluorine Chemistry, 1989, 43, 371-377) (step b). The thus obtained 1,1-difluoro-2-phenylpropane can be converted into 4-(1,1-difluoro-2-propyl)benzenesulfonyl chloride by either direct chlorosulfonylation with chlorosulfonic acid (Heterocycles, 2001, 55, 9, 1789-1803; J. Org. Chem., 2000, 65, 1399-1406) (step c) or by a two step process preparing first the sulfonic acid derivatives (step d) which are then transformed to the sulfonylchlorides (step e) by reaction with e.g. chlorosulfonic acid, phosphorous pentachloride (Eur. J. Med. Chem., 2002, 36, 809-828); through diazotisation of suitable amine precursors with sodium nitrite under acidic conditions and reaction with sulfur dioxide in acetic acid (J. Org. Chem., 1960, 25, 1824-26); oxidation of suitable heteroaryl-thiols or heteroaryl-benzyl-thioethers with chlorine (Synthesis, 1998, 36-38; J. Am. Chem. Soc., 1950, 74, 4890-92) directly to the corresponding sulfonyl chlorides.

The synthesis shown in scheme 6 can also be performed using (R)-2-phenylpropanic acid and (S)-2-phenylpropanic acid respectively to give the corresponding chiral 4-(1,1-difluoropropan-2-yl)benzene-1-sulfonyl chlorides.

Scheme 7:

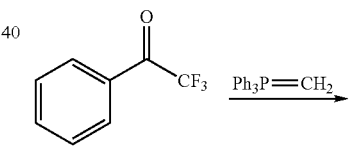

Scheme 6:

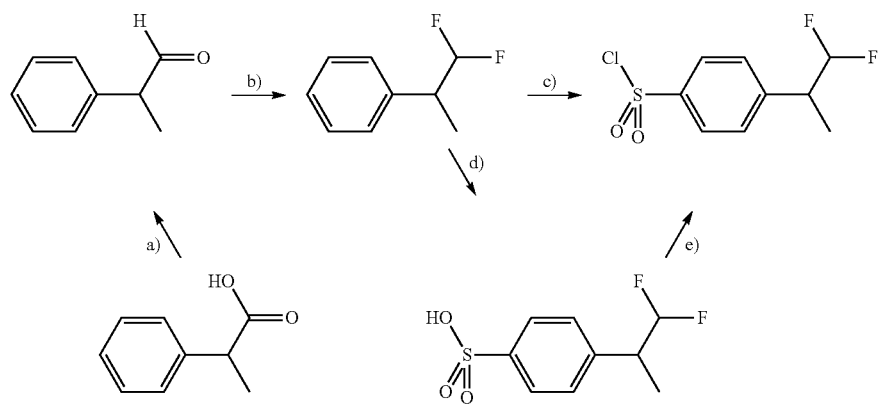

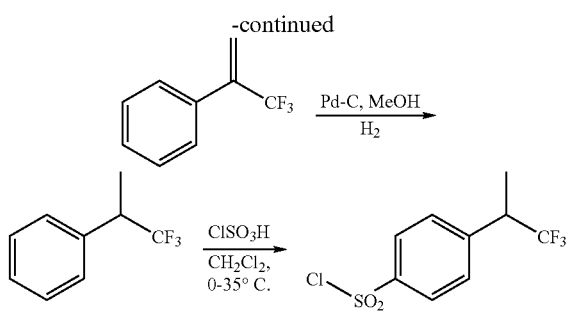

4-(1,1,1-Trifluoropropan-2-yl)benzene-1-sulfonyl chloride intermediate can be prepared from the commercially available 2,2,2-trifluoro-1-phenylethanone by a synthetic route shown in scheme 7. The ketone can be converted to the 3,3,3-trifluoro-2-phenylpropene by a Wittig reaction with a suitable ylide such as methylene-triphenylphosphane (prepared by reaction of methyltriphenylphosphonium halide and a suitable base such as lithium diisopropylamide or potassium tert-butoxide) or according to a Horner-Emmons reaction by reacting the ketone with a suitable phosphonate such as diethyl methylphosphonate and a suitable suitable base such as lithium diisopropylamide or potassium tert-butoxide. The thus obtained 3,3,3-trifluoro-2-phenylpropene can then be reduced to the saturated alkane by catalytic hydrogenation (eg Pd—C) followed by conversion to the sulfonyl chloride by the methods described in scheme 6.

The synthesis of scheme 7 can also be performed using a chiral catalyst for the alkene hydrogenation to allow the preparation of the corresponding chiral 4-(1,1,1-triifluoropropan-2-yl)benzene-1-sulfonyl chlorides.

Scheme 8:

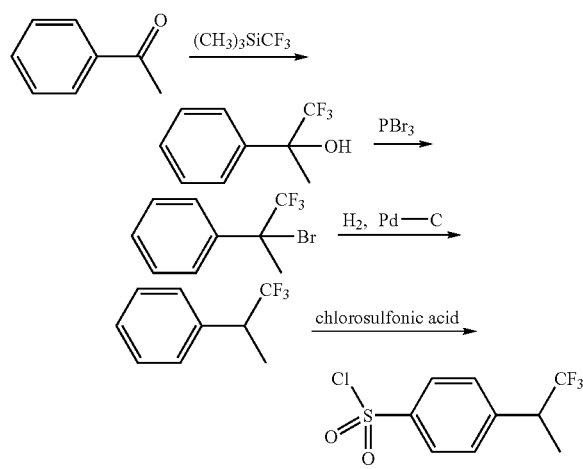

The 4-(1,1,1-trifluoropropan-2-yl)benzene-1-sulfonyl chloride can be also prepared from the commercially available 1-phenyl-ethanone by a four step procedure as shown in scheme 8. The ketone can be converted to the trifluoromethyl hydroxyl intermediate by reaction with trimethyl-trifluoromethyl-silane (Journal of Organic Chemistry, 2000, 65, 8848-8856; Journal of Fluorine Chemistry, 2003, 122, 243-246) which can then be converted to the trifluoromethyl bromide (Journal of the American Chemical Society, 1987, 109, 2435-4). Dehalogenation by catalytic hydrogenation (eg Pd—C) can then be followed by conversion to the sulfonyl chloride by the methods discussed above.

Examples of solvents which can be used are ethers, such as diethyl ether, diisopropyl ether, methyl tert-butyl ether or tetrahydrofuran, aprotic polar solvent, such as dimethyl-formamide, dimethyl sulfoxide, dimethoxyethane, and acetonitrile, aromatic hydrocarbons, such as toluene and xylene, ketones, such as acetone or methyl ethyl ketone, halohydrocarbons, such as dichloromethane, trichloromethane and dichloroethane, esters, such as ethyl acetate and methyl butyrate, carboxylic acids, such as acetic acid or propionic acid, and alcohols, such as methanol, ethanol, n-propanol, isopropanol, n-butanol, isobutanol, 2-butanol and tert.-butanol.

If desired, it is possible for a base to be present in order to neutralize protons which are released in the reactions. Suitable bases include inorganic bases, such as sodium carbonate, potassium carbonate, sodium hydrogen carbonate or potassium hydrogen carbonate, and, in addition, alkoxides, such as sodium methoxide or sodium ethoxide, alkali metal hydrides, such as sodium hydride, and also organometallic compounds, such as butyllithium compounds or alkylmagnesium compounds, or organic nitrogen bases, such as triethylamine or pyridine. The latter compounds can at the same time serve as solvents.

The crude product is isolated in a customary manner, for example by filtering, distilling off the solvent or extracting from the reaction mixture, etc. The resulting compounds can be purified in a customary manner, for example by means of recrystallizing from a solvent, by means of chromatography or by means of converting into an acid addition salt.

The acid addition salts of compounds I are prepared in a customary manner by mixing the free base with a corresponding acid, where appropriate in solution in an organic solvent, for example a lower alcohol, such as methanol, ethanol or propanol, an ether, such as methyl tert-butyl ether or diisopropyl ether, a ketone, such as acetone or methyl ethyl ketone, or an ester, such as ethyl acetate.

The compounds according to the invention of the formula I have a surprisingly high affinity for $5HT_6$ receptors. Compounds of formula I are furthermore highly selective dopamine $5HT_6$ receptor ligands which, because of their low affinity for other receptors such as $D_1$ receptors, $D_5$ receptors, $D_4$ receptors, α1-adrenergic and/or α2-adrenergic receptors, muscarinic receptors, histamine receptors, opiate receptors and, in particular, dopamine $D_2$ receptors, give rise to fewer side-effects than other, less selective $5HT_6$ ligands. Some compounds of formula I show a high affinity for $5HT_6$ receptors and optionally also for dopamine $D_3$ receptors. Because of their low affinity for other receptors such as $D_1$ receptors, $D_5$ receptors, $D_4$ receptors, α1-adrenergic and/or α2-adrenergic receptors, muscarinic receptors, histamine receptors, opiate receptors and, in particular, dopamine $D_2$ receptors, they give rise to fewer side-effects than other, less selective compounds, such as classic neuroleptics, which are $D_2$ receptor antagonists.

The compound of the invention can be a dopamine $5HT_6$ receptor agonist, including partial agonistic activity, or a dopamine $5HT_6$ receptor antagonist, including inverse agonist activity.

The high affinity of the compounds according to the invention for $5HT_6$ receptors is reflected in very low in-vitro receptor binding constants ($K_i(5HT_6)$ values) of as a rule less than 50 nM (nmol/l), preferably of less than 10 nM and, in particular of less than 5 nM. The displacement of $^3$H-LSD can, for example, be used in receptor binding studies for determining binding affinities to 5-$HT_6$ receptors and [$^{125}$I]-iodosulpride for determining binding affinities to dopamine $D_3$ receptors.

The $D_3/D_2$ selectivity of the compounds according to the invention which also have a high affinity for dopamine $D_3$ receptors, i.e. the ratio $K_i(D_2)/K_i(D_3)$ of the receptor binding constants, is as a rule at least 25, preferably at least 50, even better at least 100. The displacement of [$^3$H]SCH23390 or [$^{125}$I] spiperone can be used, for example, for carrying out receptor binding studies on $D_1$, $D_2$ and $D_4$ receptors.

Because of their binding profile, the compounds can be used for treating diseases which respond to $5HT_6$ receptor ligands and optionally to dopamine $D_3$ receptor ligands (or which are susceptible to treatment with a $5HT_6$ receptor ligand, and optionally with a dopamine $D_3$ receptor ligand), i.e. they are effective for treating those medical disorders or diseases in which exerting an influence on (modulating) the $5HT_6$ receptors, and optionally on (modulating) the dopamine $D_3$ receptors, leads to an improvement in the clinical picture or to the disease being cured. Examples of these diseases are disorders or diseases of the central nervous system.

Disorders or diseases of the central nervous system are understood as meaning disorders which affect the spinal chord and, in particular, the brain. Within the meaning of the invention, the term "disorder" denotes disturbances and/or anomalies which are as a rule regarded as being pathological conditions or functions and which can manifest themselves in the form of particular signs, symptoms and/or malfunctions. While the treatment according to the invention can be directed toward individual disorders, i.e. anomalies or pathological conditions, it is also possible for several anomalies, which may be causatively linked to each other, to be combined into patterns, i.e. syndromes, which can be treated in accordance with the invention.

The disorders which can be treated in accordance with the invention are in particular disorders which respond to a modulation of the $5HT_6$ receptor They include cognitive dysfunctions, such as a deficit in memory, cognition and learning, in particular associated with Alzheimer's disease, age-related cognitive decline and mild cognitive impairment, attention deficit disorder/hyperactivity syndrome, personality disorders, such as schizophrenia, in particular cognitive deficits related with schizophrenia, affective disorders such as depression, anxiety and obsessive compulsive disorders, motion or motor disorders such as Parkinson's disease and epilepsy, migraine, sleep disorders (including disturbances of the Circadian rhythm), feeding disorders, such as anorexia and bulimia, certain gastrointestinal disorders such as Irritable Bowl Syndrome, diseases associated with neurodegeneration, such as stroke, spinal or head trauma and head injuries, such as hydrocephalus, drug addiction and obesity.

The addiction diseases include psychic disorders and behavioral disturbances which are caused by the abuse of psychotropic substances, such as pharmaceuticals or narcotics, and also other addiction diseases, such as addiction to gaming (impulse control disorders not elsewhere classified). Examples of addictive substances are: opioids (e.g. morphine, heroin and codeine), cocaine; nicotine; alcohol; substances which interact with the GABA chloride channel complex, sedatives, hypnotics and tranquilizers, for example benzodiazepines; LSD; cannabinoids; psychomotor stimulants, such as 3,4-methylenedioxy-N-methylamphetamine (ecstasy); amphetamine and amphetamine-like substances such as methylphenidate and other stimulants including caffeine. Addictive substances which come particularly into consideration are opioids, cocaine, amphetamine or amphetamine-like substances, nicotine and alcohol.

With regard to the treatment of addiction diseases, particular preference is given to those compounds according to the invention of the formula I which themselves do not possess any psychotropic effect. This can also be observed in a test using rats, which, after having been administered compounds which can be used in accordance with the invention, reduce their self administration of psychotropic substances, for example cocaine.

Compounds of formula I having a high affinity for the $5HT_6$ receptor as well as for the dopamine $D_3$ receptor can be advantageously used for treating disorders, in particular CNS disorders, having both a dopaminergic and a serotoninergic impact. While the $5HT_6$ receptor is more related to cognitive functions, the dopamine $D_3$ receptor is associated with positive symptoms, such as delusion, hallucination, disorganized thinking, disorganized speaking, disorganized, agitated or catatonic behaviour, and negative symptoms, such as depletion of feelings, impairment of the language, loss of motivation, loss of vitality, attention deficits and social retreat. Thus, compounds of formula I having a high affinity for the $5HT_6$ receptor as well as for the dopamine $D_3$ receptor can be advantageously used for treating disorders, such as Alzheimer's disease and in particular schizophrenia, which are characterized by cognitive dysfunctions as well as by positive and negative symptoms.

According to another aspect of the present invention, the compounds according to the invention are suitable for treating disorders whose causes can at least partially be attributed to an anomalous activity of $5HT_6$ receptors.

According to another aspect of the present invention, the treatment is directed, in particular, toward those disorders which can be influenced, within the sense of an expedient medicinal treatment, by the binding of preferably exogeneously administered binding partners (ligands) to $5HT_6$ receptors.

The diseases which can be treated with the compounds according to the invention are frequently characterized by progressive development, i.e. the above-described conditions change over the course of time; as a rule, the severity increases and conditions may possibly merge into each other or other conditions may appear in addition to those which already exist.

The compounds according to the invention can be used to treat a large number of signs, symptoms and/or malfunctions which are connected with the disorders of the central nervous system and, in particular, the abovementioned conditions. These signs, symptoms and/or malfunctions include, for example, a disturbed relationship to reality, lack of insight and ability to meet customary social norms or the demands made by life, changes in temperament, changes in individual drives, such as hunger, sleep, thirst, etc., and in mood, disturbances in the ability to observe and combine, changes in personality, in particular emotional lability, hallucinations, ego-disturbances, distracted-ness, ambivalence, autism, depersonalization and false perceptions, delusional ideas, chanting speech, lack of synkinesia, short-step gait, flexed posture of trunk and limbs, tremor, poverty of facial expression, monotonous speech, depressions, apathy, impeded spontaneity and decisiveness, impoverished association ability, anxiety, nervous agitation, stammering, social phobia, panic disturbances, withdrawal symptoms in association with dependency, maniform syndromes, states of excitation and confusion, dysphoria, dyskinetic syndromes and tic disorders, e.g. Huntington's chorea and Gilles-de-la-Tourette's syndrome, vertigo syndromes, e.g. peripheral positional, rotational and oscillatory vertigo, melancholia, hysteria, hypochondria and the like.

Within the meaning of the invention, a treatment means the treatment of acute or chronic signs, symptoms and/or malfunctions. The treatment can be orientated symptomatically, for example as the suppression of symptoms. It can be effected over a short period, be orientated over the medium term or can be a long-term treatment, for example within the context of a maintenance therapy.

The compounds according to the invention are preferentially suitable for treating diseases of the central nervous system, more preferably for treating cognitive dysfunctions and in particular, for treating cognitive dysfunctions associated with schizophrenia or Alzheimer's disease.

Within the context of the treatment, the use according to the invention of the described compounds involves a method. In this method, an effective quantity of one or more compounds, as a rule formulated in accordance with pharmaceutical and veterinary practice, is administered to the individual to be treated, preferably a mammal, in particular a human being, productive animal or domestic animal. Whether such a treatment is indicated, and in which form it is to take place, depends on the individual case and is subject to medical assessment (diagnosis) which takes into consideration signs, symptoms and/or malfunctions which are present, the risks of developing particular signs, symptoms and/or malfunctions, and other factors.

As a rule, the treatment is effected by means of single or repeated daily administration, where appropriate together, or alternating, with other active compounds or active compound-containing preparations such that a daily dose of preferably from about 0.1 to 1000 mg/kg of bodyweight, in the case of oral administration, or of from about 0.1 to 100 mg/kg of bodyweight, in the case of parenteral administration, is supplied to an individual to be treated.

The invention also relates to the production of pharmaceutical compositions for treating an individual, preferably a mammal, in particular a human being, productive animal or domestic animal. Thus, the ligands are customarily administered in the form of pharmaceutical compositions which comprise a pharmaceutically acceptable excipient together with at least one compound according to the invention and, where appropriate, other active compounds. These compositions can, for example, be administered orally, rectally, transdermally, subcutaneously, intravenously, intramuscularly or intranasally.

Examples of suitable pharmaceutical formulations are solid medicinal forms, such as powders, granules, tablets, in particular film tablets, lozenges, sachets, cachets, sugar-coated tablets, capsules, such as hard gelatin capsules and soft gelatin capsules, suppositories or vaginal medicinal forms, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations, and eyedrops and eardrops. Implanted release devices can also be used for administering inhibitors according to the invention. In addition, it is also possible to use liposomes or microspheres.

When producing the compositions, the compounds according to the invention are optionally mixed or diluted with one or more excipients. Excipients can be solid, semisolid or liquid materials which serve as vehicles, carriers or medium for the active compound.

Suitable excipients are listed in the specialist medicinal monographs. In addition, the formulations can comprise pharmaceutically acceptable carriers or customary auxiliary substances, such as glidants; wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik und angrenzende Gebiete [Encyclopedia of auxiliary substances for pharmacy, cosmetics and related fields], 4$^{th}$ edition, Aulendorf: ECV-Editio-Kantor-Verlag, 1996.

It has further been found that disorders having both a dopaminergic and a serotoninergic impact can also be treated by the combined use of a dopamine $D_3$ receptor ligand and a $5HT_6$ receptor ligand. This combination surprisingly shows no adverse effects.

Accordingly, a further aspect of the invention relates to a pharmaceutical composition comprising at least one compound having an affinity for the dopamine $D_3$ receptor and at least one compound having an affinity for the $5HT_6$ receptor and optionally at least one physiologically acceptable carrier and/or auxiliary substance.

The invention also relates to the use of at least one compound having an affinity for the dopamine $D_3$ receptor together with at least one compound having an affinity for the $5HT_6$ receptor or of the pharmaceutical composition as defined above for preparing a medicament for the treatment of a disease of the central nervous system.

The compounds to be used according to the invention or in the above composition having an affinity for the dopamine $D_3$ receptor preferably have no or no significant activity for the $5HT_6$ receptors and vice versa. Preferably, the compound having an affinity for the dopamine $D_3$ receptor has a binding constant $K_i$ to the dopamine $D_3$ receptor of at most 150 nM and the compound having an affinity for the $5HT_6$ receptor has a binding constant $K_i$ to the $5HT_6$ receptor of at most 150 nM. More preferably, the compound having an affinity for the dopamine $D_3$ receptor has a selectivity for the $D_3$ dopamine receptor versus the $5HT_6$ receptor $K_i(5HT_6)/K_i(D_3)$ of at least 10, more preferably at least 25, and in particular at least 50 and the compound having an affinity for the $5HT_6$ dopamine receptor has a selectivity for the $5HT_6$ receptor versus the dopamine $D_3$ receptor $K_i(D_3)/K_i(5HT_6)$ of at least 10, more preferably at least 25, and in particular at least 50.

Compounds having an affinity for the dopamine $D_3$ receptor are widely known and are for example described in following publications:
WO 2006/058753, WO 2006/040176, WO 2006/040177, WO 2006/040178, WO 2006/040179, WO 2006/0040180, WO 2006/008592, WO 2006/015842, WO 2005/058328, WO 2004/89905, WO 2004/108706, WO 2004/080981, WO 2004/069830, WO 01/72306, WO 00/67847, WO 00/42038, WO 99/09015, WO 99/02503, WO 97/25324, WO 96/002519, the contents of which are hereby fully incorporated by reference.

Preferred compounds having an affinity for the dopamine $D_3$ receptor are dopamine $D_3$ receptor antagonists.

Compounds having an affinity for the dopamine $5HT_6$ receptor are also well known and are for example described in following publications:
WO 2006/081322, WO 2005/040124, WO 2003/080580, WO 2002/032863, WO 00/05225, WO 98/27081 and S.-H.

Zhao et al., Bioorganic and Medicinal Chemistry Letters 2007, the contents of which are hereby fully incorporated by reference.

Preferred compounds having an affinity for the dopamine $5HT_6$ receptor are dopamine $5HT_6$ receptor antagonists.

In one preferred embodiment of the invention, compounds having an affinity for the dopamine $5HT_6$ receptor are the compounds of the formula I of the present invention. More preferred compounds are compounds I mentioned above as preferred.

Surprisingly, the combination of compound having an affinity for the dopamine $D_3$ receptor and at least one compound having an affinity for the $5HT_6$ receptor does not have any adverse effects. This can be proved by the assay (microdialysis study) described in the examples. In particular, the binding affinity to the one or other receptor is not reduced.

The following examples serve to explain the invention without limiting it.

The compounds were either characterized via proton-NMR in $d_6$-dimethylsulfoxid or d-chloroform, if not stated otherwise, on a 400 MHz or 500 MHz NMR instrument (Bruker AVANCE), or by mass spectrometry, generally recorded via HPLC-MS in a fast gradient on C18-material (electrospray-ionisation (ESI) mode), or melting point.

The magnetic nuclear resonance spectral properties (NMR) refer to the chemical shifts (δ) expressed in parts per million (ppm). The relative area of the shifts in the $^1H$ NMR spectrum corresponds to the number of hydrogen atoms for a particular functional type in the molecule. The nature of the shift, as regards multiplicity, is indicated as singlet (s), broad singlet (s. br.), doublet (d), broad doublet (d br.), triplet (t), broad trip-let (t br.), quartet (q), quintet (quint.) and multiplet (m).

PREPARATION EXAMPLES

I. Preparation of the Compounds I

Example 1

3-Difluoromethoxy-N-[2-(4-methyl-piperazin-1-yl)-pyridin-4-yl]-benzene sulfonamide To a solution of 200 mg of 2-(4-methyl-piperazin-1-yl)-4-amino-pyridin (1.04 mmol) in 5 ml of pyridine 272 mg of (1.12 mmol) of 3-difluoromethoxybenzene sulfonylchloride (1.66 mmol) were added and the reaction mixture was stirred for 15 h at room temperature. The solvent was evaporated under reduced pressure and the residue was dissolved in dichloromethane. This mixture was washed with aqueous $NaHCO_3$. The organic layer was dried over magnesium sulfate, filtered, and the solvent was evaporated under reduced pressure. The crude product was purified via silica gel chromatography with ethyl dichloromethane/methanol (0-15%) as eluent, yielding 231 mg of the purified product.

ESI-MS: 399.1 $[M+H]^+$
$^1$H-NMR (DMSO): δ [ppm] 7.8 (d, 1H), 7.7 (d, 1H), 7.65 (t, 1H), 7.6 (s, 1H), 7.45 (d, 1H), 7.3 (t, 1H, $OCHF_2$), 6.4 (d, 1H), 6.35 (s, 1H), 3.35 (broad, 4H), 2.4 (broad, 4H), 2.2 (s, 3H).

Example 2

4-Isopropyl-N-[5-piperazin-1-yl-pyridin-3-yl]-benzenesulfonamide x HCl 2.1 1-Benzyl-4-(5-bromo-pyridin-3-yl)-piperazine A mixture of 1-benzyl-piperazine (1.49 g, 8.44 mmol), 3,5-dibromo-pyridine (2.00 g, 8.44 mmol), and potassium carbonate (1.17 g, 8.44 mmol) in 15 ml DMF was heated at 200° C. for 1 h under a nitrogen atmosphere. Then the mixture was diluted with 100 ml of water and was extracted twice with ethyl acetate. The combined organic layers were extracted with aqueous HCl solution. The pH of the aqueous solution was adjusted to pH 10 with aqueous NaOH. After extraction with diethylether the combined organic phases were dried with magnesium sulfate, filtered and the solvent was evaporated under reduced pressure. The so obtained oil was purified via silica gel chromatography with cyclohexane/ethyl acetate (2:1) as eluent to give 0.32 g of the product.

ESI-MS: 333.1 $[M+H]^+$ 2.2 N-[5-(4-Benzyl-piperazin-1-yl)-pyridin-3-yl]-4-isopropyl-benzenesulfonamide To a solution of 1-benzyl-4-(5-bromo-pyridin-3-yl)-piperazine (320 mg, 0.88 mmol) in 5 ml trifluoromethylbenzene under an argon atmosphere was added $Pd_2(dba)_3$ (40 mg, 0.04 mmol), and tri-tert-butyl-phosphane (27 mg, 0.13 mmol). To a solution of 4-isopropylbenzene sulfonamide (175 mg, 0.88 mol) in 10 ml trifluoromethyl benzene in a separate flask was added sodium hydride (50%, 42 mg, 0.88 mmol) at 50° C. This second solution was added after cooling to room temperature to the first solution. The mixture was heated in a microwave instrument (CEM) at 150° C. for 1 h. After evaporation of the solvent under reduced pressure the mixture was diluted with 50 ml of water and was extracted with 25 ml of ethyl acetate. The combined organic layers were extracted with aqueous HCl solution. The pH of the aqueous solution was adjusted to pH 9 with aqueous NaOH. After extraction with ethyl acetate, the combined organic phases were dried with magnesium sulfate, filtered and the solvent was evaporated under reduced pressure. The so obtained oil was purified via silica gel chromatography with cyclohexane/ethyl acetate (3:7) as eluent, yielding 100 mg of the product.

ESI-MS: 451.1 $[M+H]^+$ 2.3 4-Isopropyl-N-[5-piperazin-1-yl-pyridin-3-yl]-benzenesulfonamide x HCl A mixture of N-[5-(4-benzylpiperazin-1-yl)-pyridin-3-yl]-4-isopropyl benzene sulfonamide (100 mg, 0.22 mmol) and 10% palladium on charcoal (10 mg) in methanol (20 ml) was hydrogenated at atmospheric pressure until the consumption of hydrogen was complete. After filtration and evaporation of the solvent under reduced pressure the residue was dissolved in water and 0.5 ml 1N HCl and was lyophilized to give 78 mg of the title compound.

ESI-MS: 362.1 $[M+H]^+$

Example 3

4-Isopropyl-N-[5-(4-propyl-piperazin-1-yl)-pyridin-3-yl]-benzenesulfonamide 30 mg of 4-Isopropyl-N-[5-piperazin-1-yl-pyridin-3-yl]-benzenesulfonamide (0.08 mmol) were dissolved in 5 ml of tetrahydrofuran, and 6.9 mg of acetic acid, 4.4 mg of propionic aldehyde (0.08 mmol) and 32 mg of sodium triacetoxyborohydride (0.15 mmol) were slowly added in portions. After stirring at room temperature for 120 min., the solvent was evaporated, water was added and the pH was adjusted to pH 8. The aqueous phase was extracted three times with diethyl ether, the organic phases were combined, dried over magnesium sulphate, filtered and evaporated to dryness under reduced pressure. The residue was dissolved in 25 ml water and 0.5 ml 1N HCl and the mixture was lyophilized to yield 25 mg of the product.

ESI-MS: 404.1 $[M+H]^+$

II. Examples of Galenic Administration Forms

A) Tablets

Tablets of the following composition are pressed on a tablet press in the customary manner:
40 mg of substance from Example 8
120 mg of corn starch
13.5 mg of gelatin
45 mg of lactose
2.25 mg of Aerosil® (chemically pure silicic acid in submicroscopically fine dispersion)
6.75 mg of potato starch (as a 6% paste)

B) Sugar-Coated Tablets
20 mg of substance from Example 8
60 mg of core composition
70 mg of saccharification composition The core composition consists of 9 parts of corn starch, 3 parts of lactose and 1 part of 60:40 vinylpyrrolidone/vinyl acetate copolymer. The saccharification composition consists of 5 parts of cane sugar, 2 parts of corn starch, 2 parts of calcium carbonate and 1 part of talc. The sugar-coated tablets which had been prepared in this way are subsequently provided with a gastric juice-resistant coating.

III. Biolociical Investigations

Receptor Binding Studies:

The substance to be tested was either dissolved in methanol/Chremophor® (BASF-AG) or in dimethyl sulfoxide and then diluted with water to the desired concentration.

Human $5HT_6$ Receptor:

Characterization of the compounds of this invention to the human 5-HT6 receptor in the binding assay and the functional adenylyl cyclase assay The compounds were dissolved in a concentration of $10^{-2}$ M or $10^{-3}$ M in DMSO. Further dilutions were performed in incubation buffer.

Binding Assays

The procedure for the binding assay was based on the method of Monsma et al. (1993) Mol Pharmacol 43: 320-327. The binding reaction was carried out in a total volume of 0.250 ml for 60 min at 37° C. Membranes from HEK-293 cells stably expressing the human 5-HT6 receptor were incubated with 2 nM $^3$H-LSD in the presence or absence of various concentrations of test compound for 60 min at 37° C. Non-specific binding was defined with 100 µM Serotonin (5-HT). Assays were performed in duplicate. Bound and free radioligand was separated by filtration and bound radioactivity determined by liquid scintillation counting.

Evaluation:

The specific ligand binding to the receptors was defined as the difference between the total binding and the nonspecific binding determined in the presence of an excess of unlabelled 5-HT. The results are expressed as a percent of control specific binding obtained in the presence of compound. The $IC_{50}$ values (concentration causing a half-maximal inhibition of control specific binding) and Hill coefficients (no were determined by non-linear regression analysis of the competition curves using Hill equation curve fitting.

The inhibition constants ($K_i$) were calculated from the Cheng Prusoff equation ($K_i$=IC50/(1+(L/KD)), where L=concentration of radioligand in the assay, and KD=affinity of the radioligand for the receptor).

Functional Adenylyl Cyclase Assay

Membranes of human Hela cells stably expressing human 5-HT6 receptors were incubated for 20 min at 37° C. in HBSS, 1 mM MgCl2, 1 mM CaCl2, 100 mM IBMX, pH 7.4 in the presence and absence of test compounds. For agonistic effect, compounds were incubated alone. For antagonistic effects inhibition of 0.3 µM serotonin (5-HT)-induced cAMP increase was determined.

Evaluation: cAMP accumulation was determined by EIA quantification.

Dopamine $D_3$ Receptor:

The assay mixture (0.250 ml) was composed of membranes derived from ~$10^6$ HEK-293 cells possessing stably expressed human dopamine $D_3$ receptors, 0.1 nM [$^{125}$I]-iodosulpride and incubation buffer (total binding) or, in addition, test substance (inhibition curve) or 1 µM spiperone (nonspecific binding). Each assay mixture was run in triplicate.

The incubation buffer contained 50 mM tris, 120 mM NaCl, 5 mM KCl, 2 mM $CaCl_2$, 2 mM $MgCl_2$ and 0.1% bovine serum albumin, 10 µM quinolone and 0.1% ascorbic acid (prepared fresh daily). The buffer was adjusted to pH 7.4 with HCl.

Dopamine $D_{2L}$ Receptor:

The assay mixture (1 ml) was composed of membranes from ~$10^6$ HEK-293 cells possessing stably expressed human dopamine $D_{2L}$ receptors (long isoform) and 0.01 nM [$^{125}$I] iodospiperone and incubation buffer (total binding) or, in addition, test substance (inhibition curve) or 1 µM haloperidol (nonspecific binding). Each assay mixture was run in triplicate.

The incubation buffer contained 50 mM tris, 120 mM NaCl, 5 mM KCl, 2 mM $CaCl_2$, 2 mM $MgCl_2$ and 0.1% bovine serum albumin. The buffer was adjusted to pH 7.4 with HCl.

Measurement and Analysis:

After having been incubated at 25° C. for 60 minutes, the assay mixtures were filtered through a Whatman GF/B glass fiber filter under vacuum using a cell collecting device. The filters were transferred to scintillation viols using a filter transfer system. After 4 ml of Ultima Gold® (Packard) have been added, the samples were shaken for one hour and the radioactivity was then counted in a Beta-Counter (Packard, Tricarb 2000 or 2200CA). The cpm values were converted into dpm using a standard quench series and the program belonging to the instrument.

The inhibition curves were analyzed by means of iterative nonlinear regression analysis using the Statistical Analysis System (SAS) which is similar to the "LIGAND" program described by Munson and Rodbard.

The results of the receptor binding studies are expressed as receptor binding constants $K_i(5HT_6)$, $K_i(D_3)$ and $K_i(D_2)$, respectively, as herein before described, and given in table 6.

In these tests, the compounds according to the invention exhibit very good affinities for the $5HT_6$ receptor (<50 nM, or <10 nM, frequently <5 nM). Some of the compounds also exhibit very good affinities for the $D_3$ receptor (<50 nM, or <10 nM, frequently <5 nM) and bind selectively to the $D_3$ receptor, as compared to the affinity for the $D_2$ receptor.

IV. Assay for Testing the Compatibility of Dopamine $D_3$ and $5HT_6$ Receptor Ligands Microdialysis Studies An increase in cholinergic function is widely believed to improve cognitive performance, an increase of cortical extracellular acetylcholine (ACh) can be regarded as a bio-chemical marker for potential pro-cognitive effects.

Therefore, microdialysis studies in freely moving rats were performed. The effects of $5-HT_6$ receptor ligands, selective $D_3$ ligands or the combination of both principles, on acetylcholine release in the medial prefrontal cortex and in the hippocampus has been investigated: one guide cannula was implanted into the medial prefrontal cortex (AP=2.5; ML=0.6; DV=−0.2) and the second into the hippocampus (AP=−5.5; ML=4.5; DV=−4.5). 5 to 7 days after surgery, 2 microdialysis probes (CMA/12, 3 mm membrane length) were slowly lowered into the final position. On the day of the experiment, the test compound or its vehicle (2 ml/kg) was administered intraperitoneally. Microdialysate fractions (six 20-min fractions before and six fractions after compound administration) were analyzed for acetylcholine by high performance liquid chromatography in combination with electrochemical detection (for methods see Fox et al., J. Phamacol. Exp. Ther. 2005, 313, 176 to 190 and detailed description below).

5-$HT_6$ receptor ligands and selective $D_3$ receptor ligands increased dose-dependently extracellular ACh levels in the medial prefrontal cortex and in the hippocampus. The combination of both 5-$HT_6$ receptor ligands and $D_3$ receptor ligands resulted in an at least additive effect of both principles in the medial prefrontal cortex and in the hippo-campus, suggesting thus that the combination of both principles may offer a therapeutic benefit in CNS disorders characterized by impaired cognitive functions, including dementia and schizophrenia.

Furthermore, mixed $D_3$/5-$HT_6$ receptor ligands also increase microdialysate ACh levels in the medial prefrontal cortex and in the hippocampus. Based on dose comparisons, compounds combining $D_3$/5-$HT_6$ within the molecule are more potent in increasing cortical cholinergic function than "pure" $D_3$ receptor antagonists.

Microdialysis Experiments

Surgery

For pain prophylaxis, Rimadyl® (3 mg/kg, i.p.) was administered before surgery. Individual male Sprague-Dawley rats (290-320 g body weight) anesthetized with pentobarbital (60 mg/kg, i.p, Narcoren®, Rhone-Merieux GmbH, France) were mounted in a KOPF stereotaxic frame and two microdialysis guide cannula (CMA/12, Axel Semrau GmbH, Germany) were implanted into selected brain areas of the same animal: one guide cannula was implanted into the medial prefrontal cortex (AP=2.5; ML=0.6; DV=−0.2) and the second into the hippocampus (AP=−5.5; ML=4.5; DV=−4.5). The guide cannula were secured with dental cement (Technovit powder, Product No 5071, Technovit polymerization starter fluid, Product No 2060, Kulzer GmbH, Germany) and 4 anchor screws into the skull. The rats were allowed to recover from surgery for 5-7 days. The day before the experiment, each animal was transferred into a system allowing for free movement (CMA/120 Axel Semrau GmbH, Germany, consisting of a plastic bowl, wire attachment, counter-balance arm, swivel assembly connecting in-/outlet of the probe with the perfusion pump). Next, a CMA/12 microdialysis probe (3 mm membrane length) was slowly lowered into the final position. The probe was perfused with Ringer solution (147 mM NaCl, 4.0 mM KCl and 2.4 mM $CaCl_2$, containing 1 μM neostigmine), for about one hour (CMA/102 microdialysis pump, Axel Semrau GmbH, Germany; 1.5 μl/min). The probe was perfused again 24 hours later for at least 1 hour before microdialysate fractions were collected every 20 minutes. Six fractions before and six fractions after the intraperitoneally administration of the test compound or vehicle were analyzed for microdialysate levels of acetylcholine by HPLC with electro-chemical detection.

Assay of Microdialysate Acetylcholine Levels

10 μl of each microdialysate fraction was injected onto a reversed phase column (MF-8908 Acetylcholine SepStik Kit; microbore column, particle size 10 μm, 530×1.0 mm coupled to an immobilized enzyme reactor 50×1.0 mm, particle size 10 μm, containing acetylcholinesterase and choline oxidase; BAS, U.S.A.) using a refrigerated autosampler (HTC PAL twin injector autosampler system, Axel Semrau, Germany). The mobile phase consisted of 50 mmol/l $Na_2HPO_4$ (pH 8.5) and 5 ml/l Kathon. Flow rate was 0.14 ml/min (Rheos Flux pump, Axel Semrau GmbH, Germany), and the sample run time was less than 15 minutes. Acetylcholine and choline were measured via an electro-chemical detector (LC-4C, BAS, U.S.A.) with a platinum working electrode set at +500 mV versus an Ag/AgCl reference electrode. The system was calibrated by standard solutions (acetylcholine, choline) containing 1 μmol/10 μl injection. Acetylcholine was identified by its retention time and peak height with an external standard method using chromatography software (Chrom Perfect®, version 4.4.22, Justice Laboratory Soft-ware, U.S.A.).

Microdialysis (area under curve 0-120 min) data were evaluated for significance using one-way analysis of variance (ANOVA) followed by Dunnett's pair-wise comparison post hoc test using GraphPad Prism v 4.0 software.

We claim:

1. A compound of the formula (I)

wherein
D is a group of the formula C

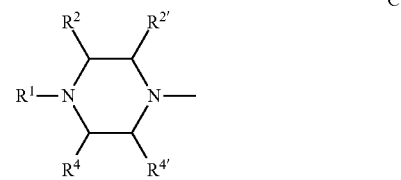

$R^1$ is H, $C_1$-$C_6$-alkyl, $C_1$-$C_6$-alkyl substituted by $C_3$-$C_6$-cycloalkyl, $C_1$-$C_6$-hydroxyalkyl, fluorinated $C_1$-$C_6$-alkyl, $C_3$-$C_6$-cycloalkyl, fluorinated $C_3$-$C_6$-cycloalkyl, $C_3$-$C_6$-alkenyl, fluorinated $C_3$-$C_6$-alkenyl, formyl, acetyl, propionyl or benzyl;

$R^2$, $R^{2'}$, $R^3$, $R^4$ and $R^{4'}$ are, independently of each other, H, methyl, fluoromethyl, difluoromethyl, or trifluoromethyl;

A is 2,4-pyridylene, 3,5-pyridylene or 2,6-pyridylene, which is optionally substituted by one, two or three substituents selected from halogen, $C_1$-$C_4$-alkyl, $C_1$-$C_4$-alkoxy, fluorinated $C_1$-$C_4$-alkyl and fluorinated $C_1$-$C_4$-alkoxy;

E is $NR^7$, wherein $R^7$ is H or $C_1$-$C_3$-alkyl;

Ar is a cyclic radical selected from the group consisting of phenyl, where the cyclic radical Ar carries 1 substituent $R^a$ in the 3-position of the phenyl ring;

each $R^a$ is $C_1$-$C_6$-hydroxyalkoxy, $C_1$-$C_6$-alkoxy-$C_1$-$C_6$-alkoxy, fluorinated $C_1$-$C_6$-alkoxy, $C_1$-$C_6$-alkylthio, or fluorinated $C_1$-$C_6$-alkylthio;

and physiologically tolerated acid addition salts thereof.

2. The compound as claimed in claim 1, wherein $R^1$ is H, $C_1$-$C_6$-alkyl, $C_1$-$C_6$-alkyl substituted by $C_3$-$C_6$-cycloalkyl, $C_1$-$C_6$-hydroxyalkyl, fluorinated $C_1$-$C_6$- alkyl, $C_3$-$C_6$-cycloalkyl, fluorinated $C_3$-$C_6$-cycloalkyl, $C_3$-$C_6$-alkenyl, fluorinated $C_3$-$C_6$-alkenyl, formyl, acetyl or propionyl.

3. The compound of claim 1, wherein $R^1$ is hydrogen, methyl, ethyl, n-propyl, 2-fluoroethyl, 3-fluoropropyl, 3-hydroxypropyl, cyclo-propylmethyl or allyl.

4. The compound as claimed in claim 3, wherein $R^1$ is n-propyl or allyl.

5. The compound of claim 1, wherein $R^2$, $R^{2'}$, $R^3$, $R^4$ and $R^{4'}$ are H.

6. The compound of claim 1, wherein A is 2,4-pyridylene or 3,5-pyridylene, which is optionally substituted by one or more substituents selected from halogen, $C_1$-$C_4$-alkyl, $C_1$-$C_4$-alkoxy, fluorinated $C_1$-$C_4$-alkyl and fluorinated $C_1$-$C_4$-alkoxy.

7. The compound as claimed in claim 6, wherein A is 3,5-pyridylene, which is optionally substituted by one or more substituents selected from halogen, $C_1$-$C_4$-alkyl, $C_1$-$C_4$-alkoxy, fluorinated $C_1$-$C_4$-alkyl and fluorinated $C_1$-$C_4$-alkoxy.

8. The compound of claim 1, wherein $R^a$ is selected from fluorinated $C_1$-$C_4$-alkoxy.

9. A compound according to claim 1 that is 3-difluoromethoxy-N-[2-(4-methyl-piperazin-1-yl)-pyridin-4-yl]-benzene sulfonamide.

10. A method for treating depression, obesity, and cognitive dysfunctions associated with Alzheimer's disease and schizophrenia, said method comprising administering an effective amount of at least one compound of claim 1 to a subject in need thereof.

11. A pharmaceutical composition comprising at least one compound according to claim 1 and at least one physiologically acceptable carrier and/or auxiliary substance.

* * * * *

UNITED STATES PATENT AND TRADEMARK OFFICE
CERTIFICATE OF CORRECTION

| | | |
|---|---|---|
| PATENT NO. | : 8,497,273 B2 | Page 1 of 1 |
| APPLICATION NO. | : 12/297328 | |
| DATED | : July 30, 2013 | |
| INVENTOR(S) | : Grandel et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 518 days.

Signed and Sealed this
Twenty-fifth Day of August, 2015

Michelle K. Lee
*Director of the United States Patent and Trademark Office*